United States Patent
Park et al.

(10) Patent No.: US 11,873,297 B2
(45) Date of Patent: Jan. 16, 2024

(54) COMPOUND AND ORGANIC LIGHT EMITTING DEVICE COMPRISING THE SAME

(71) Applicant: LG CHEM, LTD., Seoul (KR)

(72) Inventors: Seulchan Park, Daejeon (KR); Dong Hoon Lee, Daejeon (KR); Boon Jae Jang, Daejeon (KR); Sang Duk Suh, Daejeon (KR); Min Woo Jung, Daejeon (KR); Jungha Lee, Daejeon (KR); Su Jin Han, Daejeon (KR); Sunghyun Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 386 days.

(21) Appl. No.: 17/268,176

(22) PCT Filed: Nov. 15, 2019

(86) PCT No.: PCT/KR2019/015684
§ 371 (c)(1),
(2) Date: Feb. 12, 2021

(87) PCT Pub. No.: WO2020/101441
PCT Pub. Date: May 22, 2020

(65) Prior Publication Data
US 2021/0323948 A1    Oct. 21, 2021

(30) Foreign Application Priority Data

Nov. 16, 2018  (KR) .......................... 10-2018-0142001
Nov. 14, 2019  (KR) .......................... 10-2019-0145979

(51) Int. Cl.
C07D 405/14    (2006.01)
C07D 409/14    (2006.01)
H10K 85/60     (2023.01)

(52) U.S. Cl.
CPC ......... *C07D 405/14* (2013.01); *C07D 409/14* (2013.01); *H10K 85/654* (2023.02);
(Continued)

(58) Field of Classification Search
CPC .. C07D 405/14; C07D 409/14; H10K 85/654; H10K 85/6572; H10K 85/6574; H10K 85/6576
See application file for complete search history.

(56) References Cited

U.S. PATENT DOCUMENTS 11,515,484 B2 * 11/2022  Park ..................... C07D 405/14
2004/0251816 A1  12/2004  Leo et al.
(Continued)

FOREIGN PATENT DOCUMENTS

JP            6319228        5/2018
KR     10-2000-0051826       8/2000
(Continued)

OTHER PUBLICATIONS

Machine-generated English-language translation of KR 20190064773A.*
(Continued)

*Primary Examiner* — Vu A Nguyen
(74) *Attorney, Agent, or Firm* — Bryan Cave Leighton Paisner LLP

(57) ABSTRACT

Provided is a novel compound of Chemical Formula 1:

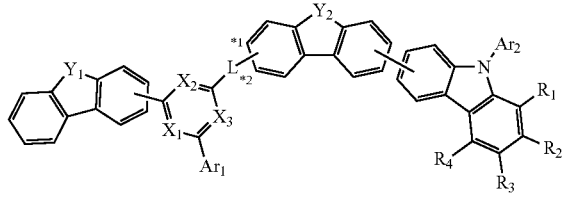

wherein:
$X_1$ to $X_3$ are each independently N or CH, provided that at least two are N,
$Y_1$ and $Y_2$ are independently O or S,
L is a single bond, or a substituted or unsubstituted $C_{6-60}$ arylene or $C_{2-60}$ heteroarylene, provided that L is bonded to a position *1 or *2,
(Continued)

$Ar_1$ and $Ar_2$ are independently a substituted or unsubstituted $C_{6-60}$ aryl or $C_{2-60}$ heteroaryl containing one or more of N, O, and S, and $R_1$ to $R_4$ are each independently hydrogen, deuterium, halogen, cyano, nitro, amino, silyl, or a substituted or unsubstituted: $C_{1-60}$ alkyl, $C_{1-60}$ haloalkyl, $C_{1-60}$ alkoxy, $C_{1-60}$ haloalkoxy, $C_{3-60}$ cycloalkyl, $C_{2-60}$ alkenyl, $C_{6-60}$ aryl, $C_{6-60}$ aryloxy, $C_{2-60}$ heteroaryl containing one or more of N, O, and S, or adjacent substituents combine to form a $C_{6-60}$ aromatic or non-aromatic ring, or a $C_{2-60}$ heteroaromatic ring, and an organic light emitting device including the same.

8 Claims, 1 Drawing Sheet

(52) U.S. Cl.
CPC ..... *H10K 85/6572* (2023.02); *H10K 85/6574* (2023.02); *H10K 85/6576* (2023.02)

(56) References Cited

U.S. PATENT DOCUMENTS

| | | |
|---|---|---|
| 2016/0248023 A1 | 8/2016 | Parham et al. |
| 2017/0186965 A1 | 6/2017 | Parham et al. |
| 2018/0037546 A1 | 2/2018 | Sugino et al. |
| 2019/0084967 A1 | 3/2019 | Parham et al. |
| 2020/0119285 A1 | 4/2020 | No et al. |
| 2020/0266355 A1 | 8/2020 | Park et al. |

FOREIGN PATENT DOCUMENTS

| | | | | |
|---|---|---|---|---|
| KR | 10-1447961 | | 10/2014 | |
| KR | 10-1730779 | | 4/2017 | |
| KR | 10-2017-0102000 | | 9/2017 | |
| KR | 10-2018-0045798 | | 5/2018 | |
| KR | 10-2018-0055688 | | 5/2018 | |
| KR | 10-2018-0061076 | | 6/2018 | |
| KR | 10-2018-0073672 | | 7/2018 | |
| KR | 10-2018-0108425 | | 10/2018 | |
| KR | 10-2019-0030963 | | 3/2019 | |
| KR | 20190030963 A * | 3/2019 | ........... C07D 405/04 |
| KR | 20190064773 A * | 6/2019 | ........... C07D 405/14 |
| KR | 20190087279 A * | 7/2019 | ........... C07D 405/14 |
| WO | 2003-012890 | | 2/2003 | |
| WO | 2015-051869 | | 4/2015 | |
| WO | 2018-101691 | | 6/2018 | |
| WO | 2018-174681 | | 9/2018 | |
| WO | 2019-054833 | | 3/2019 | |

OTHER PUBLICATIONS

International Search Report and the Written Opinion of PCT/KR2019/015684, dateed Mar. 9, 2020.

* cited by examiner

[FIG. 1]
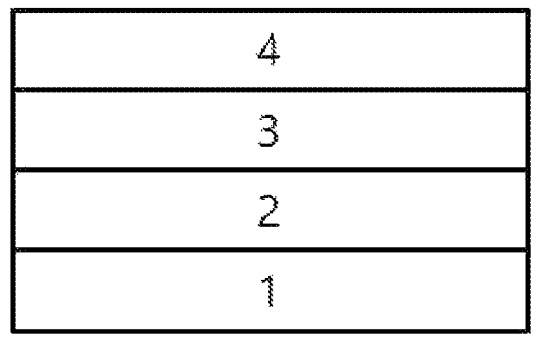
[FIG. 2]
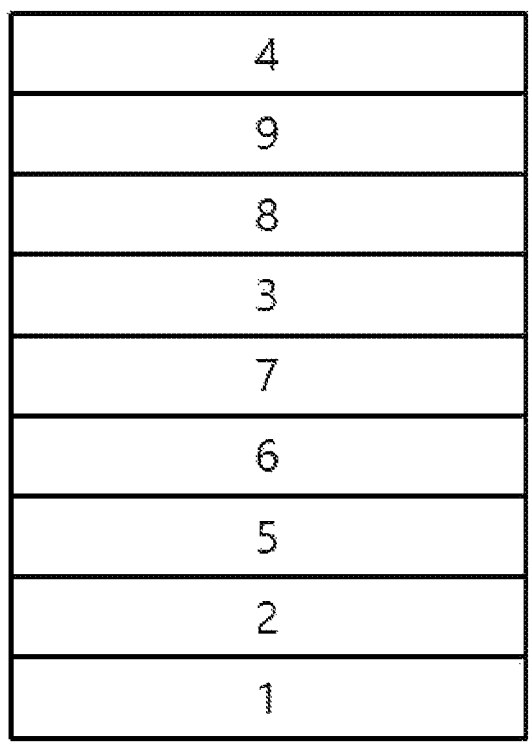

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/015684 filed on Nov. 15, 2019, which claims priority to and the benefits of the filing dates of Korean Patent Application No. 10-2018-0142001 filed with the Korean Intellectual Property Office on Nov. 16, 2018, and Korean Patent Application No. 10-2019-0145979 filed with the Korean Intellectual Property Office on Nov. 14, 2019, the entire contents of which are incorporated herein by reference.

TECHNICAL FIELD

The present disclosure relates to novel compounds and organic light emitting devices including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, holes are injected from an anode into the organic material layer and electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 0001) Korean Patent Laid-open Publication No. 10-2000-0051826

BRIEF DESCRIPTION

Technical Problem

It is an object of the present invention to provide a novel compound and an organic light emitting device including the same.

Technical Solution

In one aspect of the disclosure, provided is a compound of Chemical Formula 1:

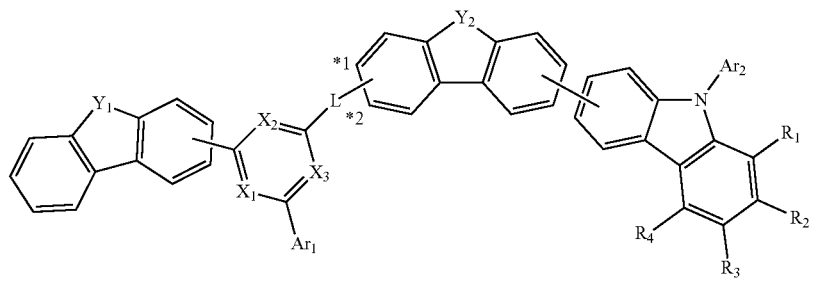

Chemical Formula 1 wherein, in Chemical Formula 1:
$X_1$ to $X_3$ are each independently N or CH, provided that at least two of $X_1$ to $X_3$ are N;
$Y_1$ and $Y_2$ are each independently O or S;
L is a single bond, a substituted or unsubstituted $C_{6-60}$ arylene, or a substituted or unsubstituted $C_{2-60}$ heteroarylene containing one or more heteroatoms selected from the group consisting of N, O, and S, provided that L is bonded to a position *1 or a position *2;
$Ar_1$ and $Ar_2$ are each independently a substituted or unsubstituted $C_{6-60}$ aryl; or a substituted or unsubstituted $C_{2-60}$ heteroaryl containing one or more heteroatoms selected from the group consisting of N, O, and S; and
$R_1$ to $R_4$ are each independently hydrogen, deuterium, a halogen, cyano, nitro, amino, silyl, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{2-60}$ heteroaryl containing one or more heteroatoms selected from the group consisting of N, O, and S, or adjacent substituents are combined with each other to form a $C_{6-60}$ aromatic ring, a $C_{6-60}$ non-aromatic ring, or a $C_{2-60}$ heteroaromatic ring containing one or more heteroatoms selected from the group consisting of N, O, and S.

In another aspect of the disclosure, there is provided an organic light emitting device including: a first electrode; a second electrode provided opposite to the first electrode; and one or more organic material layers provided between the first electrode and the second electrode, wherein one or more layers of the organic material layers includes the compound of Chemical Formula 1.

Advantageous Effects

The compound of Chemical Formula 1 described above can be used as a material of an organic material layer of an organic light emitting device, and can improve efficiency, achieve a low driving voltage, and/or improve lifetime characteristics in the organic light emitting device.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, an electron blocking layer 7, a light emitting layer 3, a hole blocking layer 8, an electron injection and transport layer 9, and a cathode 4.

DETAILED DESCRIPTION

Hereinafter, the present disclosure will be described in more detail to help understanding of the present disclosure.

In the present specification,

denotes a bond connected to another substituent, and a single bond denotes a case in which no separate atom exists in the portion represented by L.

As used herein, the term "substituted or unsubstituted" means being unsubstituted or substituted with one or more substituents selected from the group consisting of deuterium, a halogen group, a cyano group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group containing at least one of N, O, and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group, and can be interpreted as a substituent to which two phenyl groups are linked.

As used herein, the number of carbon atoms of a carbonyl group is not particularly limited, but is preferably 1 to 40. Specifically, the carbonyl group can be a group having the following structural formulae, but is not limited thereto:

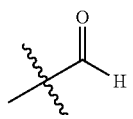
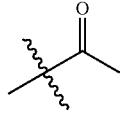
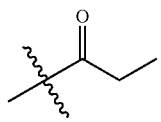
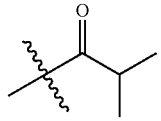
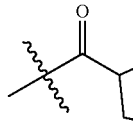
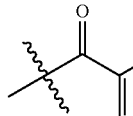
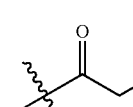

As used herein, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a group having the following structural formulae, but is not limited thereto:

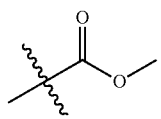
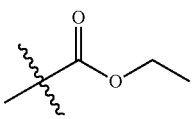
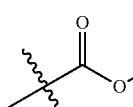
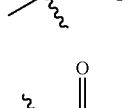
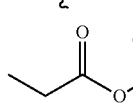
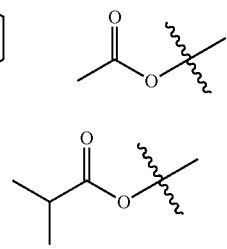
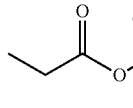

-continued

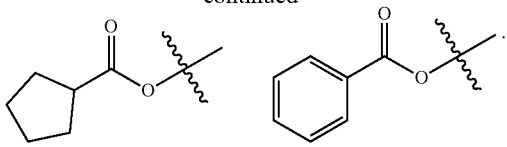

As used herein, the number of carbon atoms of an imide group is not particularly limited, but is preferably 1 to 25. Specifically, the imide group can be a group having the following structural formulae, but is not limited thereto:

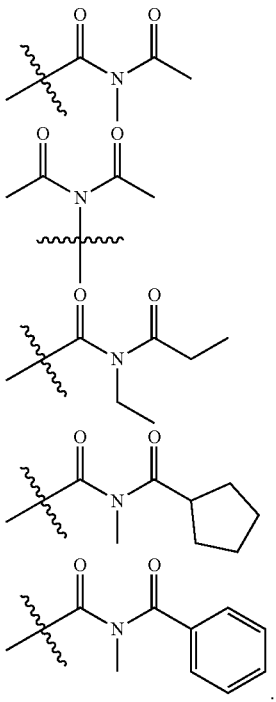

As used herein, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

As used herein, a boron group specifically includes a trimethylboron group, a triethylboron group, a t-butyldimethylboron group, a triphenylboron group, and a phenylboron group, but is not limited thereto.

As used herein, examples of a halogen group include fluorine, chlorine, bromine, and iodine.

As used herein, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to a further embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

As used herein, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

As used herein, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

As used herein, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group, or the like, but are not limited thereto.

As used herein, a fluorenyl group can be substituted, and two substituent groups can be bonded to each other to form a spiro structure. In the case where the fluorenyl group is substituted,

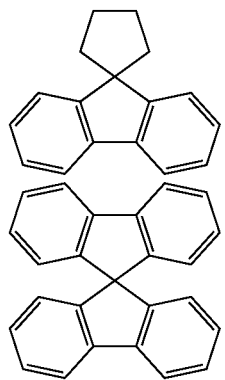

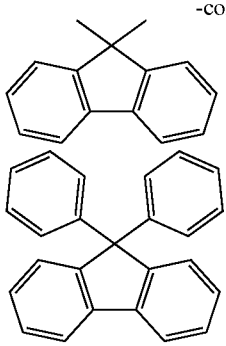

and the like can be formed. However, the structure is not limited thereto.

As used herein, a heteroaryl is a heteroaryl including one or more of O, N, Si, and S as a heteroatom, and the number of carbon atoms thereof is not particularly limited, but is preferably 2 to 60. Examples of the heteroaryl include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

As used herein, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heteroaryl group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heteroaryl group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heteroaryl is not a monovalent group but is formed by combining two substituent groups.

As used herein, an aromatic ring is a condensed monocyclic or polycyclic ring in which the entire molecule has aromaticity while containing only carbon as a ring forming atom. The aromatic ring is not particularly limited, but preferably has 6 to 60 carbon atoms, or 6 to 30 carbon atoms, or 6 to 20 carbon atoms. Further, examples of the aromatic ring include a benzene ring, a naphthalene ring, an anthracene ring, a phenanthrene ring, a pyrene ring, or the like, but are not limited thereto.

As used herein, a non-aromatic ring is a condensed monocyclic or polycyclic ring in which the entire molecule has non-aromaticity while containing only carbon as a ring forming atom. The non-aromatic ring is not particularly limited, but preferably has 6 to 60 carbon atoms, or 6 to 30 carbon atoms, or 6 to 20 carbon atoms. Further, examples of the non-aromatic ring include an indene ring, a fluorene ring, or the like, but are not limited thereto. In this regard, the indene ring, the fluorene ring, or the like are unsubstituted or substituted with one or more substituents, and the type of the substituent is referred to above.

As used herein, a heteroaromatic ring is a condensed monocyclic or polycyclic ring in which the entire molecule has aromaticity while containing one or more heteroatoms selected from the group consisting of N, O, and S other than carbon as a ring forming atom. The heteroaromatic ring is not particularly limited, but preferably has 2 to 60 carbon atoms, or 2 to 30 carbon atoms, or 2 to 20 carbon atoms. Further, examples of the heteroaromatic ring include a benzofuran ring, a benzothiophene ring, an indole ring, a carbazole ring, or the like, but are not limited thereto.

Meanwhile, in the present disclosure, there is provided the compound of Chemical Formula 1. In particular, the compound has the structure in which two or three N atom-containing 6-membered heterocyclic groups are bonded to a position *1 or a position *2 of dibenzofuran (when $Y_2$ is O)/dibenzothiophene (when $Y_2$ is S) by a linker L. When the compound is used as a host for an organic light emitting device, the organic light emitting device exhibits improved efficiency, low driving voltage, and/or improved lifetime characteristics.

However, when the compound in which two or three N atom-containing 6-membered heterocyclic groups are bonded to a position other than *1 and *2 of dibenzofuran (when $Y_2$ is O)/dibenzothiophene (when $Y_2$ is S) by linker L in Chemical Formula 1 is used as a host for an organic light emitting device, there is a problem that both the efficiency and lifetime characteristics of the organic light emitting device are deteriorated. This is, when the oxygen atom of dibenzofuran (or sulfur atom of dibenzothiophene) corresponding to the HOMO and the N atom-containing 6-membered heterocyclic group bonded to L corresponding to the LUMO are located in the same direction, or in the opposite direction, it seems that the balance of holes and electrons in the light emitting layer decreases as the electron/hole transfer characteristics are relatively reduced.

Further, when the compound in which both the N atom-containing 6-membered heterocyclic group and the carbazolyl group are bonded to the same benzene ring of dibenzofuran (when $Y_2$ is O)/dibenzothiophene (when $Y_2$ is S) is used as a host for an organic light emitting device, there is a problem that both the efficiency and lifetime characteristics of the organic light emitting device are deteriorated. It is believed that the stability of the compound decreases due to the repulsive force among the non-bonding electrons of an oxygen atom of dibenzofuran (or a sulfur atom of dibenzothiophene), that of N atoms in the 6-membered heterocycle, and that of N atoms in the carbazole group.

Specifically, the compound of Chemical Formula 1 can be Chemical Formula 1A when the linker L is bonded to the position *1, and can be Chemical Formula 1B when the linker L is bonded to the position *2 according to a bonding position of L:

Chemical Formula 1A

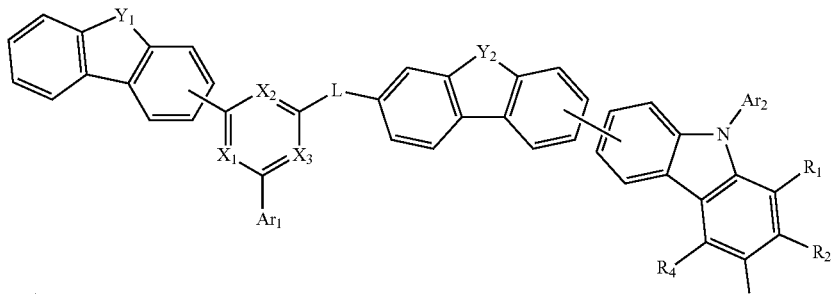

Chemical Formula 1B

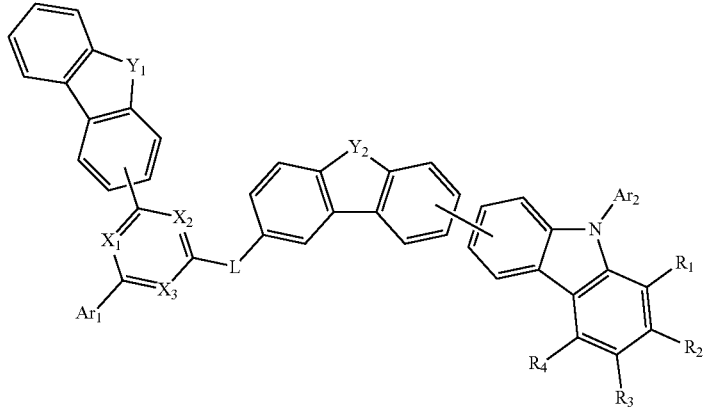

wherein, in Chemical Formula 1A and 1B:
$X_1$ to $X_3$, $Y_1$, $Y_2$, L, $Ar_1$, $Ar_2$, and $R_1$ to $R_4$ are as defined in Chemical Formula 1 above.

Preferably, $X_1$ to $X_3$ can be N.

Preferably, L can be a single bond, phenylene, biphenylylene, naphthylene, dibenzofuranylene, dibenzothiophenylene, or carbazolylene. More preferably, L can be 1,4-phenylene, 2,2'-biphenylylene, 4,4'-biphenylylene, 1,2-naphthylene, 1,4-naphthylene, 2,7-naphthylene, 1,4-dibenzofuranylene, 4,6-dibenzofuranylene, 1,6-dibenzothiophenylene, 4,6-dibenzothiophenylene, or 4,9-carbazolylene.

Preferably, $Ar_1$ and $Ar_2$ can each be independently phenyl, biphenylyl, dibenzofuranyl, dibenzothiophenyl, or carbazolyl. More preferably, $Ar_1$ can be phenyl, biphenylyl, dibenzofuranyl, dibenzothiophenyl, or carbazolyl, and $Ar_2$ can be phenyl.

Preferably, $R_1$ to $R_4$ can each be independently hydrogen or phenyl, more preferably $R_1$, $R_2$, and $R_4$ are hydrogen and $R_3$ is phenyl, or two adjacent substituents of $R_1$ to $R_4$ can be combined with each other to form a structure of Chemical Formula 2:

Chemical Formula 2

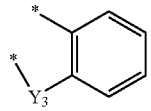

wherein, in Chemical Formula 2:
$Y_3$ is $CZ_1Z_2$, O, S, or $NZ_3$;
$Z_1$ to $Z_3$ are each independently a $C_{1-10}$ alkyl or a $C_{6-20}$ aryl; and
means a bonding position with two adjacent carbon atoms of each carbon atom bonded to $R_1$ to $R_4$.

Specifically, when two adjacent substituents of $R_1$ to $R_4$ are combined with each other to form a structure of Chemical Formula 2, two adjacent carbon atoms of each carbon atom bonded to $R_1$ to $R_4$ in Chemical Formula 1 are combined with * of Chemical Formula 2 to form a fused ring, wherein Chemical Formula 1 can be any one of the following Chemical Formulae 3-1 to 3-6:

Chemical Formula 3-1

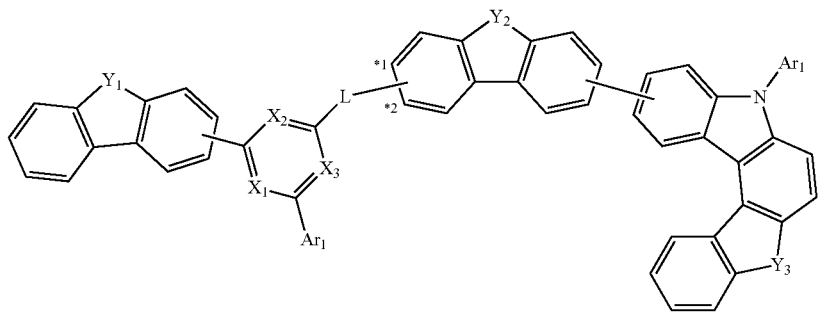

-continued
Chemical Formula 3-2
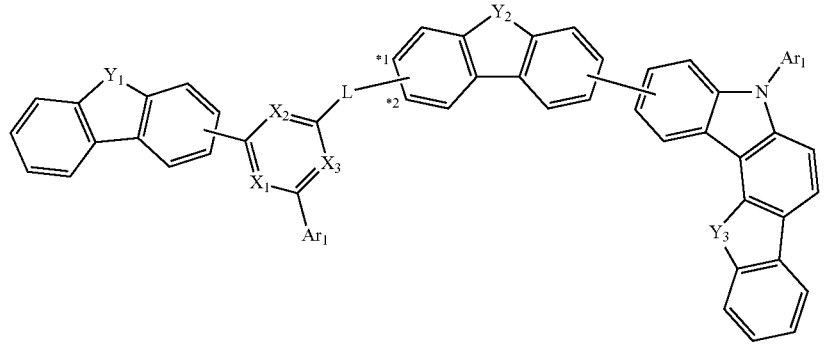
Chemical Formula 3-3
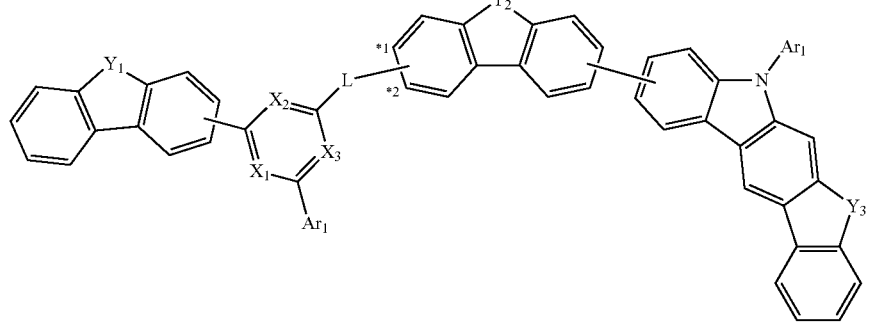
Chemical Formula 3-4
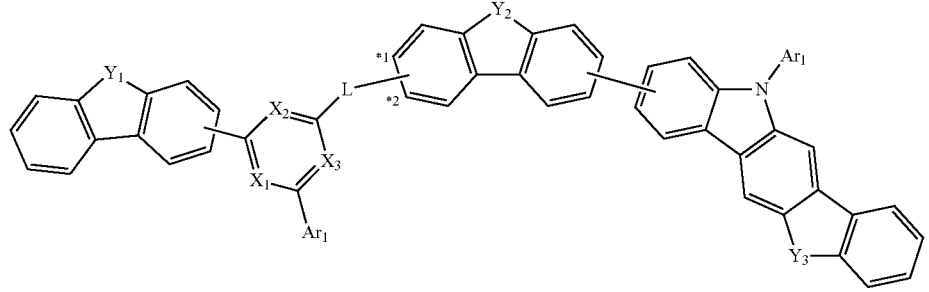
Chemical Formula 3-5
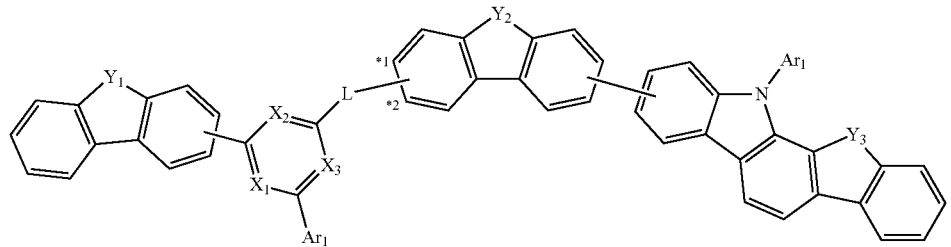
Chemical Formula 3-6
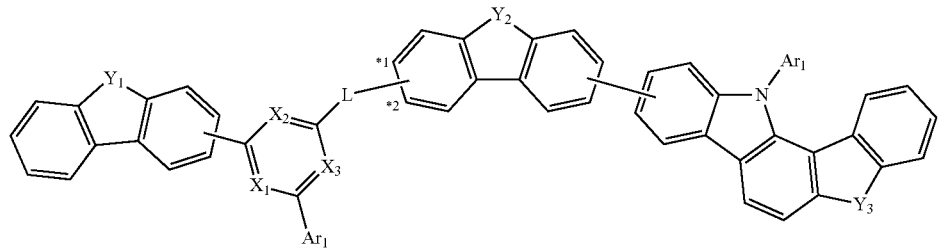

wherein, in Chemical Formula 3-1 to 3-6:
$Y_3$ is $CZ_1Z_2$, O, S, or $NZ_3$;
$Z_1$ to $Z_3$ are each independently a $C_{1-10}$ alkyl or a $C_{6-20}$ aryl; and
$X_1$ to $X_3$, $Y_1$, $Y_2$, L, $Ar_1$, and $Ar_2$ are as defined in Chemical Formula 1 above.

More preferably, $Z_1$ to $Z_3$ can each independently be methyl or phenyl, and most preferably, $Z_1$ and $Z_2$ can be methyl and $Z_3$ can be phenyl.

Preferably, the compound of Chemical Formula 1 is any one of the following Chemical Formulae 1-1 to 1-6:

Chemical Formula 1-1

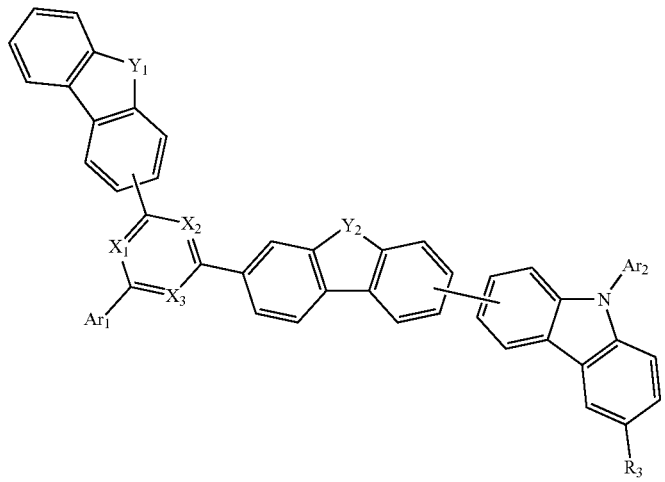

Chemical Formula 1-2

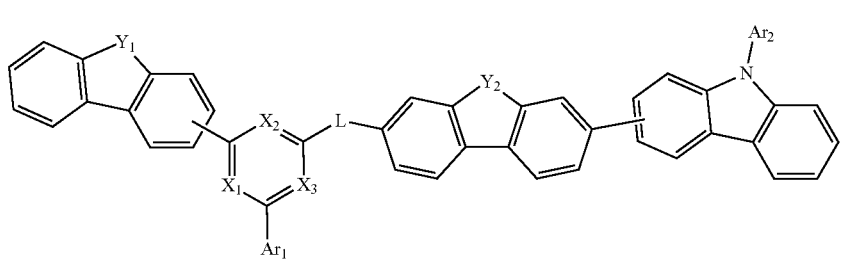

Chemical Formula 1-3

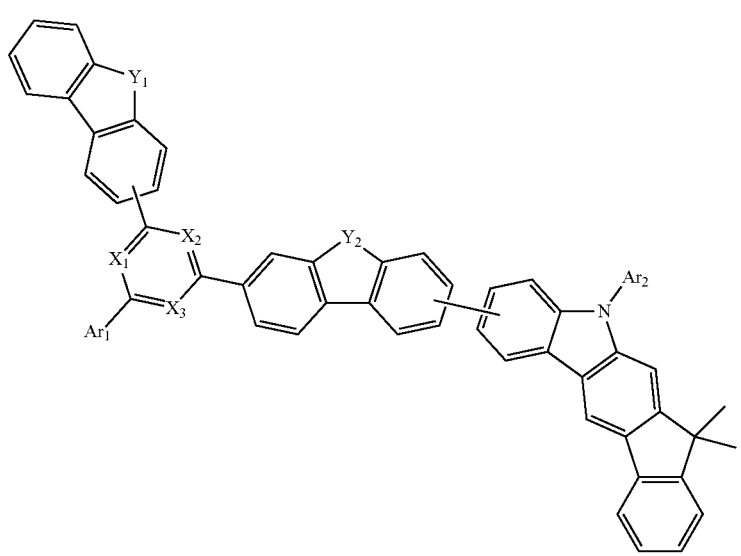

Chemical Formula 1-4

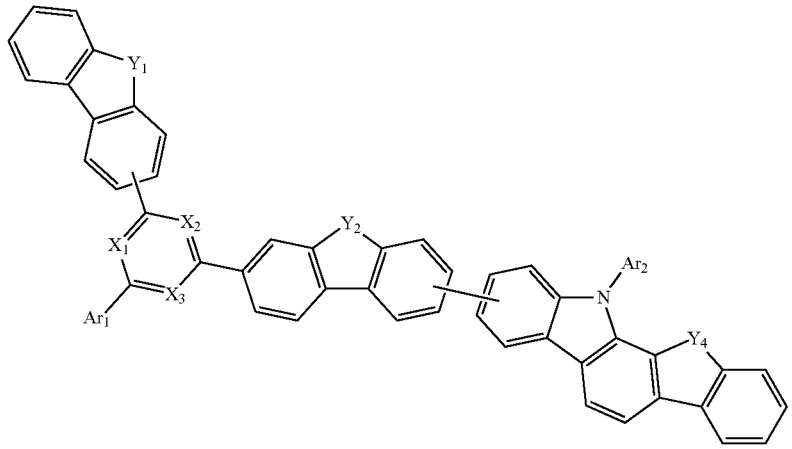

Chemical Formula 1-5

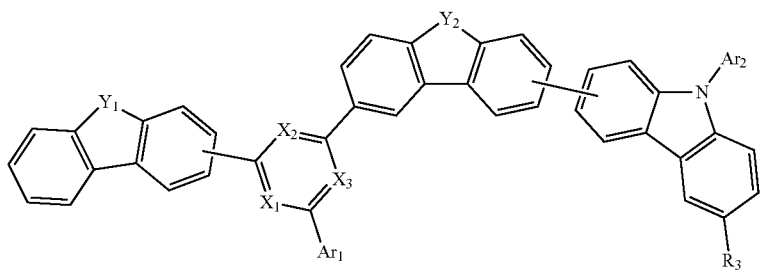

Chemical Formula 1-6

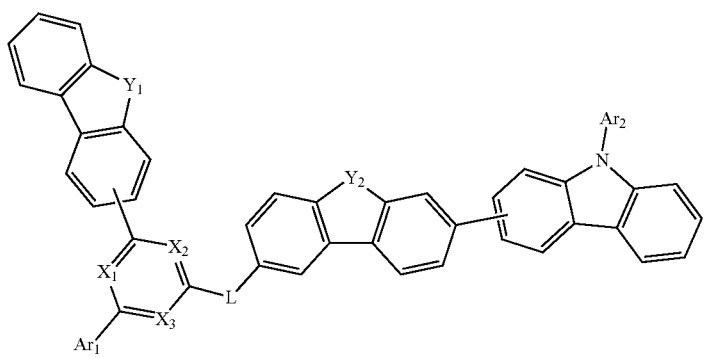

wherein, in Chemical Formulae 1-1 to 1-6:
L is a substituted or unsubstituted $C_{6-60}$ arylene, or a substituted or unsubstituted $C_{2-60}$ heteroarylene containing one or more heteroatoms selected from the group consisting of N, O, and S;
$R_3$ is hydrogen or phenyl;
$Y_4$ is O, S, or N(phenyl); and
$X_1$ to $X_3$, $Y_1$, $Y_2$, $Ar_1$, and $Ar_2$ are as defined in Chemical Formula 1 above.

For example, the above-mentioned compound can be any one compound selected from the group consisting of the following compounds:

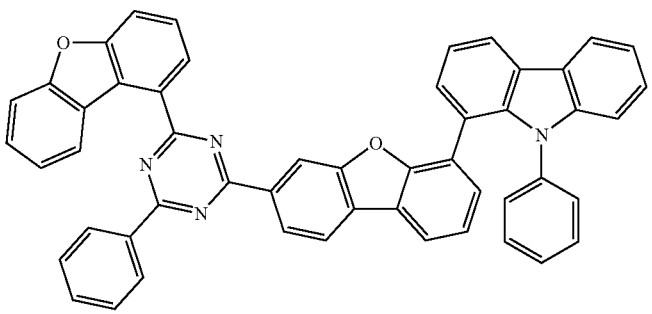

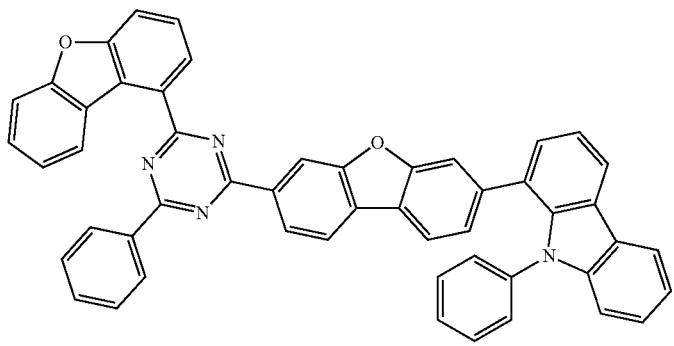
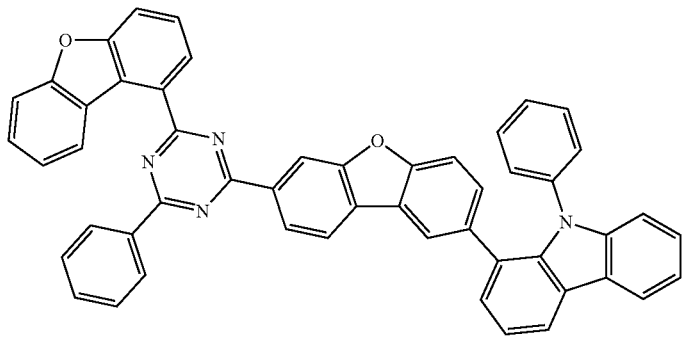
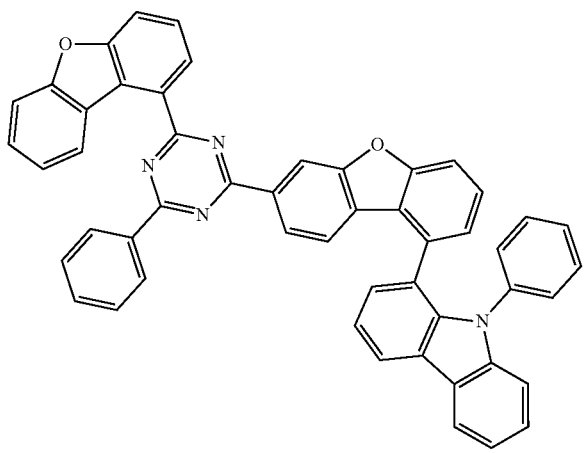
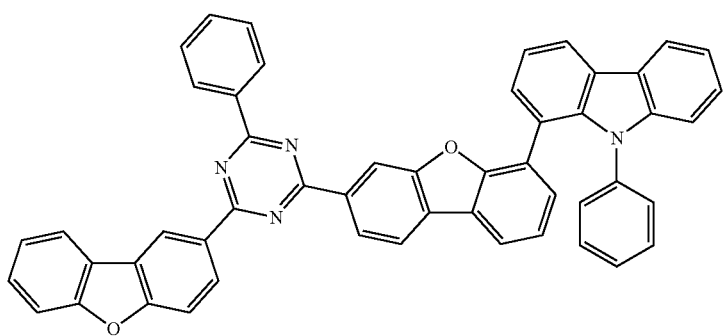

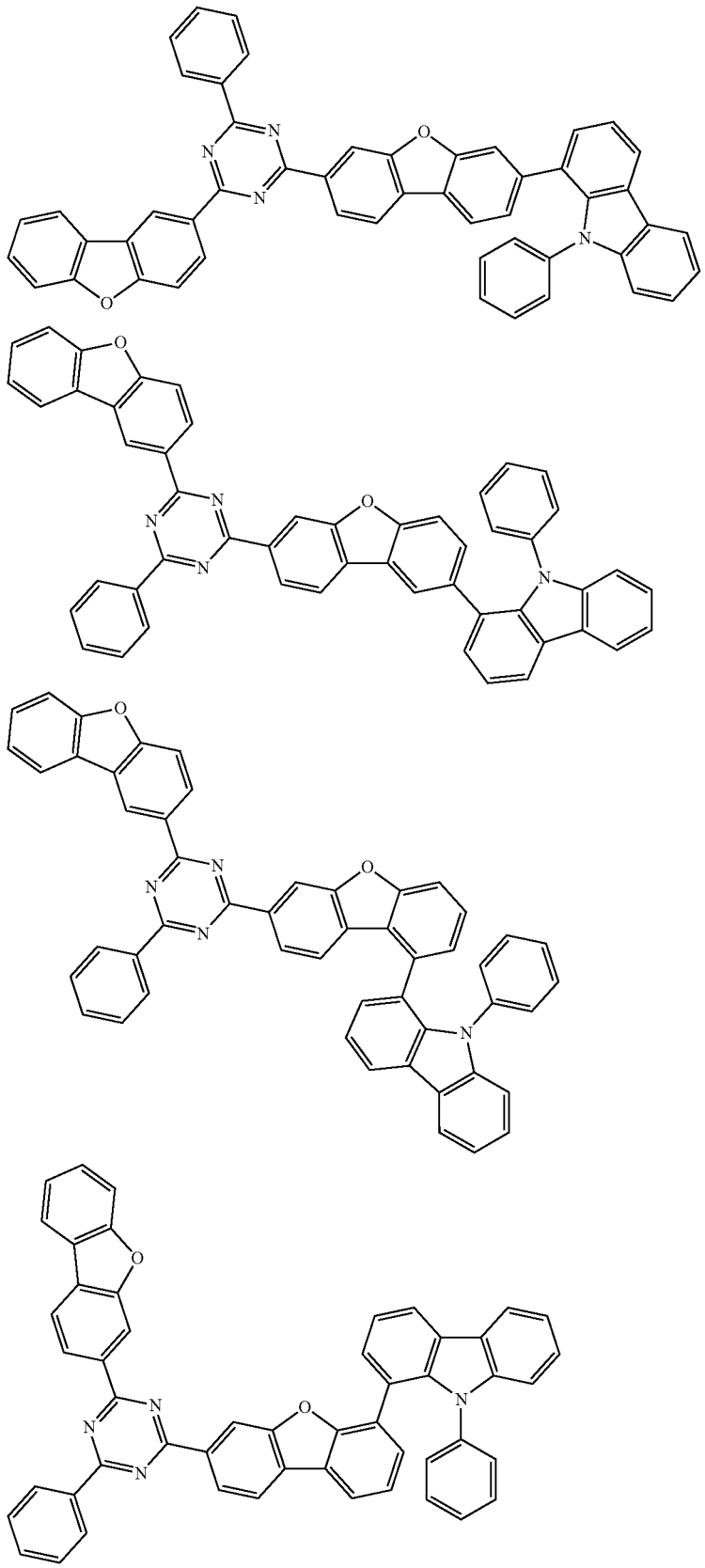

-continued
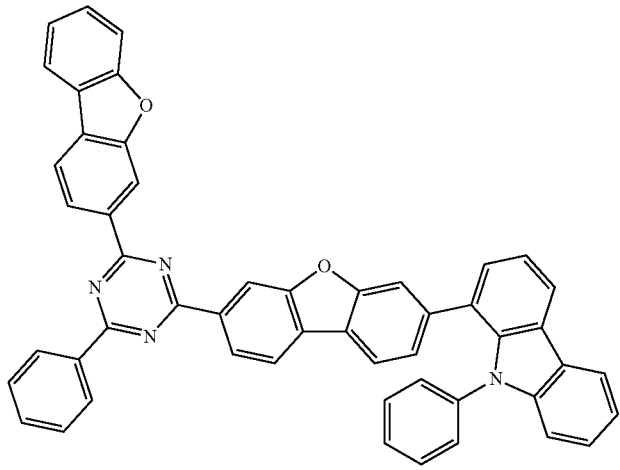
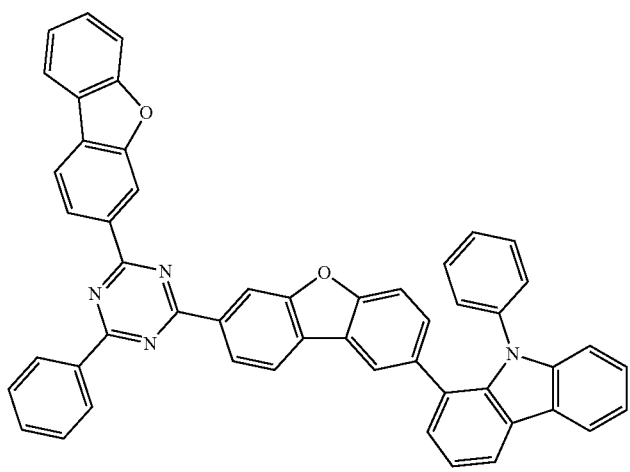
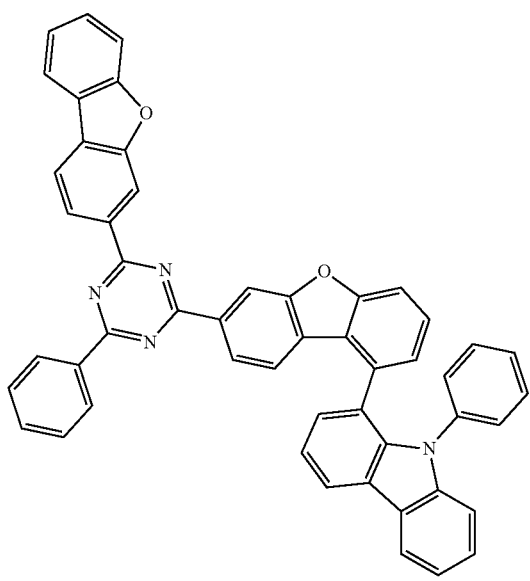

-continued
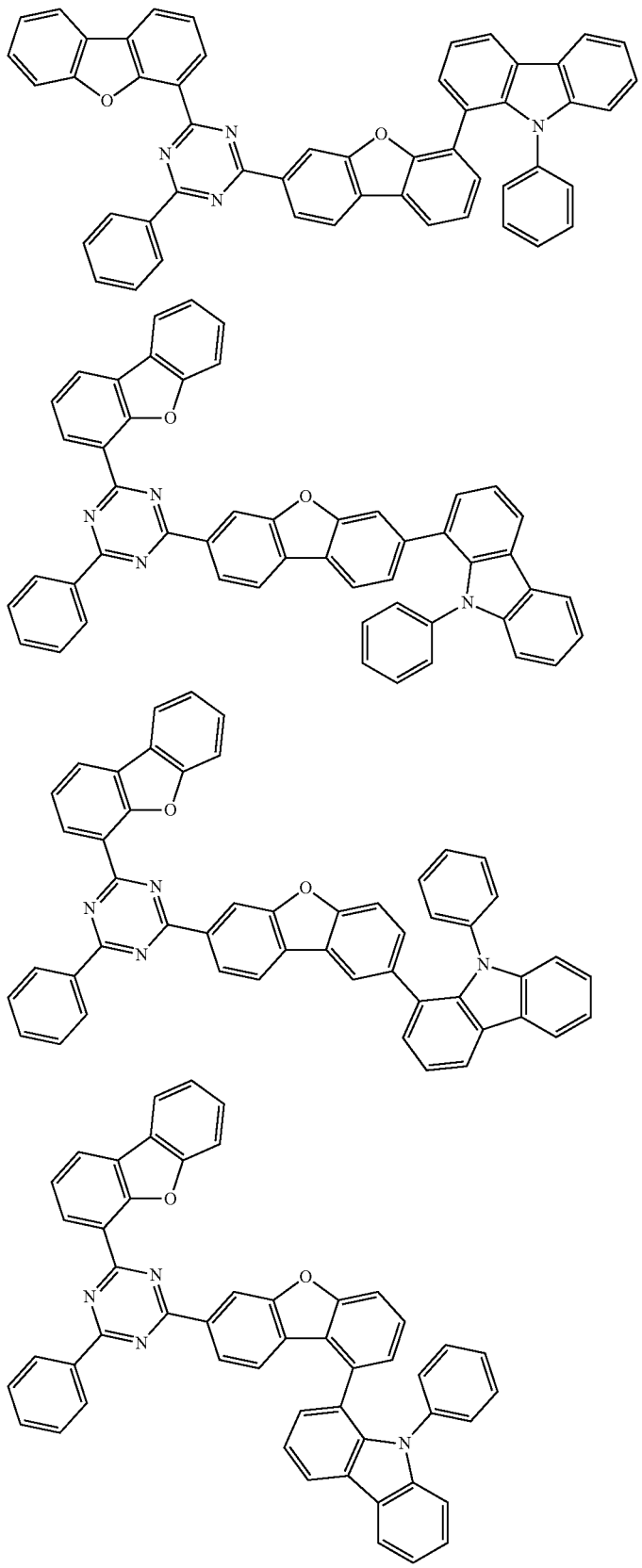

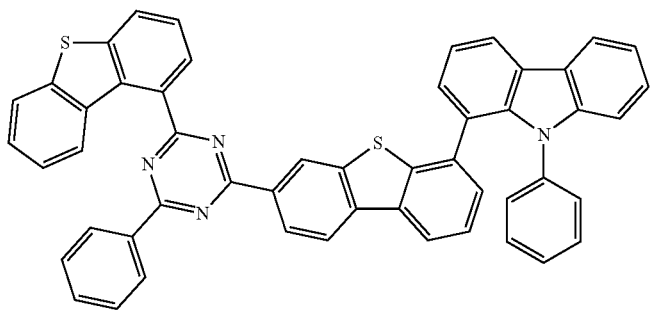
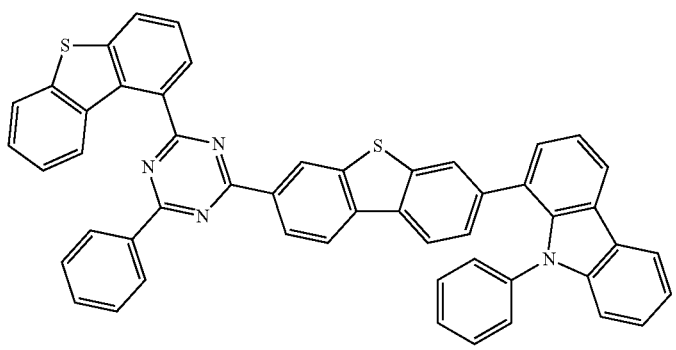
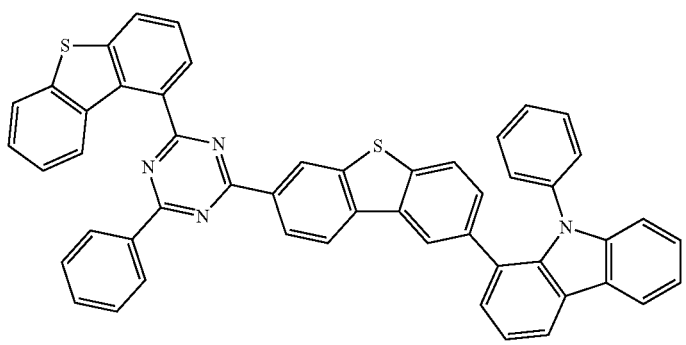
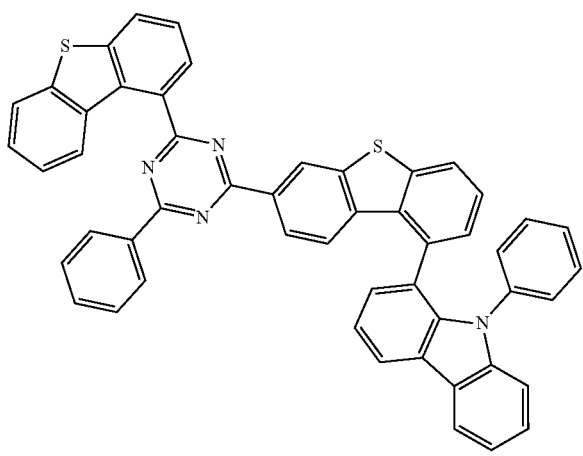

-continued
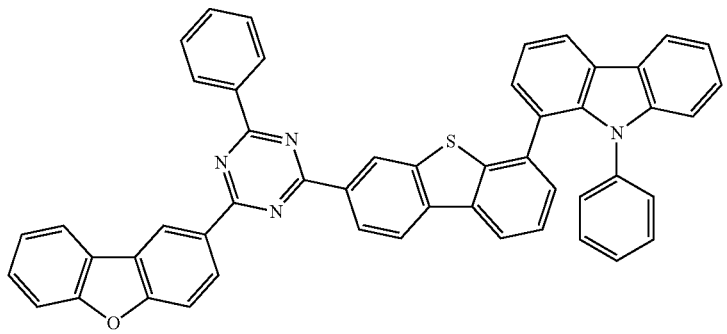
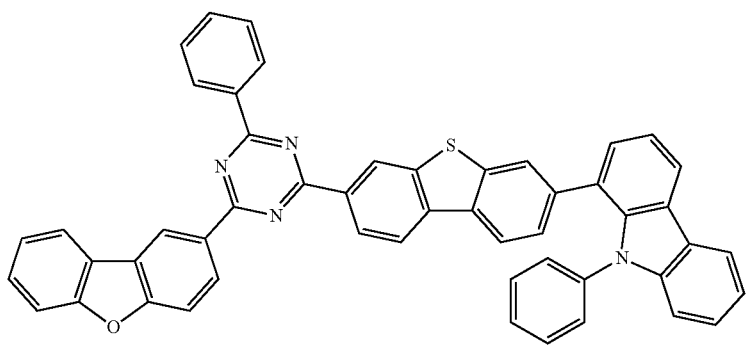
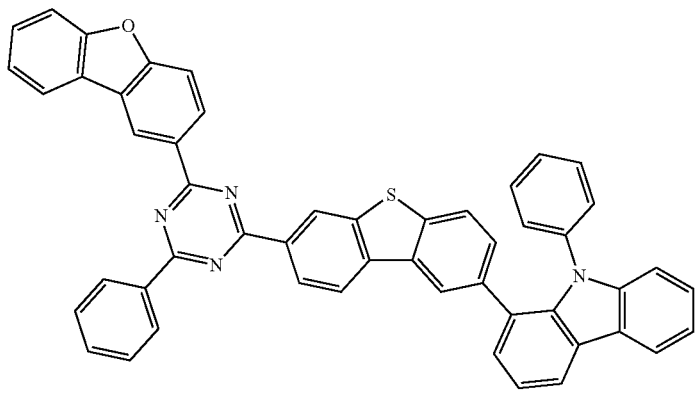
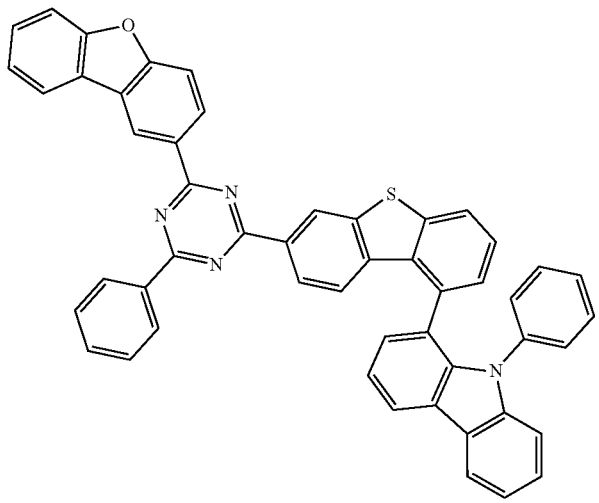

-continued
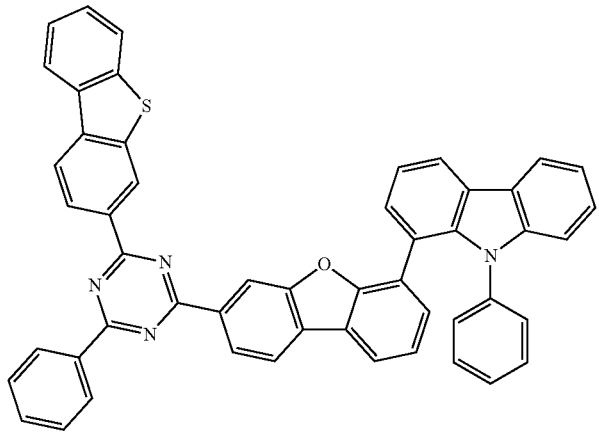
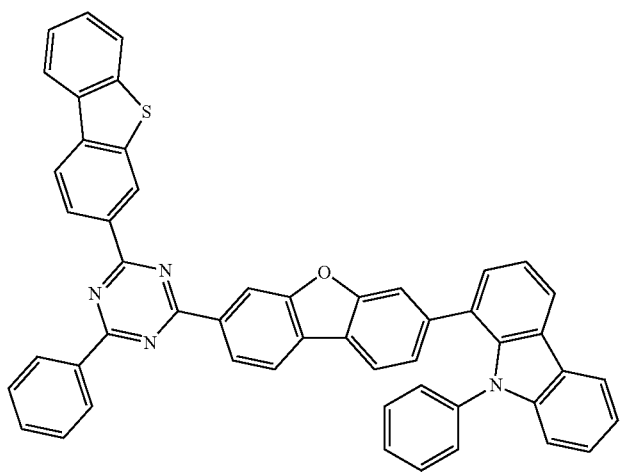
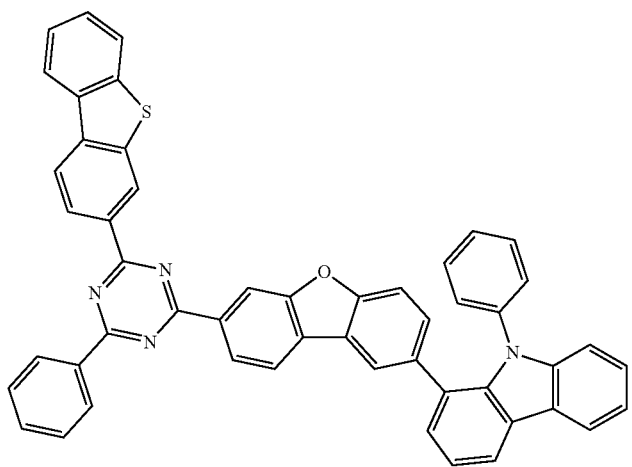

-continued
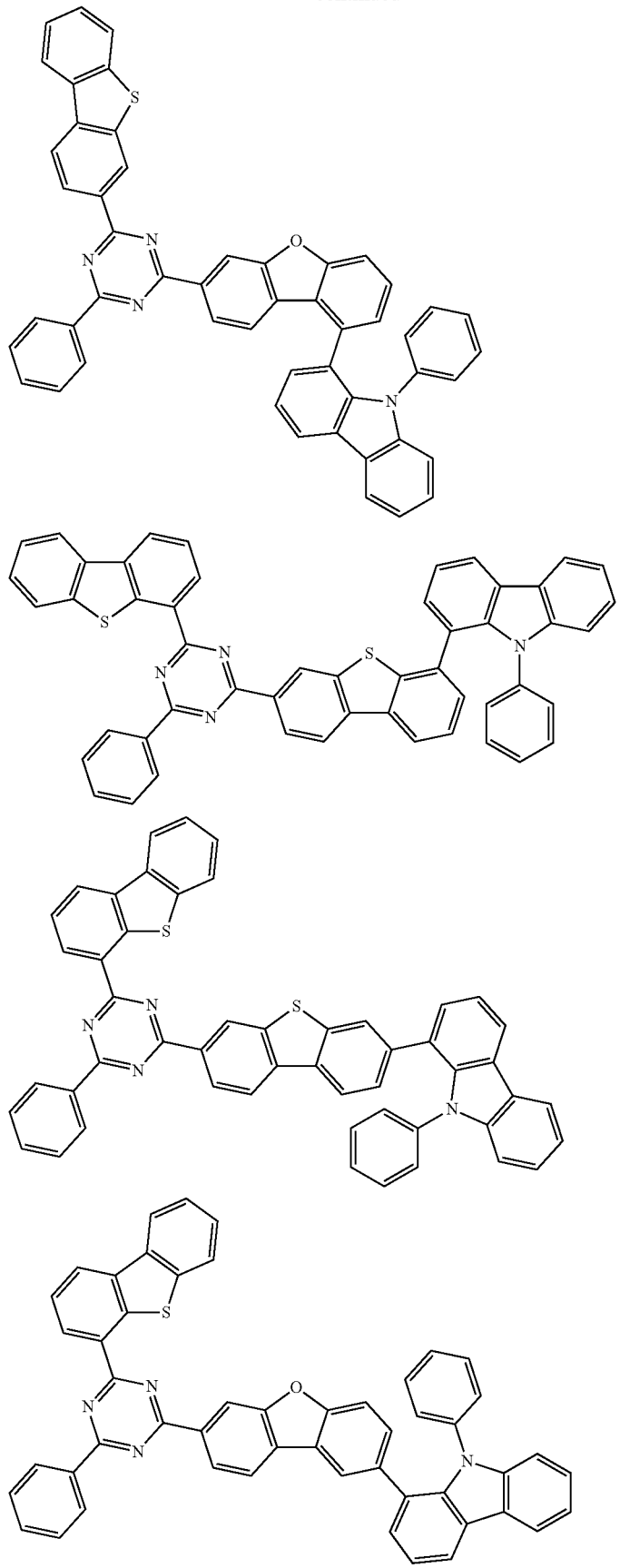

-continued
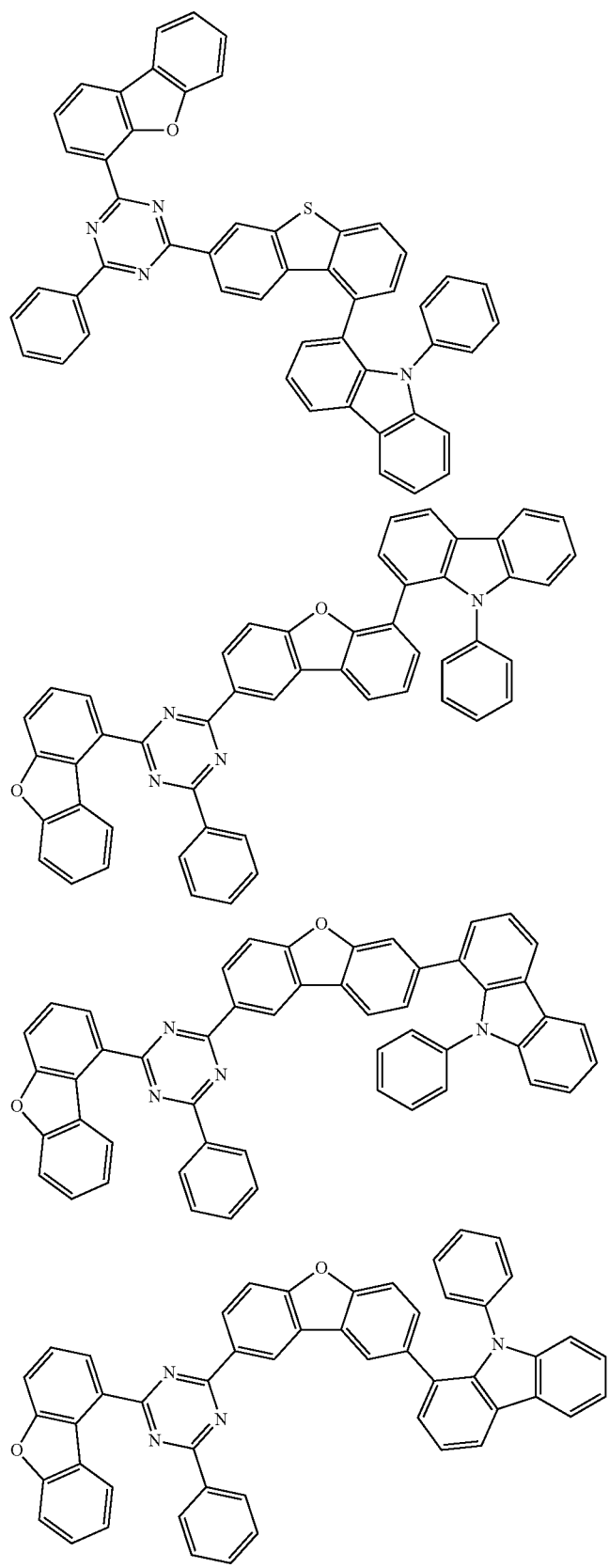

-continued
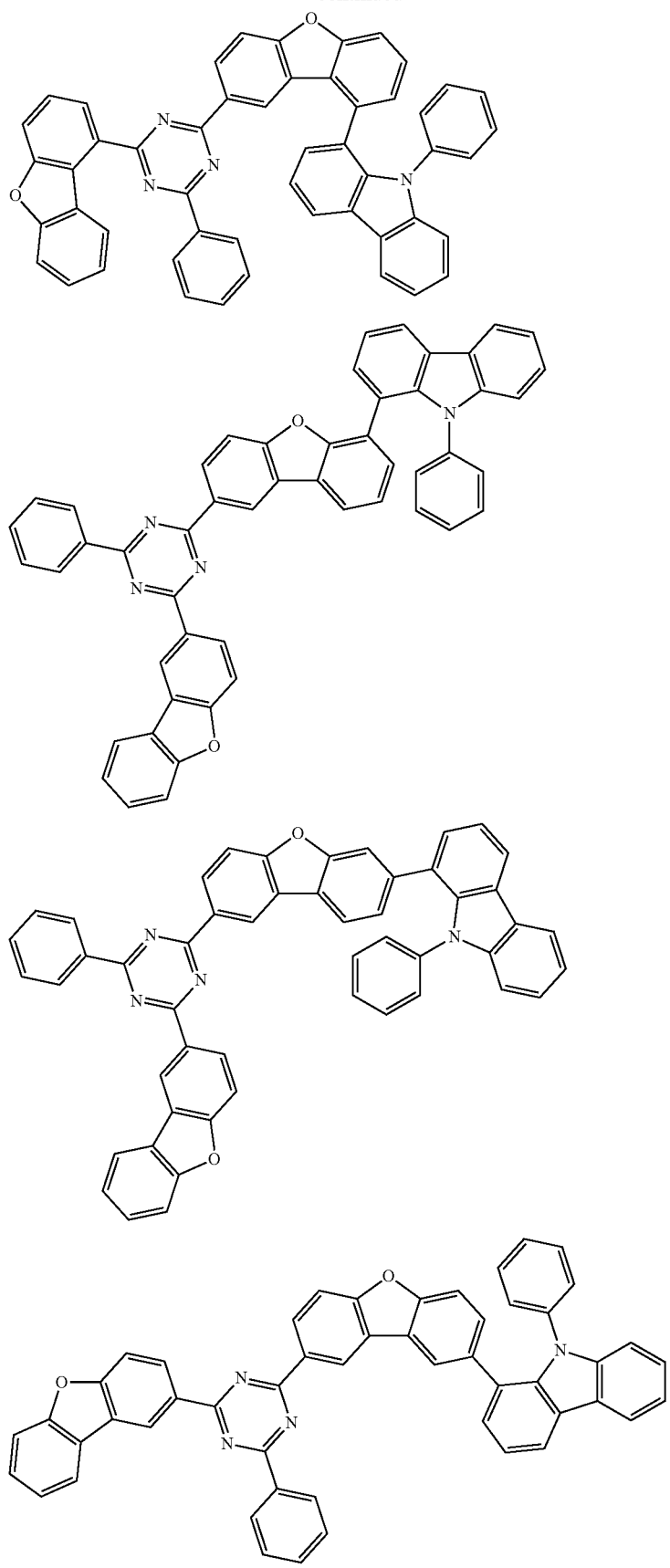

-continued
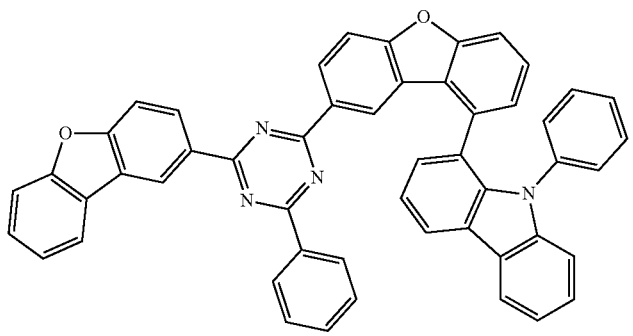
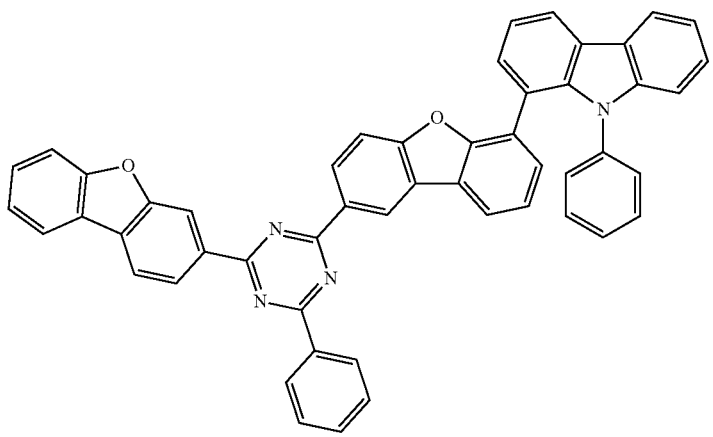
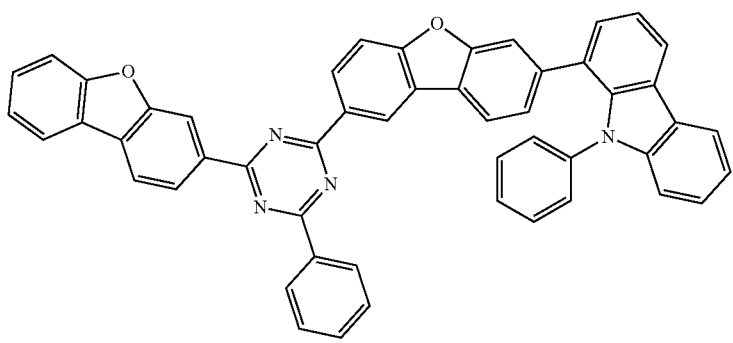
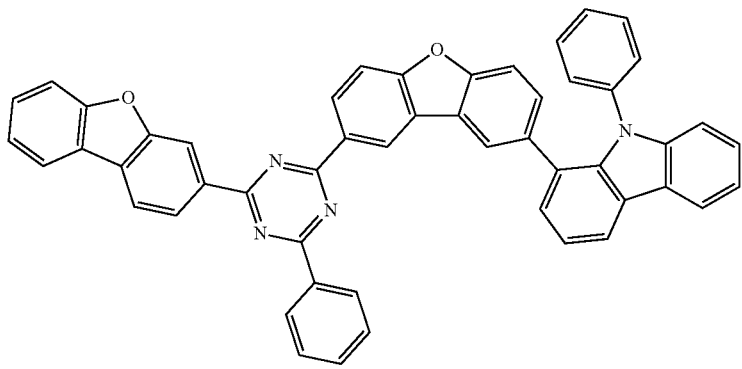

-continued
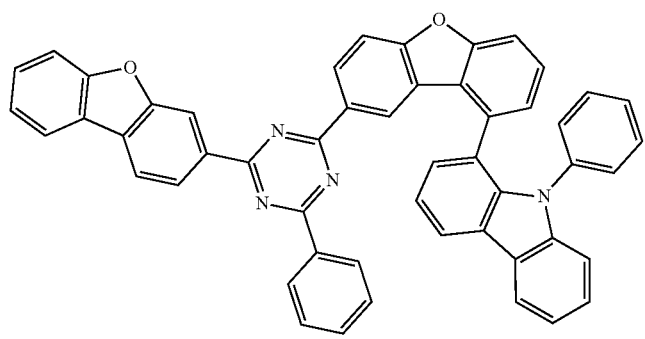
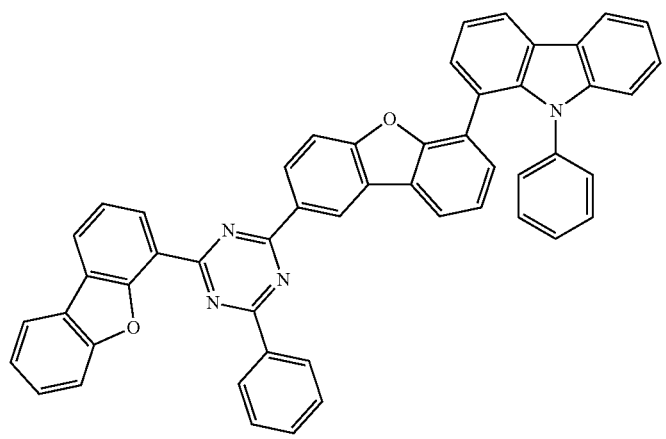
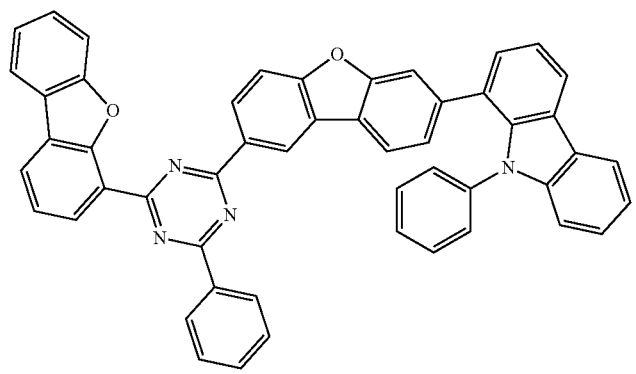
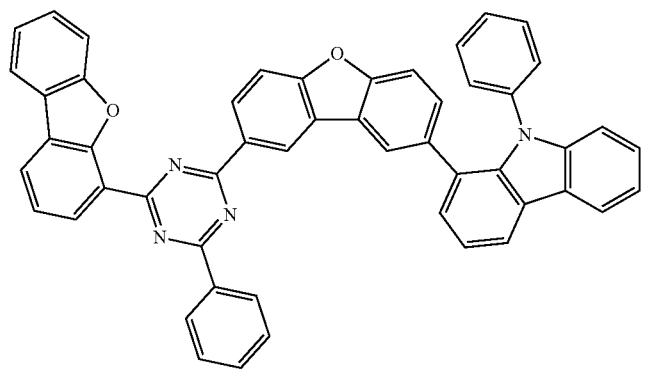

-continued
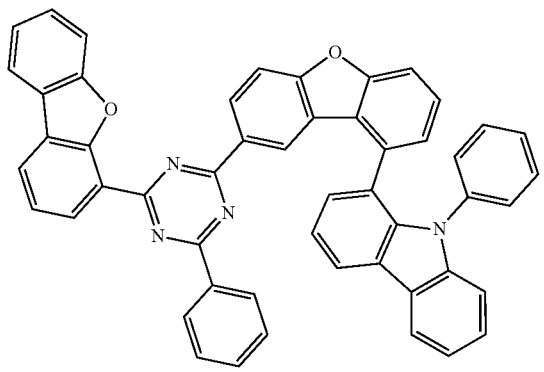
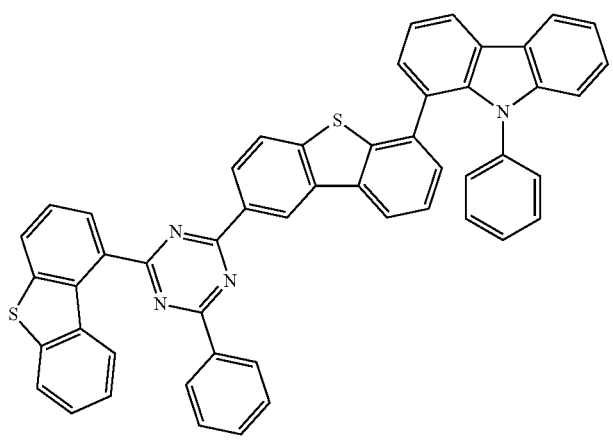
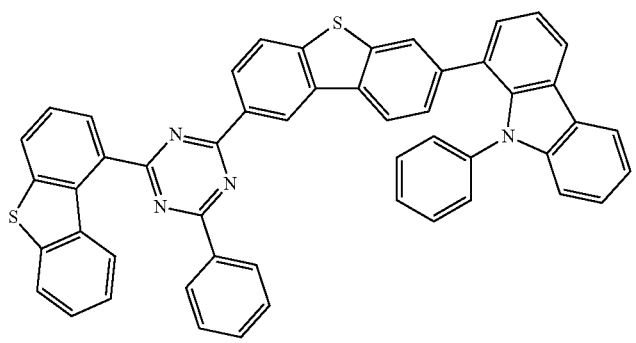
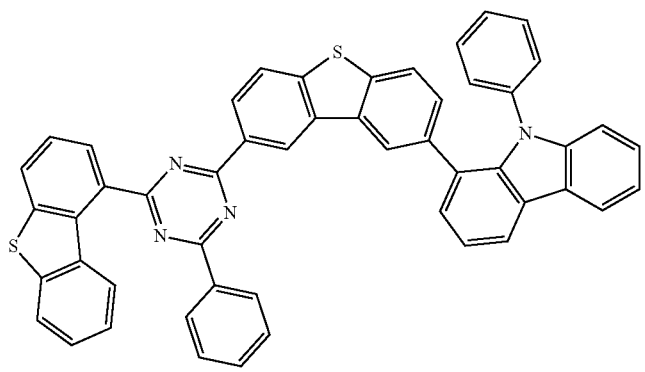

-continued
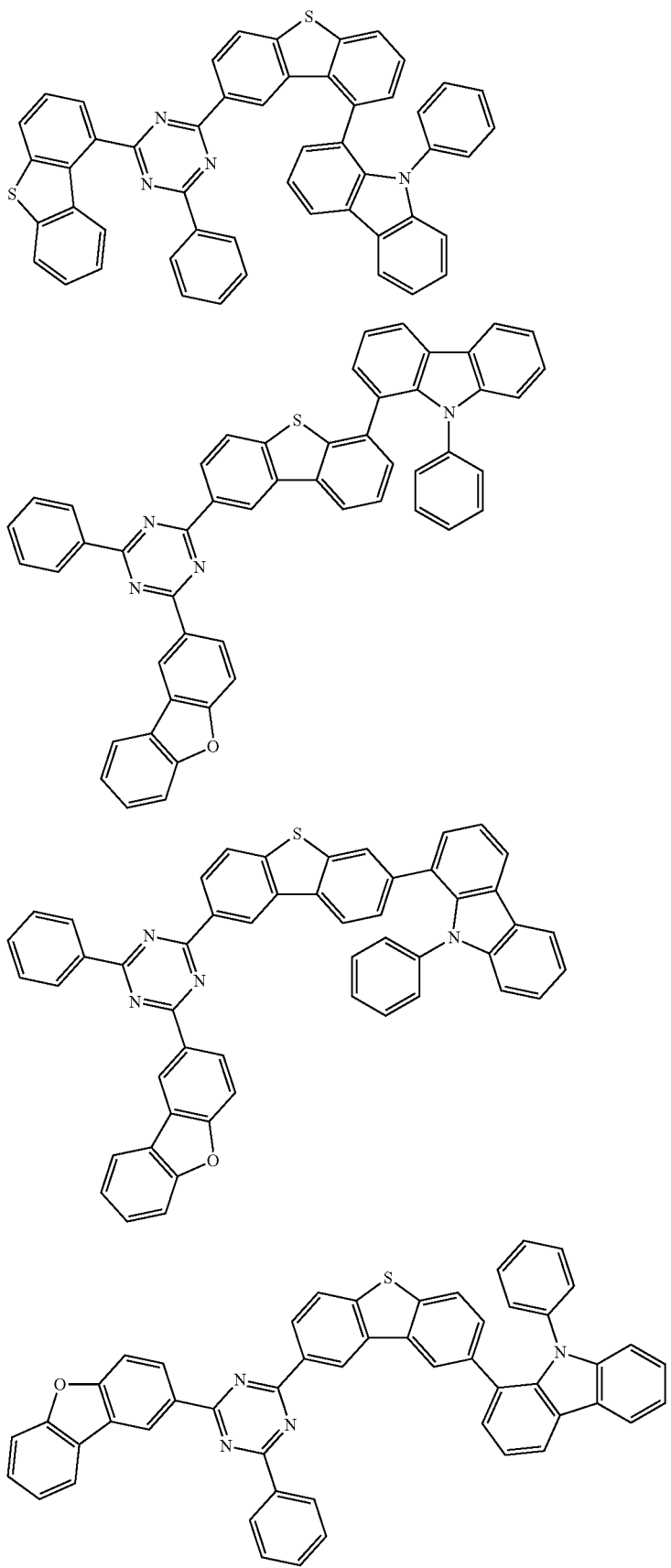

-continued
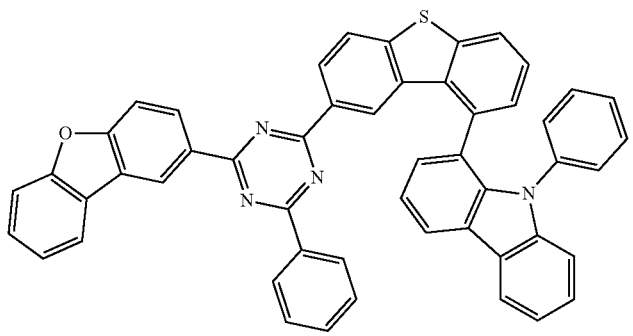
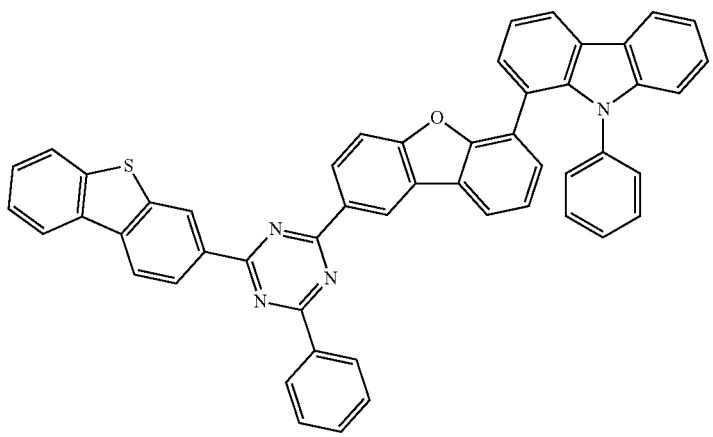
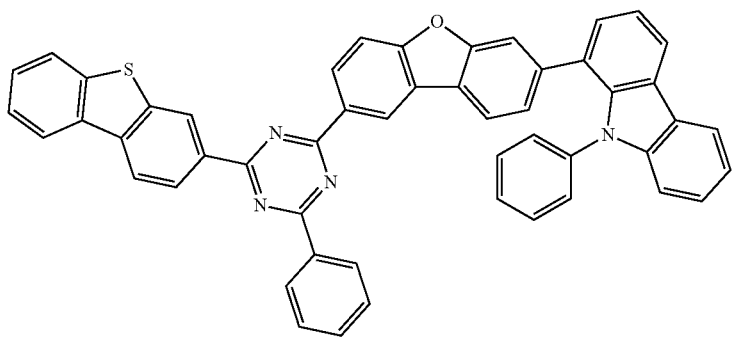
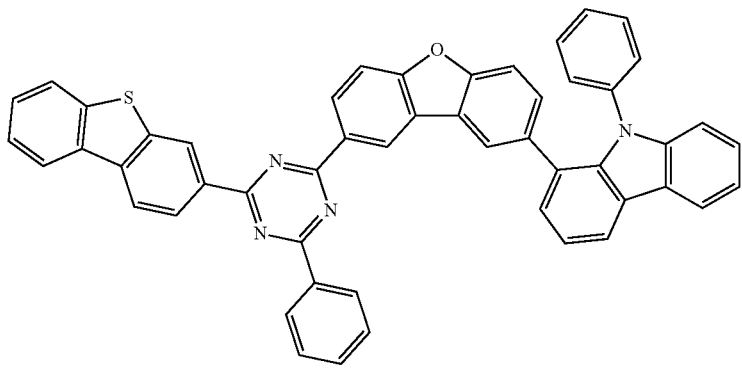

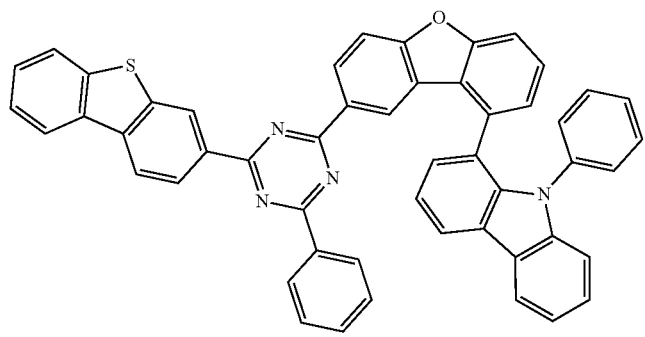
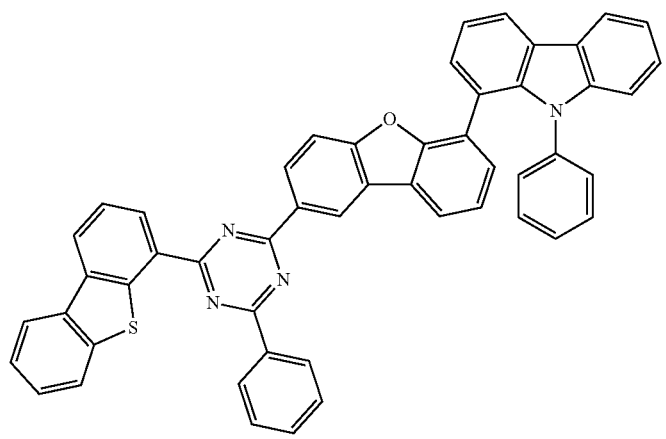
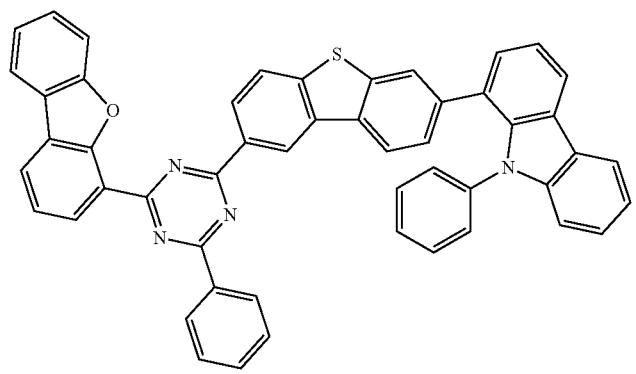
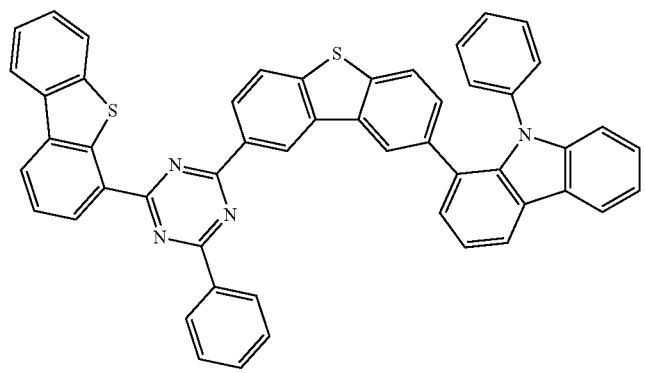

-continued
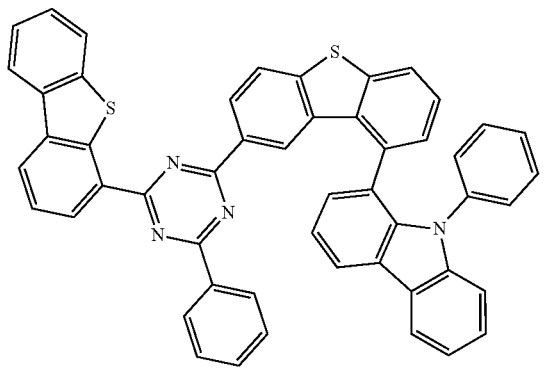
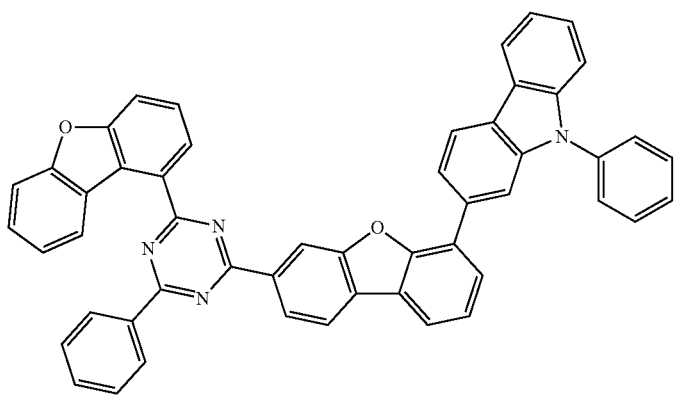
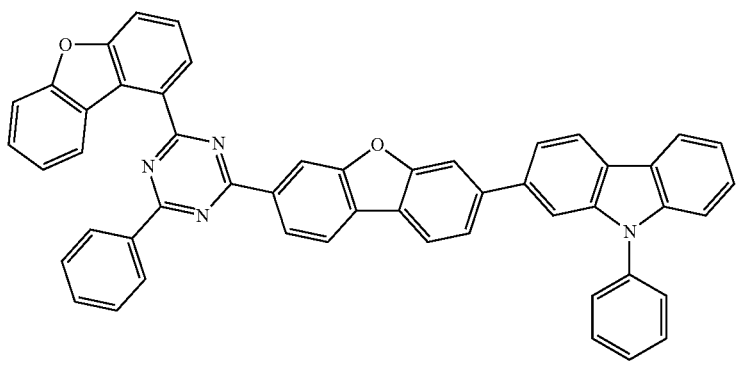
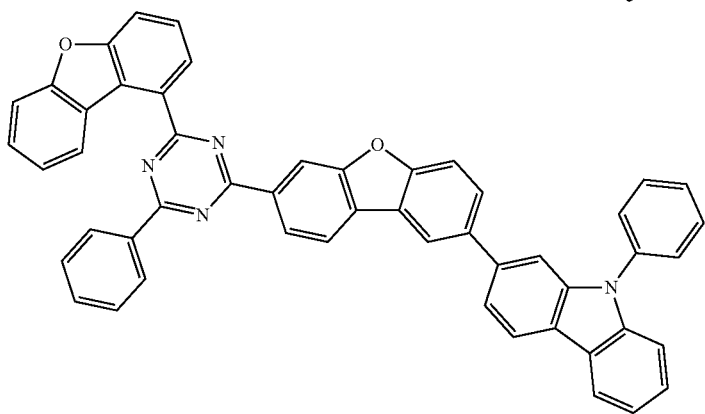

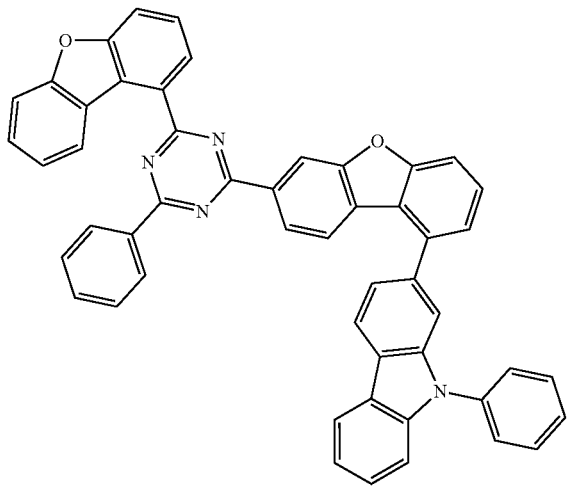
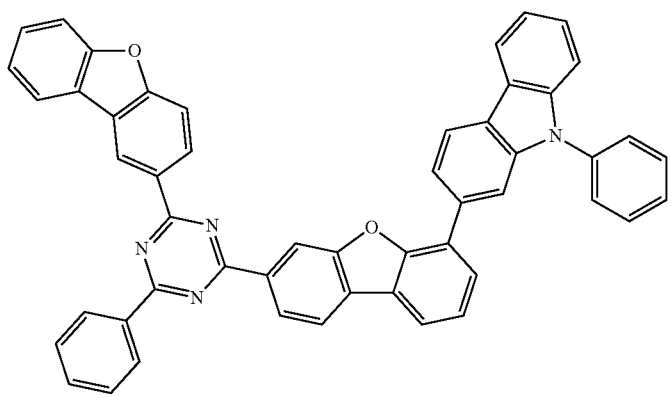
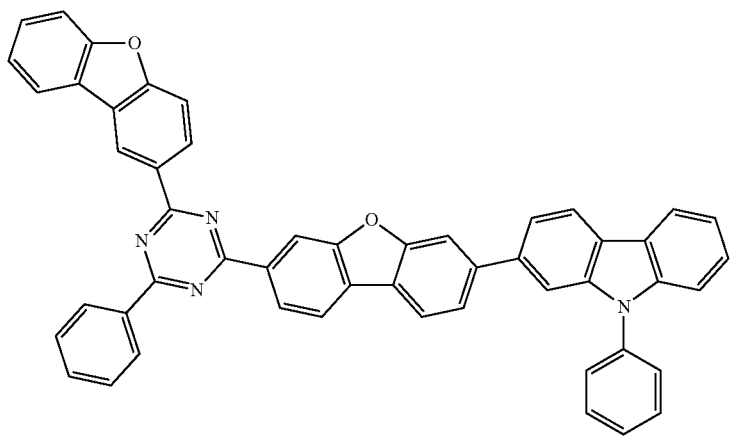

-continued
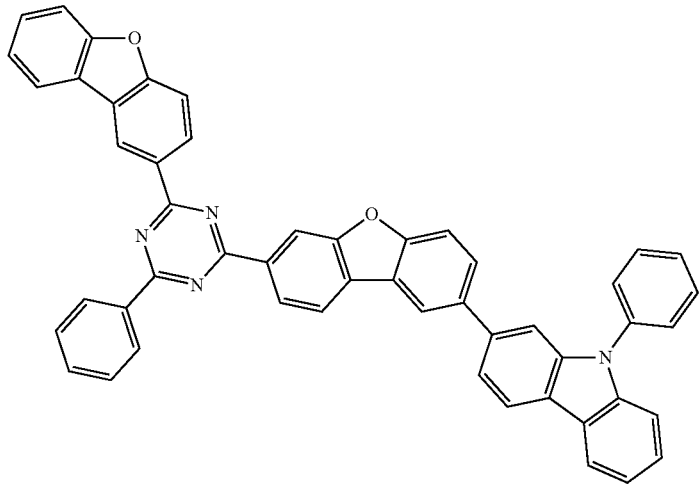
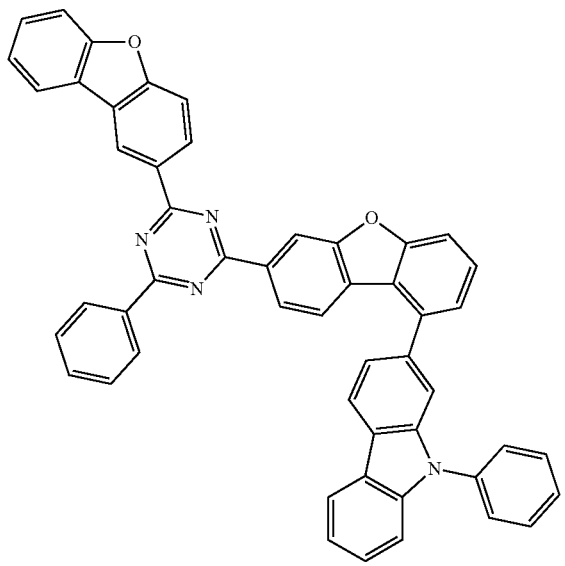
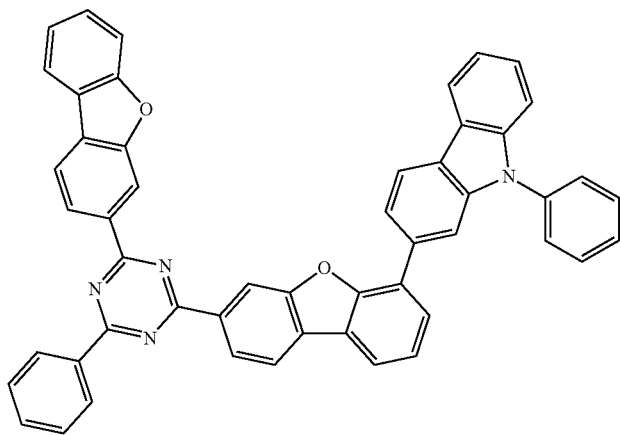

-continued
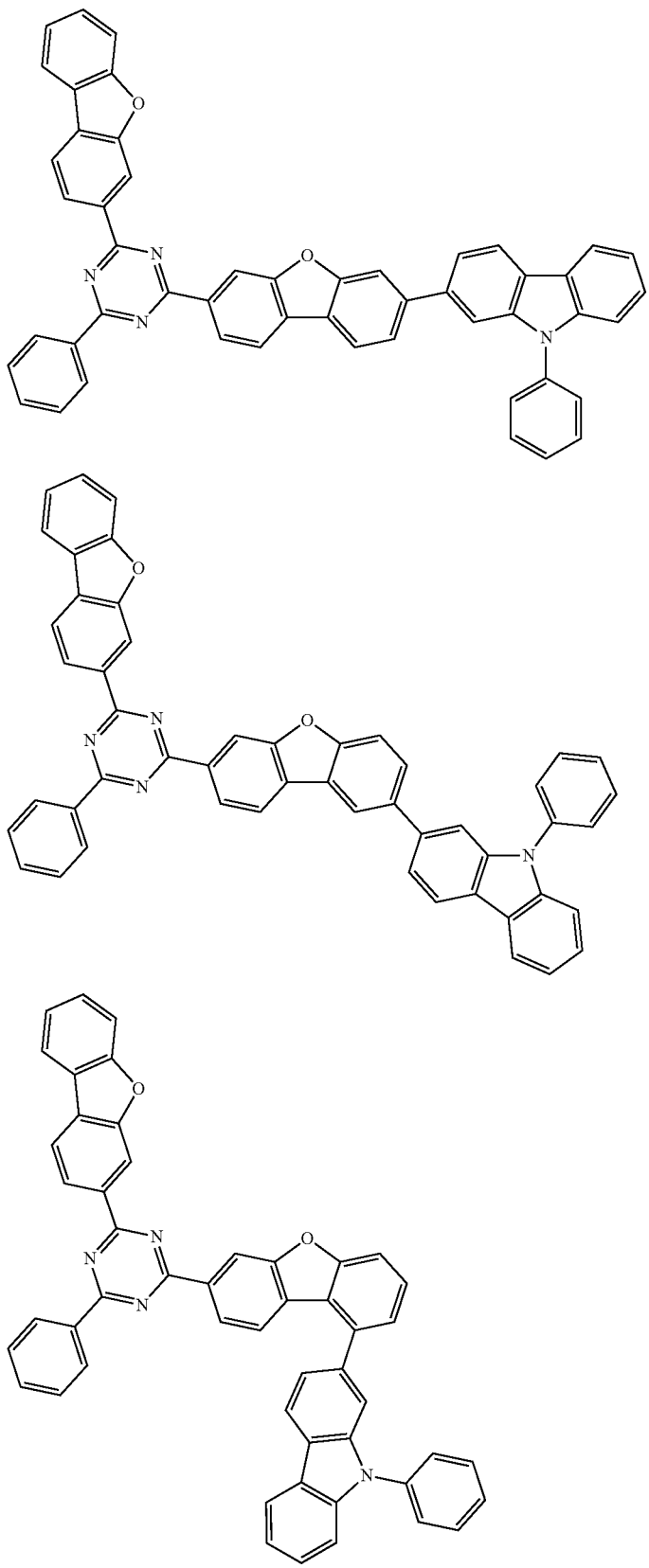

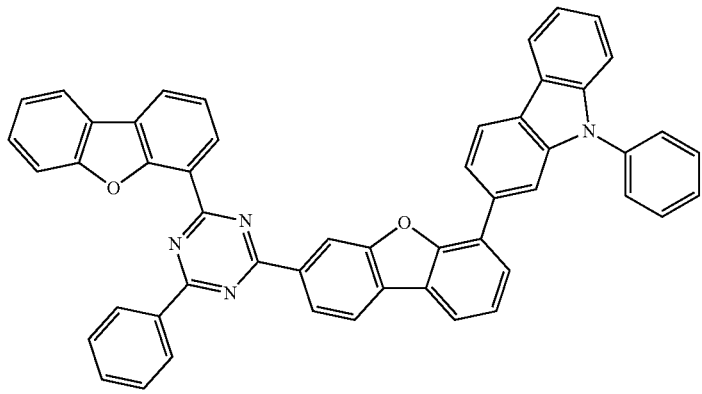
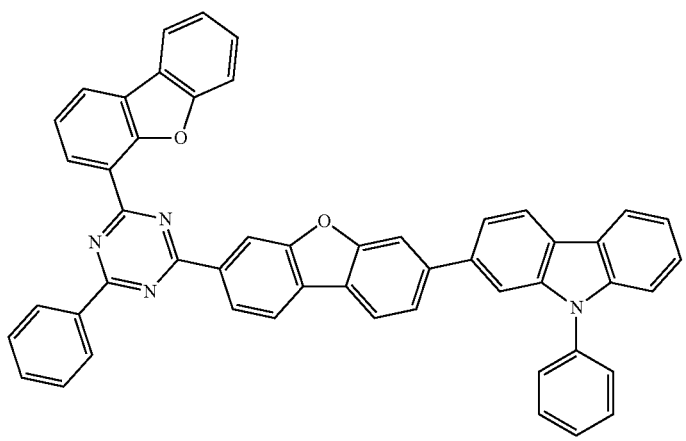
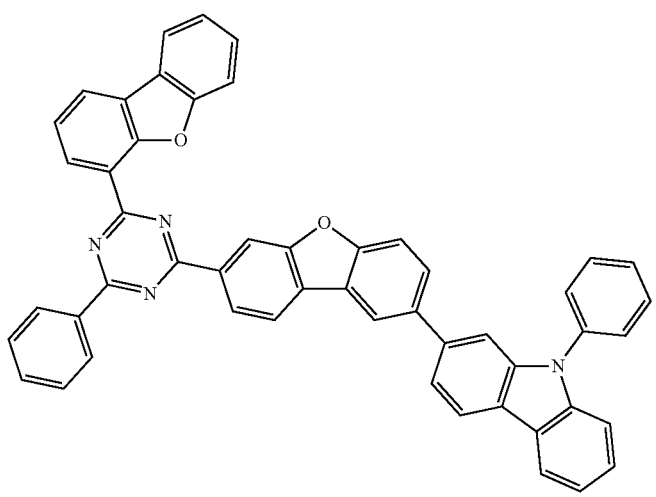

-continued
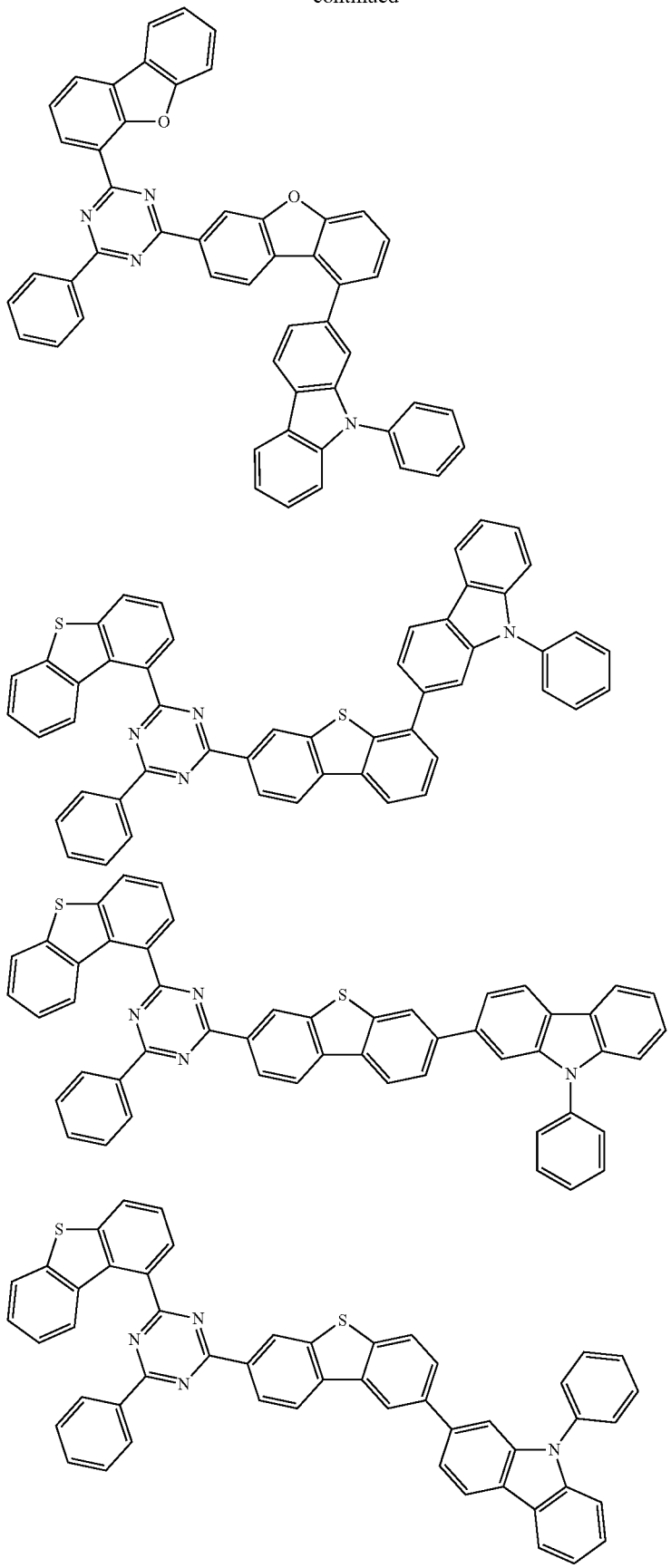

-continued
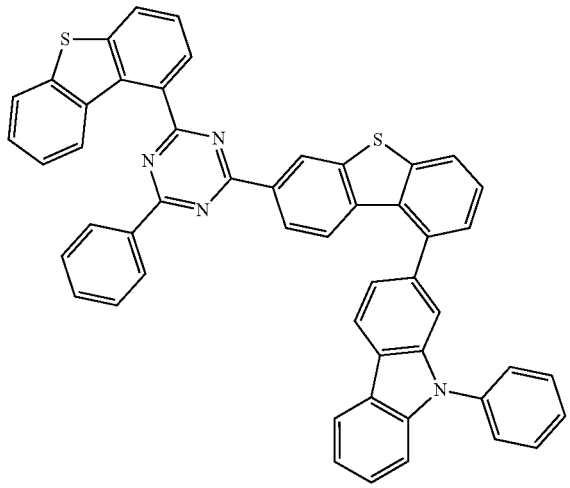
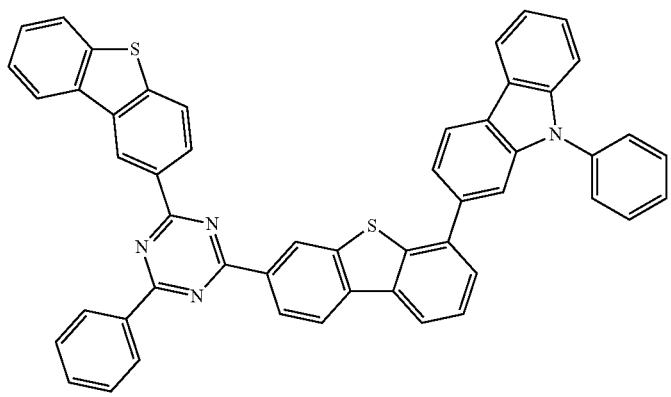
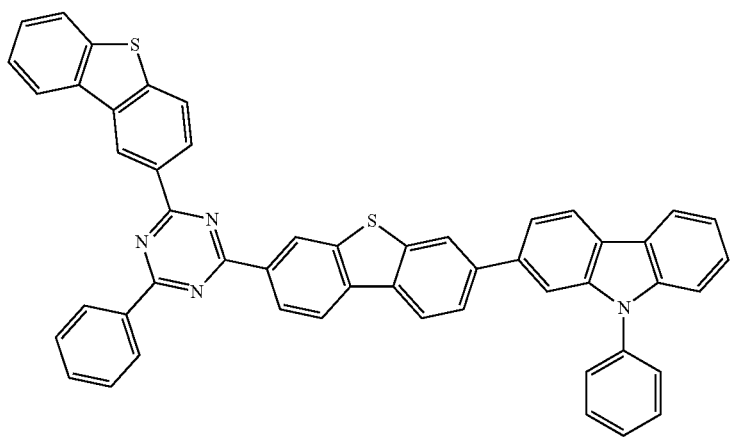

-continued
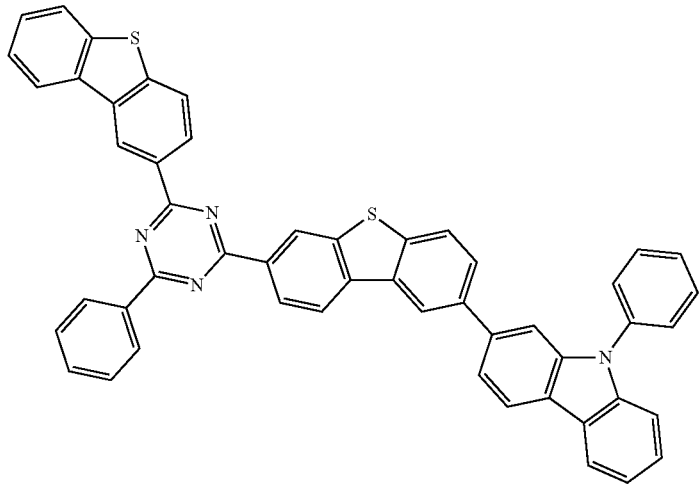
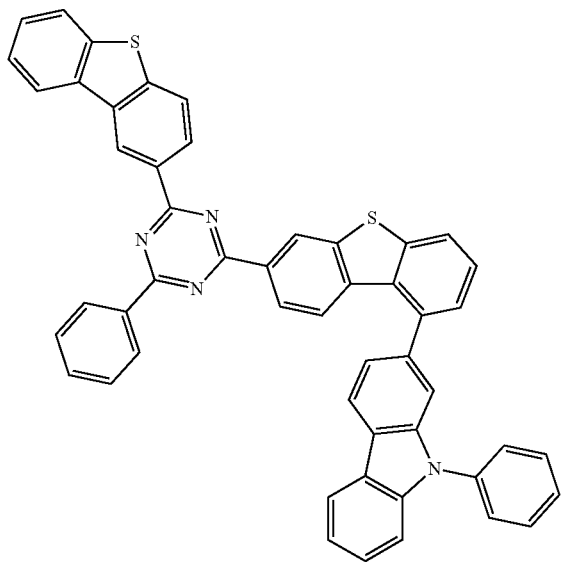
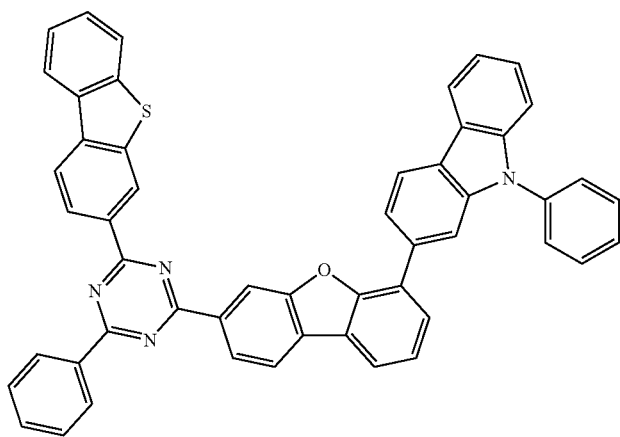

-continued
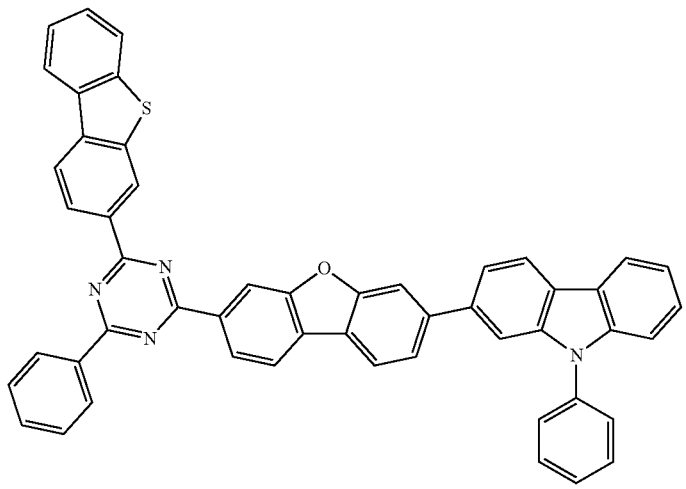
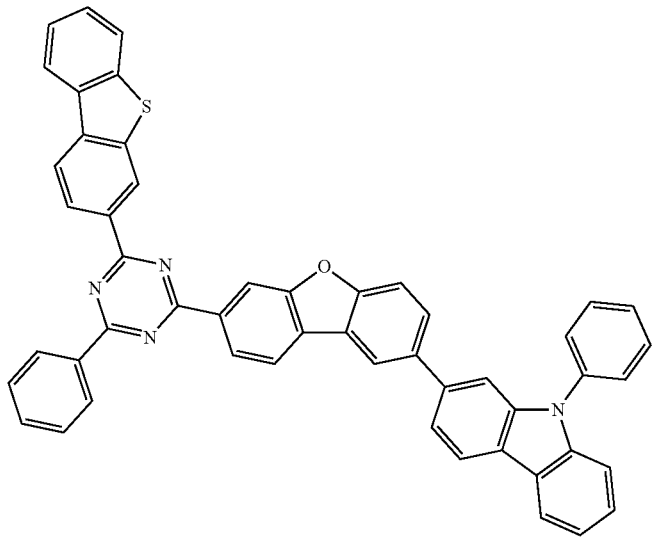
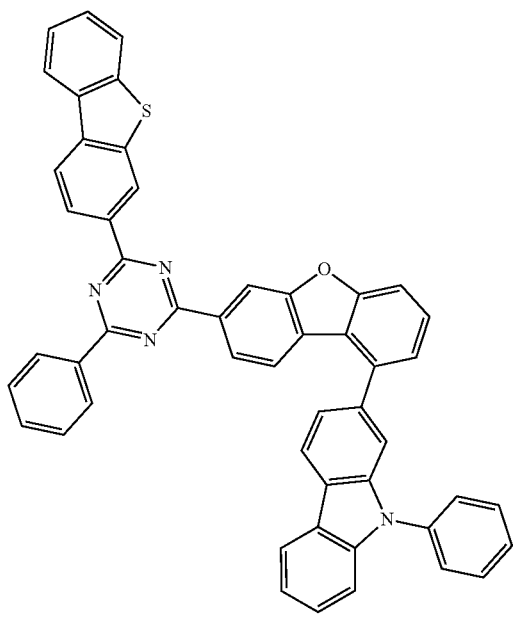 [SMILES: c1ccc(-c2nc(-c3ccc4c(c3)oc3ccccc34)nc(-c3ccc4c(c3)oc3cccc(-c5ccc6c7ccccc7n(-c7ccccc7)c6c5)c34)n2)cc1]

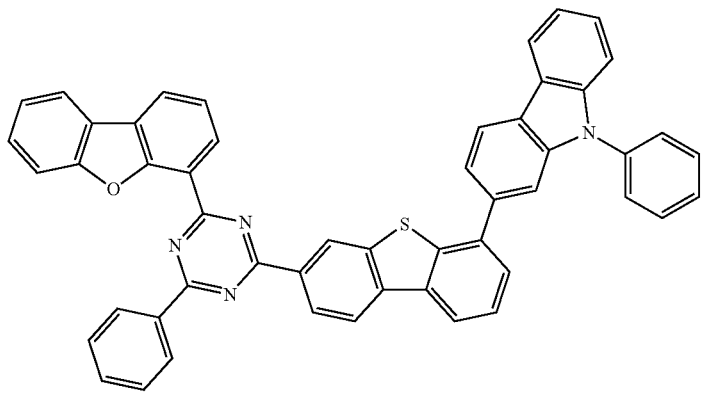
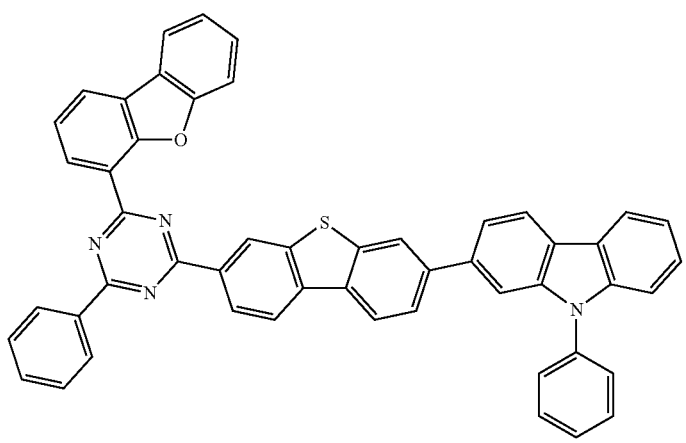
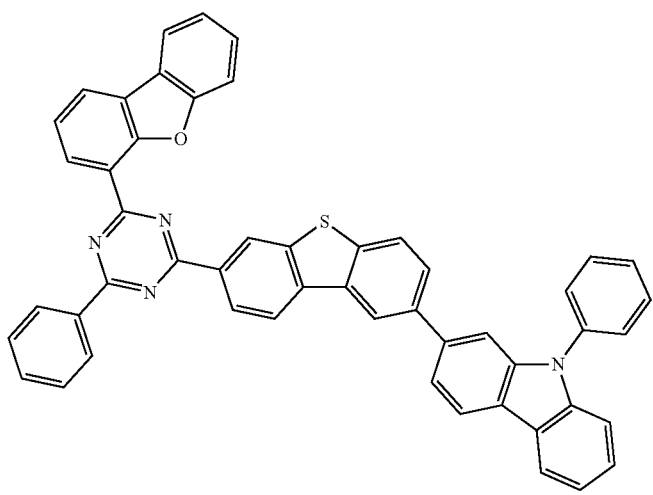

-continued
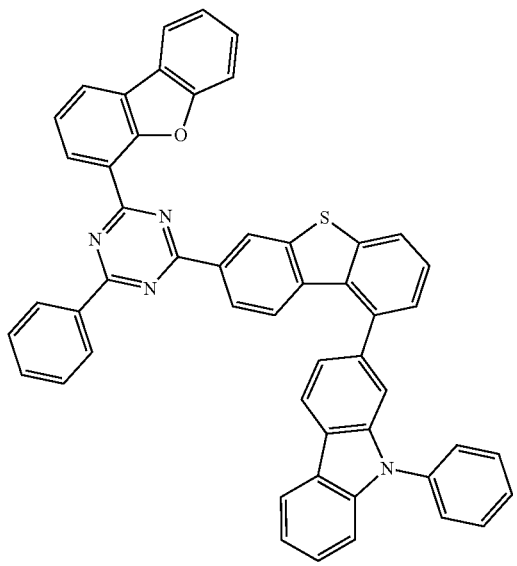
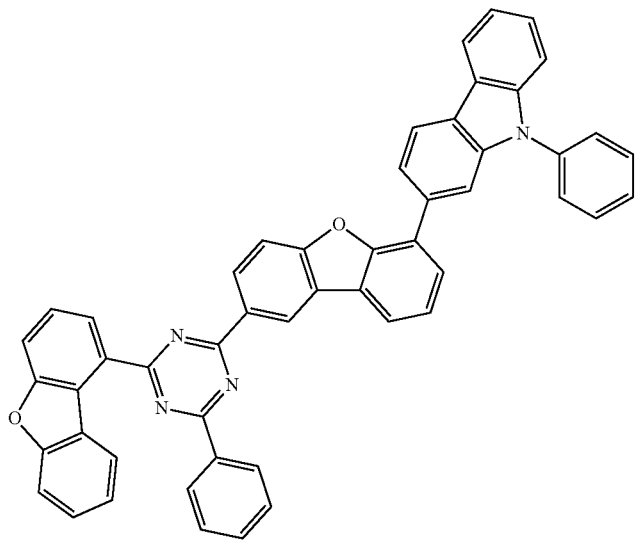
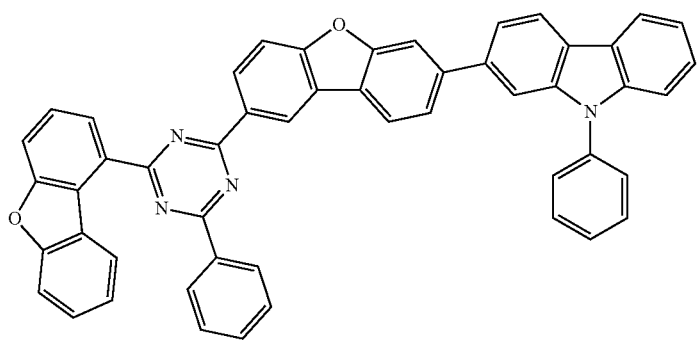

-continued
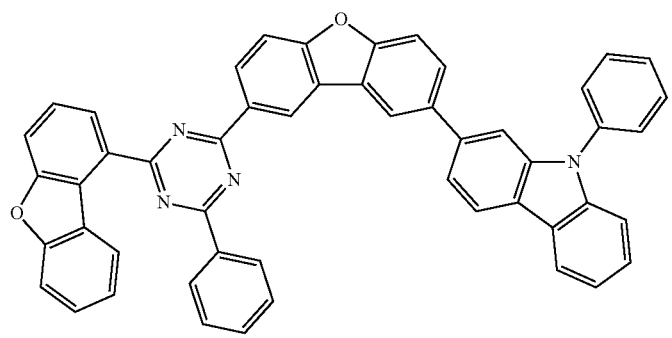
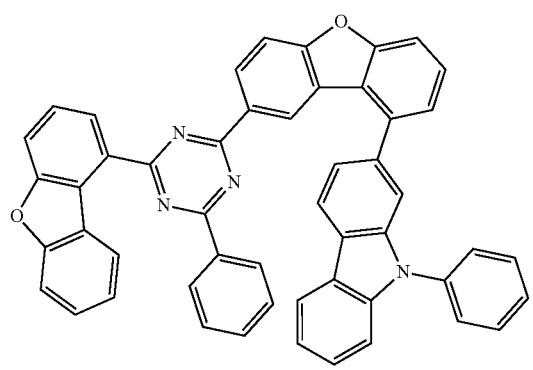
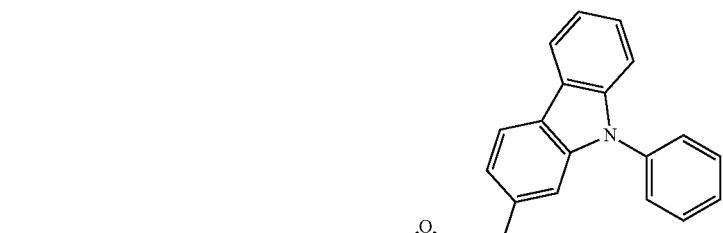
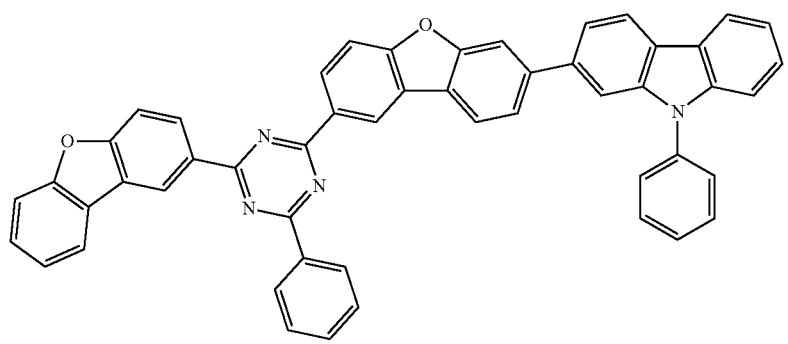

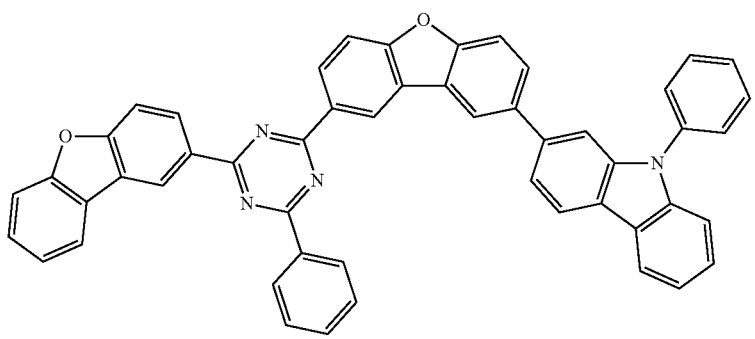
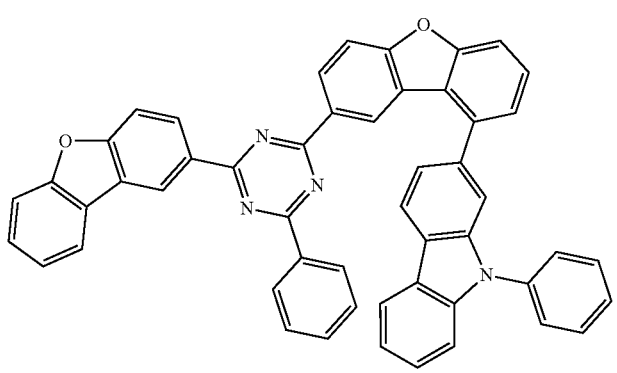
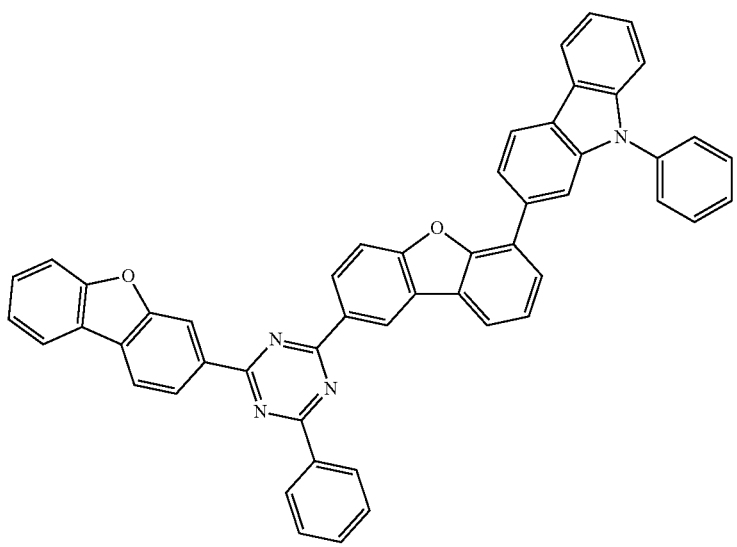
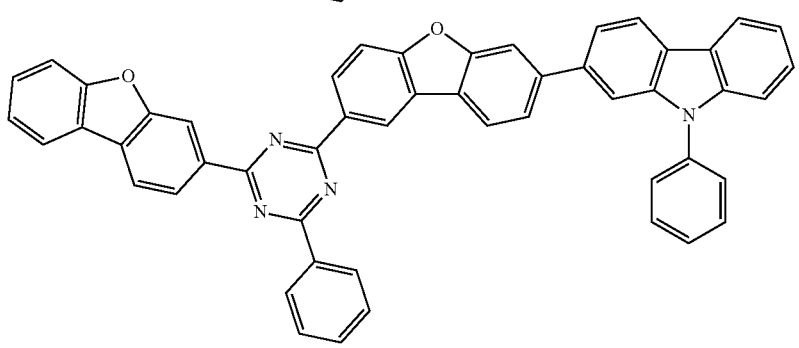

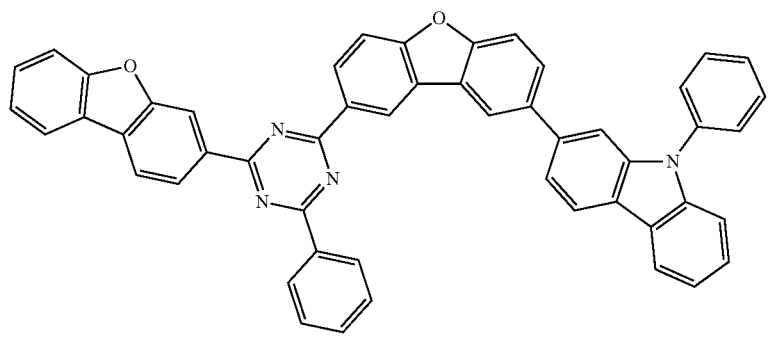
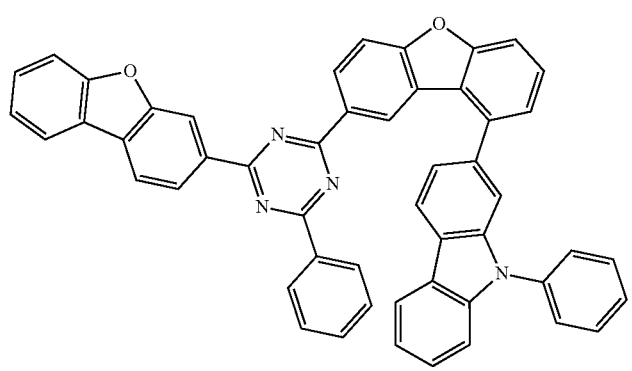
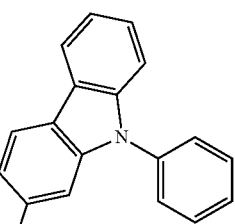
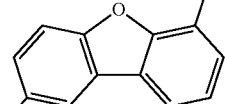
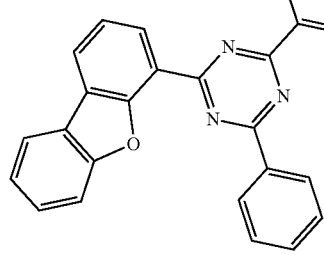
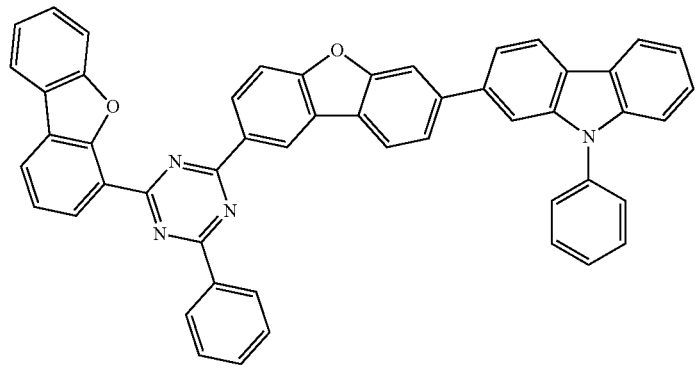

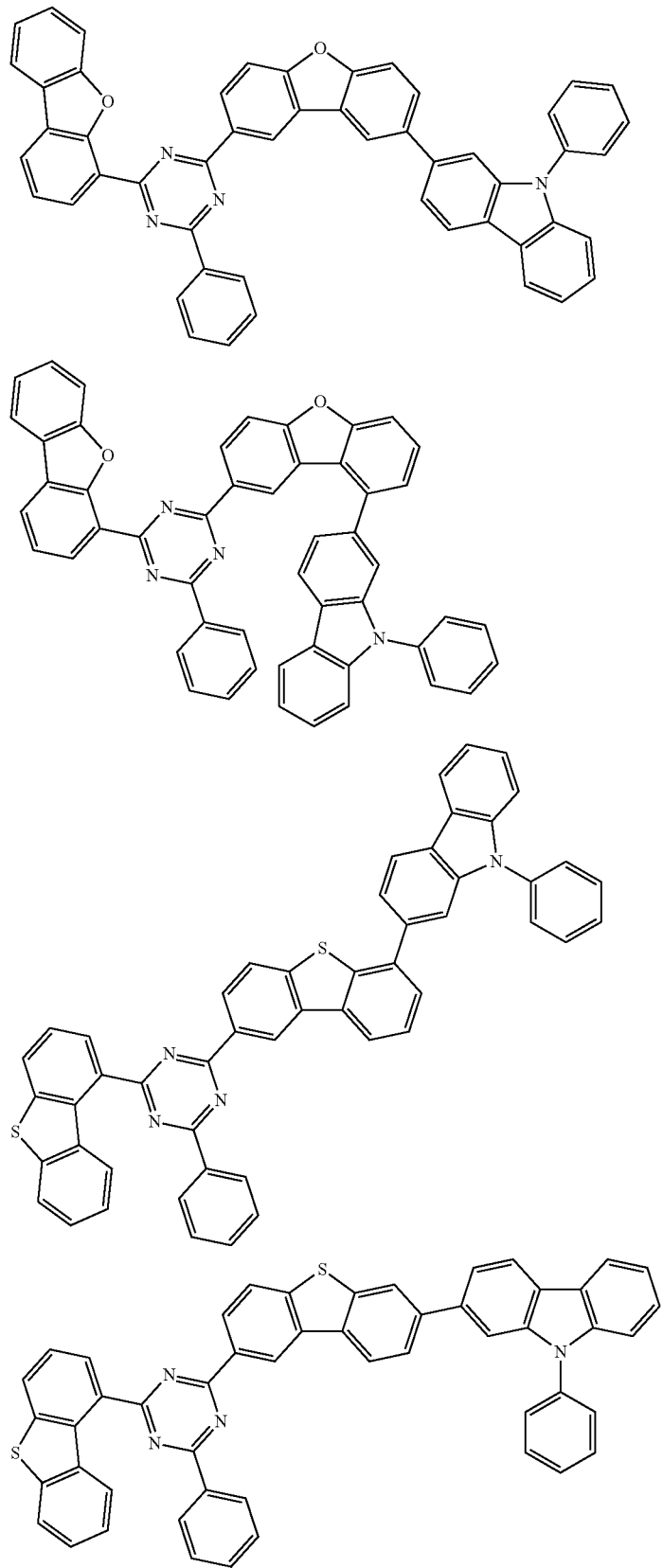

-continued
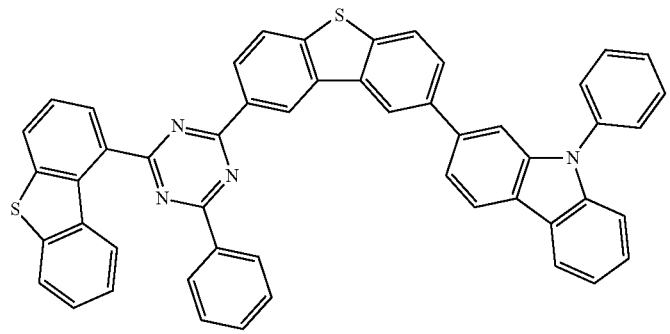
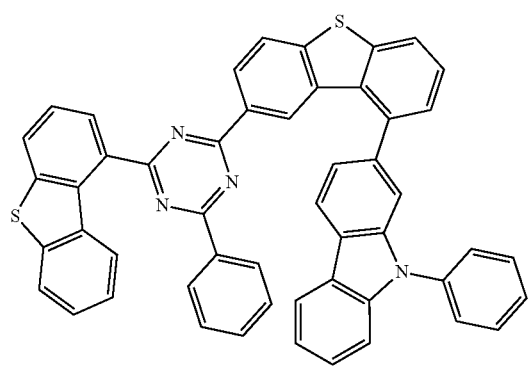
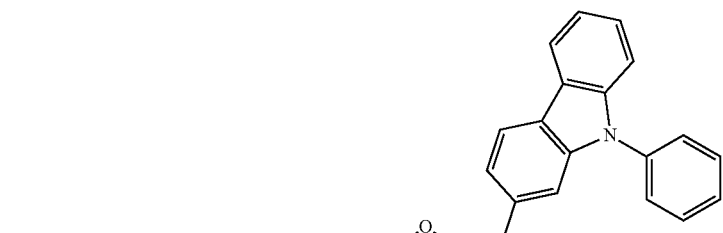
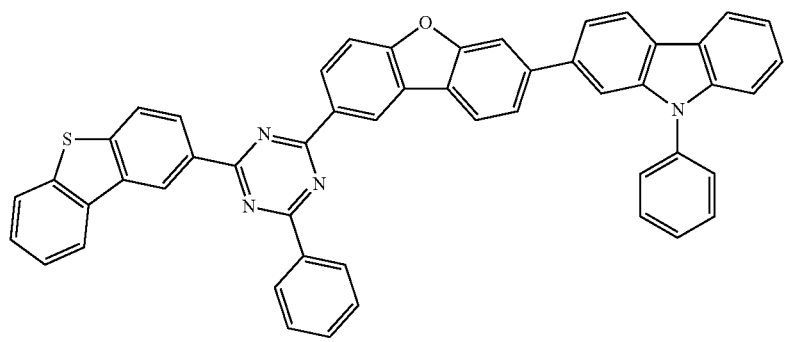

-continued
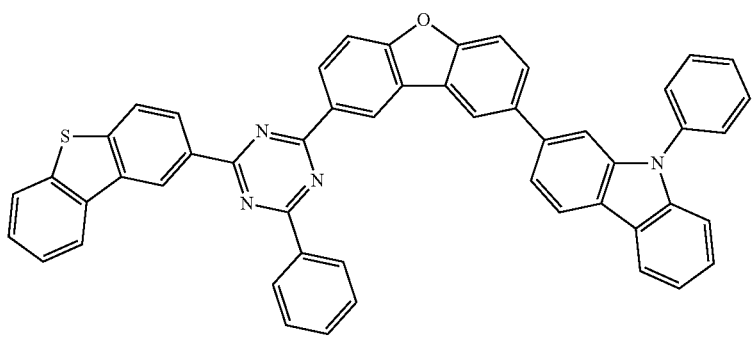

-continued
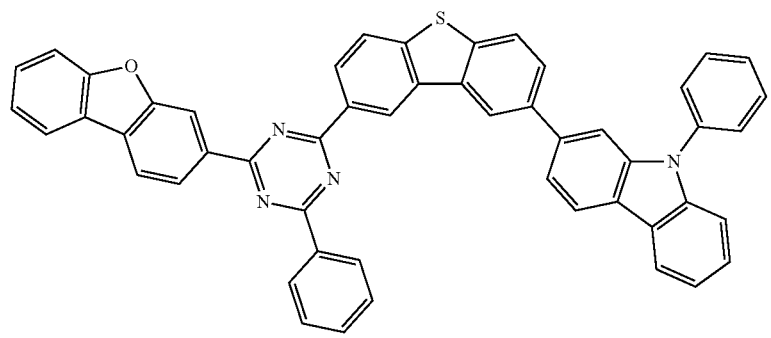
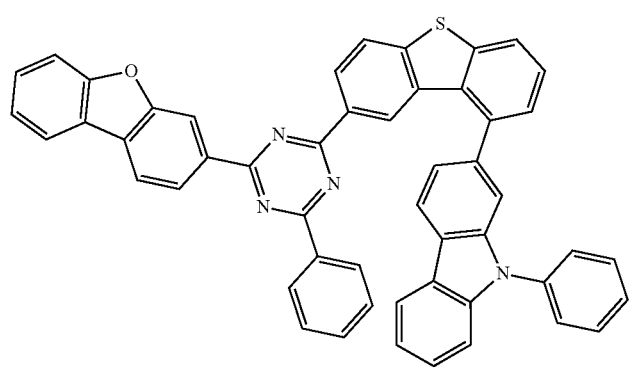
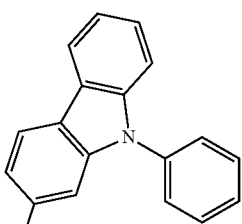
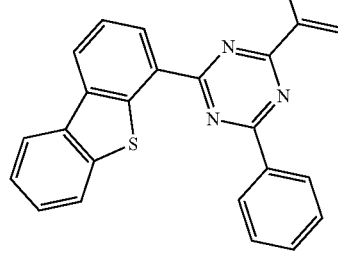
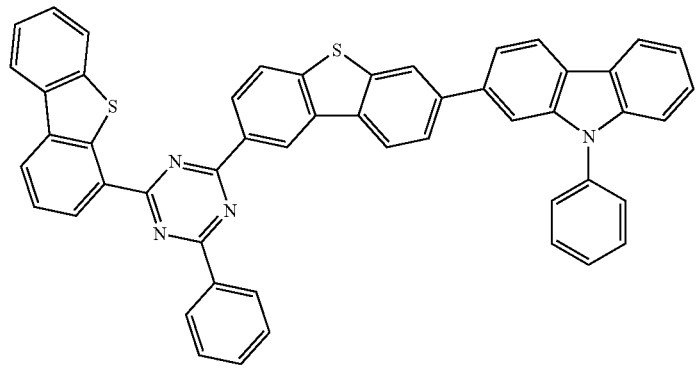

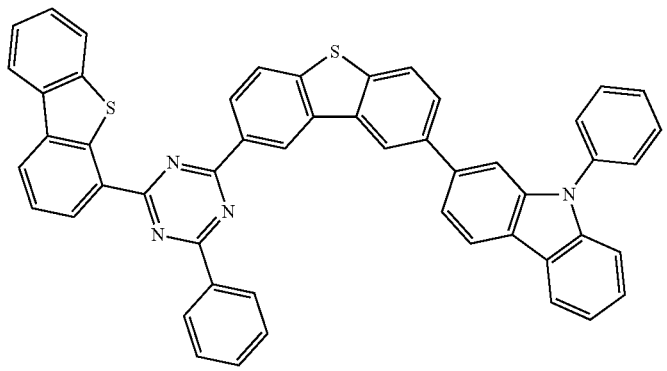
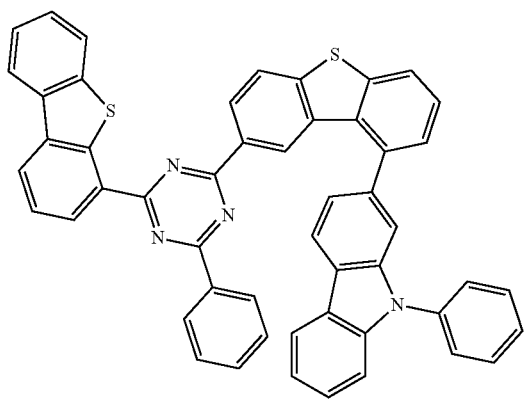
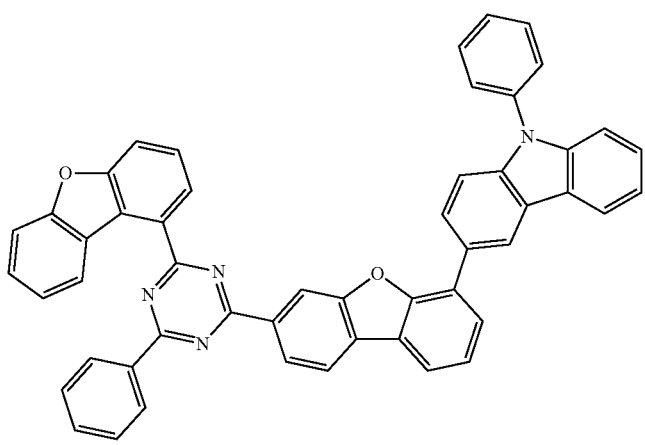
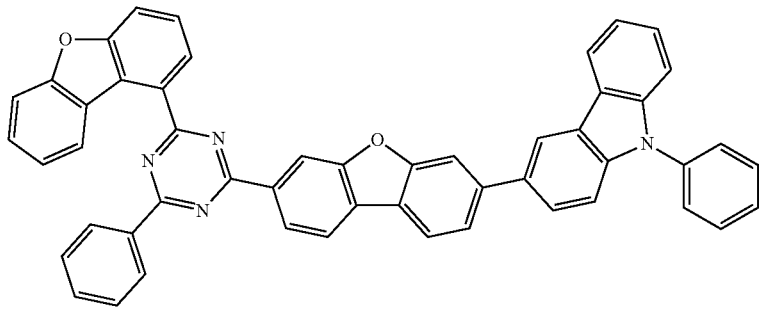

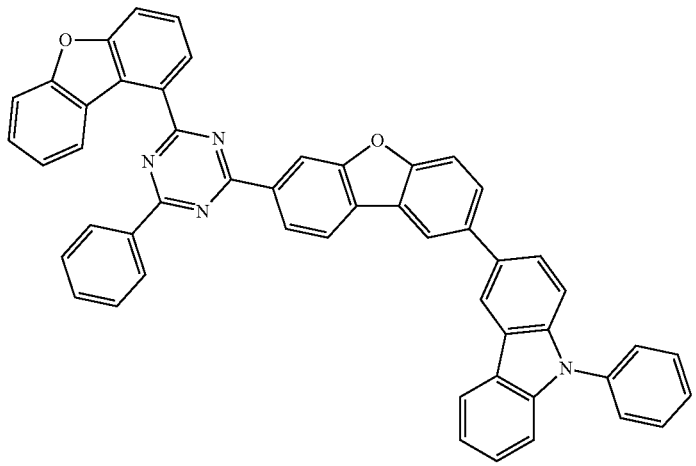
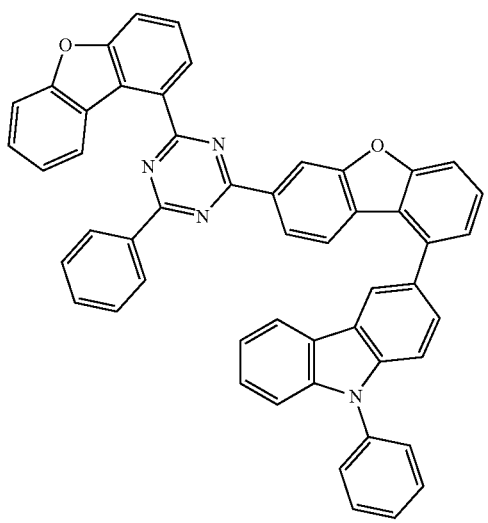
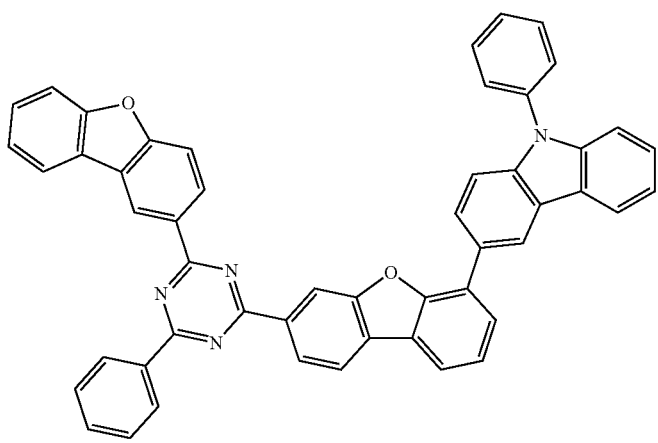

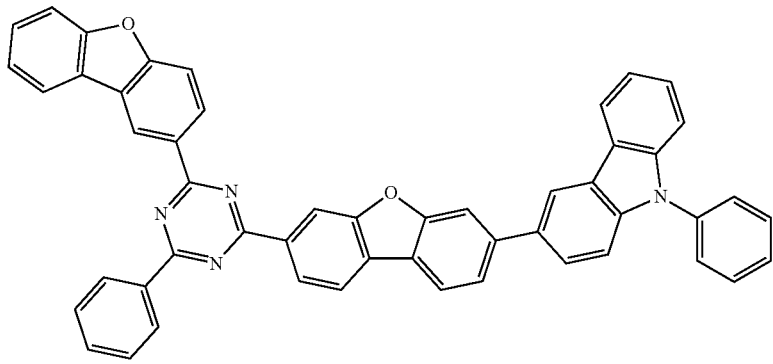
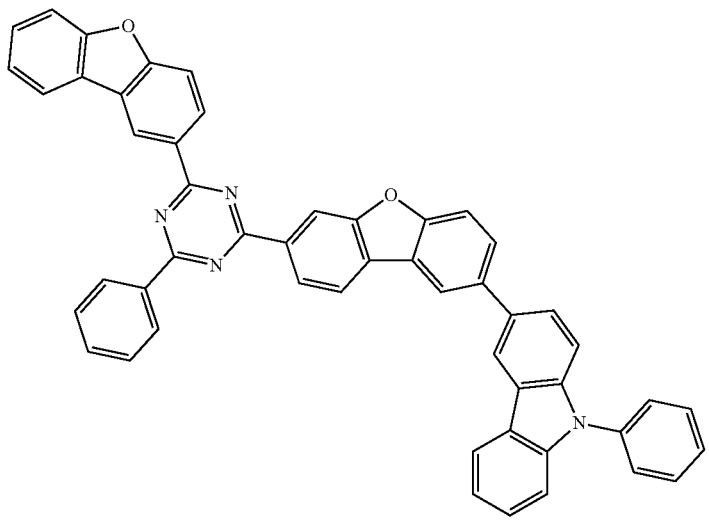
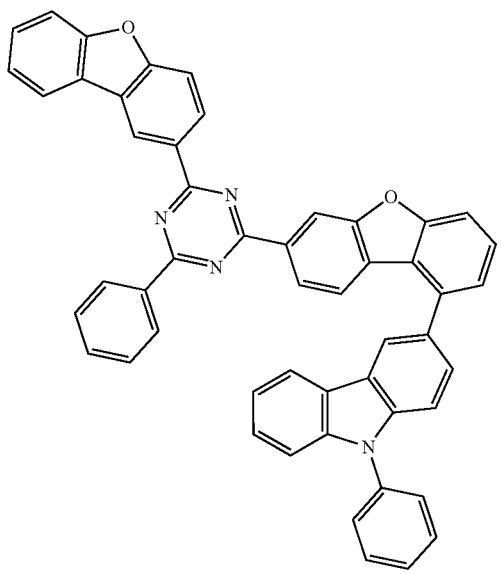

-continued
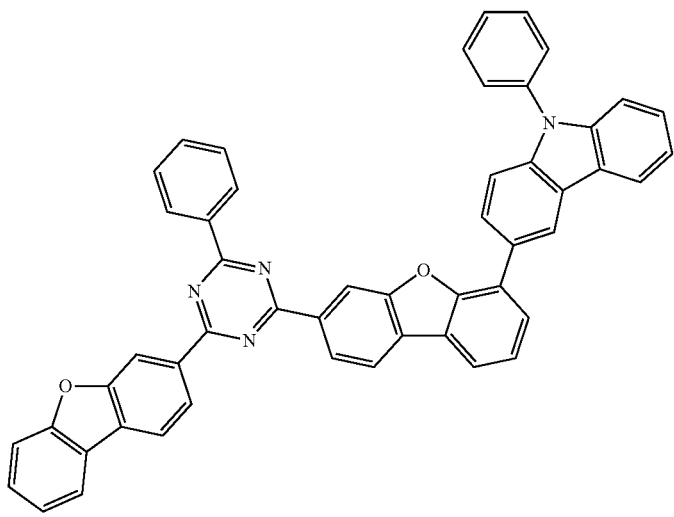
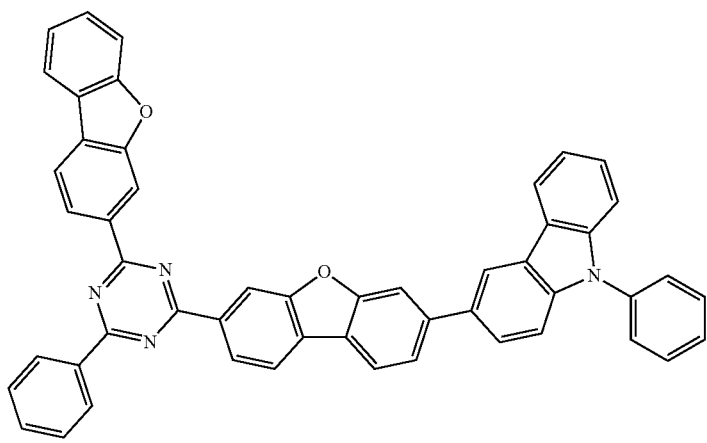
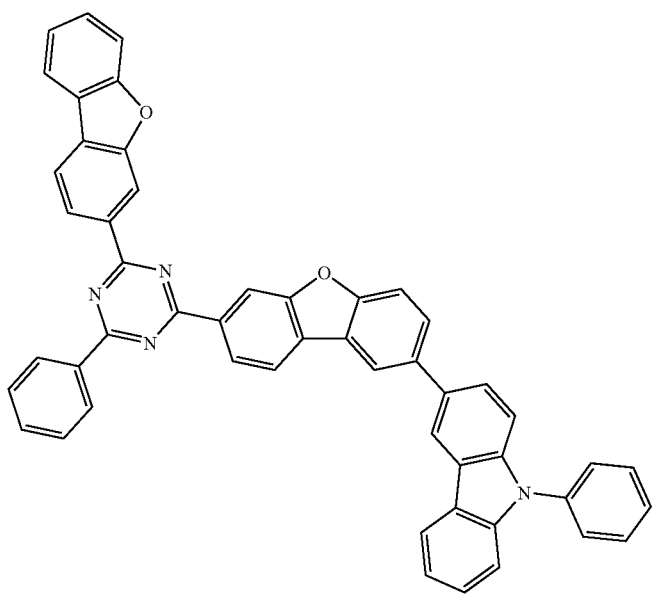

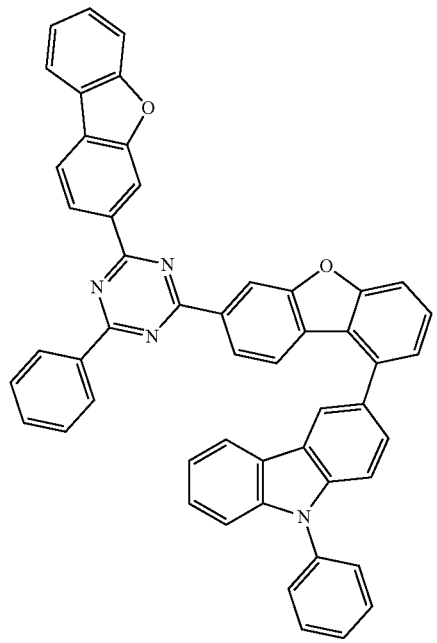 [SMILES: c1ccc(-c2nc(-c3ccc4c(c3)oc3ccccc34)nc(-c3ccc4c(c3)oc3cccc(-c5ccc6c(c5)c5ccccc5n6-c5ccccc5)c34)n2)cc1]
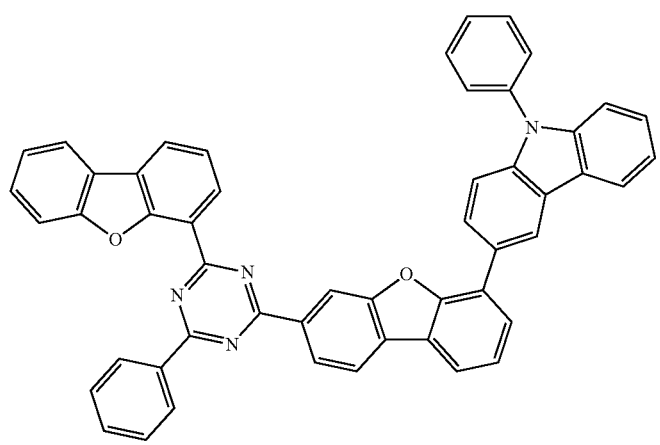
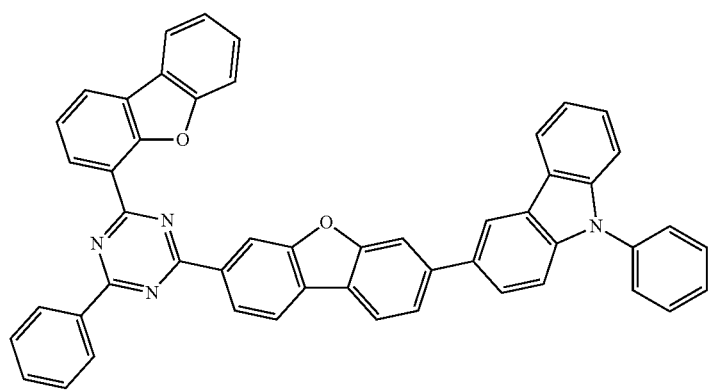

-continued
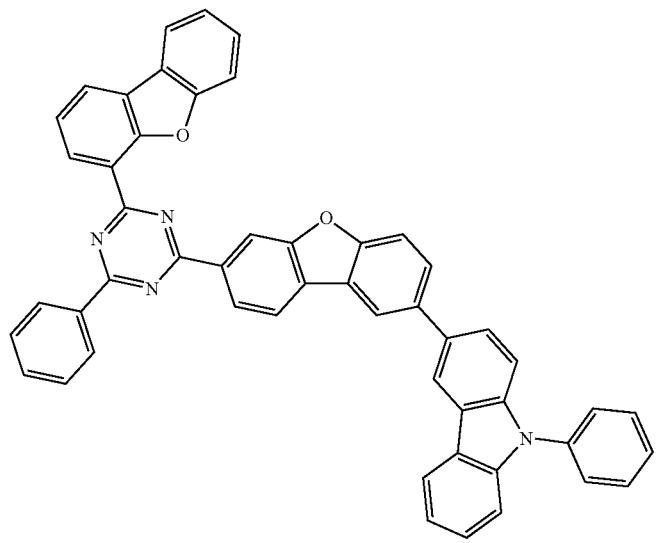
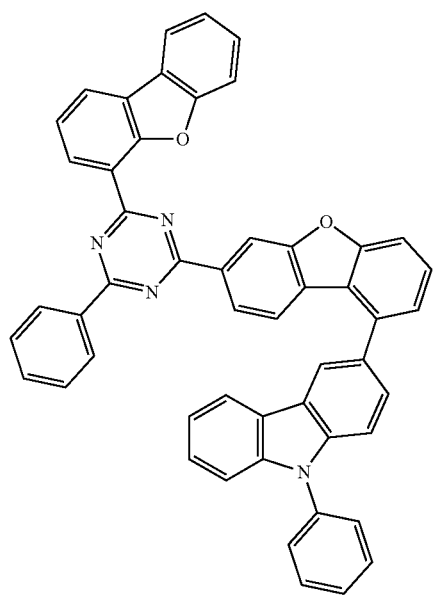 [SMILES: c1ccc(-c2nc(-c3ccc4c(c3)oc3cccc(-c5ccc6c(c5)c5ccccc5n6-c5ccccc5)c34)nc(-c3cccc4c3oc3ccccc34)n2)cc1]
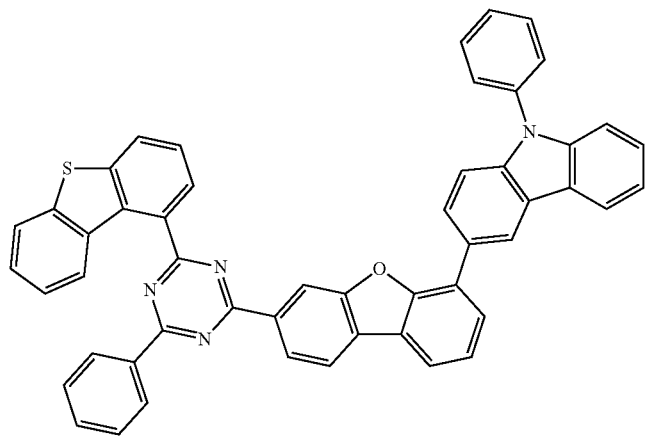

-continued
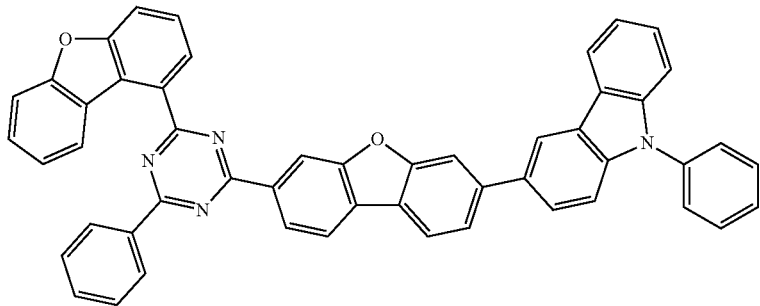
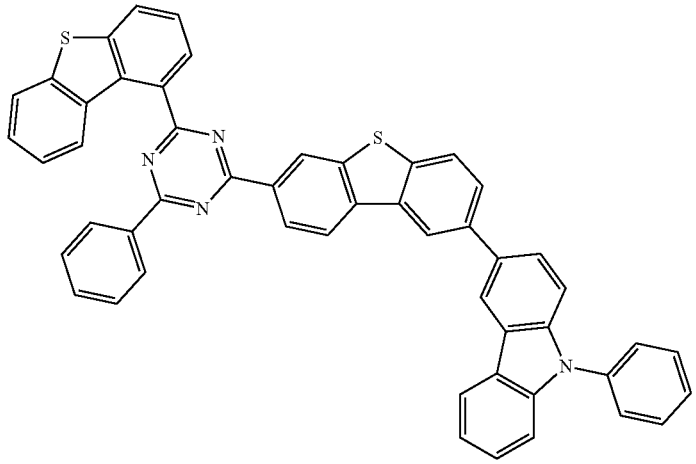
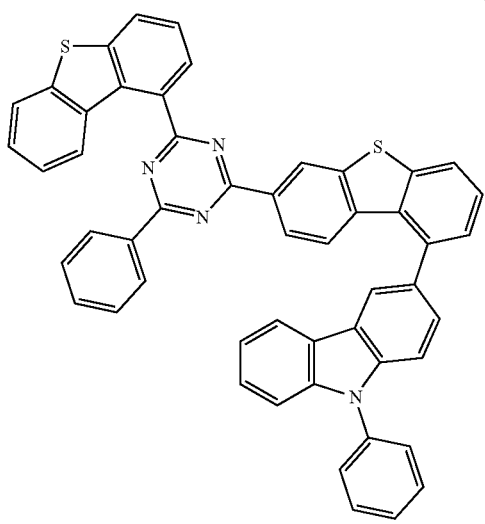
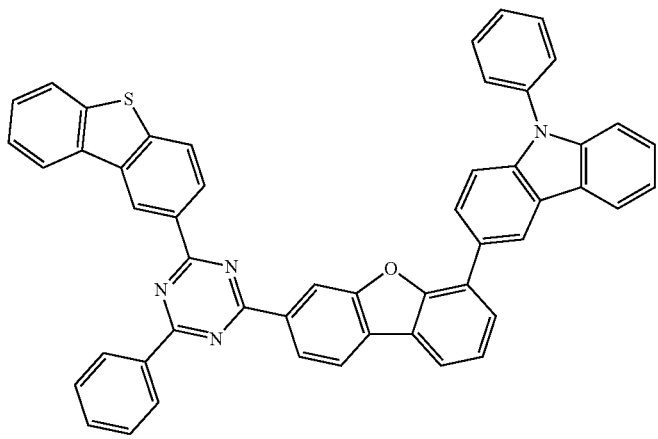

-continued
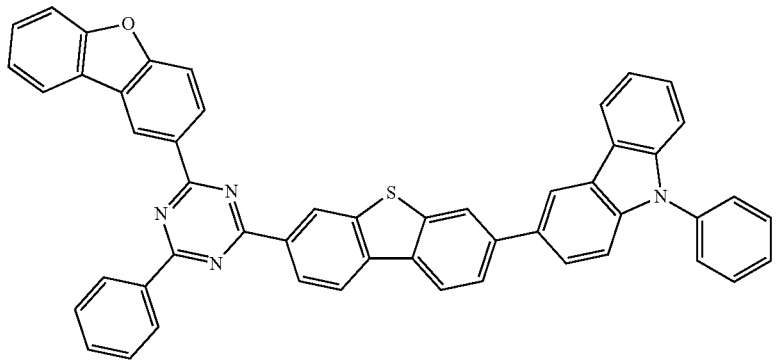
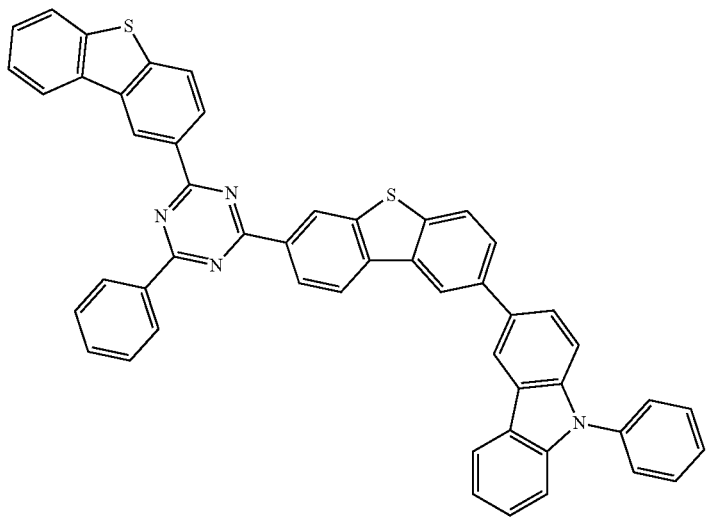
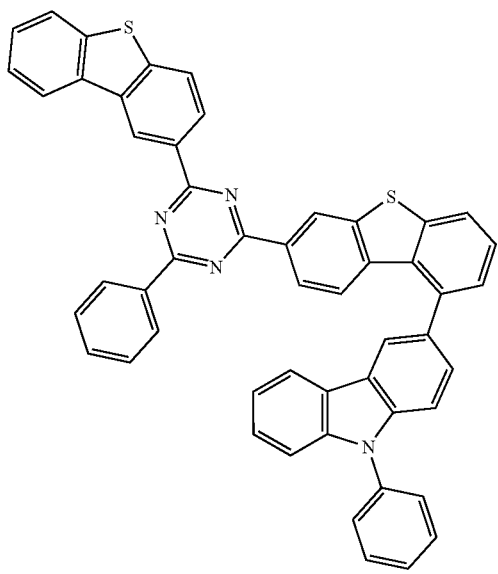

-continued
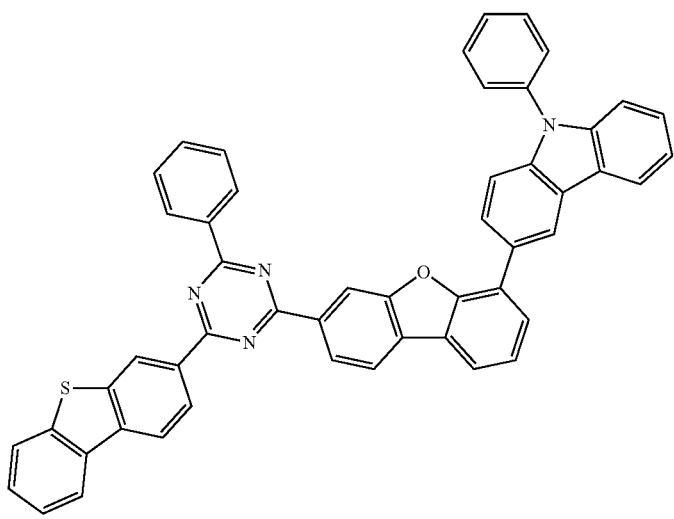
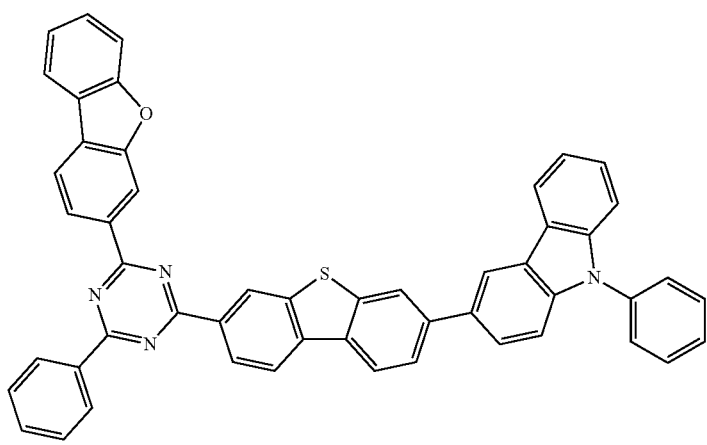
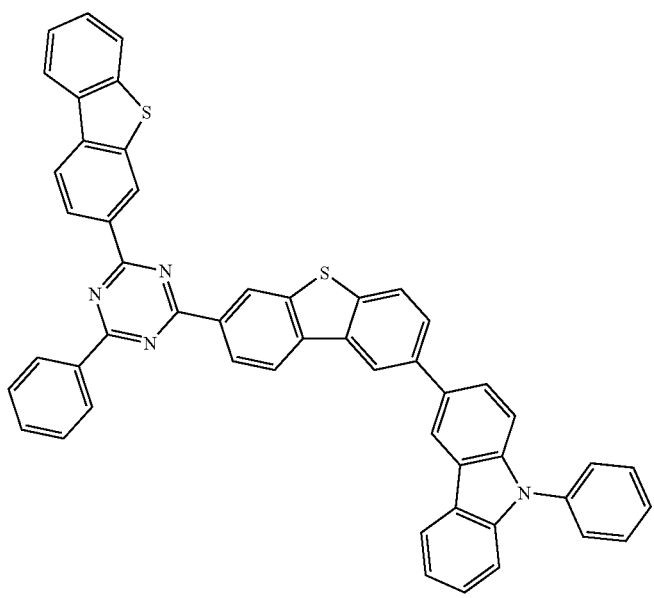

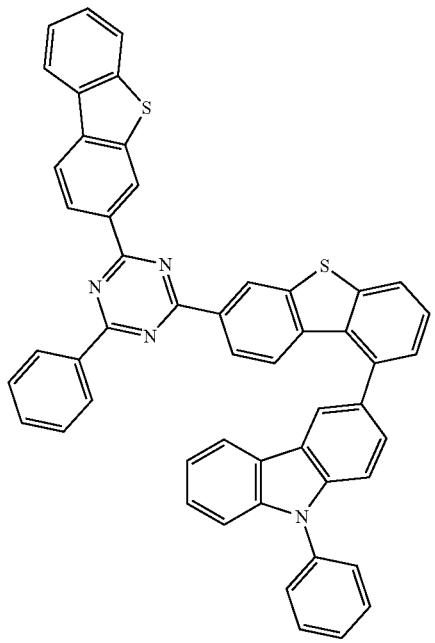 [SMILES: c1ccc(-c2nc(-c3ccc4c(c3)sc3ccccc34)nc(-c3ccc4c(c3)sc3cccc(-c5ccc6c(c5)c5ccccc5n6-c5ccccc5)c34)n2)cc1]
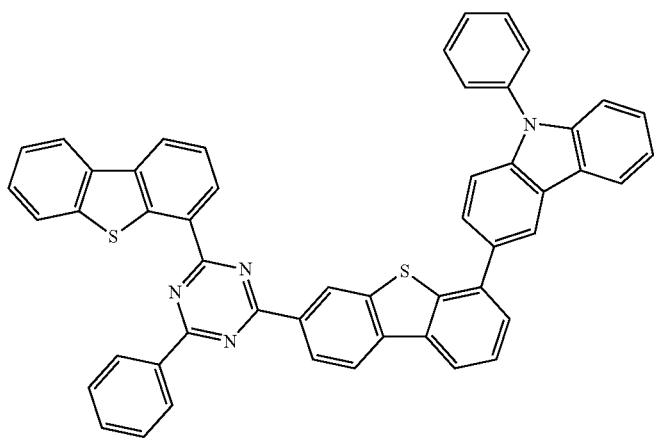
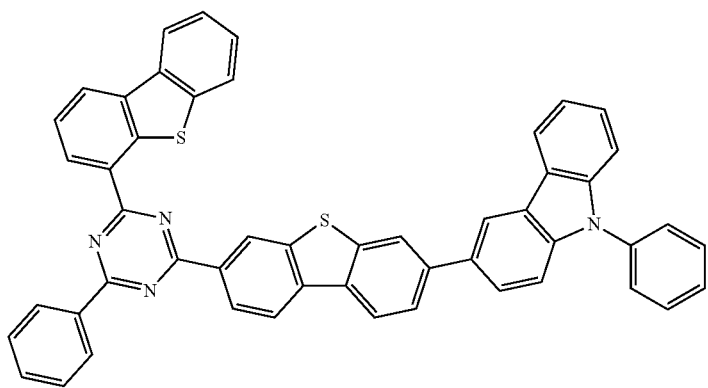

-continued
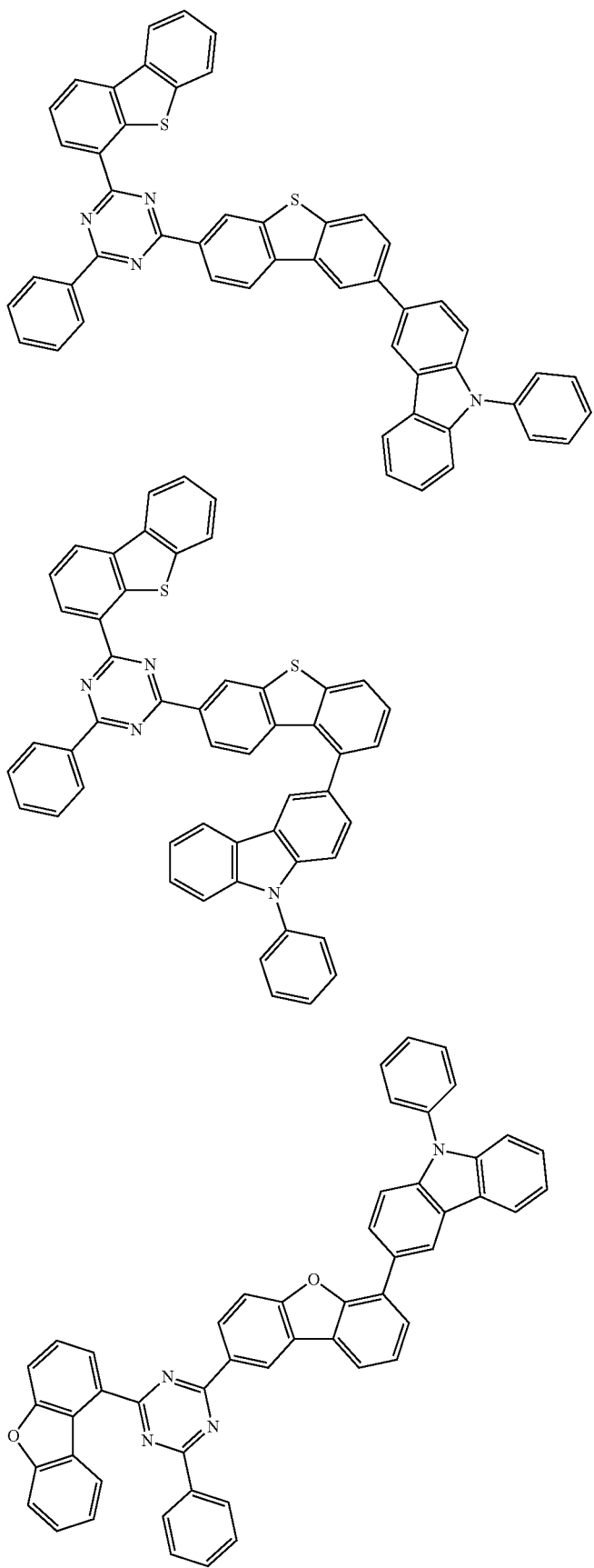

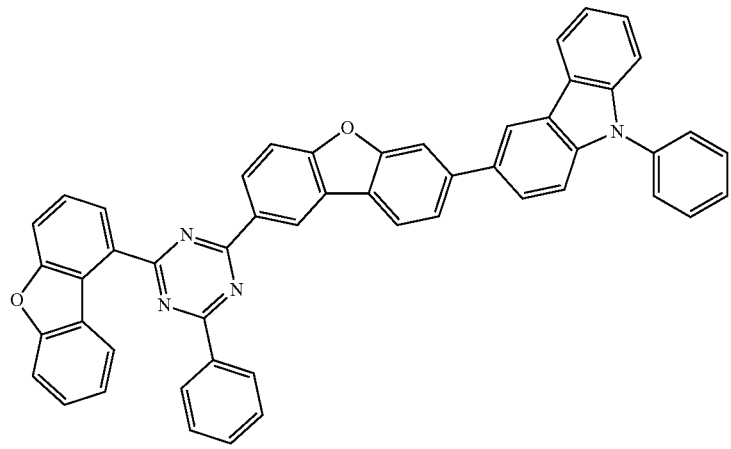
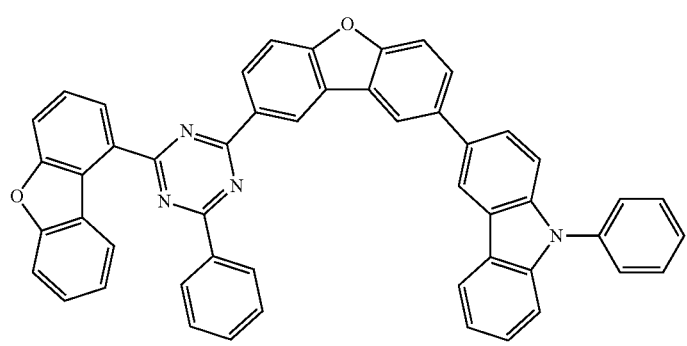
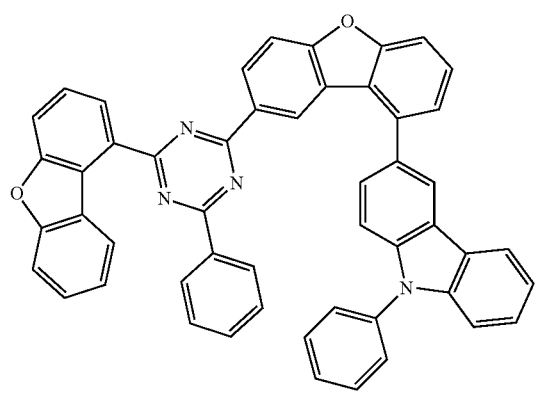

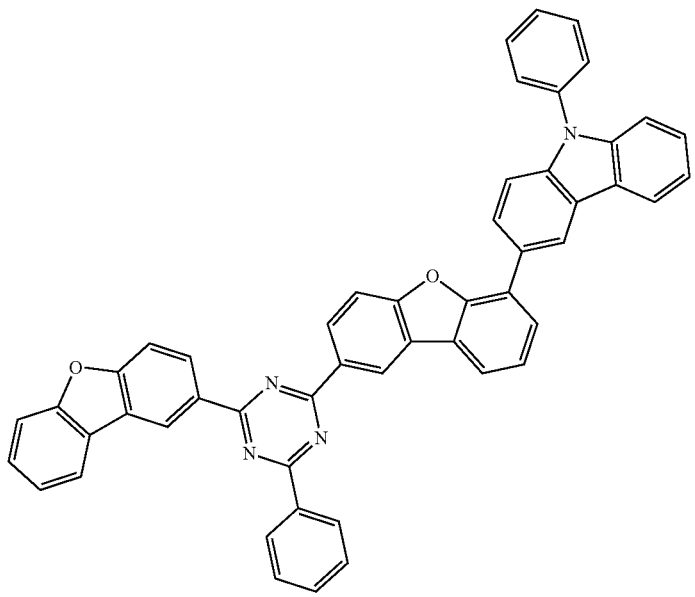
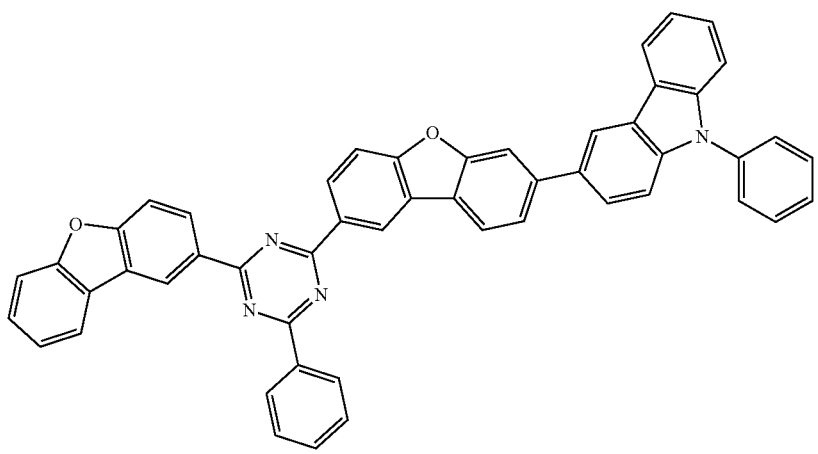
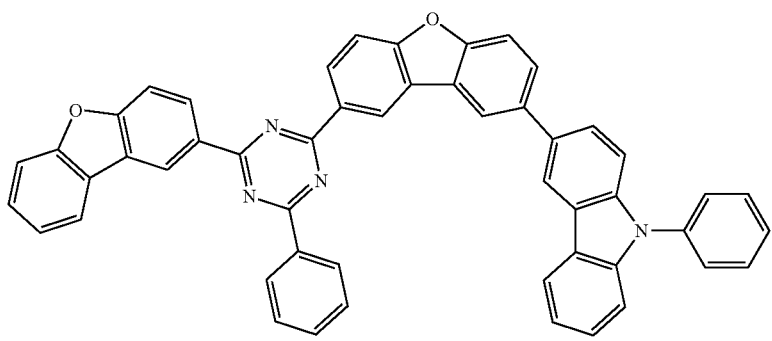

-continued
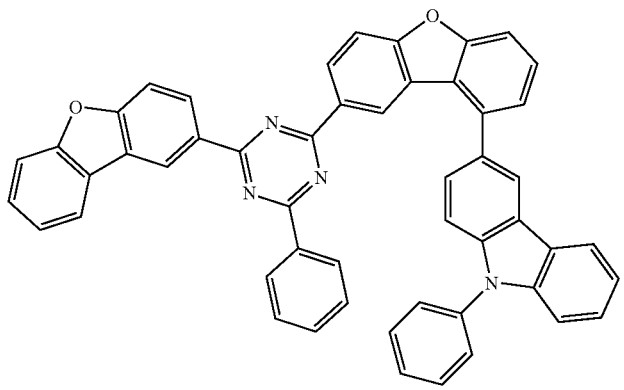
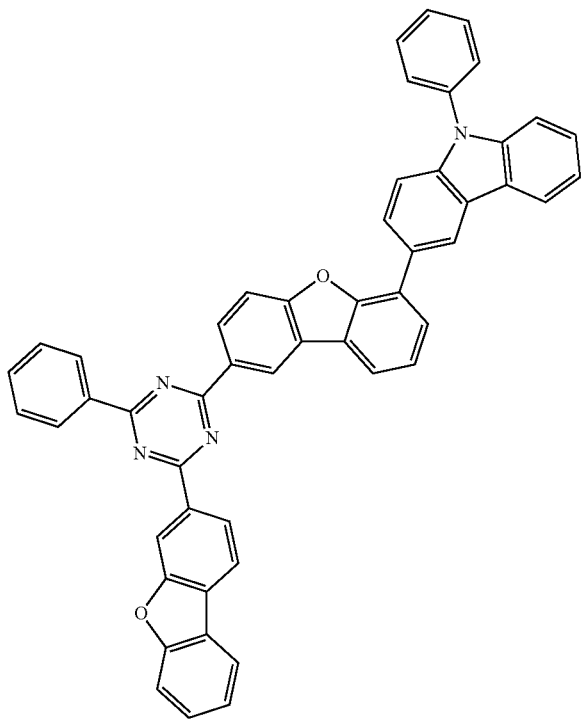
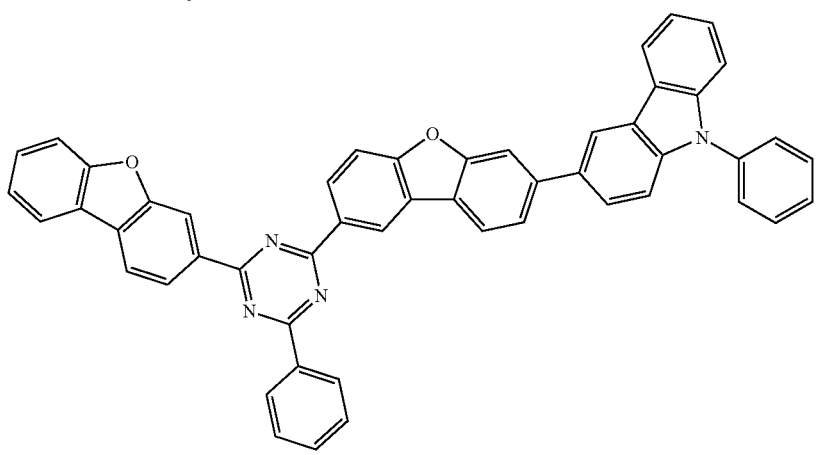

-continued
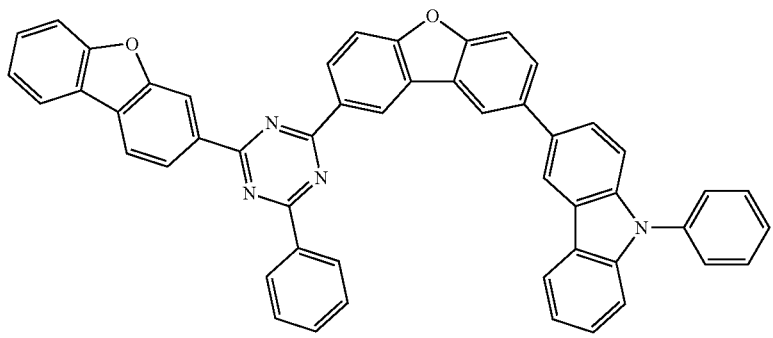
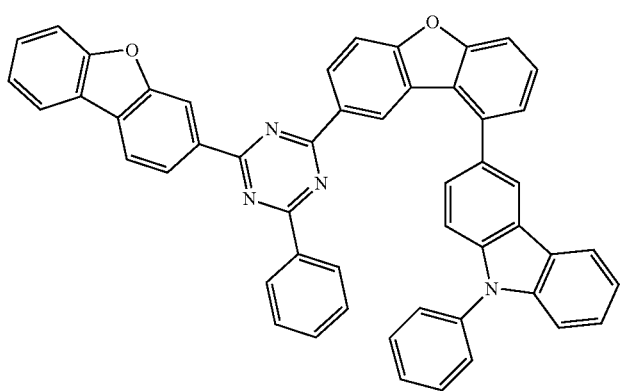
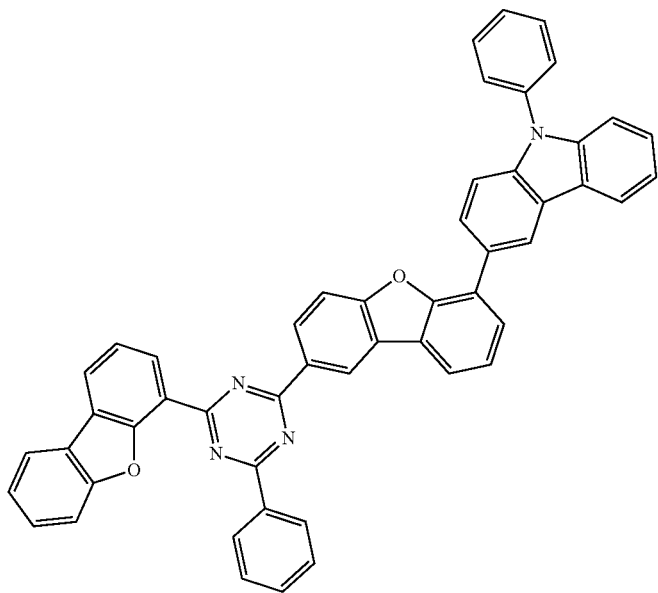

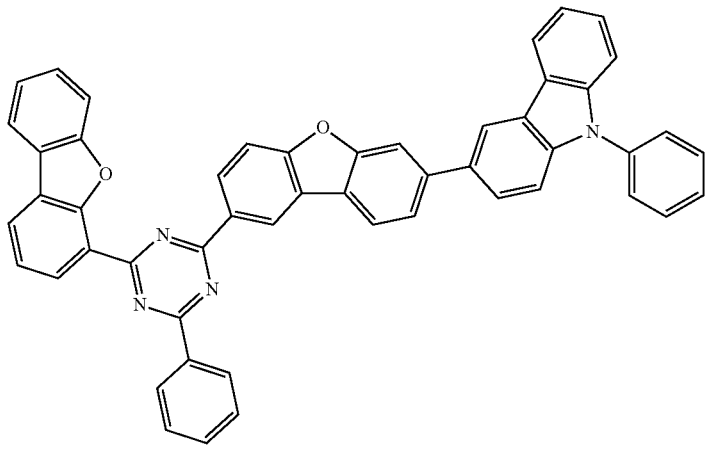
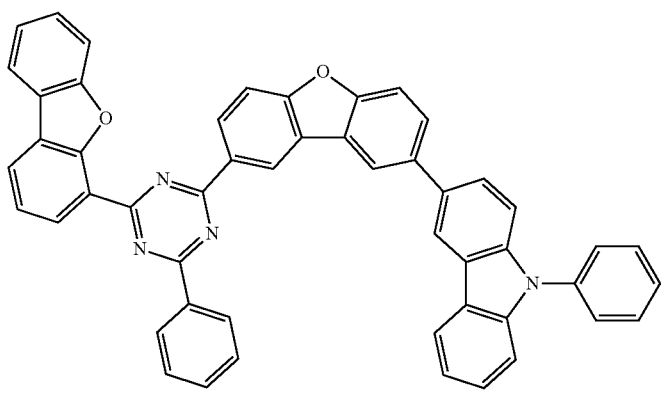
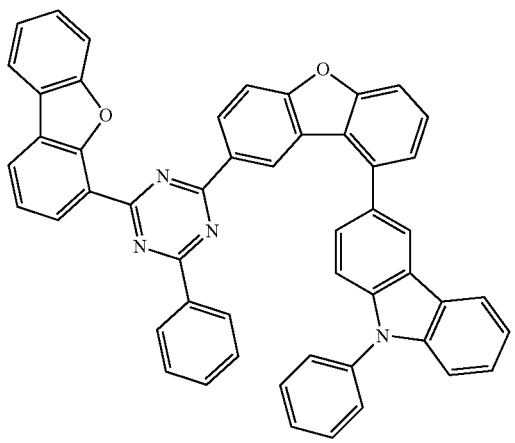

-continued
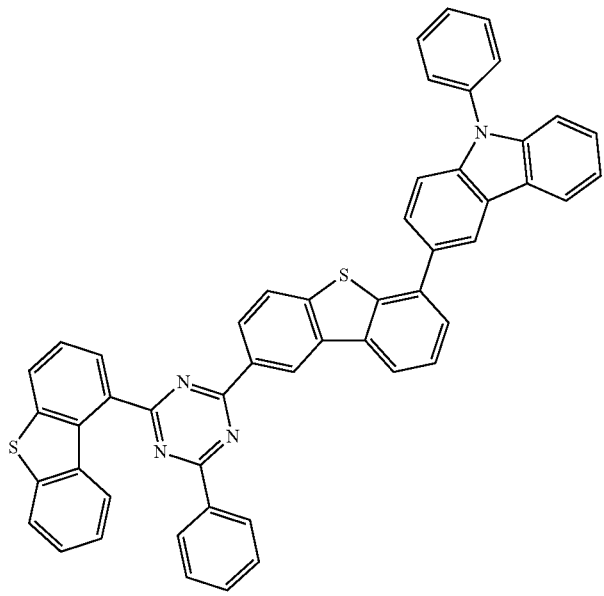
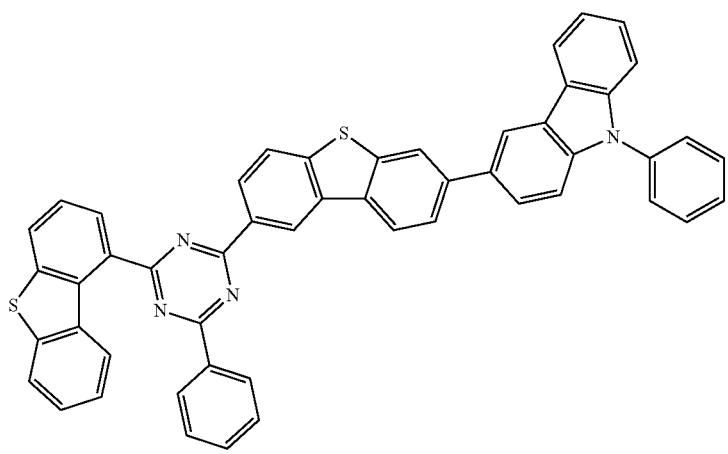
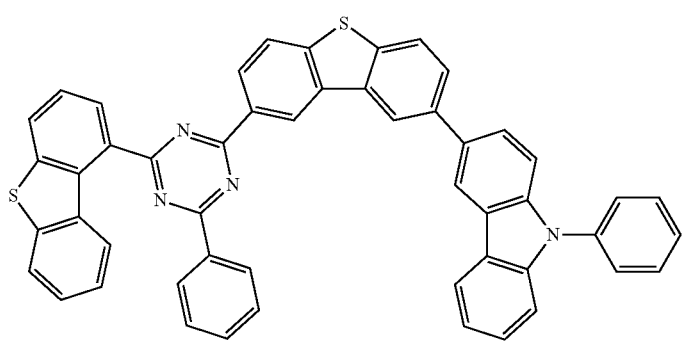

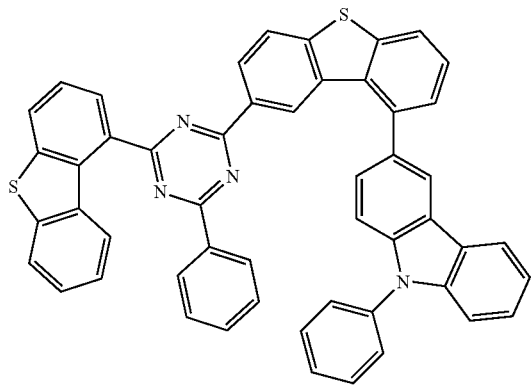
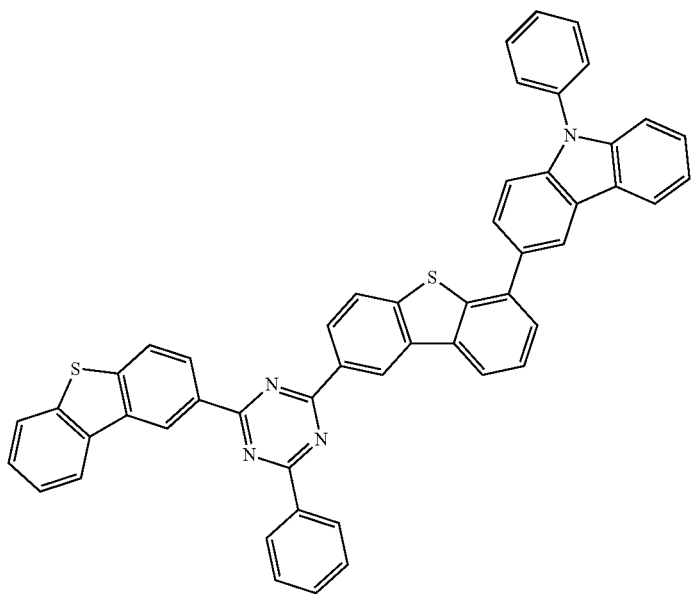
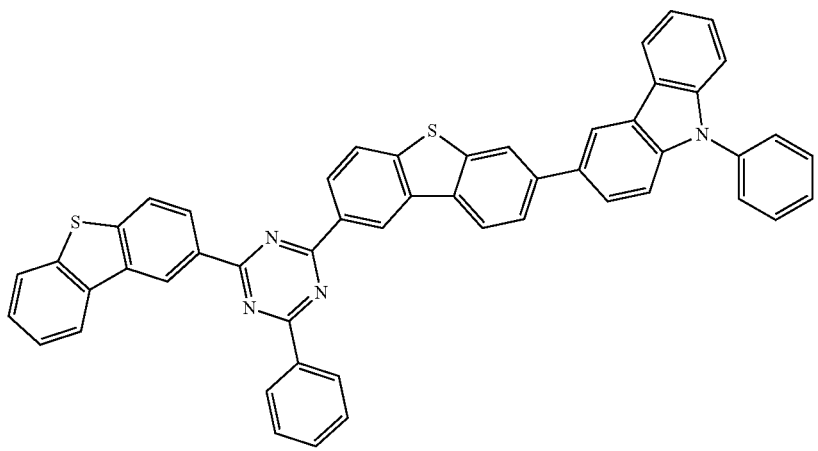

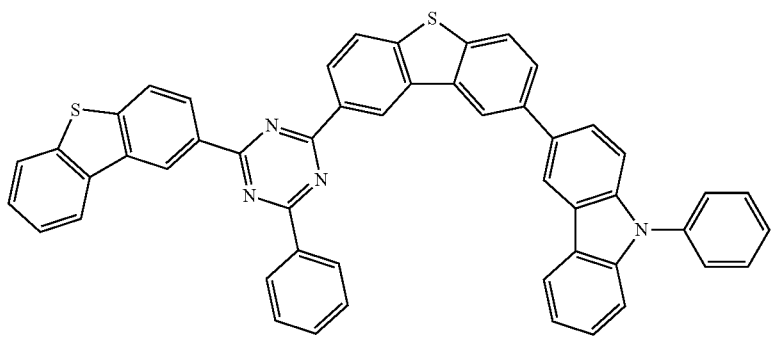
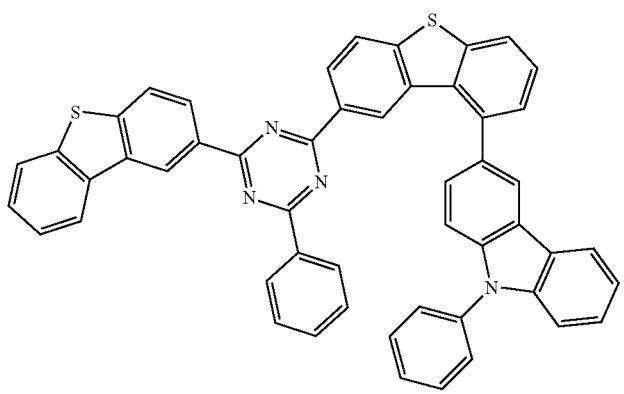
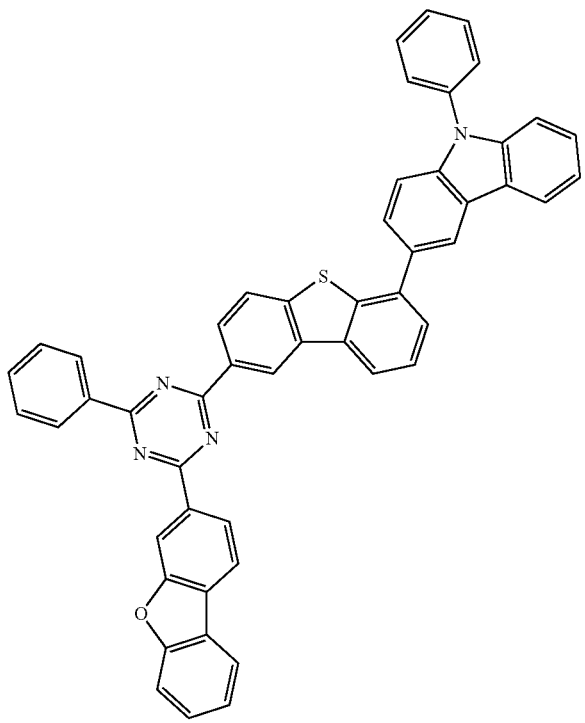

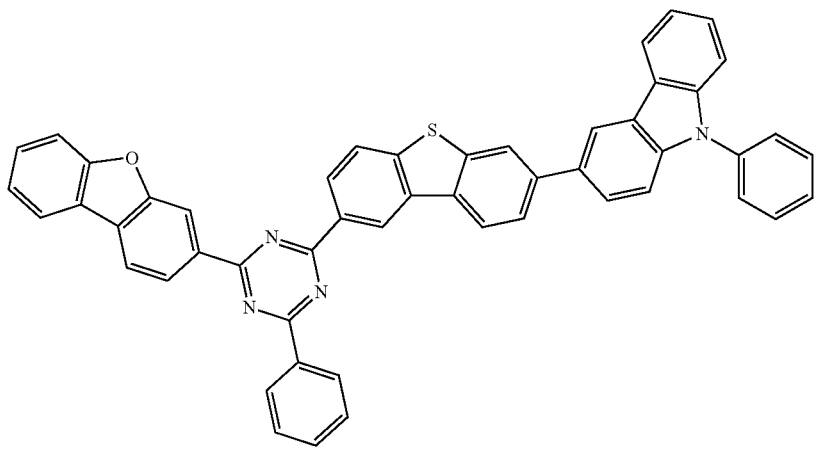
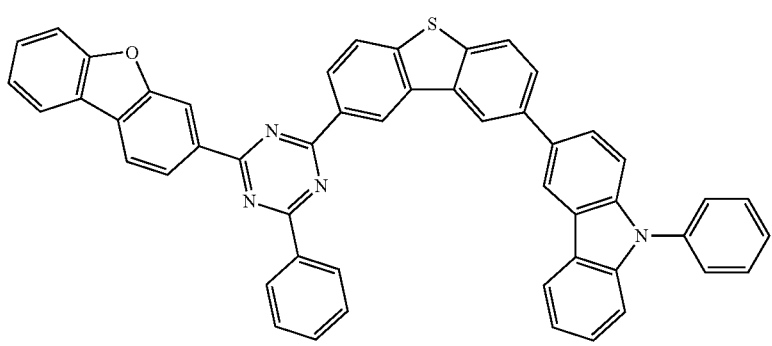
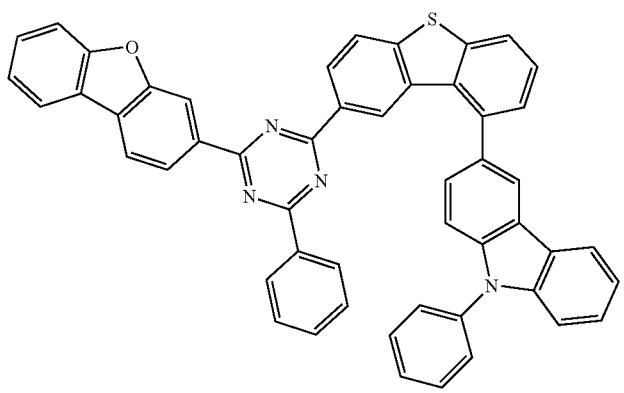

-continued
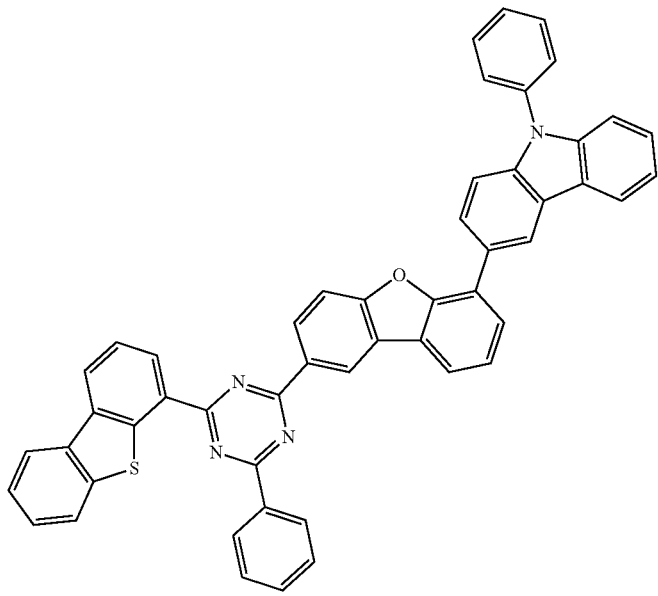
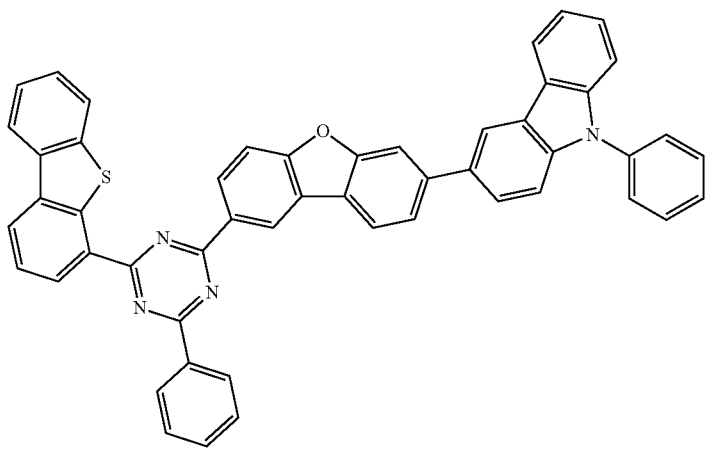
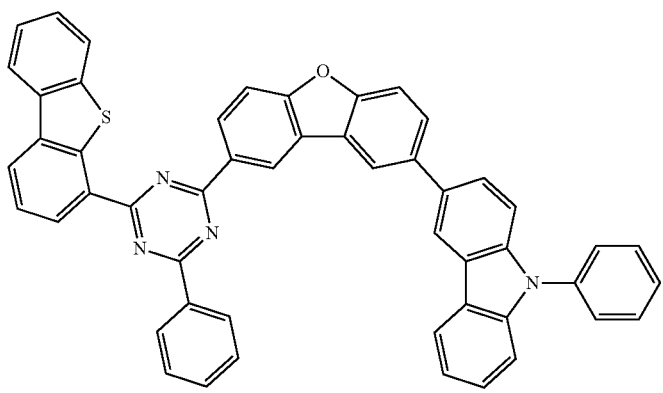

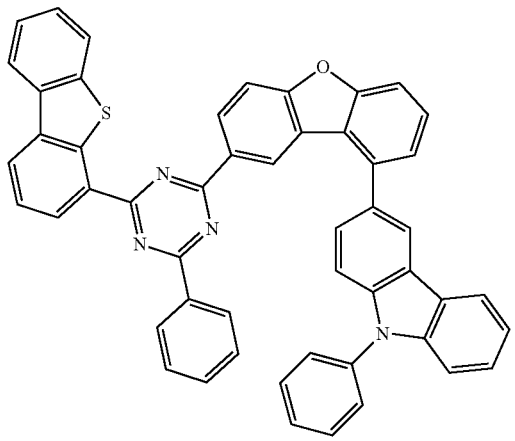
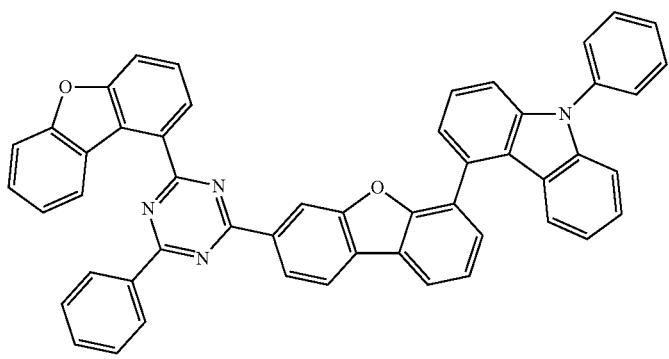
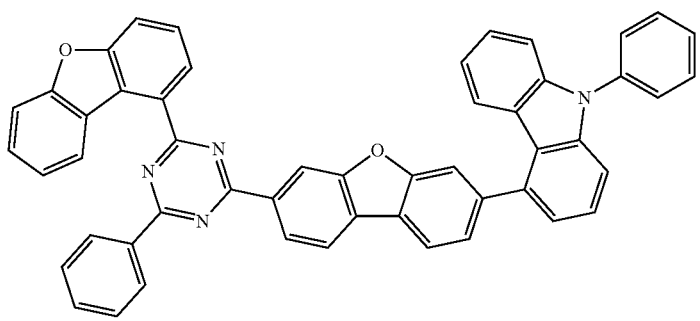
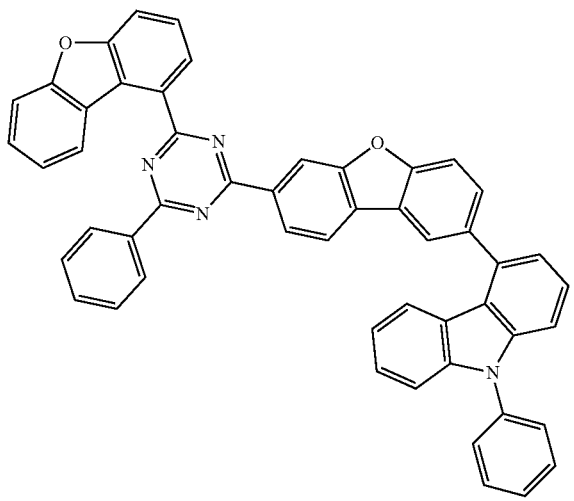

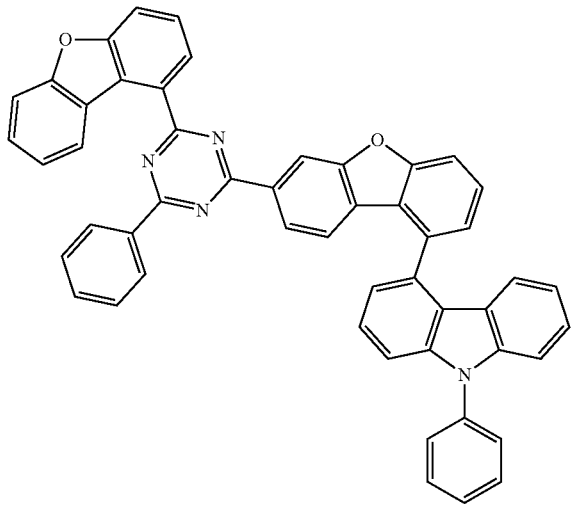
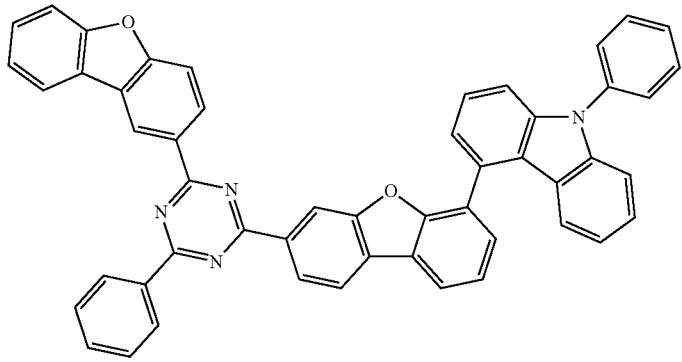
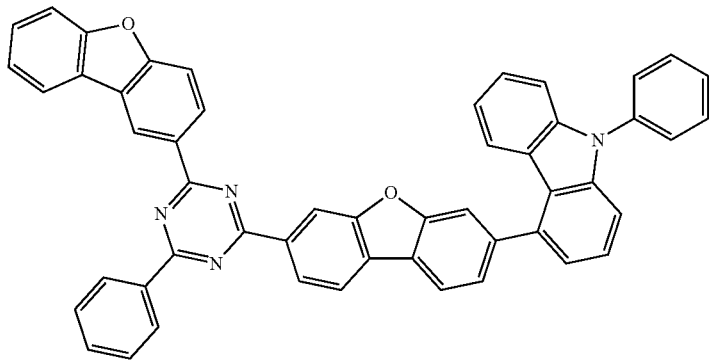

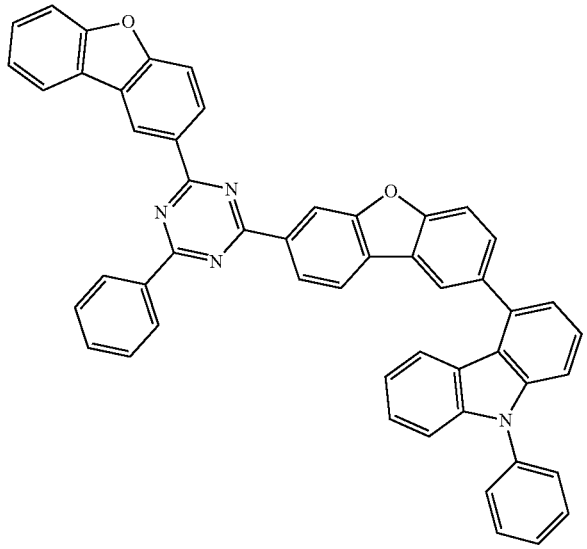
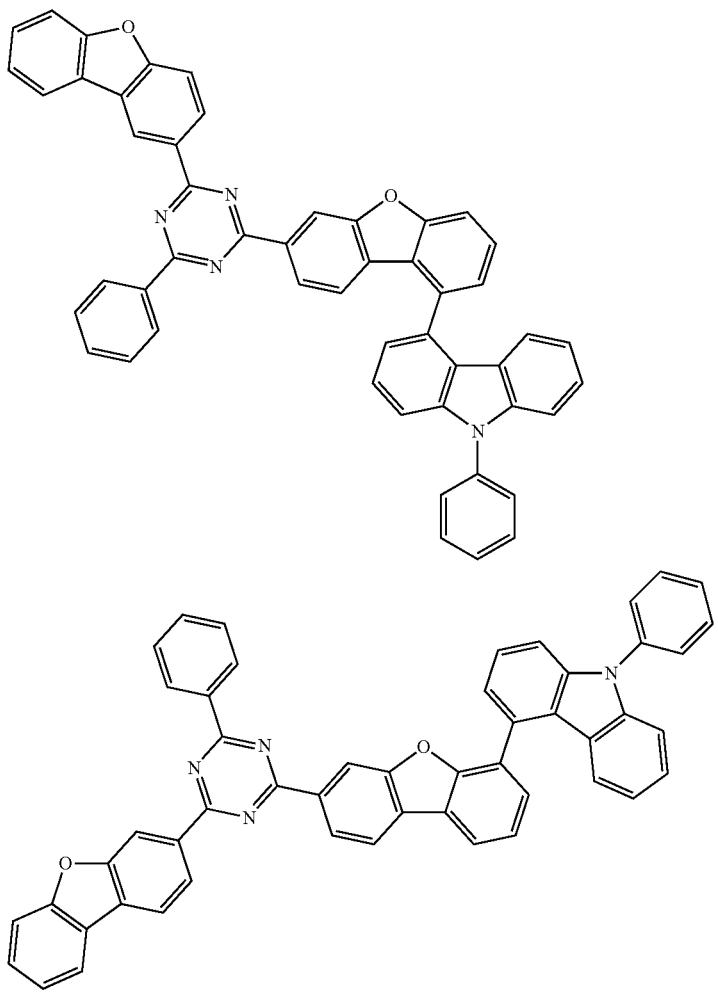

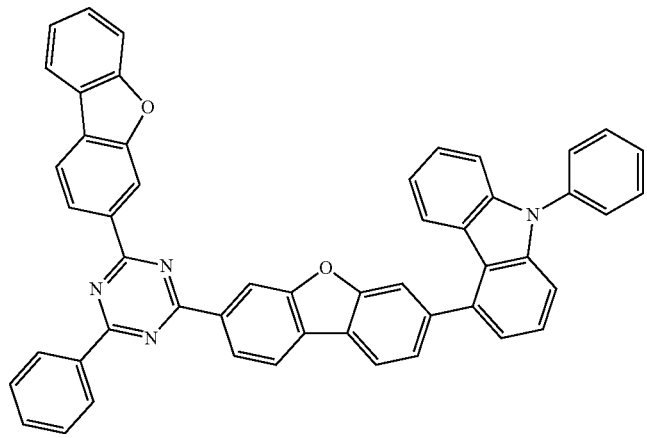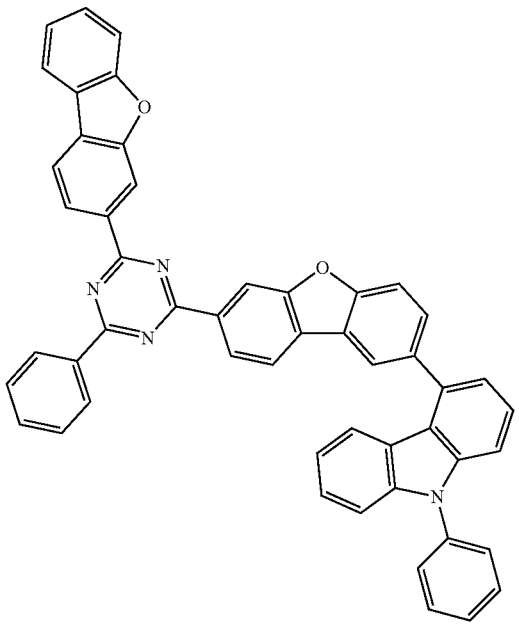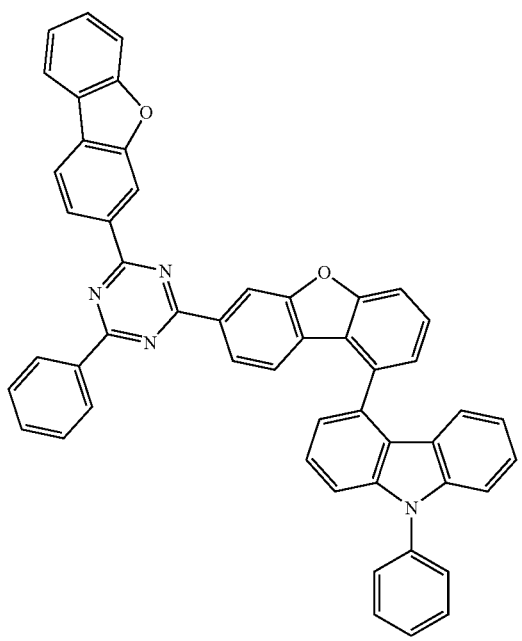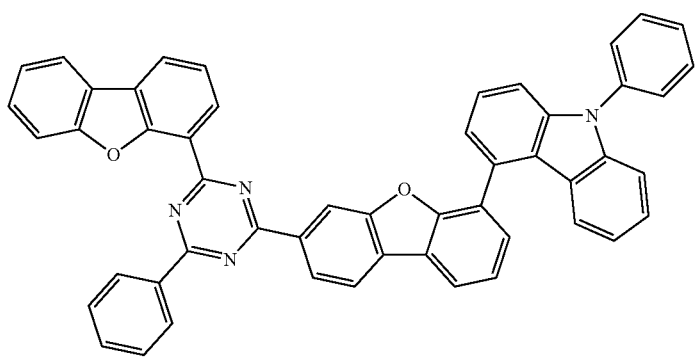

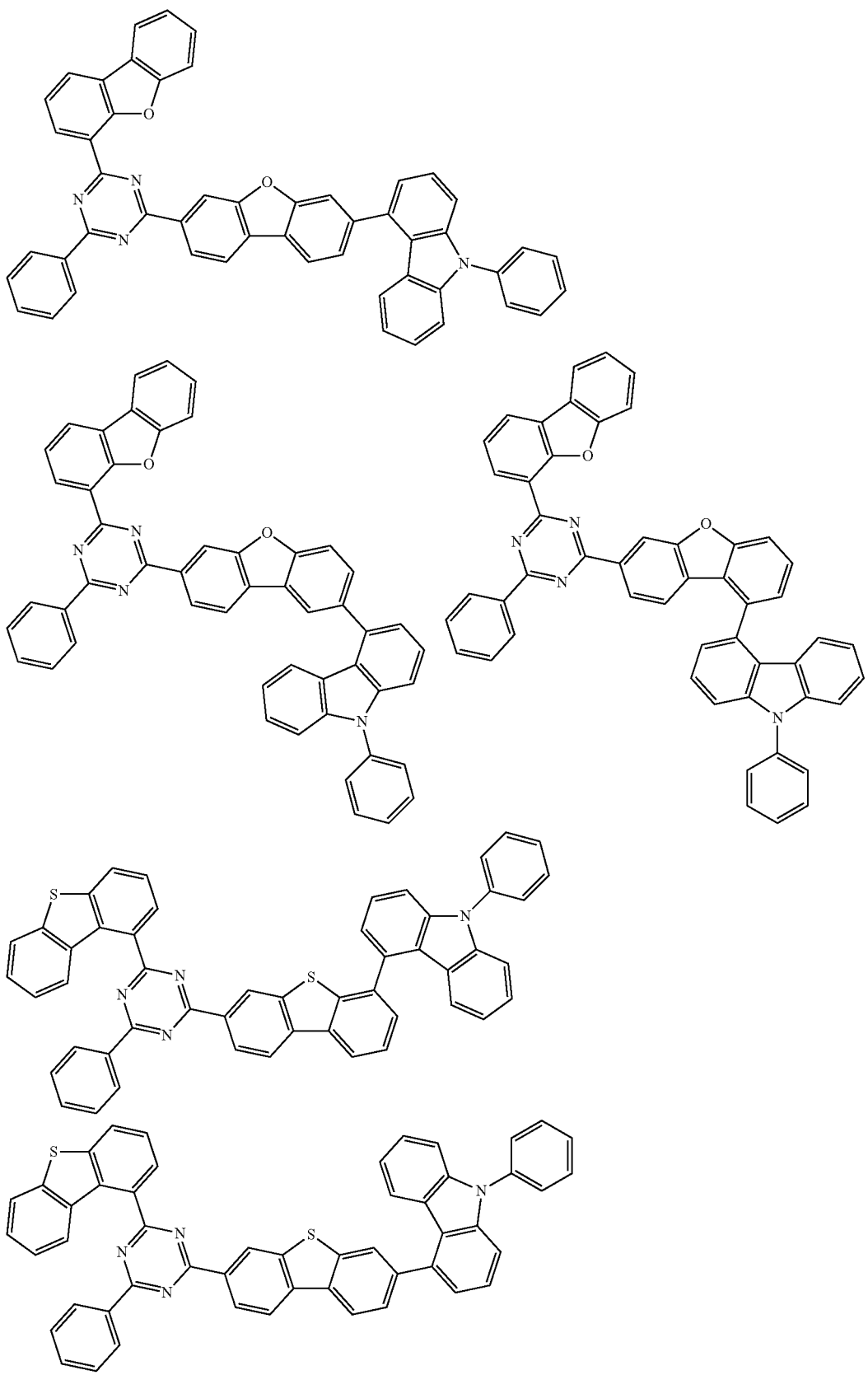

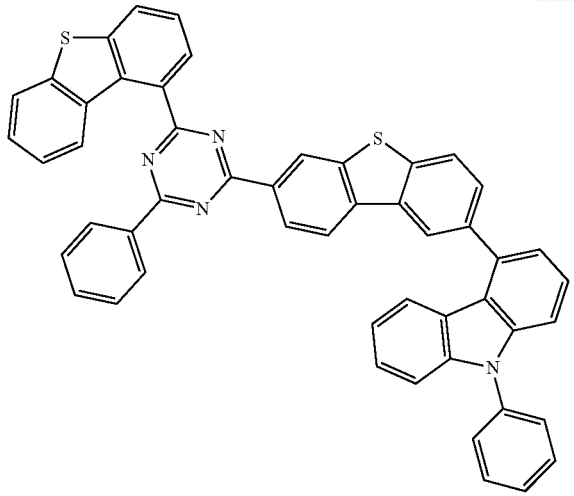
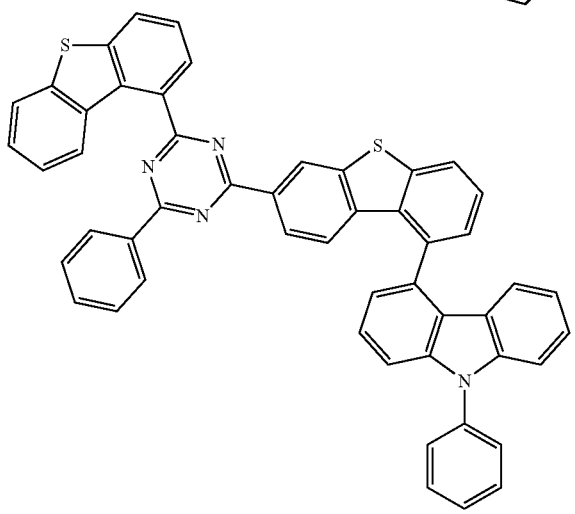
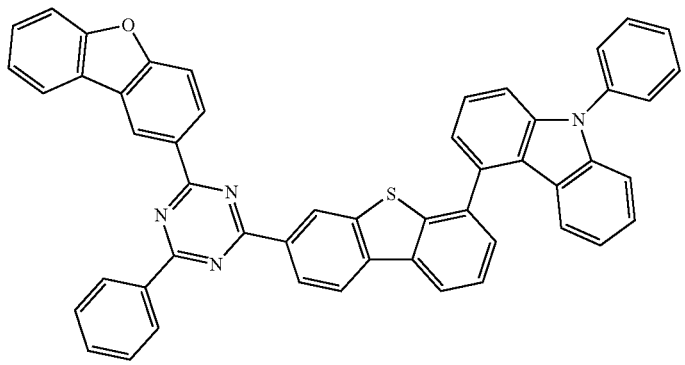
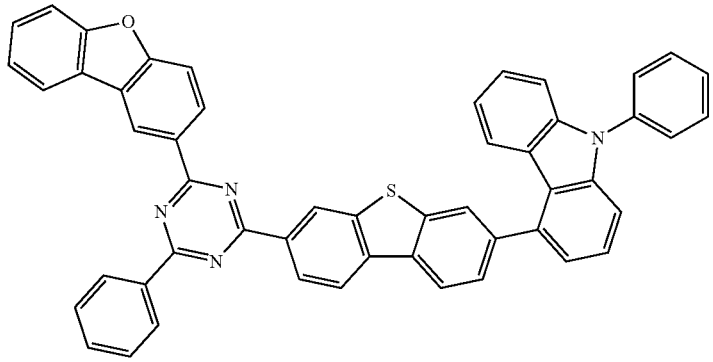

-continued
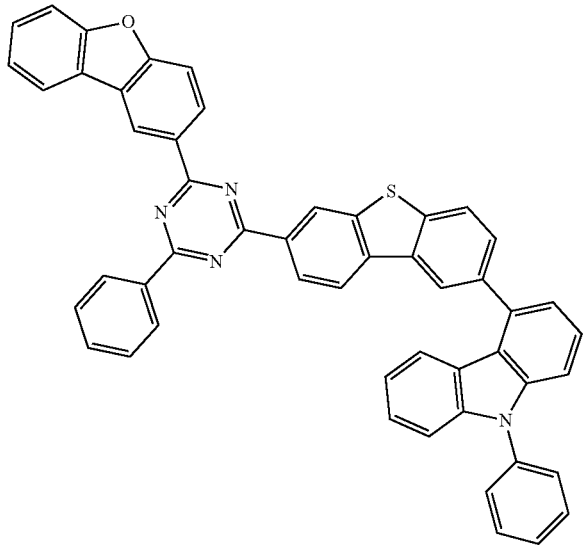
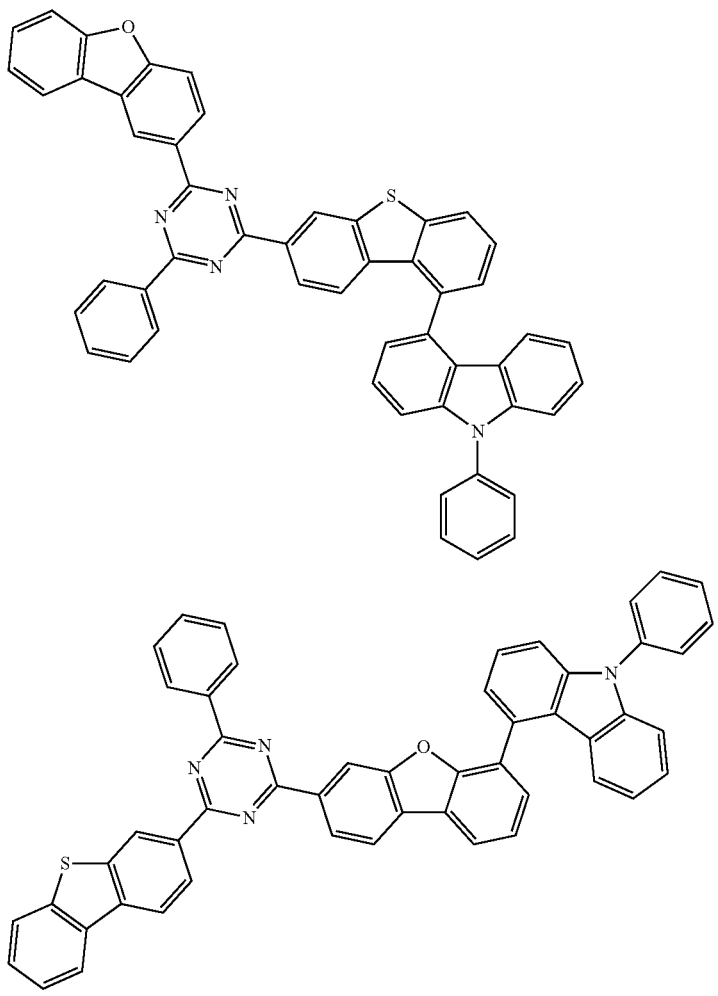

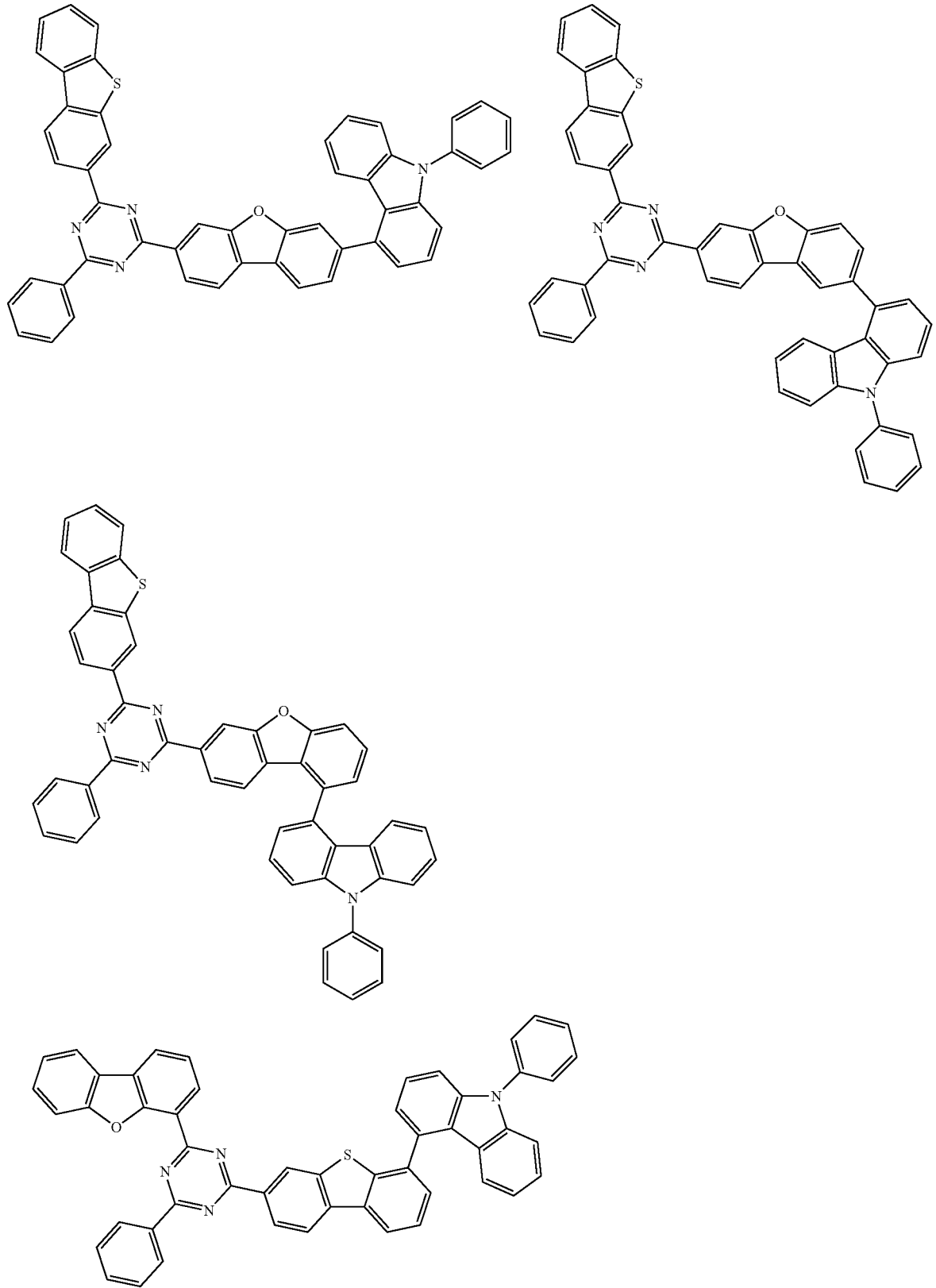

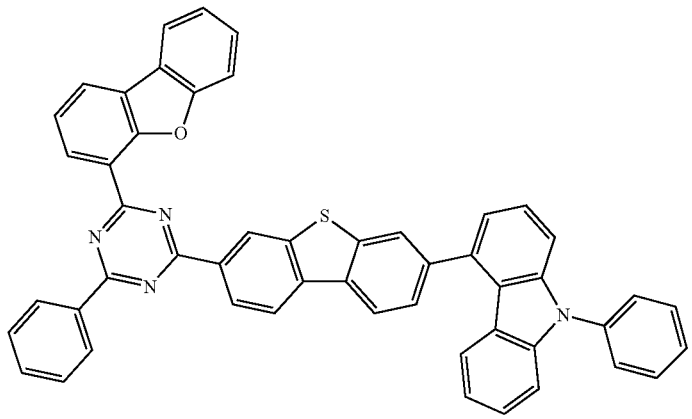
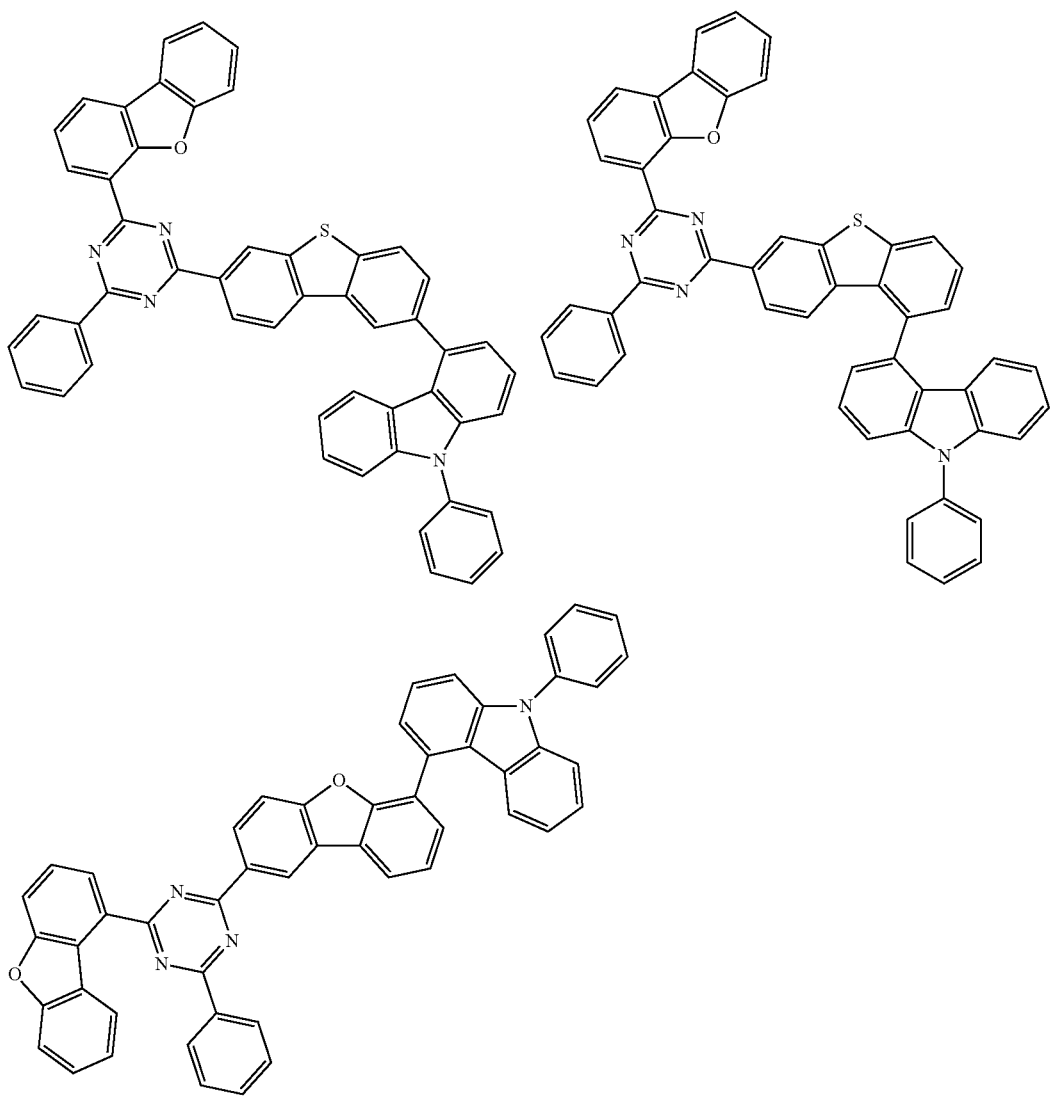

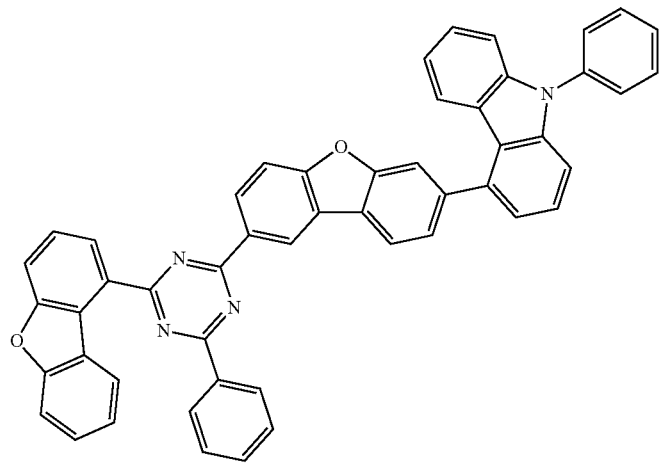
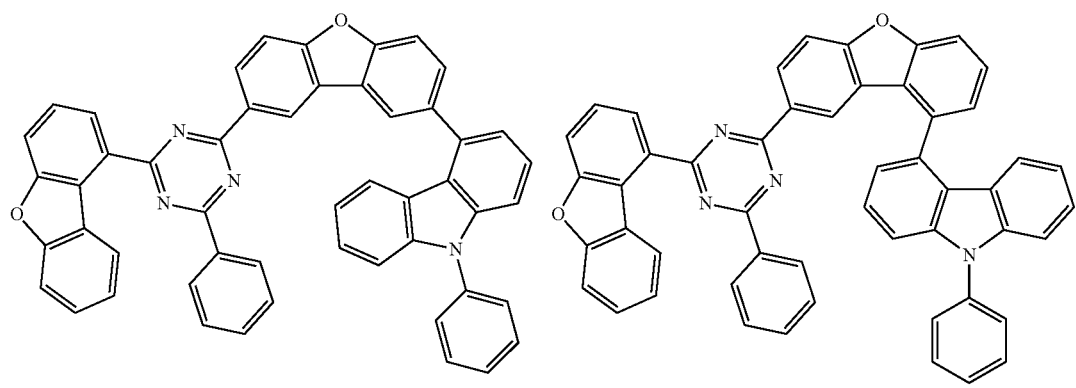
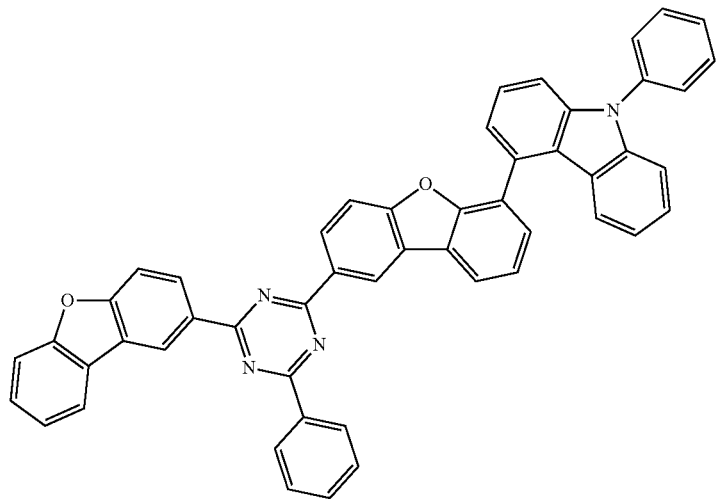

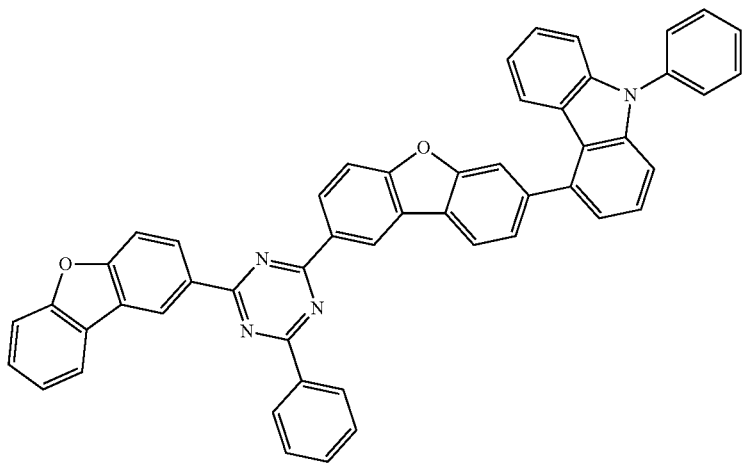
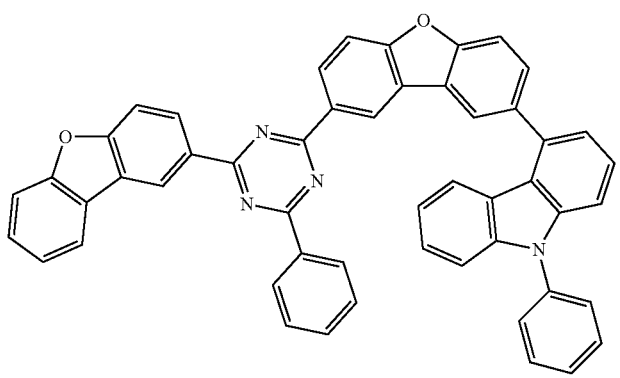
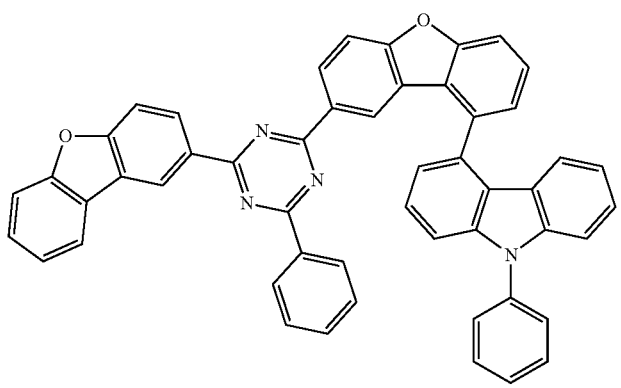

-continued
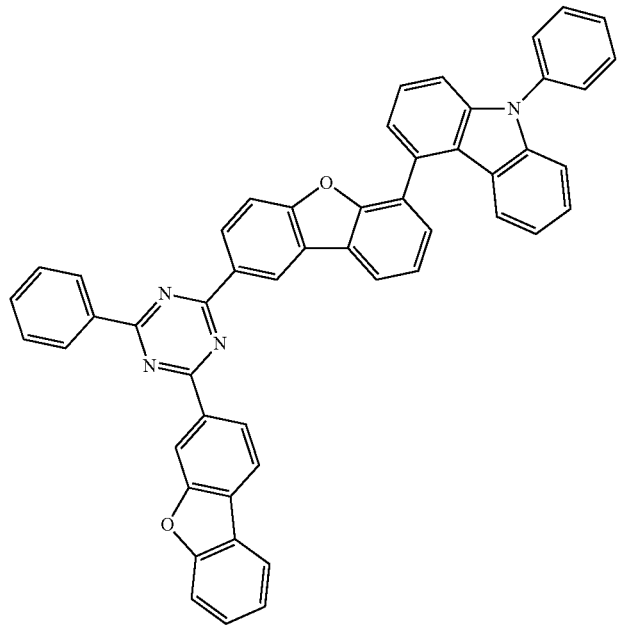
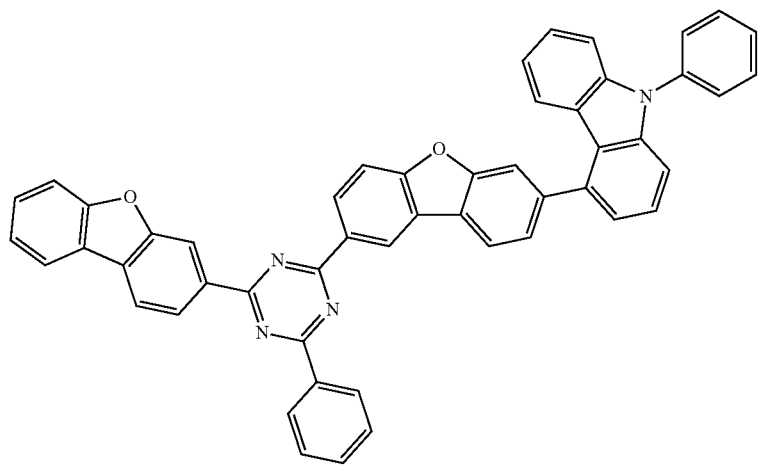
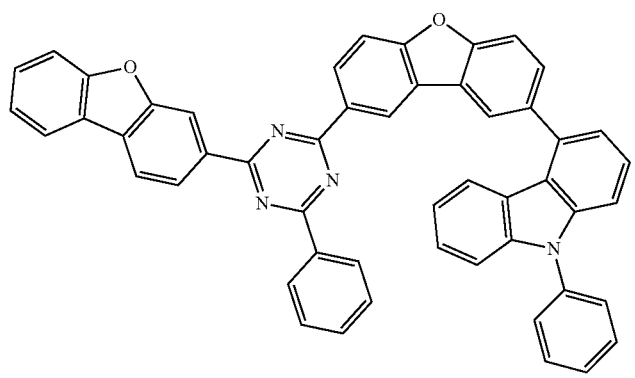

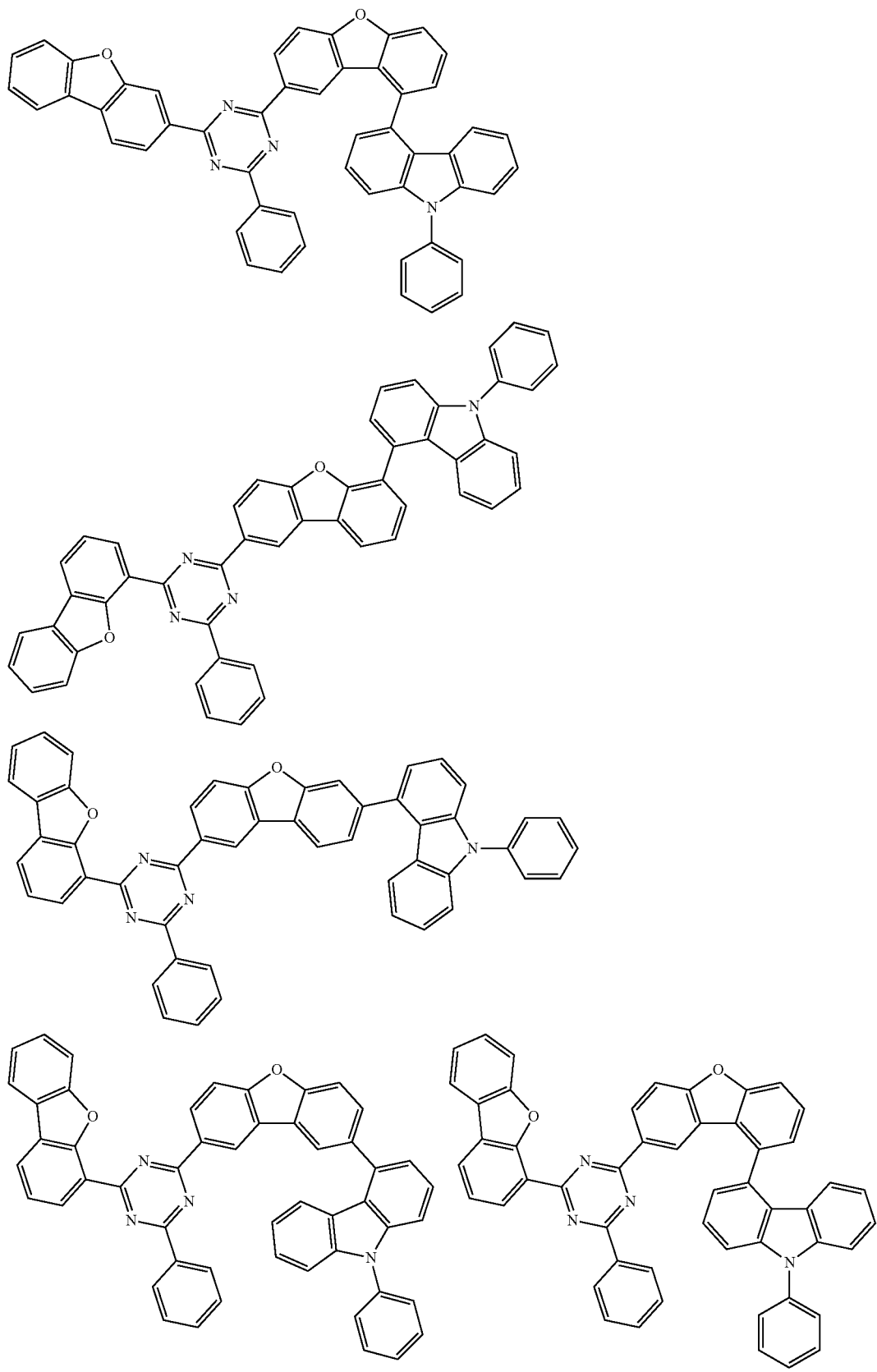

-continued
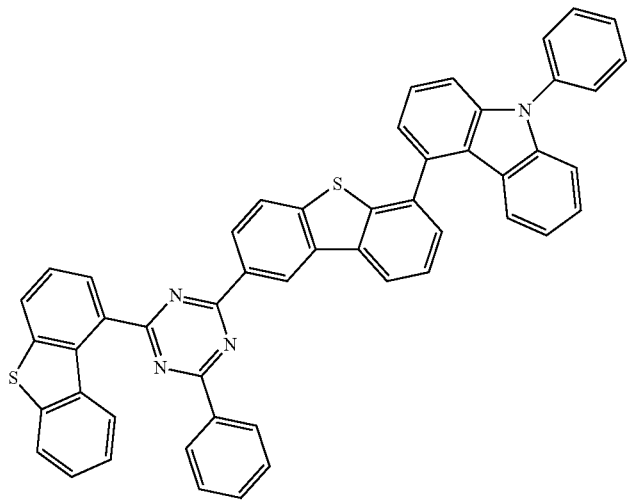
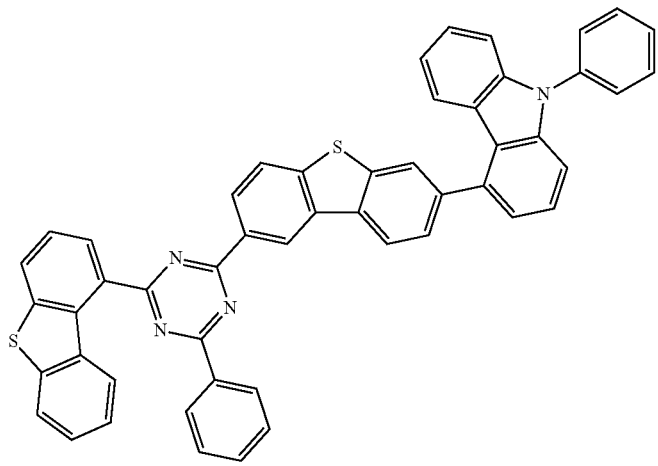
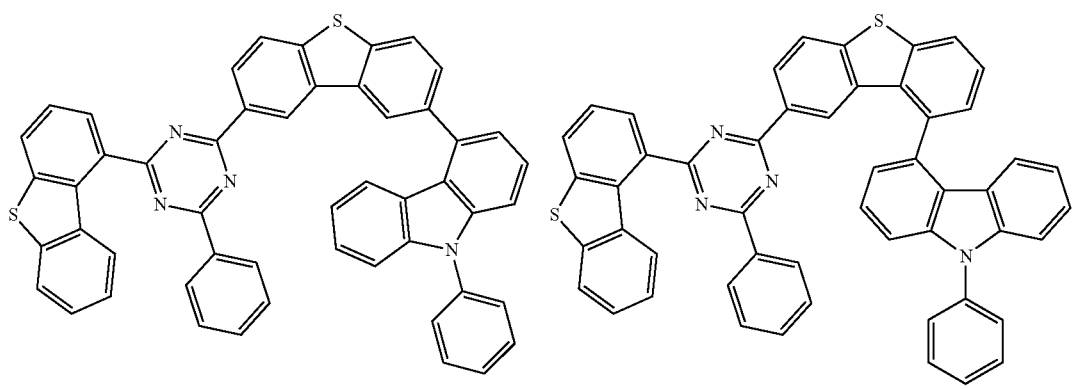

-continued
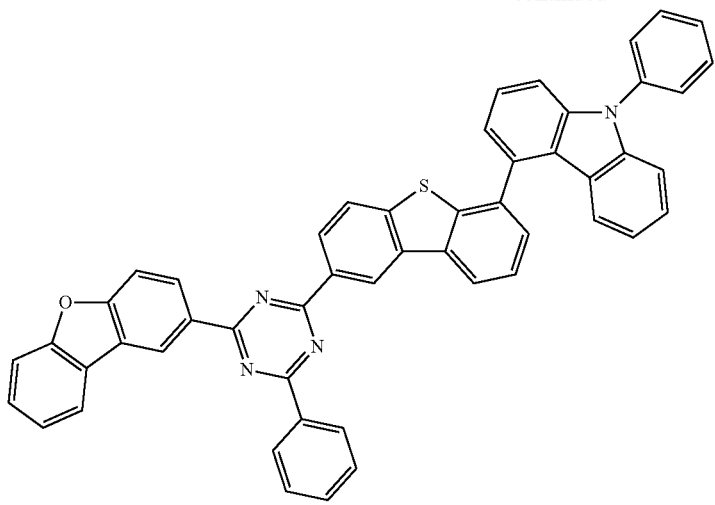
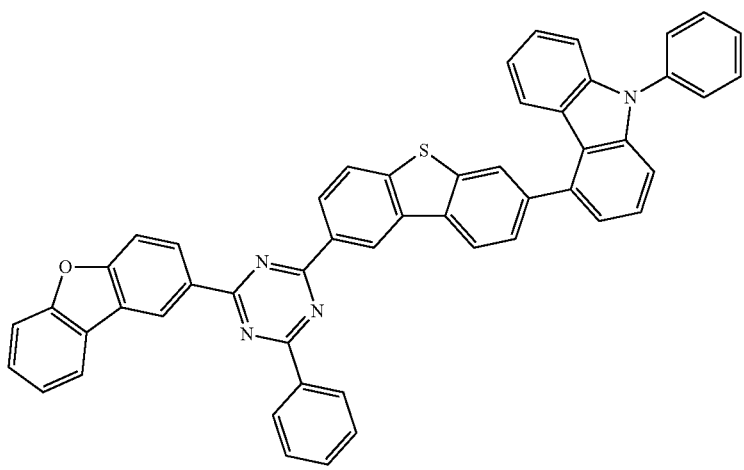
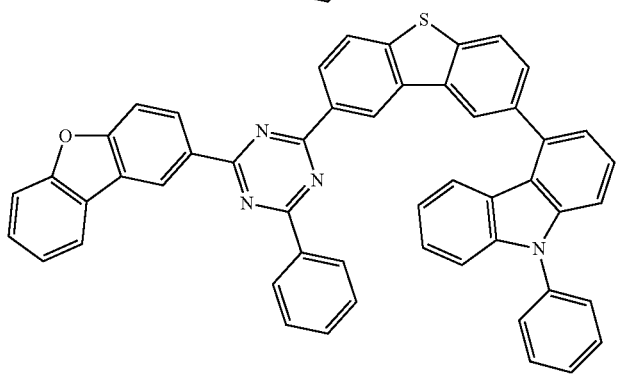
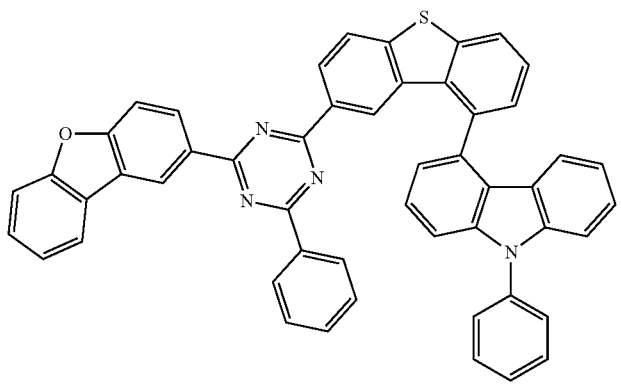

-continued
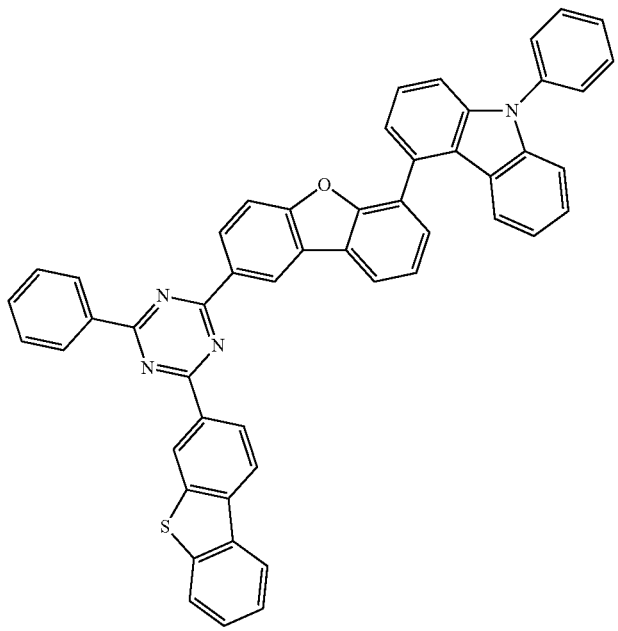
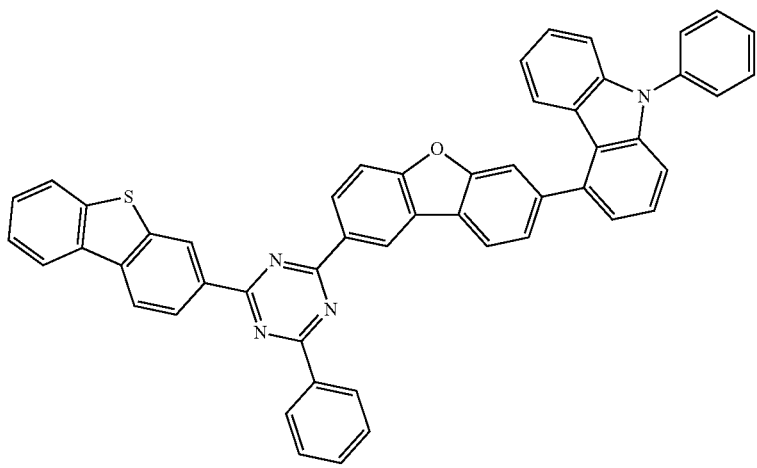
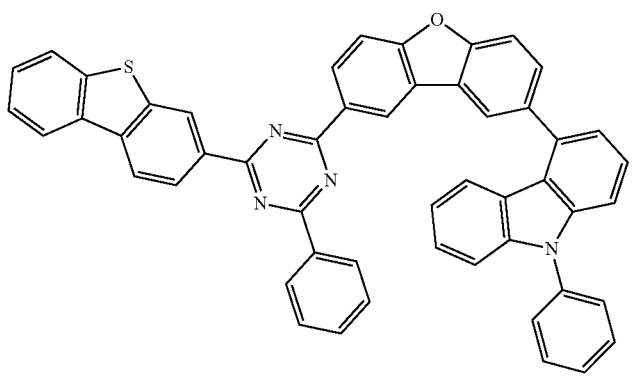

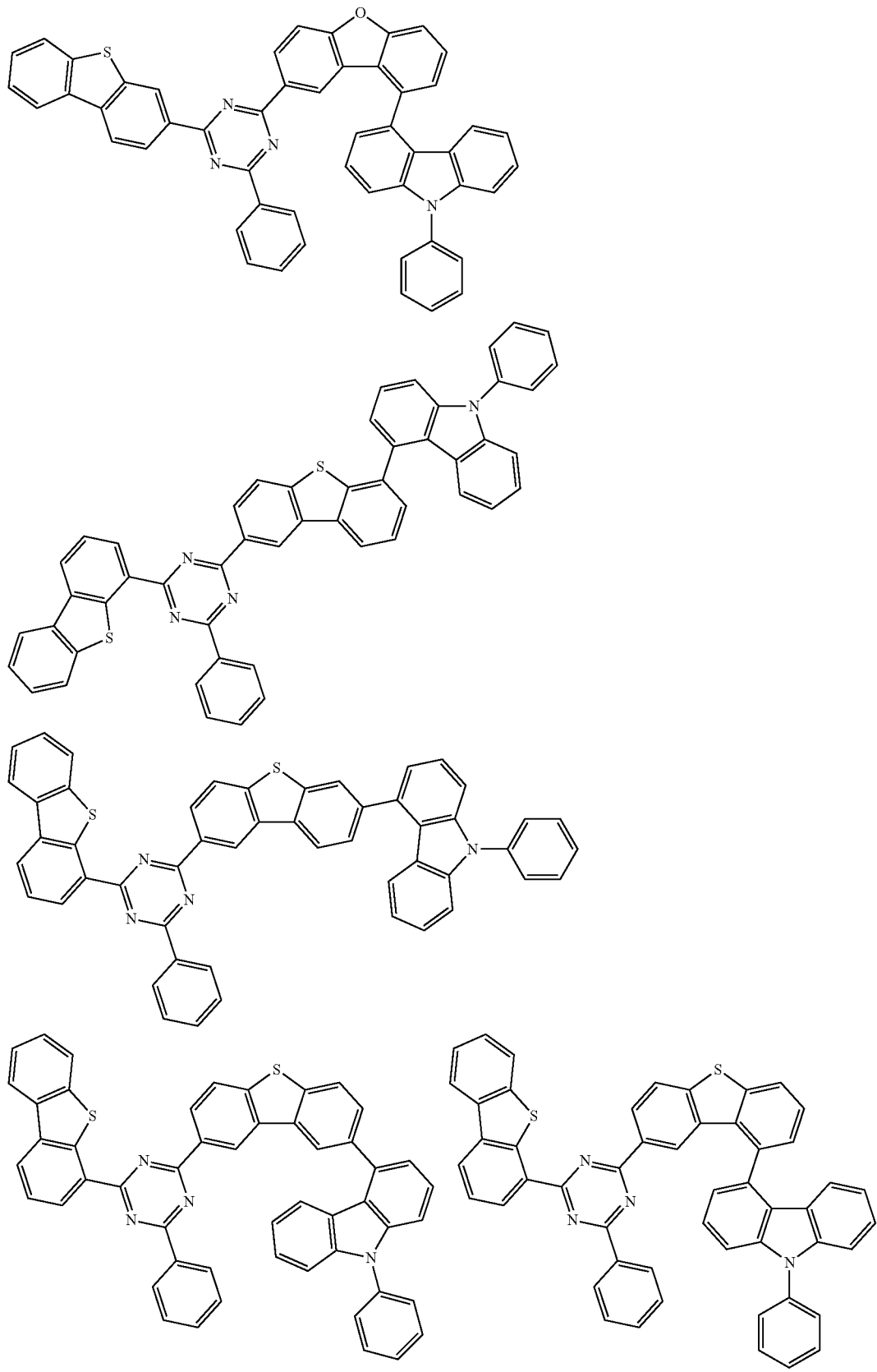

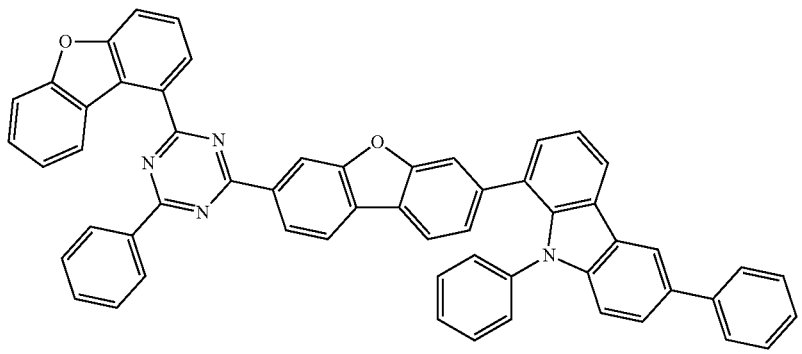
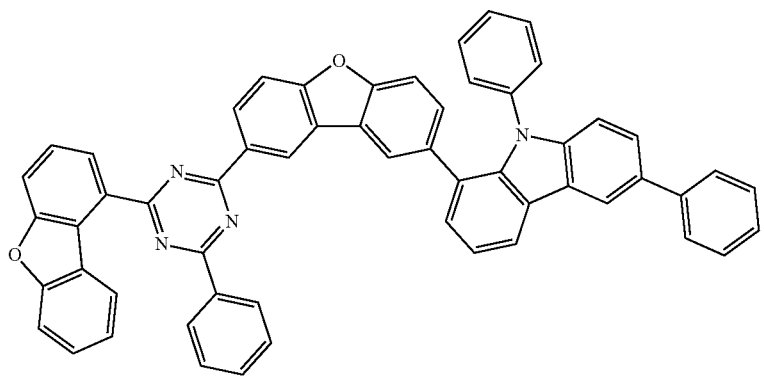
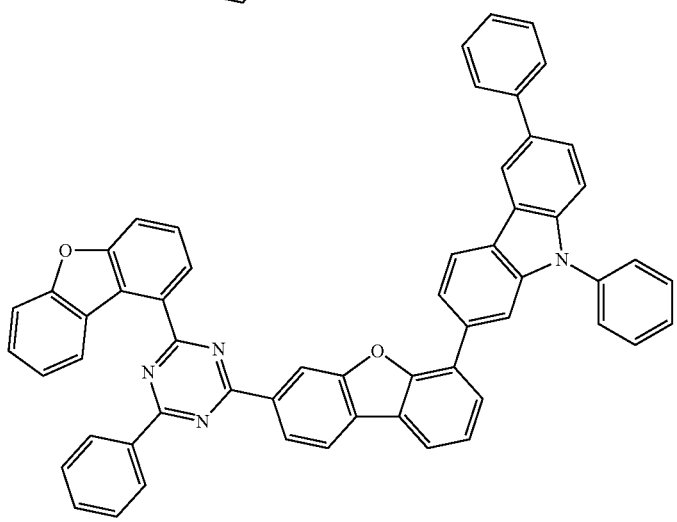
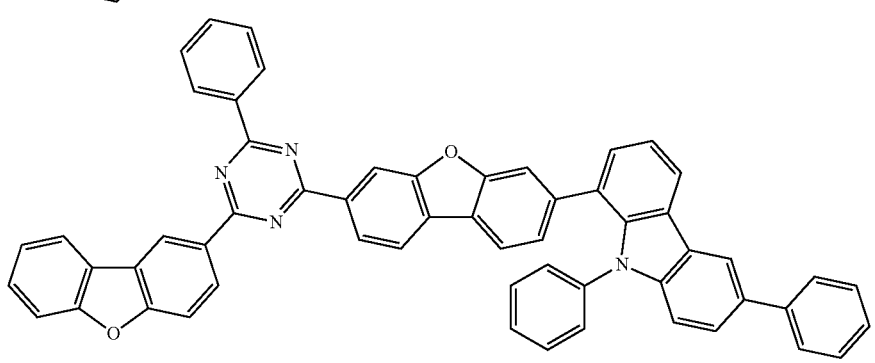

-continued
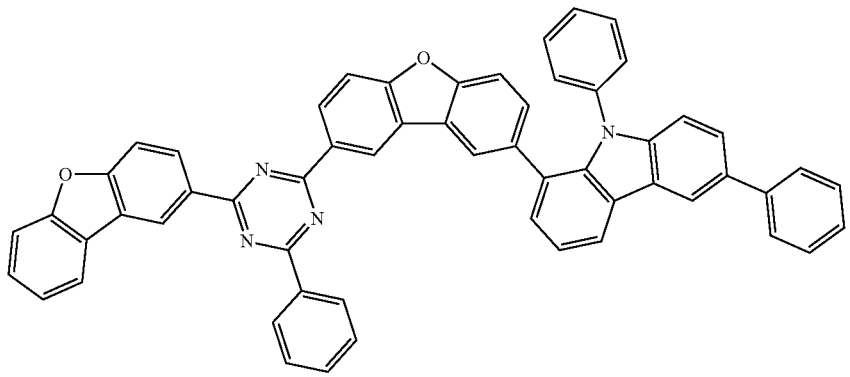
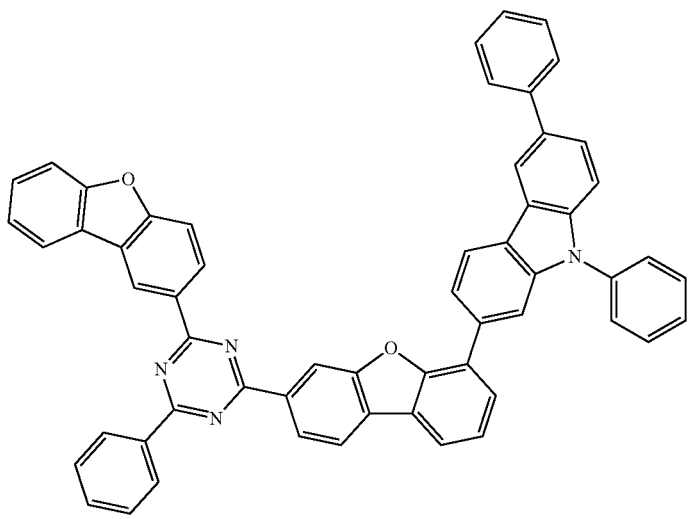
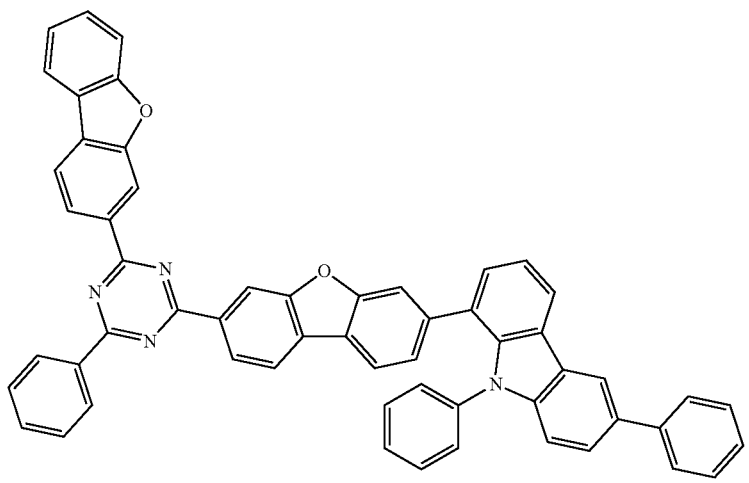

-continued
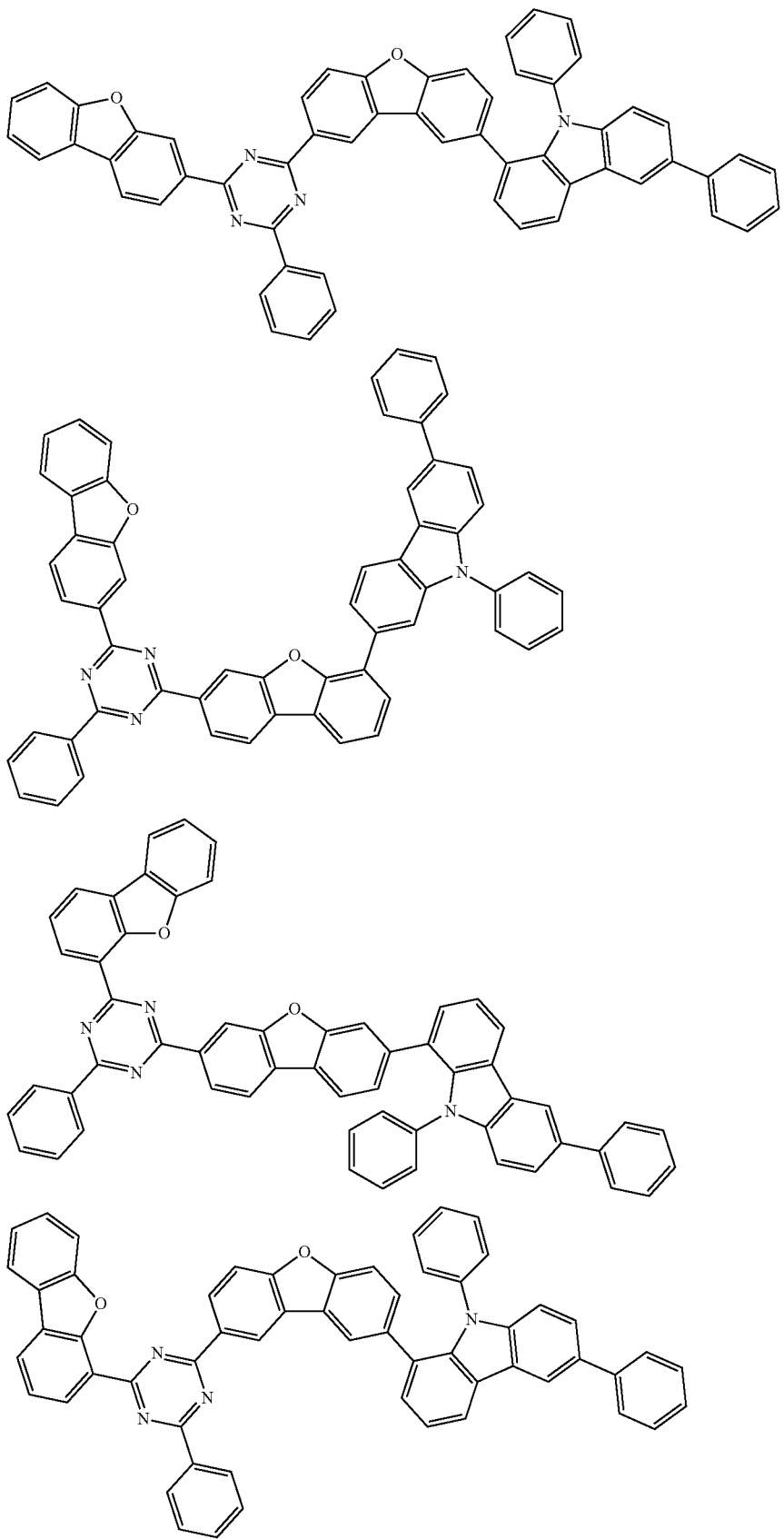

-continued
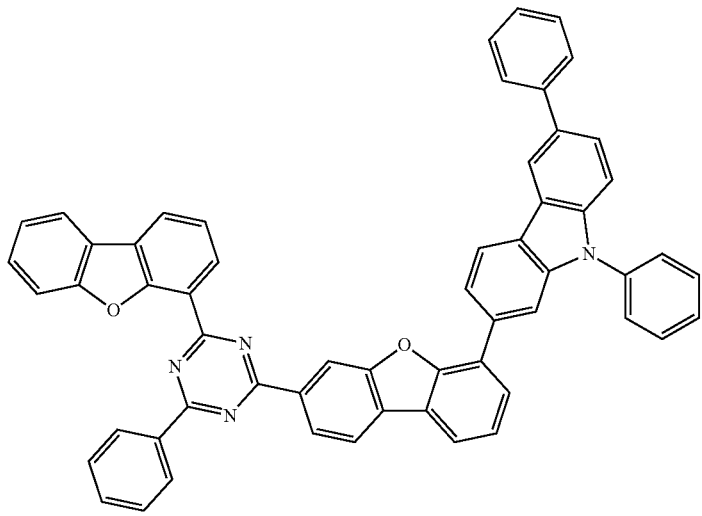
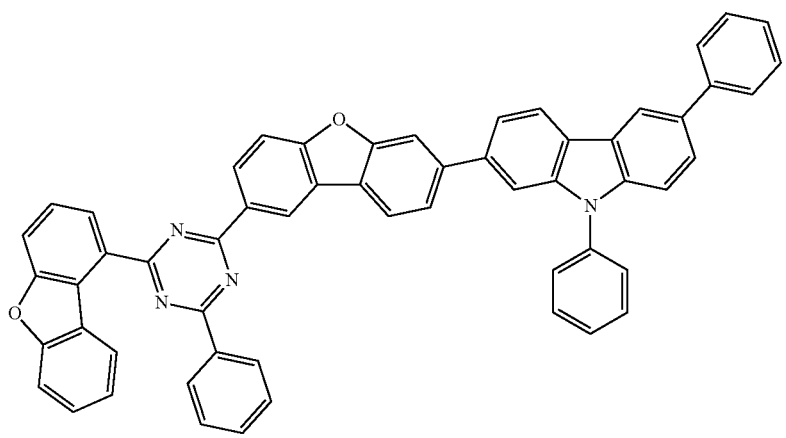
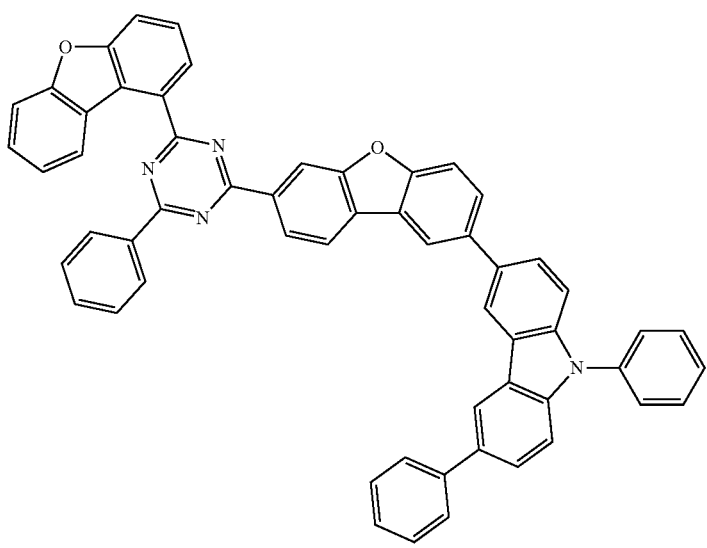

-continued
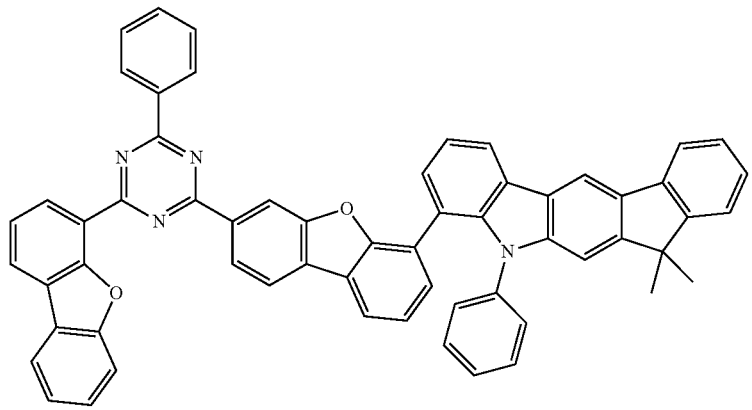
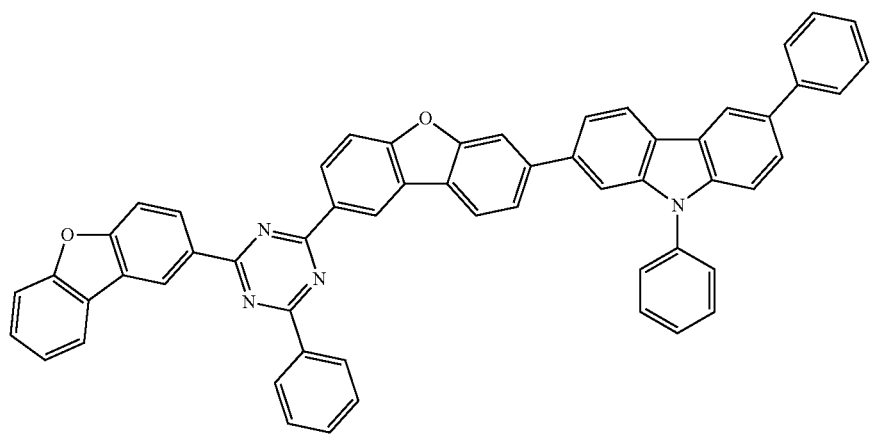
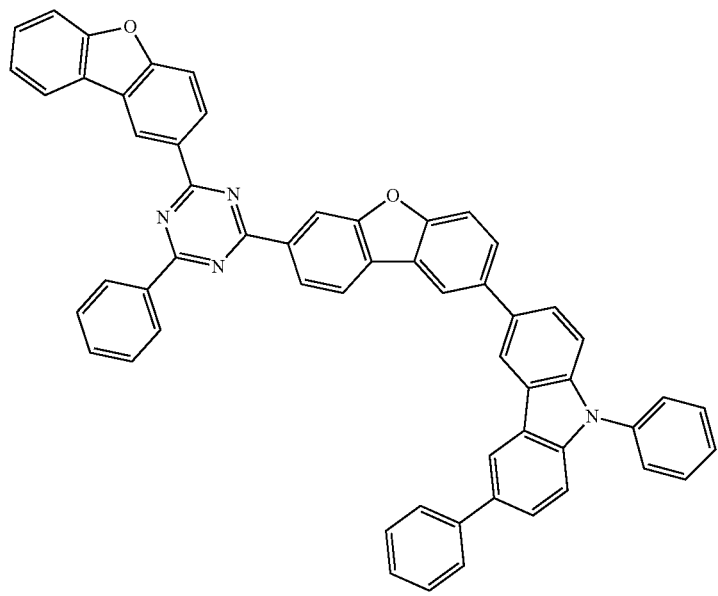

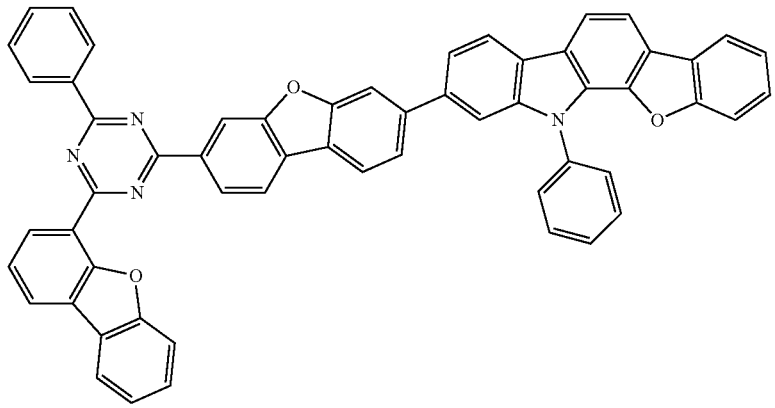
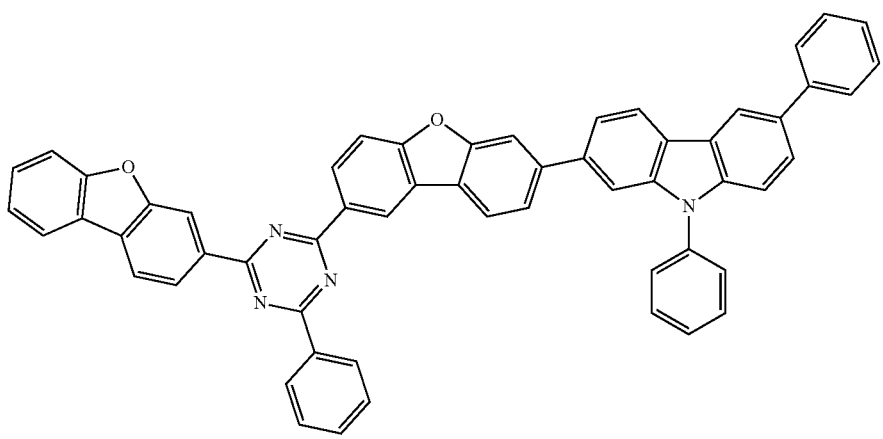
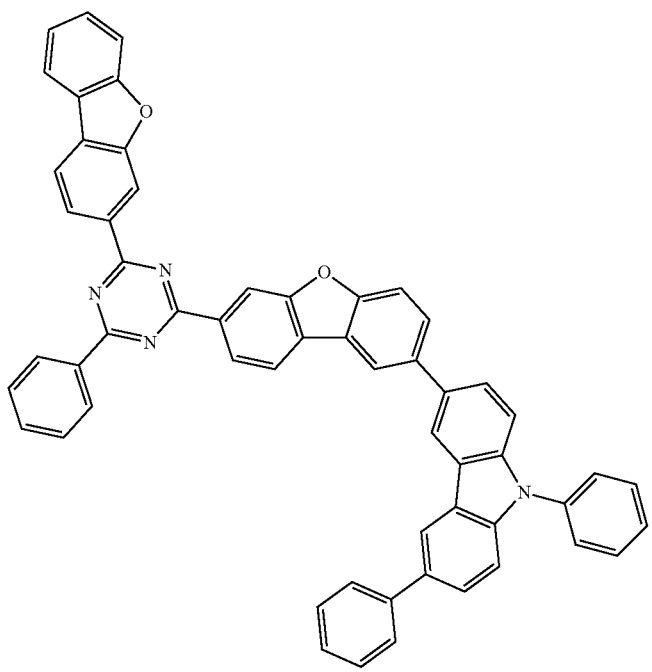

-continued
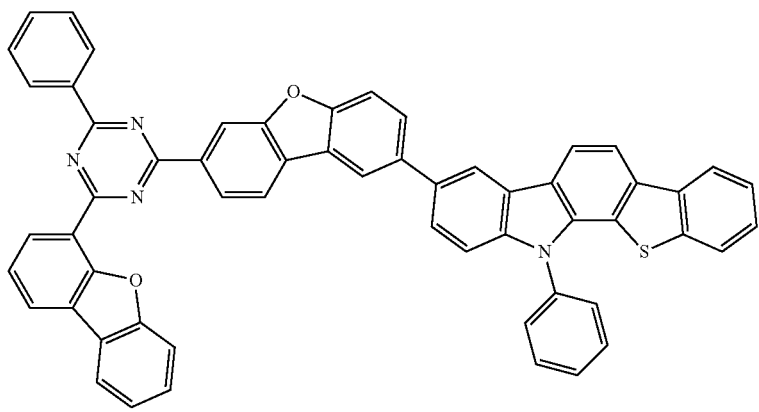
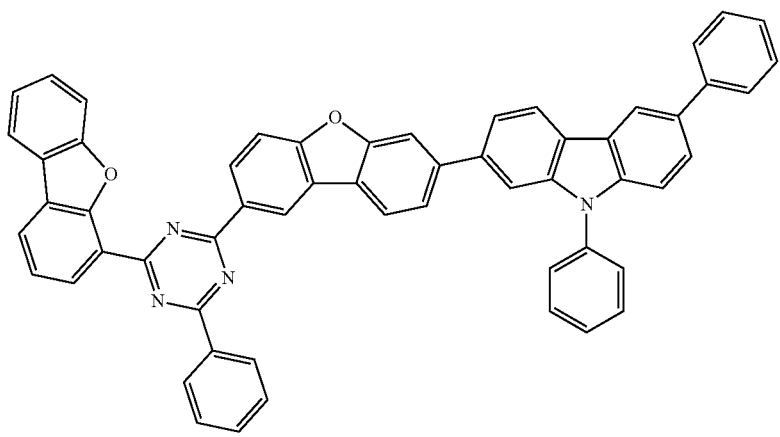
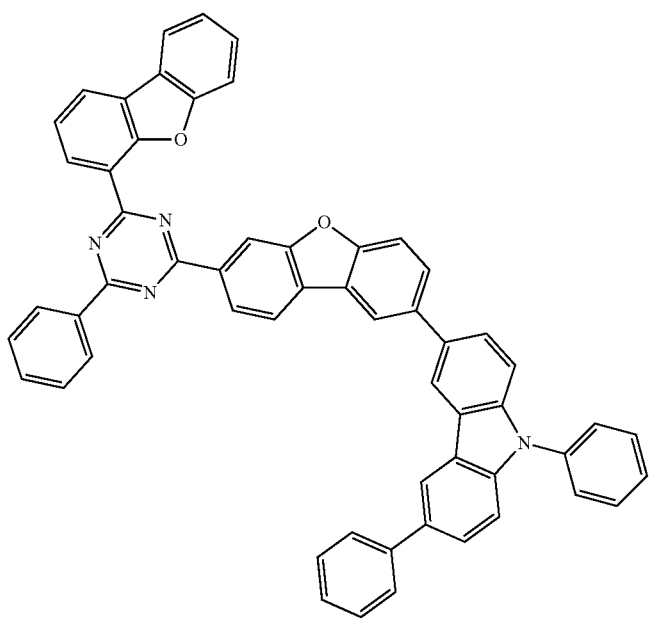

-continued
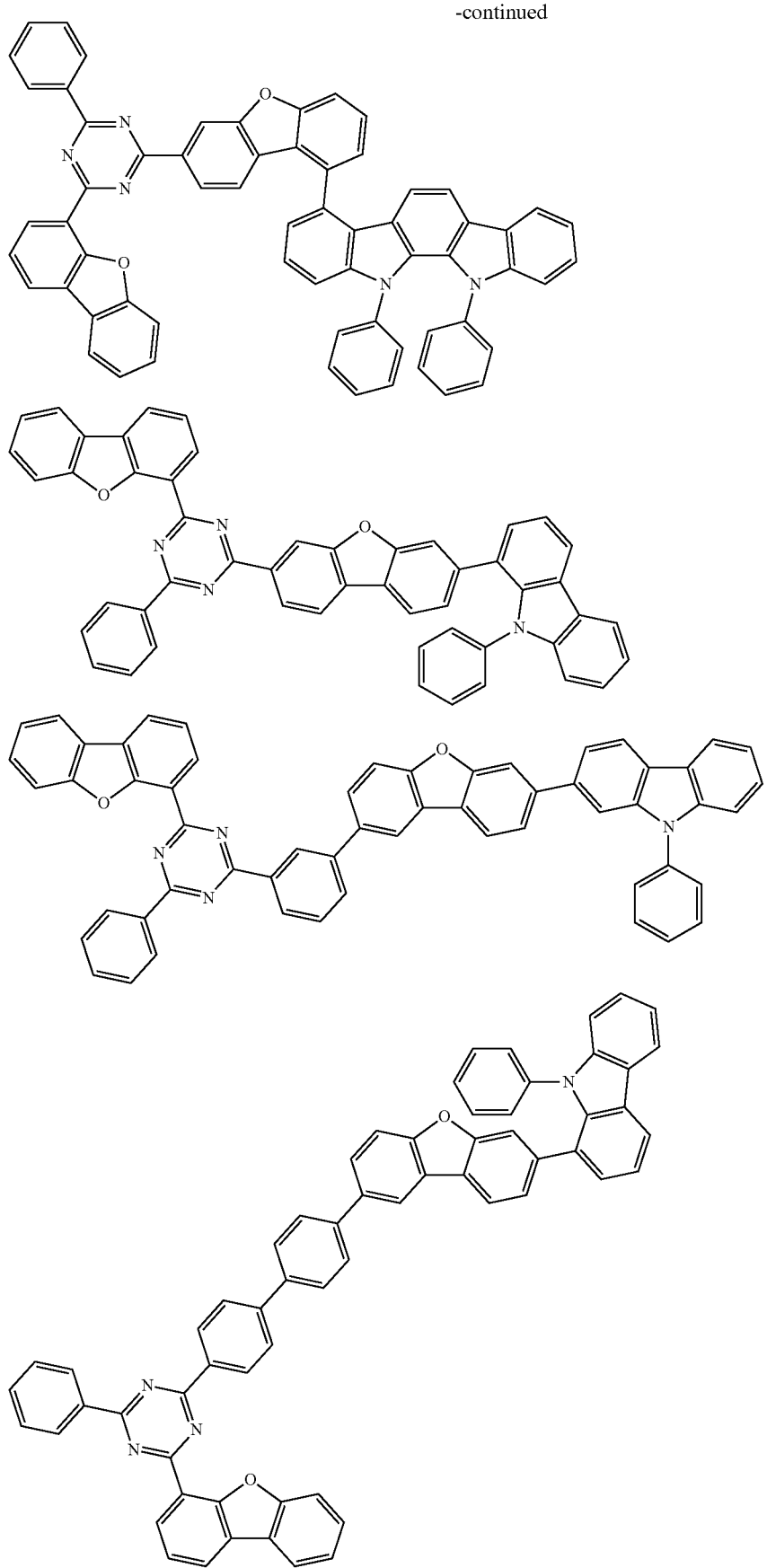

-continued
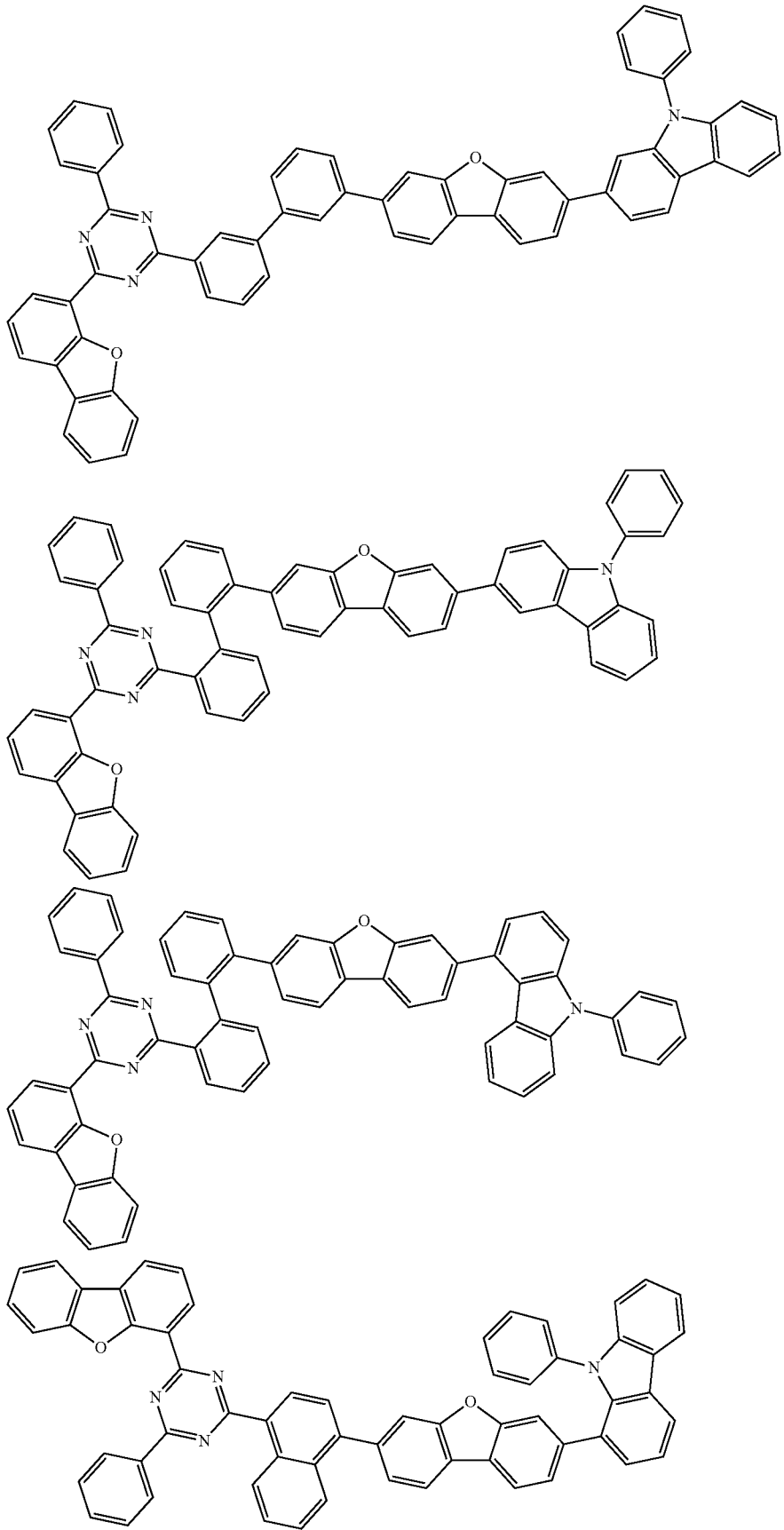

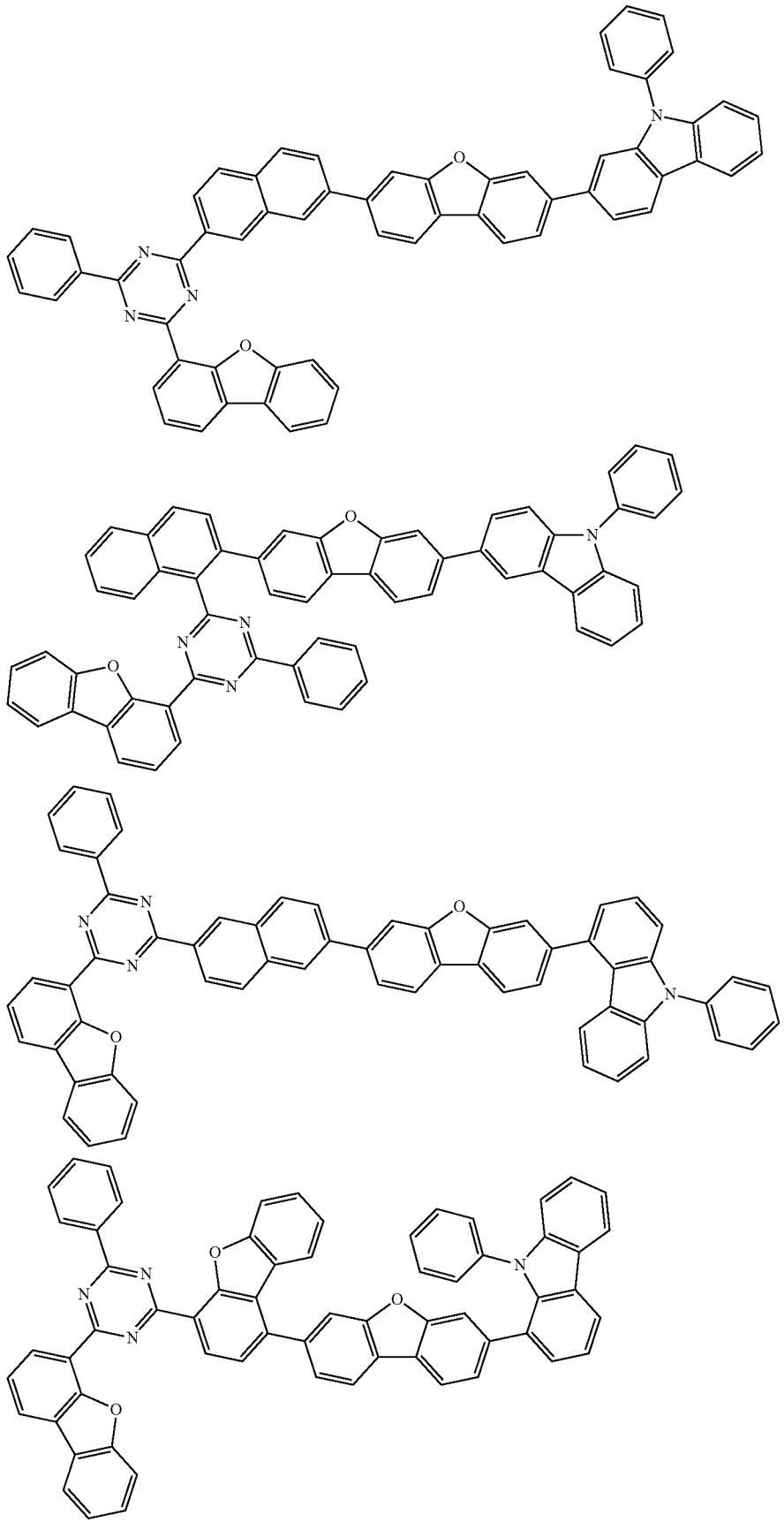

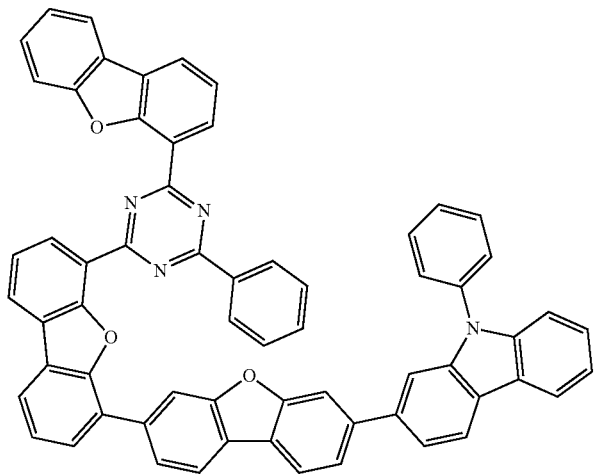
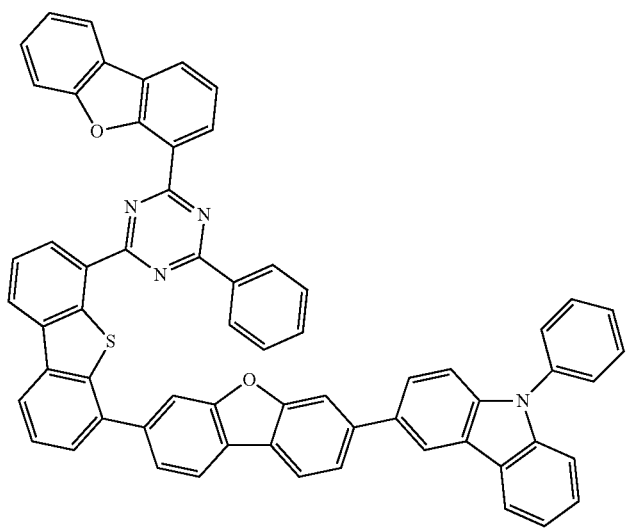
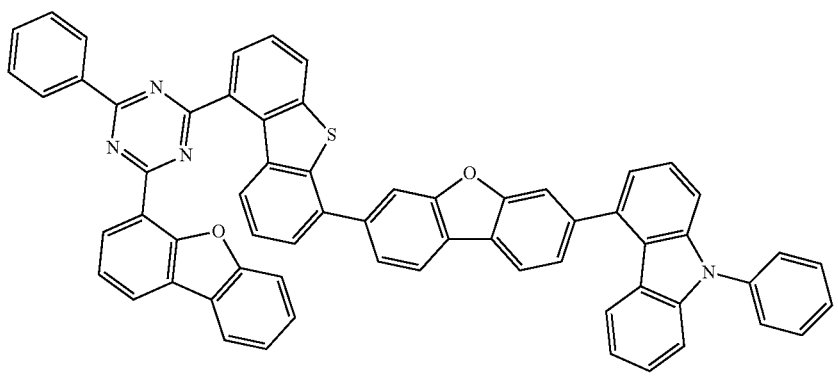

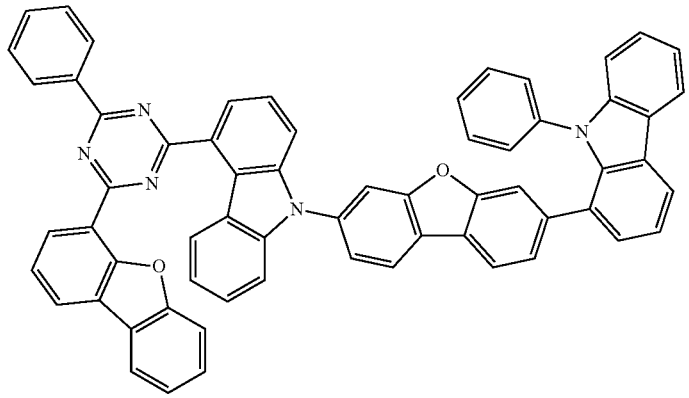
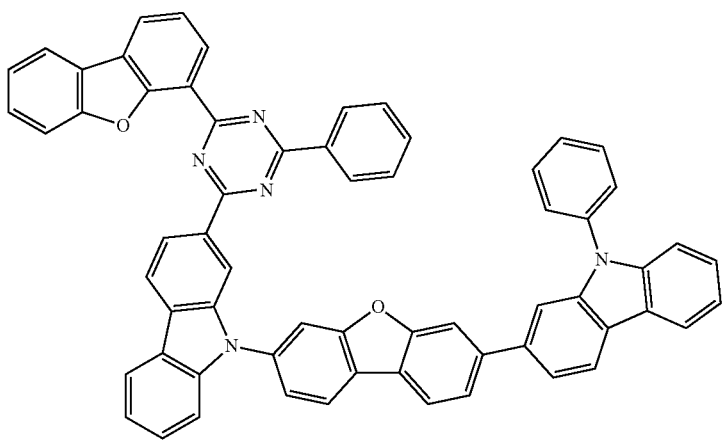
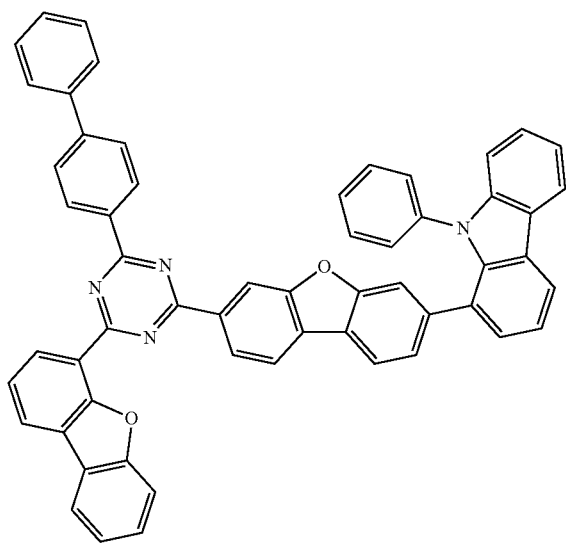

-continued
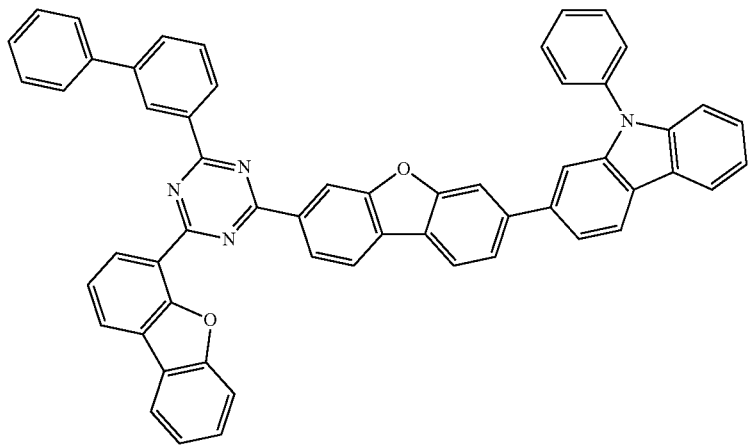
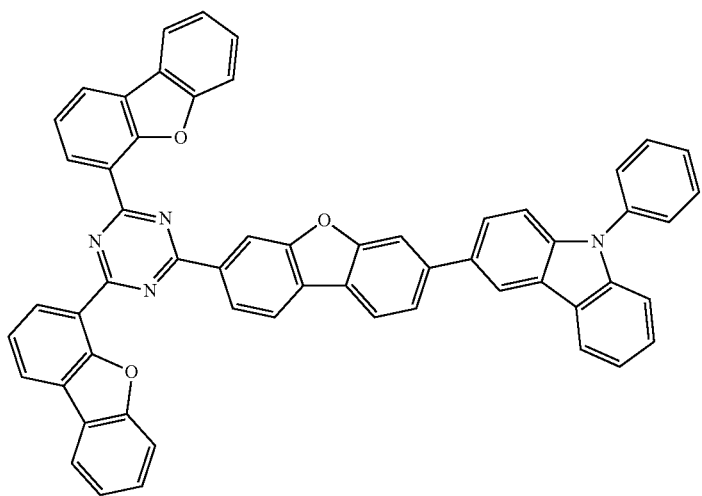
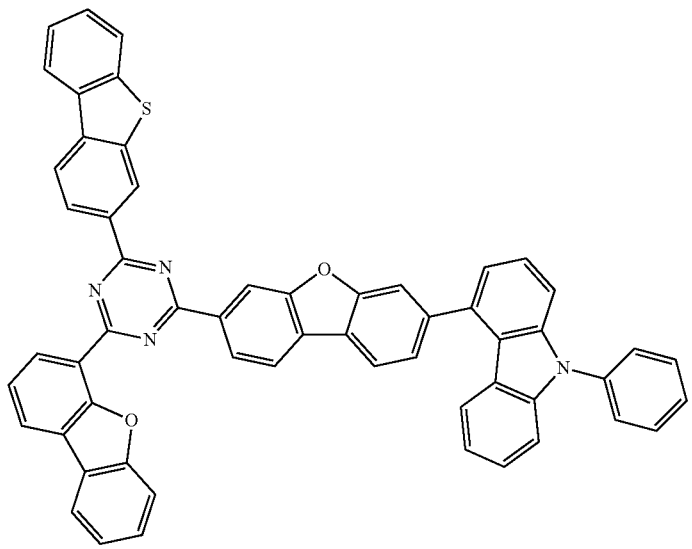

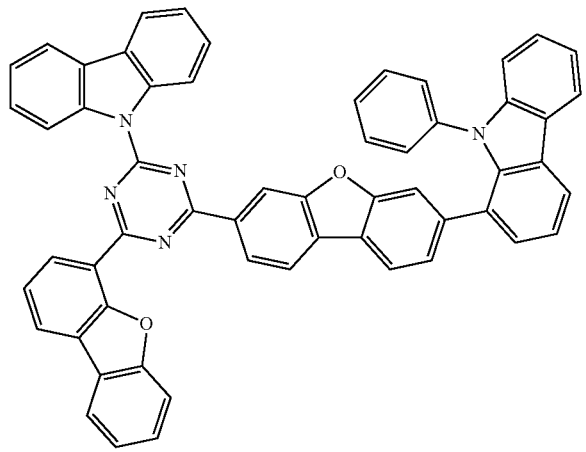
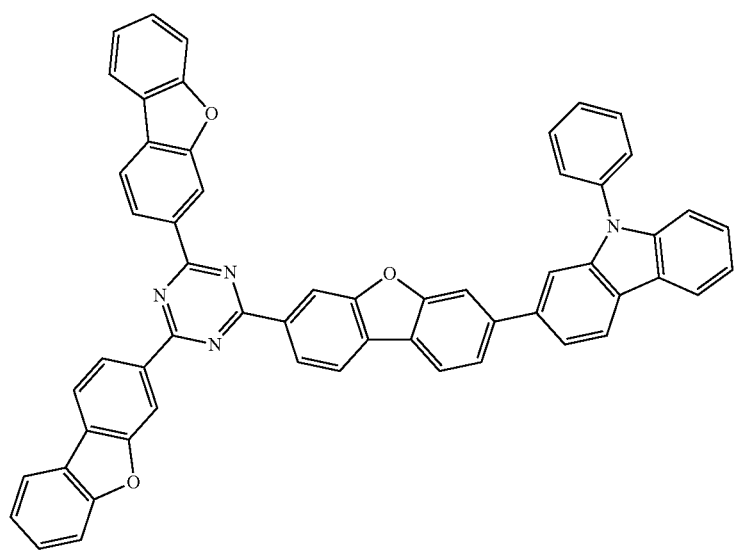
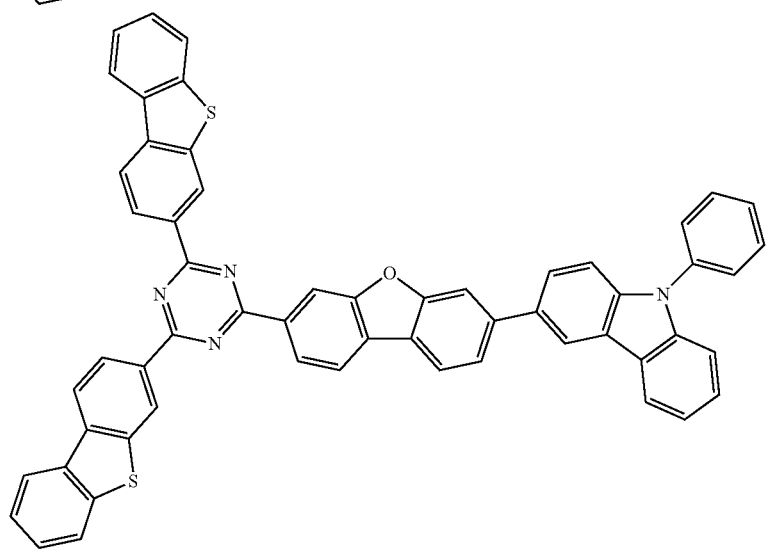

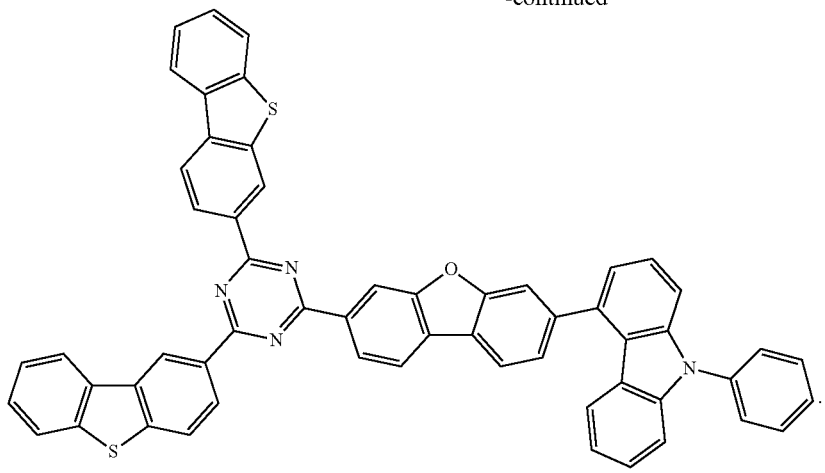
Meanwhile, the compound of Chemical Formula 1 can be prepared, for example, according to the preparation method as shown in the following Reaction Scheme 1.
<Reaction Scheme 1>
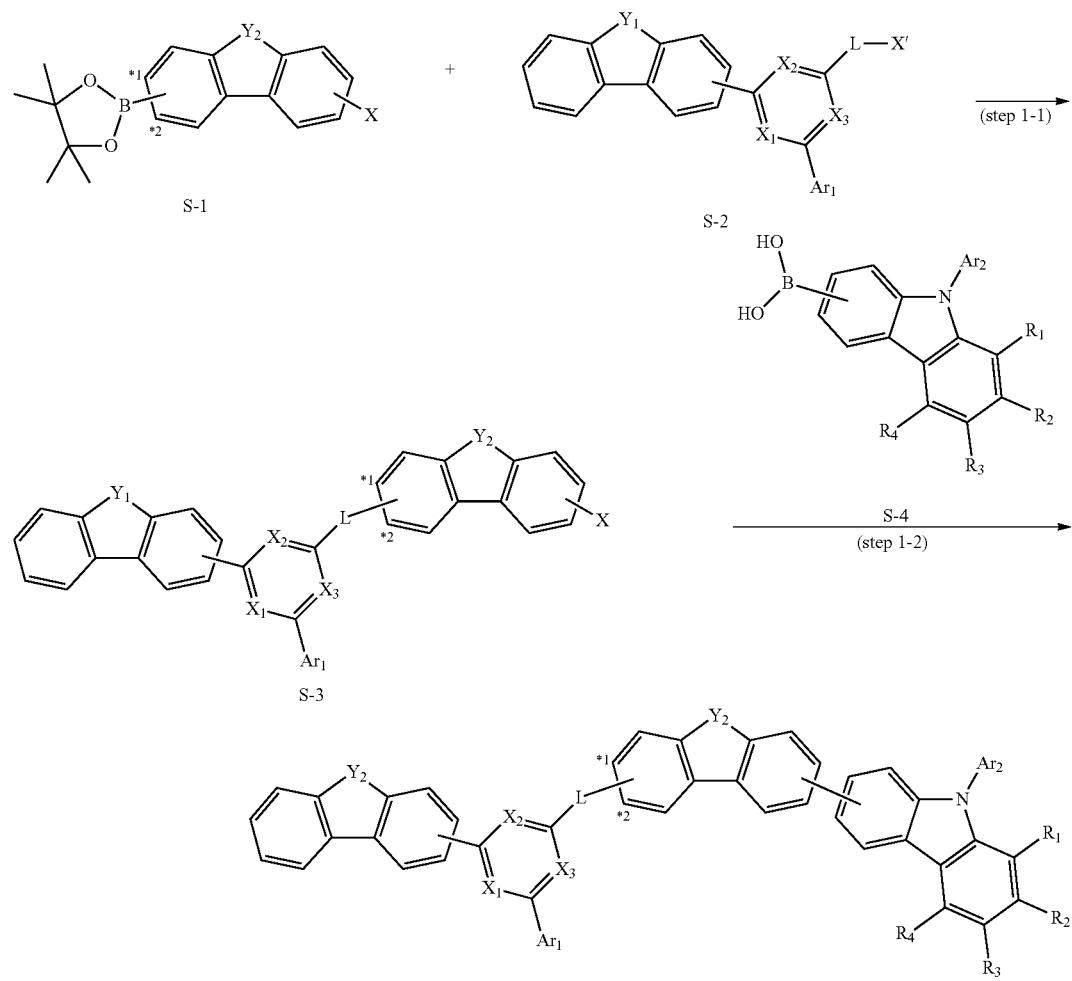

In Reaction Scheme 1, X and X' are each independently a halogen, preferably bromo or chloro, and the definition of each substituent is as defined above.

The step 1-1 is a step of preparing the compound S-3 by the Suzuki-coupling reaction of the compounds S-1 and S-2, and the step 1-2 is a step of preparing the compound of Chemical Formula 1 by the Suzuki-coupling reaction of the compounds S-3 and S-4. At this time, the Suzuki coupling reaction is preferably performed under a palladium catalyst and a base, and the reactive group for the reaction can be modified into a reactive group known in the art. Such a preparation method can be further specified in preparation examples described hereinafter.

In another embodiment of the invention, there is provided an organic light emitting device including the compound of Chemical Formula 1 described above. As an example, there is provided an organic light emitting device including: a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present invention can have a single layer structure, or it can have a multilayered structure in which two or more organic material layers are stacked. For example, the organic light emitting device of the present invention can have a structure including a hole injection layer, a hole transport layer, a light emitting layer, an electron transport layer, an electron injection layer, and the like as the organic material layer. However, the structure of the organic light emitting device is not limited thereto, and it can include a smaller number of organic layers.

Further, the organic material layer can include a light emitting layer, wherein the light emitting layer includes a compound of Chemical Formula 1. In particular, the compound according to the present invention can be used as a host in a light emitting layer. Specifically, the compound according to the present invention can be used as a green phosphorescent host in the light emitting layer.

Further, the organic material layer can include an electron transport layer or an electron injection layer, wherein the electron transport layer or the electron injection layer can include a compound of Chemical Formula 1.

The organic material layer of the organic light emitting device of the present invention can have a single layer structure, or it can have a multilayered structure in which two or more organic material layers are stacked. For example, the organic light emitting device of the present invention can have a structure further including a hole injection layer and a hole transport layer provided between the first electrode and the light emitting layer, and an electron transport layer and an electron injection layer provided between the light emitting layer and the second electrode, in addition to the light emitting layer. However, the structure of the organic light emitting device is not limited thereto, and it can include a smaller number of organic layers or a larger number of organic layers.

Further, the organic light emitting device according to the present invention can be a normal type of organic light emitting device in which an anode, one or more organic material layers, and a cathode are sequentially stacked on a substrate. In addition, the organic light emitting device according to the present invention can be an inverted type of organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound of Chemical Formula 1 can be included in the light emitting layer, FIG. 2 shows an example of an organic light emitting device including a substrate 1, an anode 2, a hole injection layer 5, a hole transport layer 6, an electron blocking layer 7, a light emitting layer 3, a hole blocking layer 8, electron injection and transport layer 9, and a cathode 4. In such a structure, the compound of Chemical Formula 1 can be included in one or more layers of the hole injection layer, the hole transport layer, the light emitting layer, and the electron transport layer. For example, the compound of Chemical Formula 1 can be included in the light emitting layer.

The organic light emitting device according to the present invention can be manufactured by materials and methods known in the art, except that one or more layers of the organic material layers include the compound of Chemical Formula 1. In addition, when the organic light emitting device includes a plurality of organic material layers, the organic material layers can be formed of the same material or different materials.

For example, the organic light emitting device according to the present invention can be manufactured by sequentially stacking a first electrode, an organic material layer, and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer, and an anode material on a substrate.

Further, the compound of Chemical Formula 1 can be formed into an organic material layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device can be manufactured by sequentially depositing a cathode material, an organic material layer, and an anode material on a substrate (International Publication WO2003/012890). However, the manufacturing method is not limited thereto.

As an example, the first electrode is an anode and the second electrode is a cathode, or alternatively the first electrode is a cathode and the second electrode is an anode.

As the anode material, generally, a material having a large work function is preferably used so that holes can be smoothly injected into the organic material layer.

Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as $ZnO:Al$ or $SnO_2:Sb$; conductive polymers such as poly(3-methylthiophene), poly[3,4-(ethylene-1,2-dioxy)-thiophene] (PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al; and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. The compound of Chemical Formula 1 is used as a hole transport material, or an arylamine-based organic material, a conductive polymer, a block copolymer in which a conjugate portion and a non-conjugate portion are present together, and the like, are used as a hole transport material, but are not limited thereto.

The electron blocking layer refers to a layer that is formed on the hole transport layer and is preferably disposed in contact with the light emitting layer to adjust hole mobility, prevent excessive movement of electrons, and increase the probability of hole-electron bonding, thereby serving to improve the efficiency of an organic light emitting device. The electron blocking layer includes an electron blocking material, and examples of such electron blocking materials include the compound of Chemical Formula 1, or arylamine-based organic materials and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex ($Alq_3$); a carbazole-based compound; a dimerized styryl compound; BAlq; a 10-hydroxybenzoquinoline-metal compound; a benzoxazole-, benzothiazole-, and benzimidazole-based compound; a poly(p-phenylene vinylene) (PPV)-based polymer; a spiro compound; polyfluorene, rubrene, and the like; but are not limited thereto.

The light emitting layer can include a host material and a dopant material as described above. The light emitting layer can include a fused aromatic ring derivative, a heterocyclic-containing compound, or the like as the host material. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The hole blocking layer is formed on the light emitting layer, preferably provided in contact with the light emitting layer. The hole blocking layer serves as layer to improve the efficiency of the organic light emitting device by controlling electron mobility and preventing excessive movement of holes to increase the probability of hole-electron bonding. The hole blocking layer includes a hole blocking material, and examples of such hole blocking material include azine derivatives including triazine; triazole derivatives; oxadiazole derivatives; phenanthroline derivatives; compounds having an electron withdrawing group such as a phosphine oxide derivative, and the like can be used, but are not limited thereto.

The electron injection and transport layer is a layer that simultaneously serves as an electron transport layer and an electron injection layer that injects electrons from an electrode and transports the received electrons to the light emitting layer, and is formed on the light emitting layer or the hole blocking layer. As such an electron injecting and transporting material, a compound which is a material capable of receiving electrons from a cathode well and transferring them to a light emitting layer, is a material having high mobility for electrons. Specific examples thereof include: an Al complex of 8-hydroxyquinoline, a complex including $Alq_3$, an organic radical compound, a hydroxyflavone-metal complex, and the like, but are not limited thereto. Further, fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, together with the above the electron injecting and transporting material can be used, but are not limited thereto.

Further, the electron injection and transport layer can be formed of separate layers such as an electron injection layer and an electron transport layer. In this case, the electron transport layer is formed on the light emitting layer or the hole blocking layer, and the above electron injecting and transporting material can be used as the electron transport material included in the electron transport layer. In addition, the electron injection layer is formed on the electron transport layer, and the electron injection materials included in the electron injection layer include LiF, NaCl, CsF, $Li_2O$, BaO, fluorenone, anthraquinodimethane, diphenoquinone, and thiopyran dioxide, oxazole, oxadiazole, triazole, imidazole, perylenetetracarboxylic acid, fluorenylidene methane, anthrone, and the like, and their derivatives, metal complex compounds, nitrogen-containing 5-membered ring derivatives, and the like can be used.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention can be a front side emission type, a back side emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples.

However, these examples are presented for illustrative purposes only, and are not intended to limit the scope of the present invention.

Preparation Example 1: Preparation of Compound 1

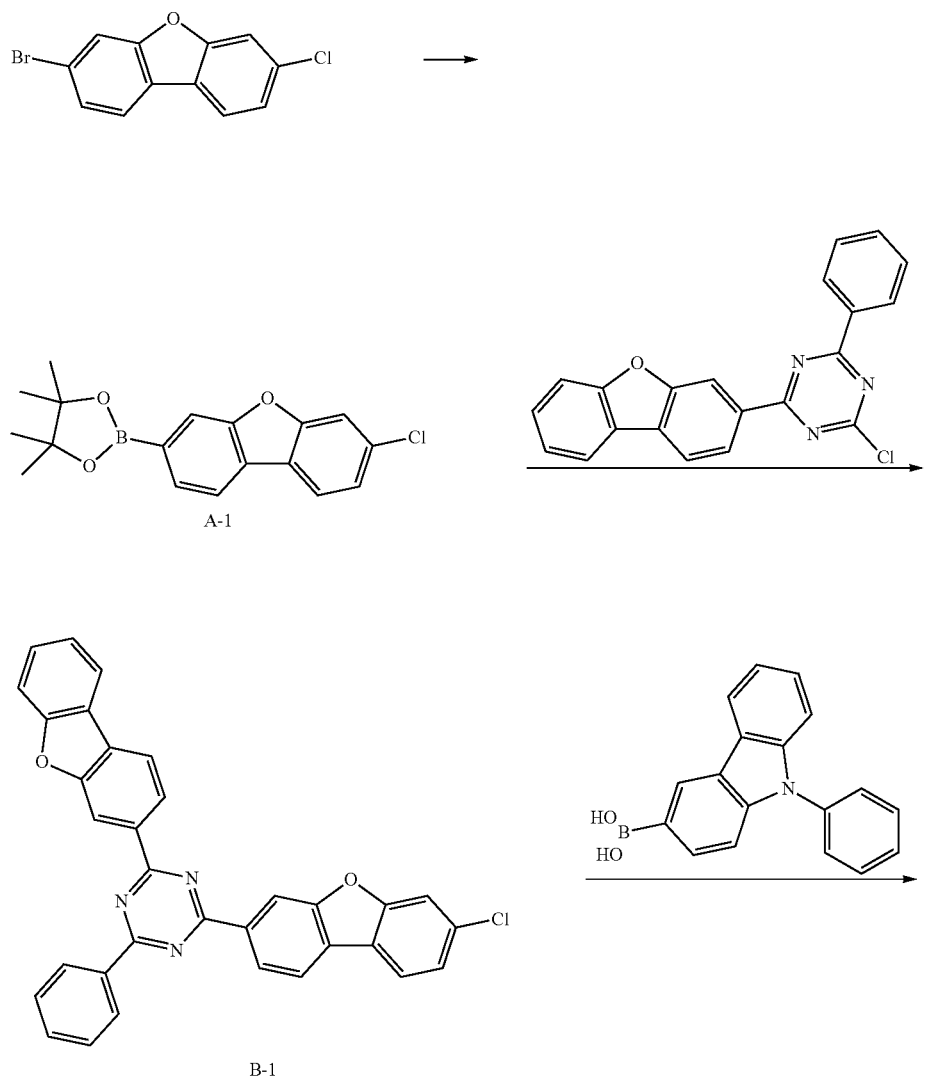

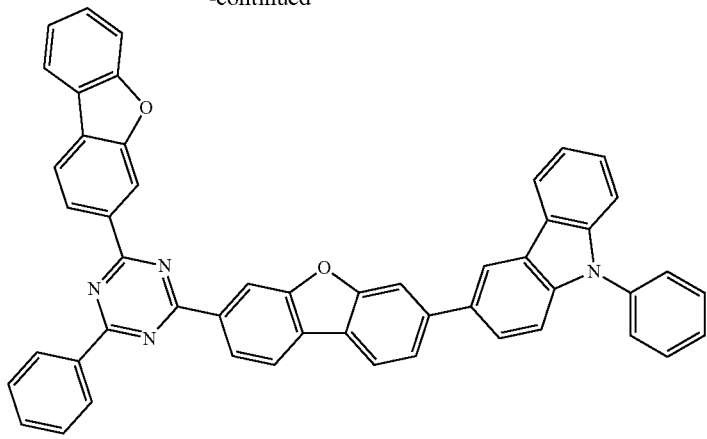

Step 1) Synthesis of Intermediate A-1

Under a nitrogen atmosphere, 3-bromo-7-chlorodibenzo[b,d]furan (20 g, 71 mmol) and bis(pinacolato)diboron (28.1 g, 71 mmol) were added to 400 ml of 1,4-dioxane (Diox), which were stirred and refluxed. After that, potassium triphosphate (45.2 g, 213.1 mmol) was added and stirred sufficiently, followed by bis(dibenzylideneacetone)palladium (1.2 g, 2.1 mmol) and tricyclohexylphosphine (1.2 g, 4.3 mmol). After reaction for 3 hours, and after cooling to room temperature, the organic layer was filtered to remove a salt, and then the filtered organic layer was distilled. The distillate was again dissolved in 233 mL of 10 times chloroform, washed twice with water, and the organic layer was separated. After adding anhydrous magnesium sulfate and stirring, the filtrate was distilled under reduced pressure. The concentrated compound was recrystallized by chloroform and ethanol to prepare a white solid compound A-1 (12.4 g, 53%).

MS: $[M+H]^+=329.6$

Step 2) Synthesis of Intermediate B-1

Under a nitrogen atmosphere, A-1 (20 g, 60.9 mmol) and 2-chloro-4-(dibenzo[b,d]furan-3-yl)-6-phenyl-1,3,5-triazine (21.8 g, 60.9 mmol) was added to 400 ml of tetrahydrofuran, which were stirred and refluxed. Subsequently, potassium carbonate (25.2 g, 182.6 mmol) was dissolved in 25 ml of water, stirred thoroughly, and then tetrakis(triphenylphosphine)palladium (2.1 g, 1.8 mmol) was added thereto. After reaction for 3 hours, and after cooling to room temperature, the organic layer and the water layer were separated, and then the organic layer was distilled. The distillate was again dissolved in 638 ml of 20 times chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound B-1 (21 g, 66%).

MS: $[M+H]^+=525$

Step 3) Synthesis of Compound 1

In a nitrogen atmosphere, B-1 (20 g, 38.2 mmol) and (9-phenyl-9H-carbazol-3-yl) boronic acid (11 g, 38.2 mmol) were added to 400 ml of 1,4-dioxane (Diox, which were stirred and refluxed. After that, potassium triphosphate (24.3 g, 114.5 mmol) was dissolved in was dissolved in 24 ml of water, stirred thoroughly, and then dibenzylidene acetone palladium (0.7 g, 1.1 mmol) and tricyclohexylphosphine (0.6 g, 2.3 mmol) were added thereto. After the reaction for 8 hours, and after cooling to room temperature, the resulting solid was filtered. The filtrate was dissolved in 763 mL of 30 times 1,2-dichlorobenzene (DCB), washed twice with water, and the organic layer was separated. After adding anhydrous magnesium sulfate and stirring, the filtrate was distilled under reduced pressure. The concentrated compound was recrystallized by DCB and ethyl acetate to prepare a fluorescent solid Compound 1 (10.9 g, 52%).

MS: $[M+H]^+=731.8$

Preparation Example 2: Preparation of Compound 2

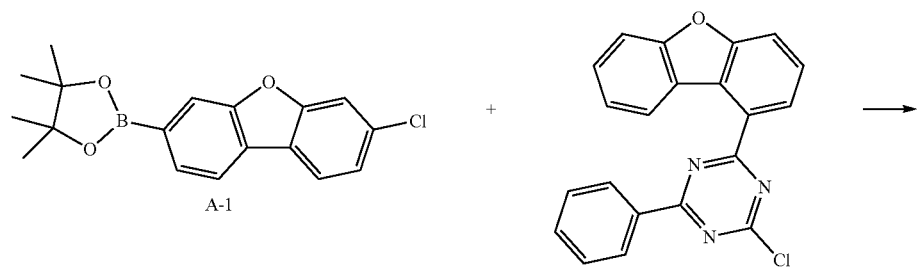

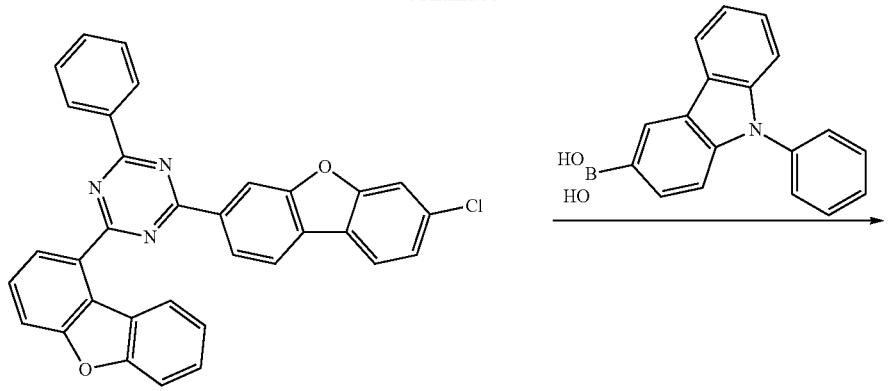
B-2
2
A fluorescent solid Compound 2 was prepared in the same manner as in Preparation Example 1, except that Intermediate B-2 is prepared using 2-chloro-4-(dibenzo[b,d]furan-1-yl)-6-phenyl-1,3,5-triazine instead of 2-chloro-4-(dibenzo-[b,d]furan-3-yl)-6-phenyl-1,3,5-triazine in the step 2 of Preparation Example 1 (15.3 g, 73%).
MS: [M+H]$^+$=731.8
Preparation Example 3: Preparation of Compound 3
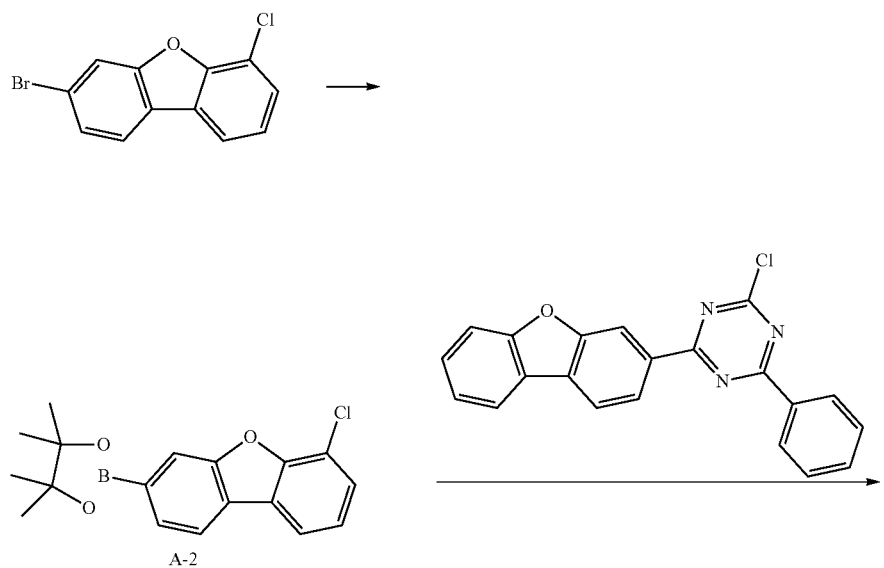
A-2

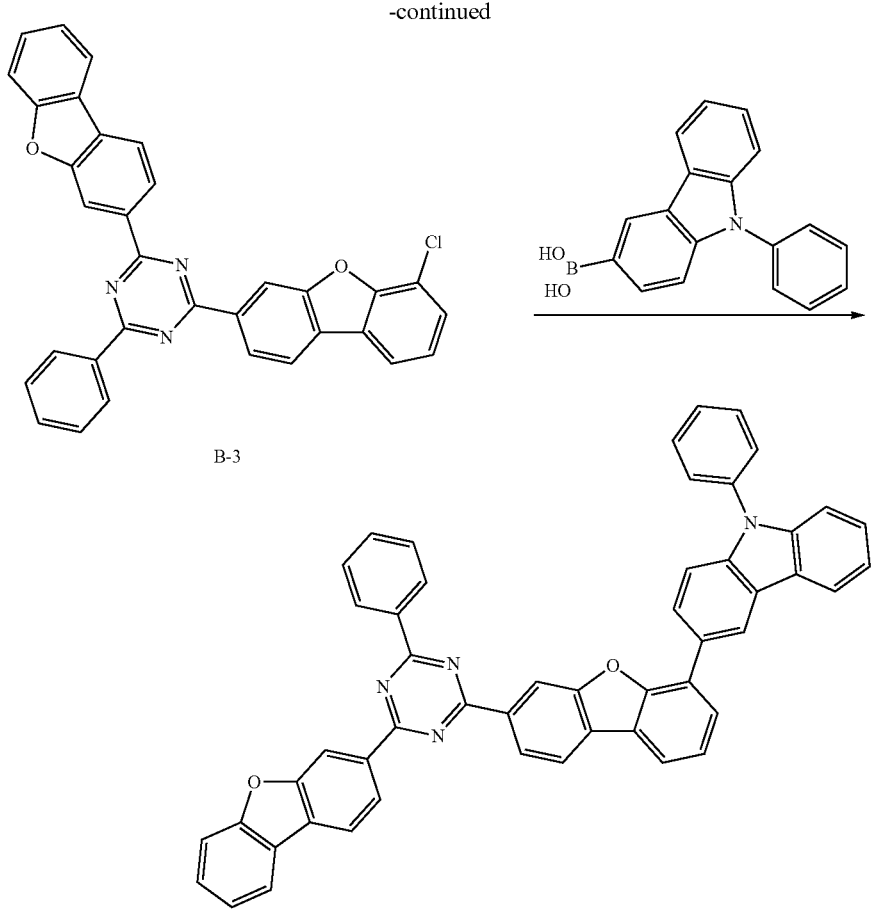

A fluorescent solid Compound 3 was prepared in the same manner as in Preparation Example 1, except that Intermediate A-2 is prepared using 3-bromo-6-chlorodibenzo[b,d]furan instead of 3-bromo-7-chlorodibenzo[b,d]furan in the step 1 of Preparation Example 1, and the prepared Intermediate A-2 is used instead of Intermediate A-1 in the step 2 of Preparation Example 1 (13.8 g, 66%).

MS: [M+H]$^+$=731.8

Preparation Example 4: Preparation of Compound 4

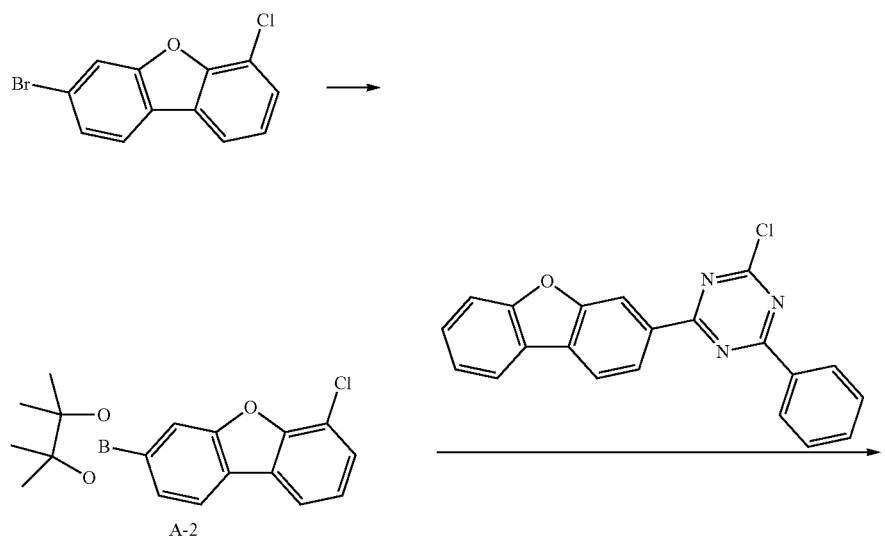

-continued

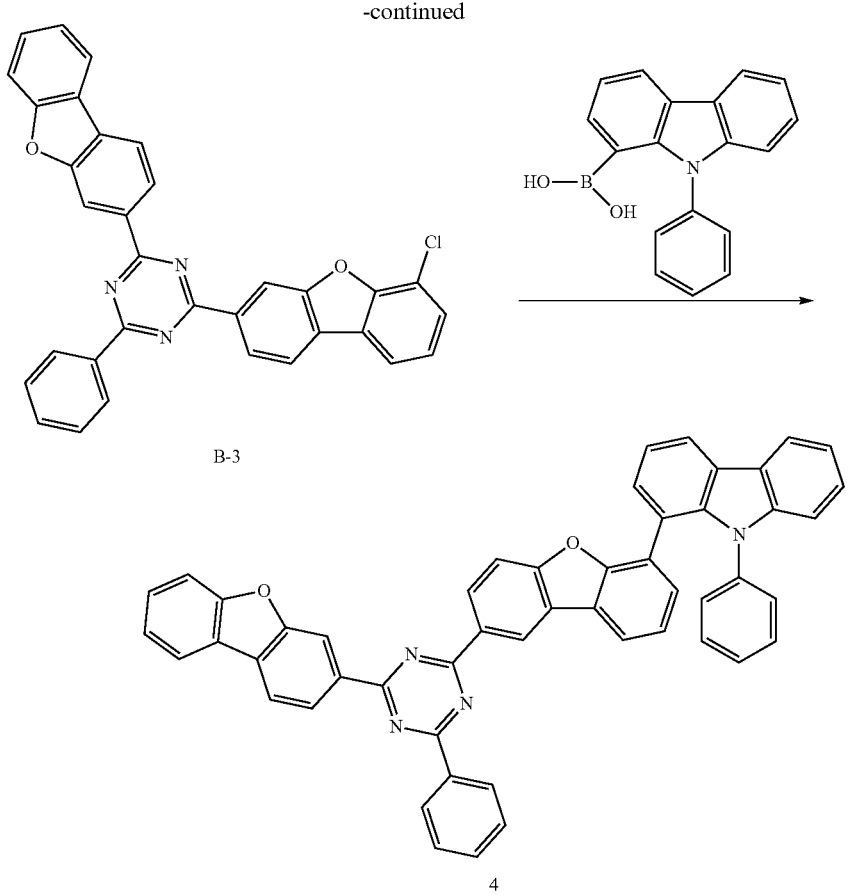

B-3

4

A fluorescent solid Compound 4 was prepared in the same manner as in Preparation Example 1, except that Intermediate A-2 is prepared using 3-bromo-6-chlorodibenzo[b,d]furan instead of 3-bromo-7-chlorodibenzo[b,d]furan in the step 1 of Preparation Example 1, and the prepared Intermediate A-2 is used instead of Intermediate A-1 and (9-phenyl-9H-carbazol-1-yl)boronic acid is used instead of (9-phenyl-9H-carbazol-3-yl)boronic acid in the step 2 of Preparation Example 1 (11.7 g, 56%).

MS: $[M+H]^+$=731.8

Preparation Example 5: Preparation of Compound 5

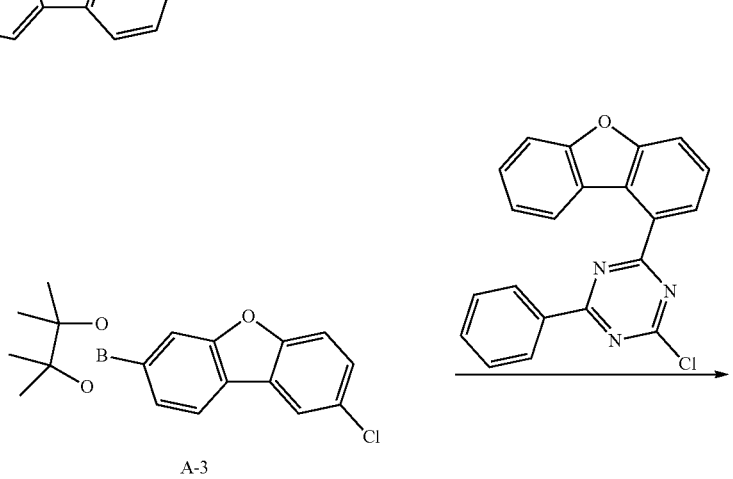

A-3

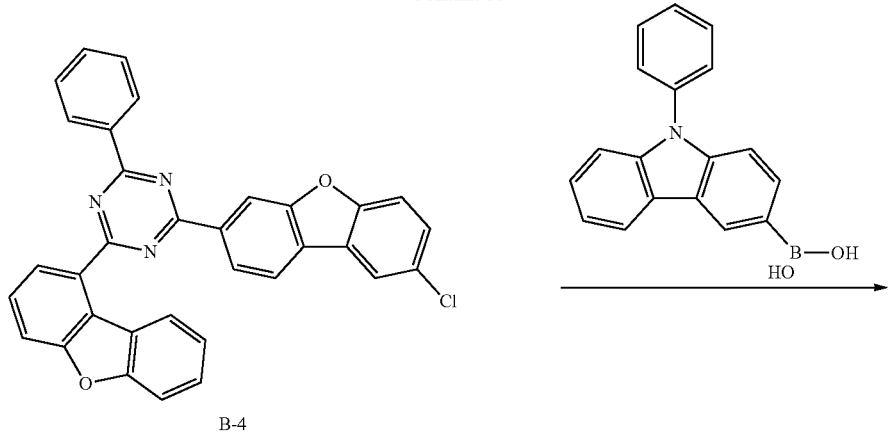

B-4

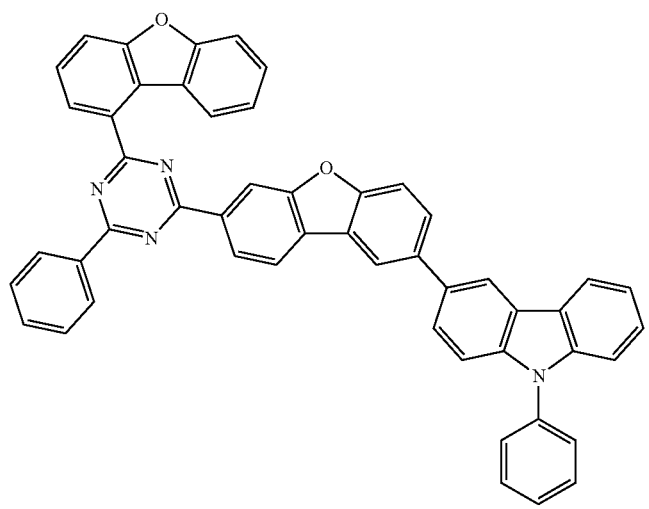

5

A fluorescent solid Compound 5 was prepared in the same manner as in Preparation Example 1, except that Intermediate A-3 is prepared using 7-bromo-2-chlorodibenzo[b,d]furan instead of 3-bromo-7-chlorodibenzo[b,d]furan in the step 1 of Preparation Example 1, and Intermediate B-4 is prepared using the prepared Intermediate A-3 instead of Intermediate A-1 in the step 2 of Preparation Example 1 (12.1 g, 58%).

MS: $[M+H]^+$=731.8

Example 1

A glass substrate on which ITO (indium tin oxide) was coated as a thin film to a thickness of 1400 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. In addition, the substrate was cleaned for 5 minutes using oxygen plasma, and then transferred to a vacuum depositor.

On the ITO transparent electrode thus prepared, the following HT-A compound and the following PD compound were thermally vacuum-deposited to a thickness of 100 Å at a weight ratio of 95:5 to form a hole injection layer, and then only the following HT-A compound was deposited to a thickness of 1150 Å to form a hole transport layer. On the hole transport layer, the following HT-B compound was thermally vacuum-deposited to a thickness of 450 Å to form an electron blocking layer.

On the electron blocking layer, Compound 1 prepared in the previous Preparation Example 1 and the following GD compound were vacuum-deposited to a thickness of 400 Å at a weight ratio of 85:15 to form a light emitting layer.

On the light emitting layer, the following ET-A compound was vacuum deposited to a thickness of 50 Å to form a hole blocking layer. On the hole blocking layer, the following ET-B compound and the following Liq compound were thermally vacuum-deposited to a thickness of 250 Å at a weight ratio of 2:1, and then LiF and magnesium were vacuum-deposited at a thickness of 30 Å at a weight ratio of 1:1 to form an electron injection and transport layer. On the electron injection and transport layer, magnesium and silver were deposited at a weight ratio of 1:4 to a thickness of 160 Å to form a cathode, thereby producing an organic light emitting device.

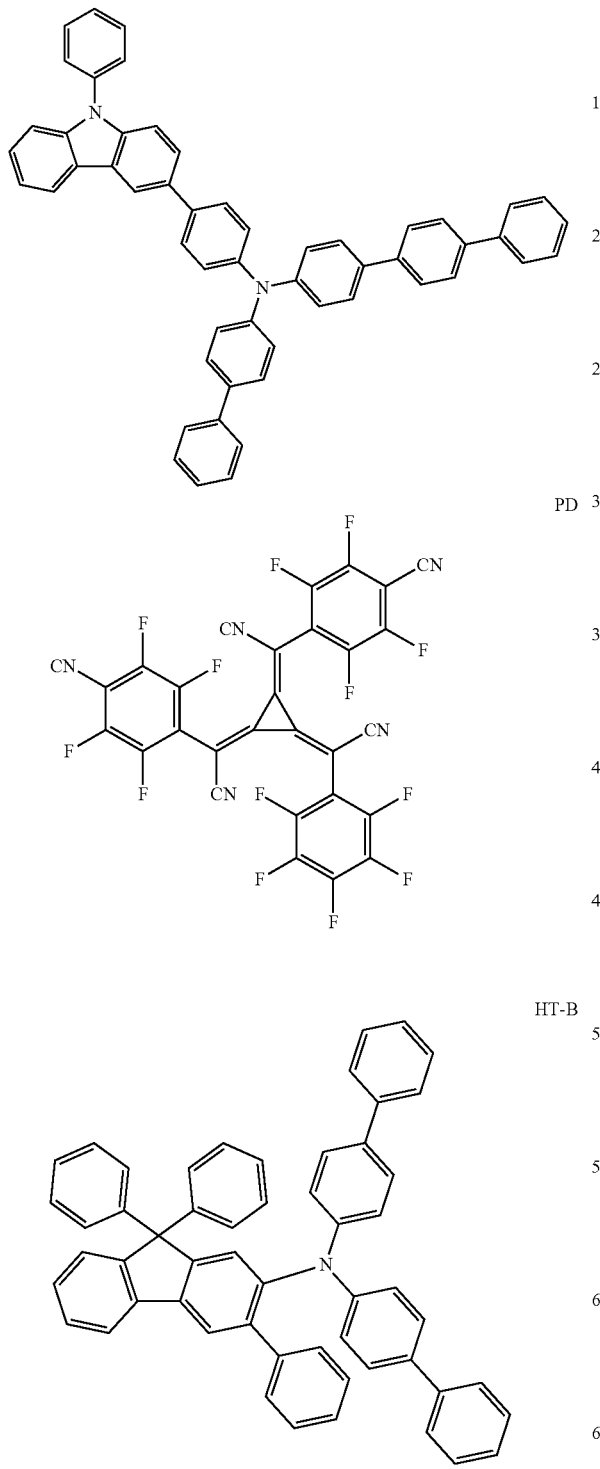

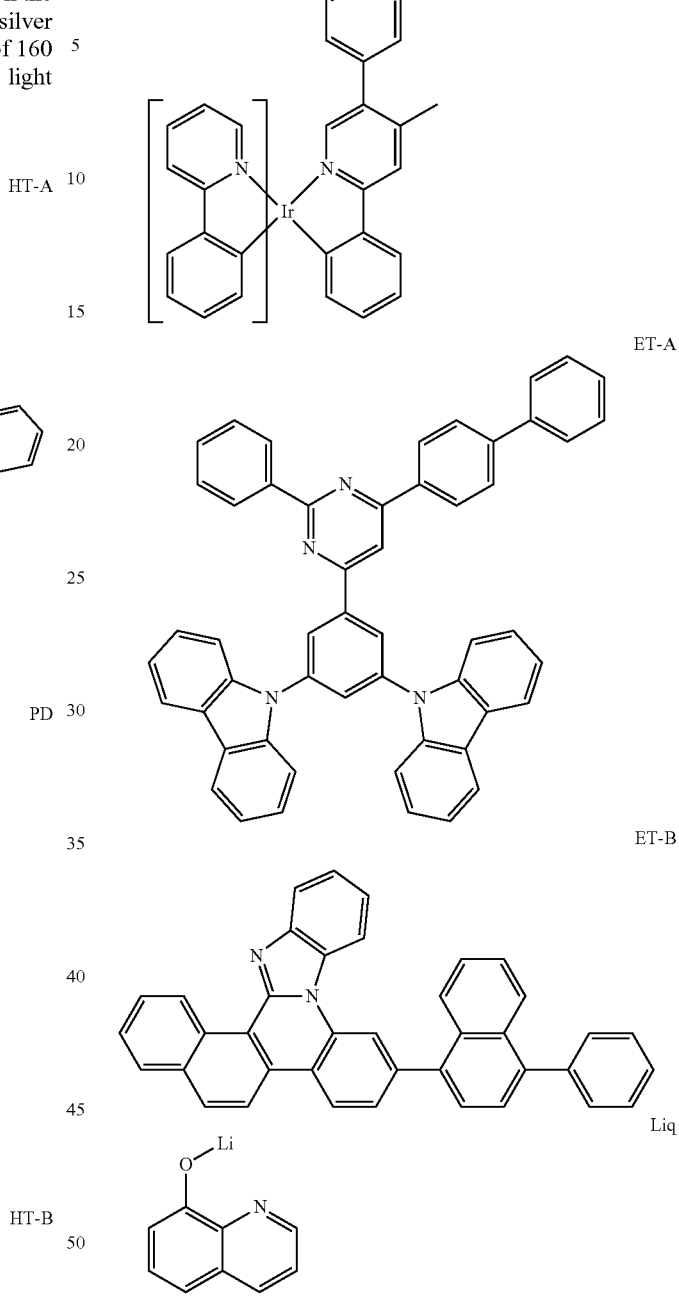

In the above-mentioned process, the vapor deposition rate of the organic material was maintained at 0.4 to 0.7 Å/s, the vapor deposition rate of lithium fluoride of cathode was maintained at 0.3 Å/s, the deposition rates of silver and magnesium were maintained at 2 Å/s, and the degree of vacuum during the deposition was maintained at $2 \times 10^{-7} \sim 5 \times 10^{-6}$ Torr, thereby producing an organic light emitting device.

Example 2 to Example 5

An organic light emitting device was manufactured in the same manner as in Example 1, except that the compounds shown in Table 1 below were used instead of Compound 1. The structures of the compounds used in the Examples 1 to 5 are as follows:

1

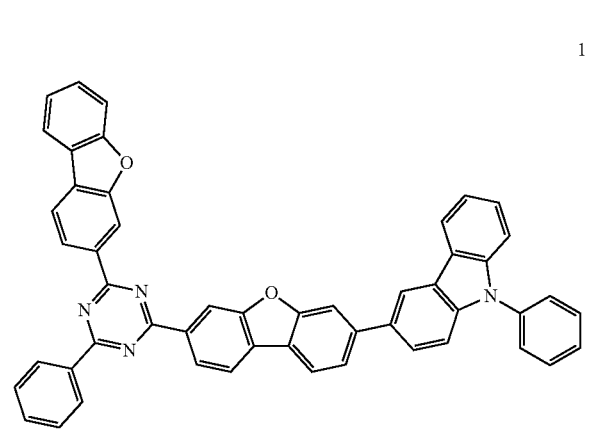

2

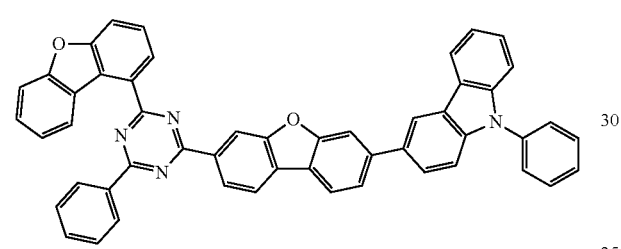

3

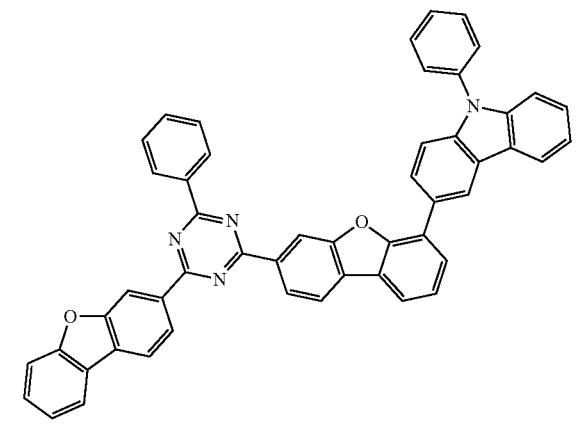

4

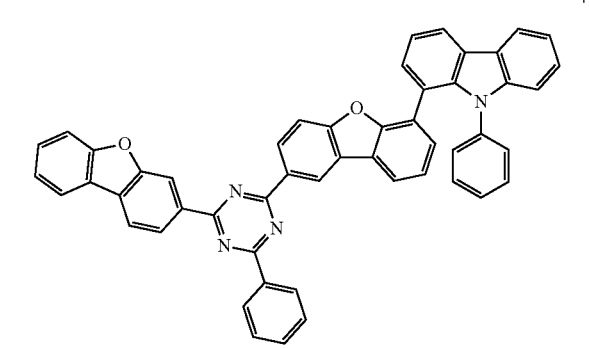

5

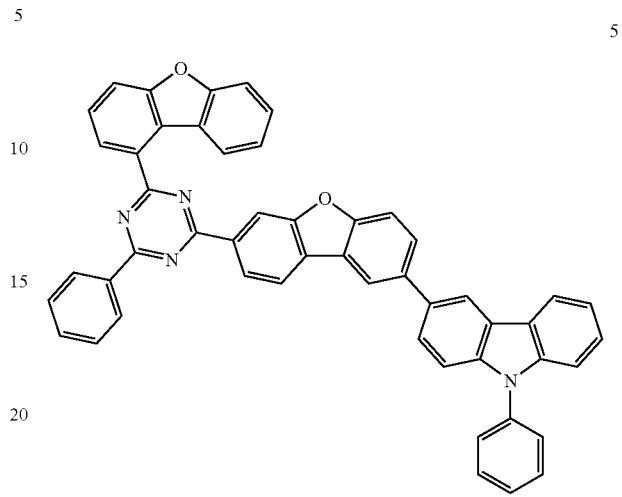

Comparative Examples 1 and 2

An organic light emitting device was manufactured in the same manner as in Example 1, except that the compounds shown in Table 1 below were used instead of Compound 1. The structures of the compounds GH-A and GH-B in Table 1 below are as follows:

GH-A

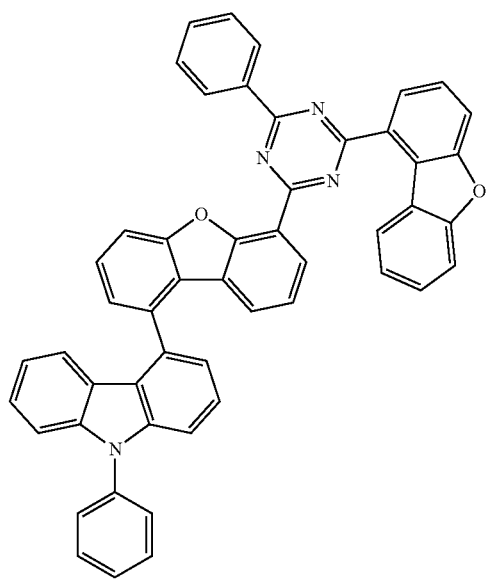

GH-B

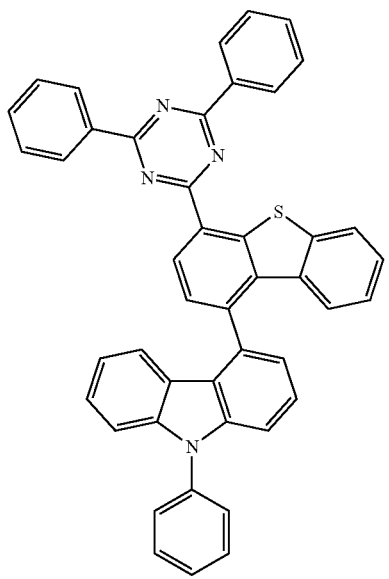

The driving voltage, efficiency, and lifetime (T95) were measured by applying a current to the organic light emitting devices manufactured in the examples and comparative examples above, and the results are shown in Table 1 below. At this time, voltage and efficiency were measured by applying a current density of 10 mA/cm². In addition, T95 in Table 1 below means the time required for the luminance to be reduced to 95% of the initial luminance at a current density of 20 mA/cm².

TABLE 1

| | Compound (host of light emitting layer) | Voltage (V) | Efficiency (cd/A) | Lifetime (T95, h) |
|---|---|---|---|---|
| Example 1 | Compound 1 | 4.12 | 51 | 128 |
| Example 2 | Compound 2 | 4.55 | 63 | 88 |
| Example 3 | Compound 3 | 4.23 | 58 | 90 |
| Example 4 | Compound 4 | 4.78 | 66 | 92 |
| Example 5 | Compound 5 | 4.32 | 59 | 80 |
| Comparative Example 1 | GH-A | 5.91 | 33.4 | 42 |
| Comparative Example 2 | GH-B | 5.88 | 27.5 | 52 |

As shown in Table 1, the organic light-emitting devices of the examples using the compound of the present disclosure as a host material of the light emitting layer exhibited excellent device properties in terms of driving voltage, efficiency, and lifetime, as compared with an organic light emitting device of Comparative Examples 1 and 2 employing the comparative compounds GH-A and GH-B in which the triazinyl group is substituted at a position different from the compound of the present disclosure, each of which used as a host material. In general, considering that the luminous efficiency and lifetime characteristics of the organic light emitting devices have a trade-off relationship with each other, it can be seen that the organic light emitting devices employing the compound of the present disclosure exhibit significantly improved device characteristics as compared with the devices of the comparative examples.

<Explanation of Signs>

1: substrate
2: anode
3: light emitting layer
4: cathode
5: hole injection layer
6: hole transport layer
7: electron blocking layer
8: hole blocking layer
9: electron injection and transport layer

The invention claimed is:
1. A compound of Chemical Formula 1:

Chemical Formula 1

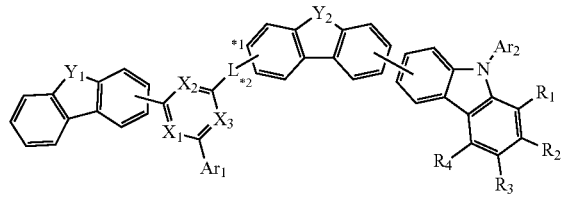

wherein, in Chemical Formula 1:
$X_1$ to $X_3$ are each independently N or CH, provided that at least two of $X_1$ to $X_3$ are N;
$Y_1$ and $Y_2$ are each independently O or S;
L is a single bond, a substituted or unsubstituted $C_{6-60}$ arylene, or a substituted or unsubstituted $C_{2-60}$ heteroarylene containing one or more heteroatoms selected from the group consisting of N, O, and S, provided that L is bonded to a position *2;
$Ar_1$ and $Ar_2$ are each independently a substituted or unsubstituted $C_{6-60}$ aryl, or a substituted or unsubstituted $C_{2-60}$ heteroaryl containing one or more heteroatoms selected from the group consisting of N, O, and S; and
$R_1$ to $R_4$ are each independently hydrogen, deuterium, a halogen, cyano, nitro, amino, silyl, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{2-60}$ heteroaryl containing one or more heteroatoms selected from the group consisting of N, O, and S, or adjacent substituents are combined with each other to form a $C_{6-60}$ aromatic ring, a $C_{6-60}$ non-aromatic ring, or a $C_{2-60}$ heteroaromatic ring containing one or more heteroatoms selected from the group consisting of N, O, and S.

2. The compound according to claim 1, wherein $X_1$ to $X_3$ are N.

3. The compound according to claim 1, wherein L is a single bond, phenylene, biphenylylene, naphthylene, dibenzofuranylene, dibenzothiophenylene, or carbazolylene.

4. The compound according to claim 1, wherein $Ar_1$ and $Ar_2$ are each independently phenyl, biphenylyl, dibenzofuranyl, dibenzothiophenyl, or carbazolyl.

5. The compound according to claim 1, wherein:
R$_1$ to R$_4$ are each independently hydrogen or phenyl, or two adjacent substituents of R$_1$ to R$_4$ are combined with each other to form a structure of Chemical Formula 2:

Chemical Formula 2

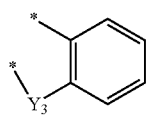

wherein, in Chemical Formula 2:
Y$_3$ is CZ$_1$Z$_2$, O, S, or NZ$_3$;
Z$_1$ to Z$_3$ are each independently a C$_{1-10}$ alkyl or a C$_{6-20}$ aryl; and
* means a bonding position with two adjacent carbon atoms of each carbon atom bonded to R$_1$ to R$_4$.

6. The compound according to claim 1, wherein the compound is one of the following Chemical Formulae 1-5 or 1-6:

Chemical Formula 1-5

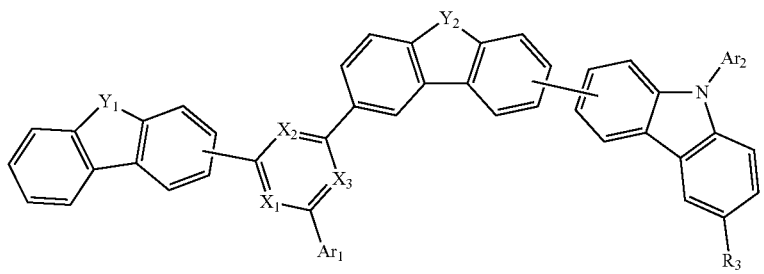

Chemical Formula 1-6

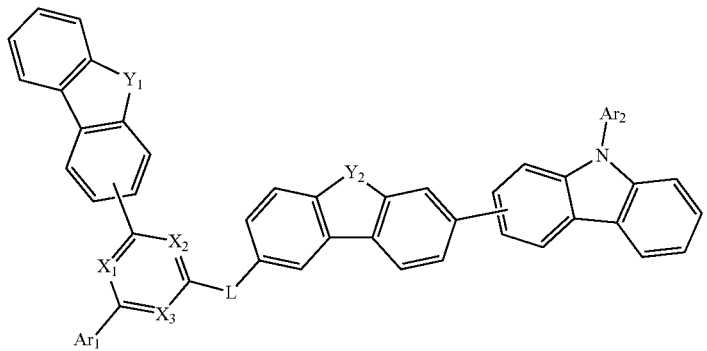

wherein, in Chemical Formulae 1-5 or 1-6:
L is a substituted or unsubstituted C$_{6-60}$ arylene, or a substituted or unsubstituted C$_{2-60}$ heteroarylene containing one or more heteroatoms selected from the group consisting of N, O, and S;
R$_3$ is hydrogen or phenyl; and
X$_1$ to X$_3$, Y$_1$, Y$_2$, Ar$_1$, and Ar$_2$ are as defined in claim 1.

7. The compound according to claim 1,
wherein the compound is any one compound selected from the group consisting of the following compounds:

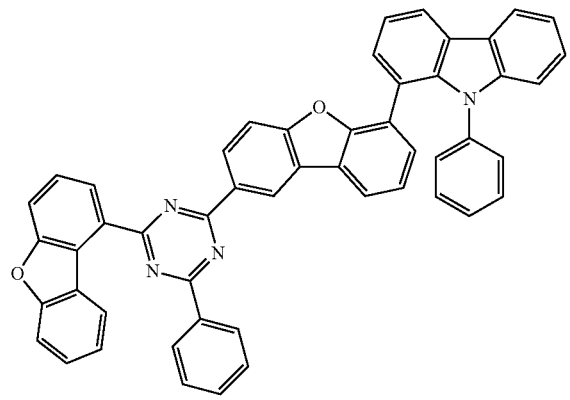

-continued

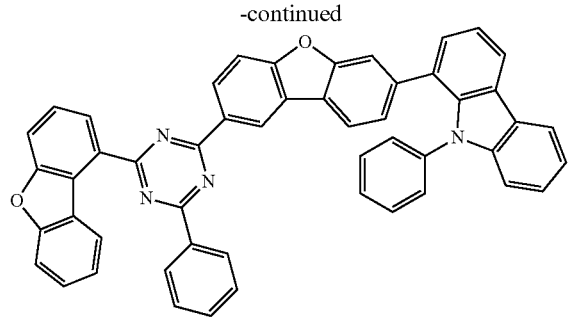

215
-continued
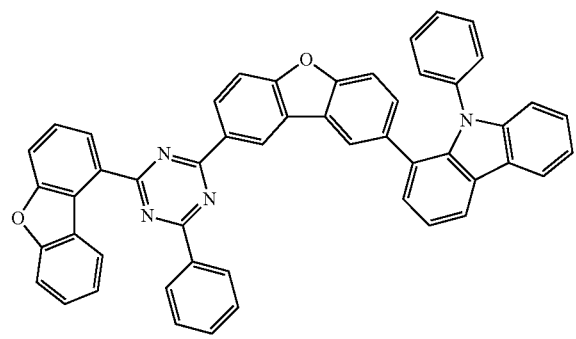
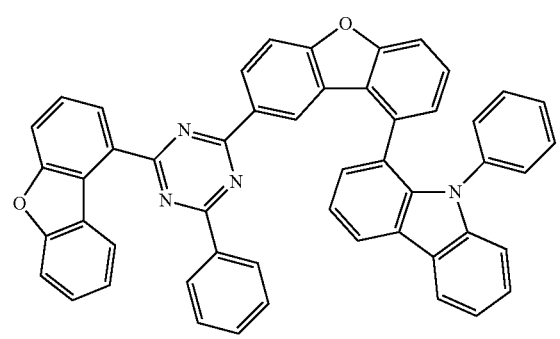
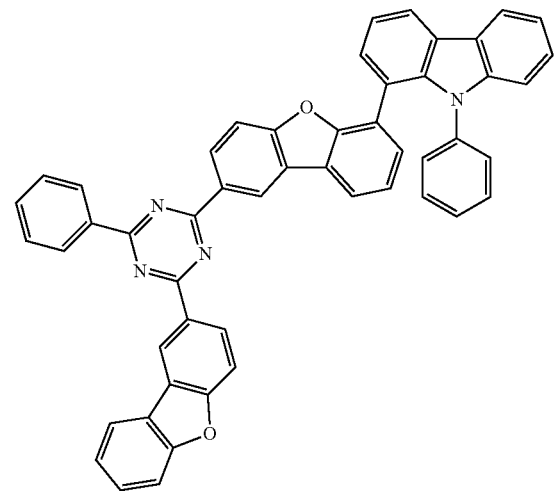
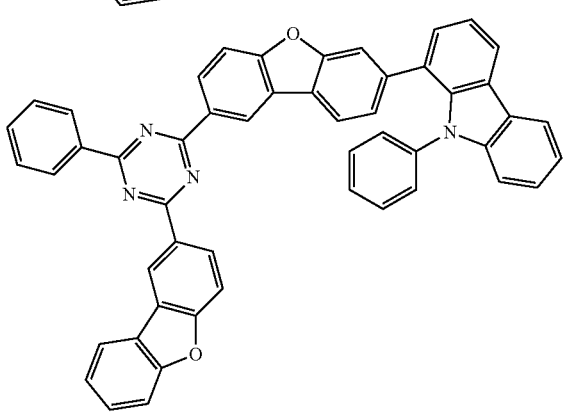
216
-continued
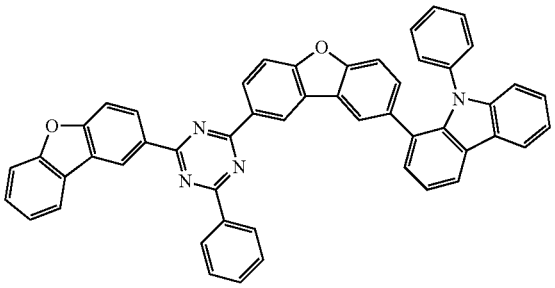
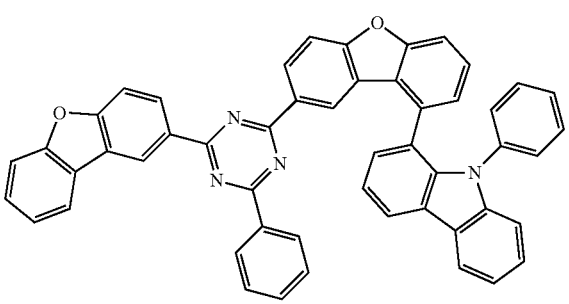
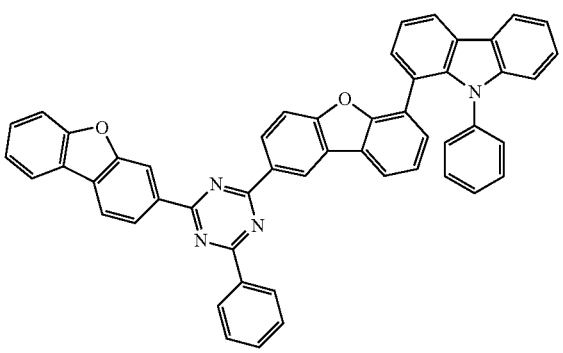
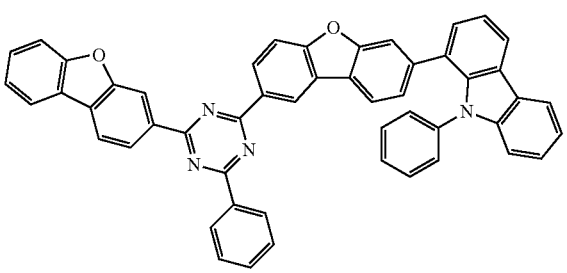
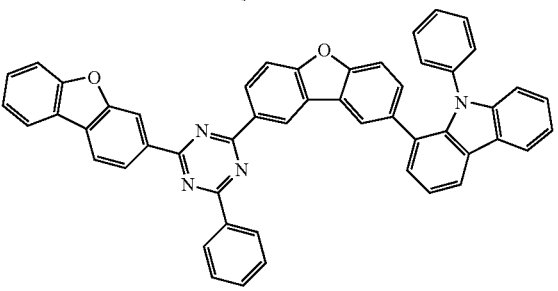

217
-continued
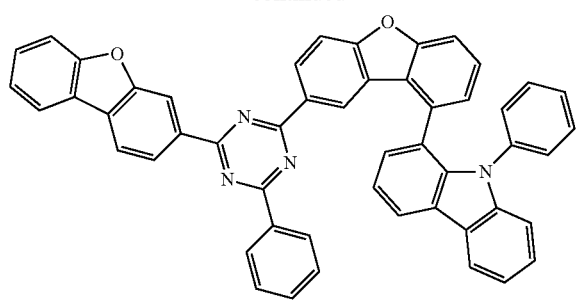
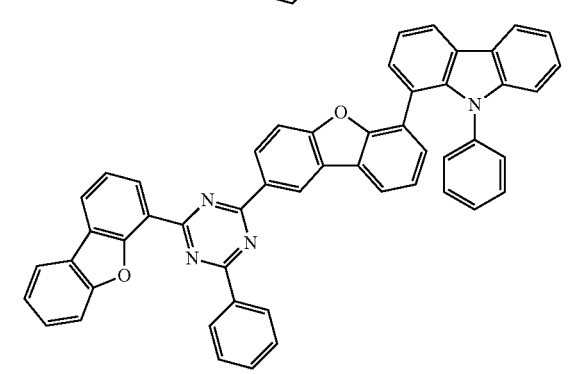
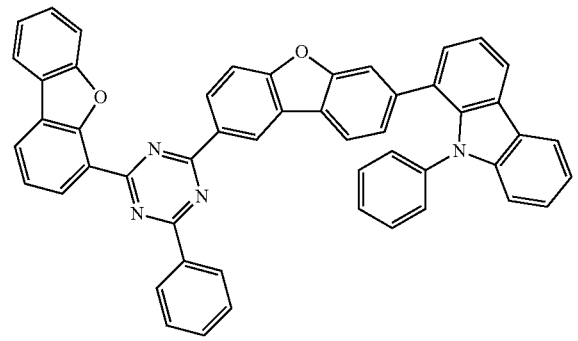
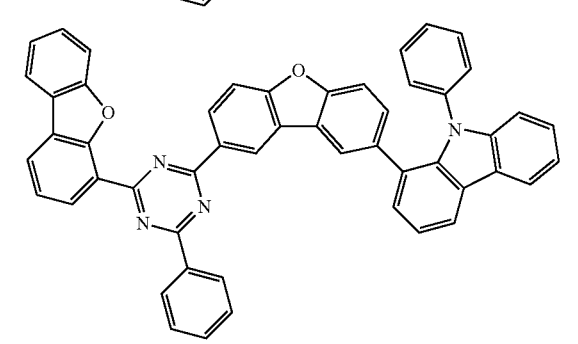
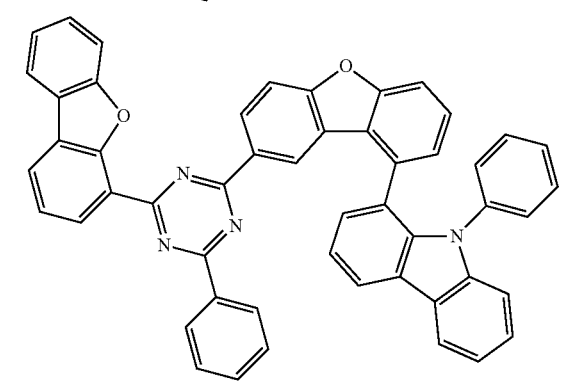
218
-continued
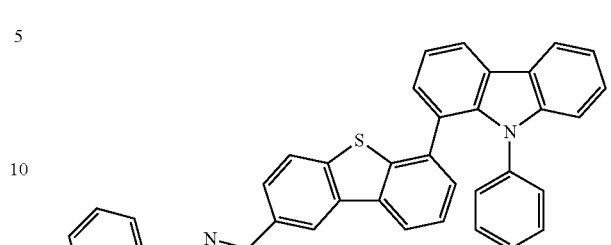

219
-continued
220
-continued
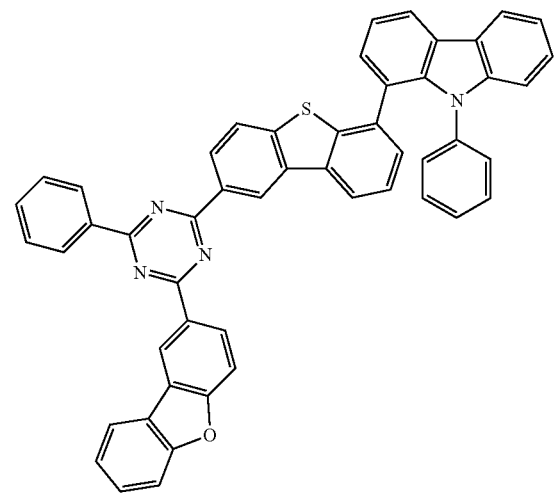
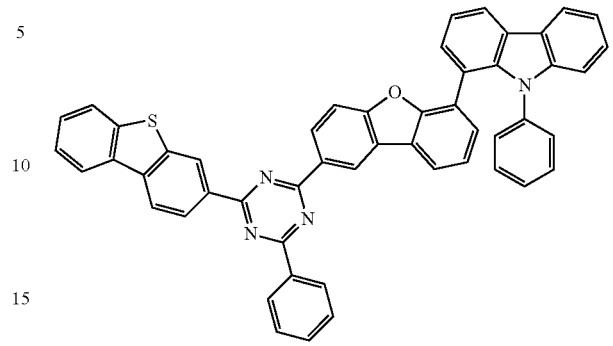
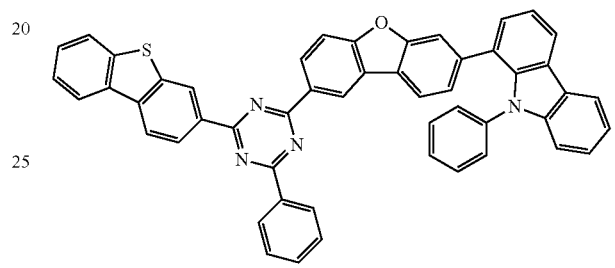
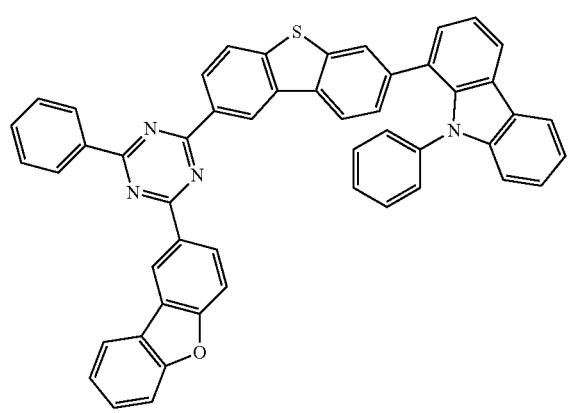
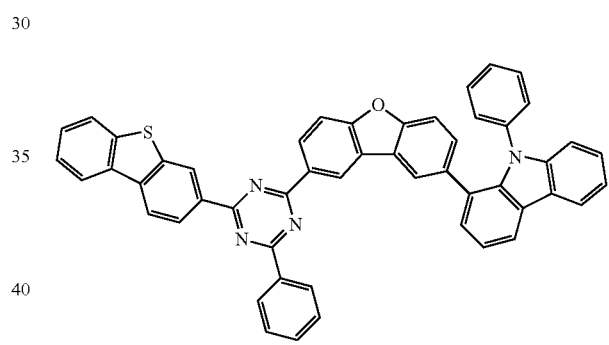
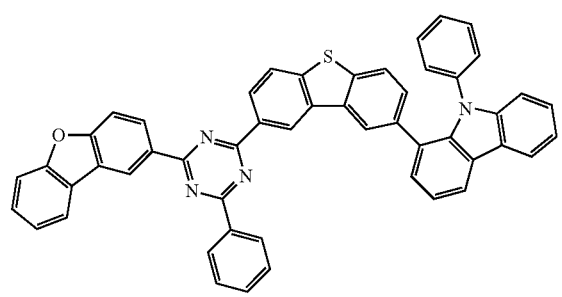
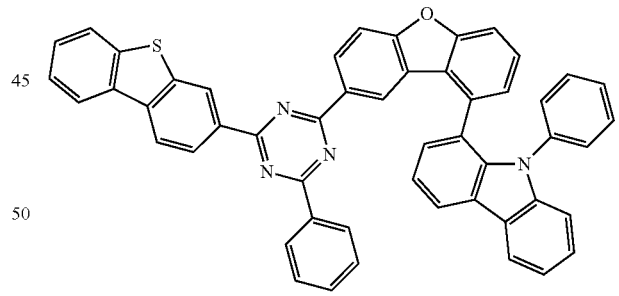
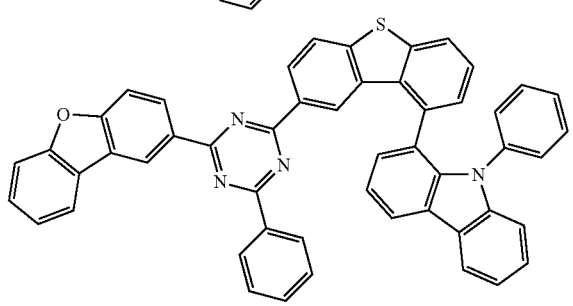
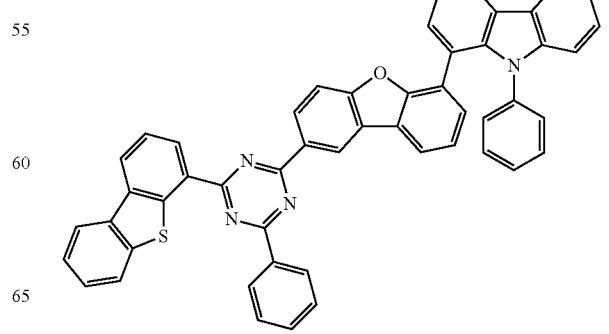

221
-continued
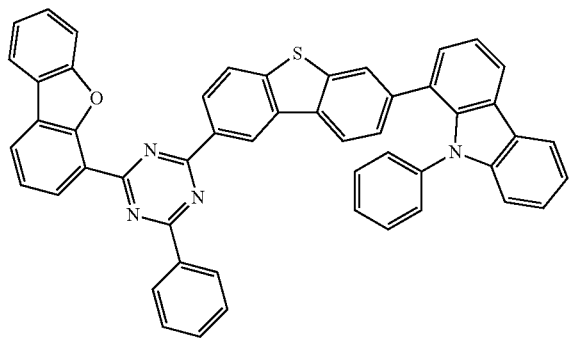
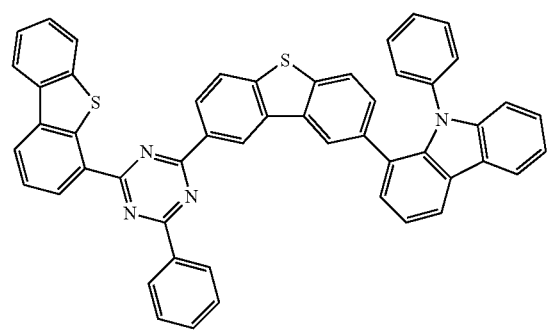
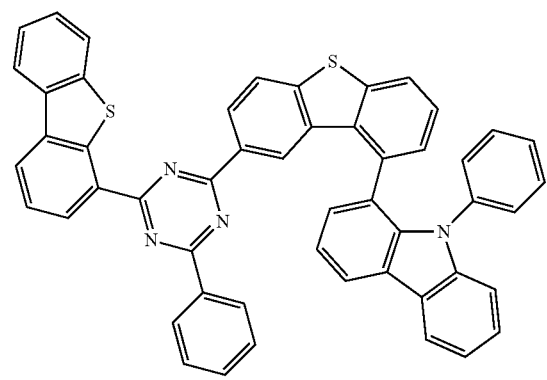
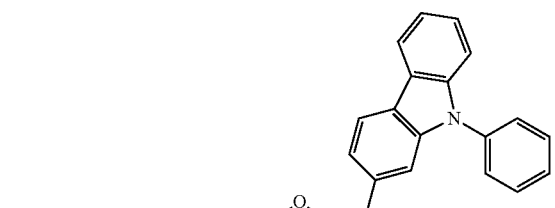
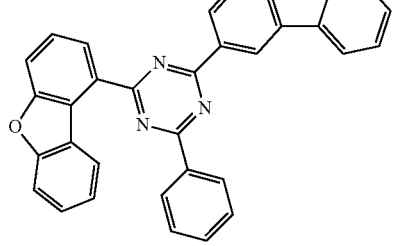
222
-continued
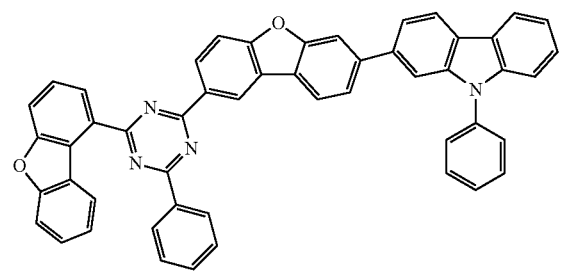
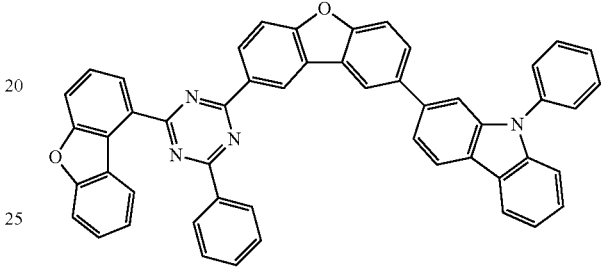
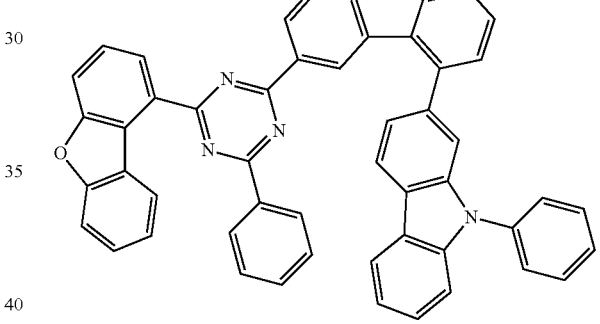
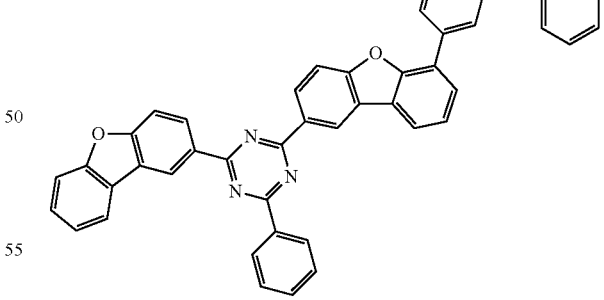
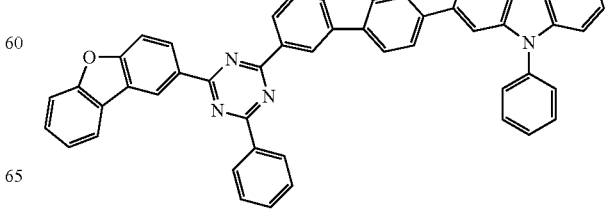

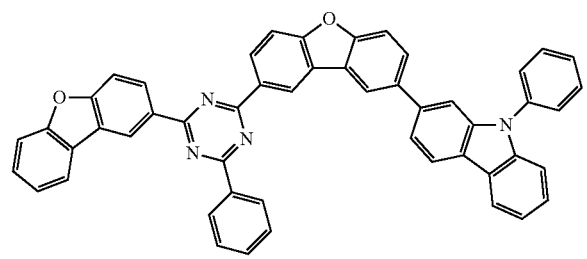
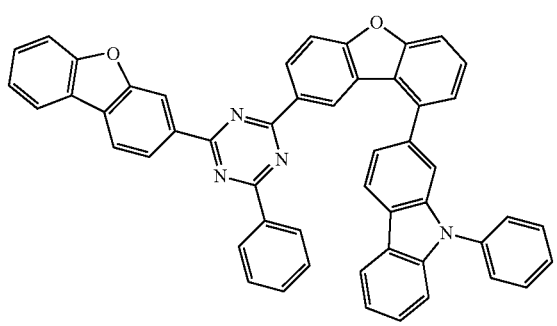
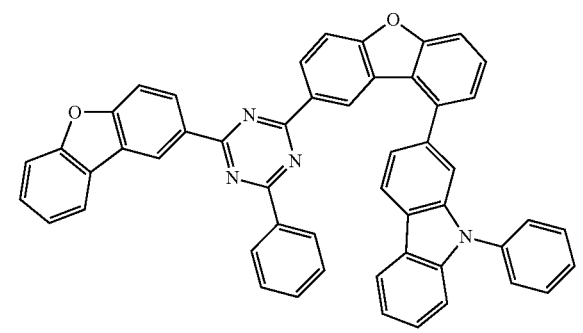
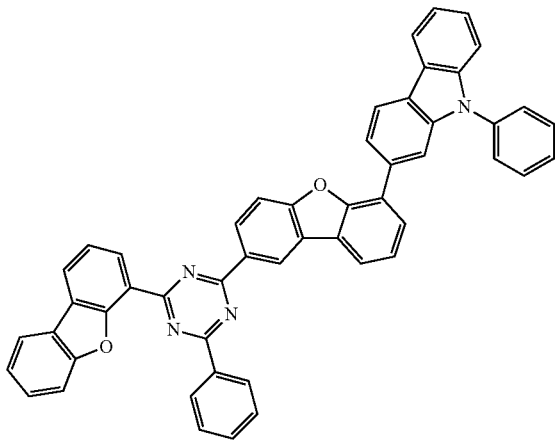
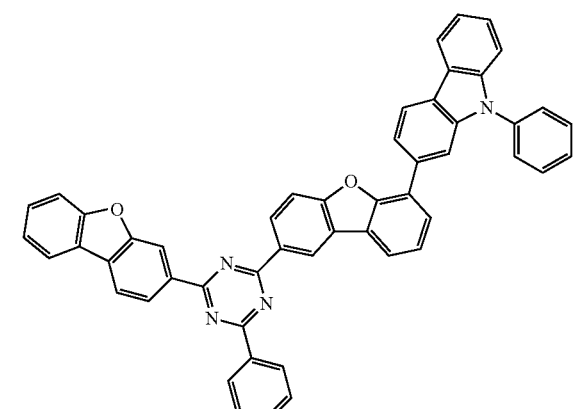
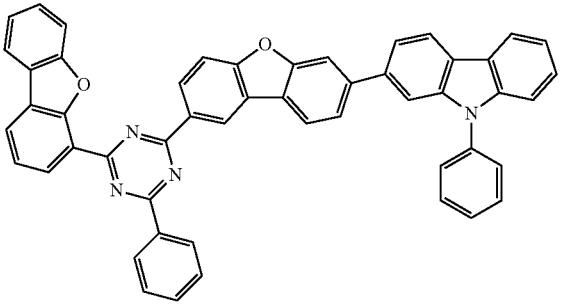
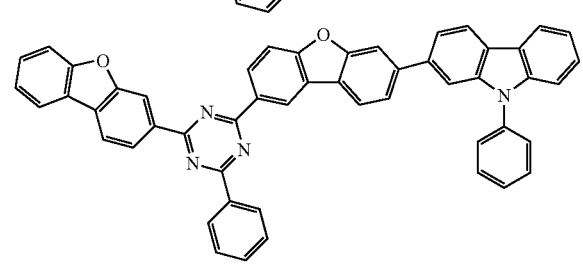
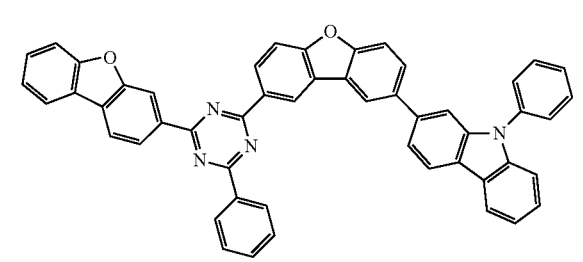
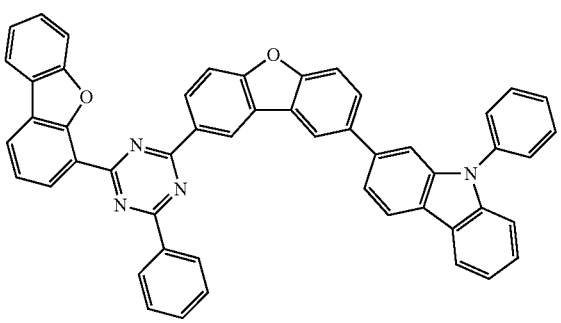

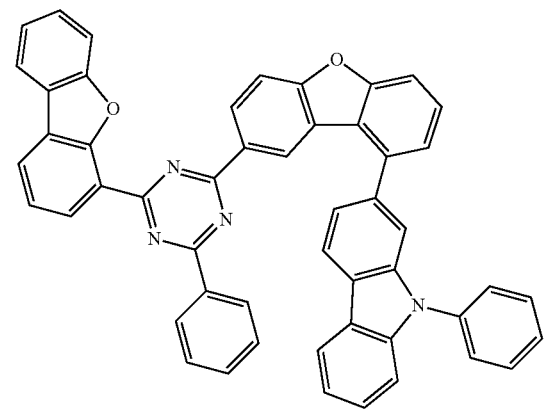
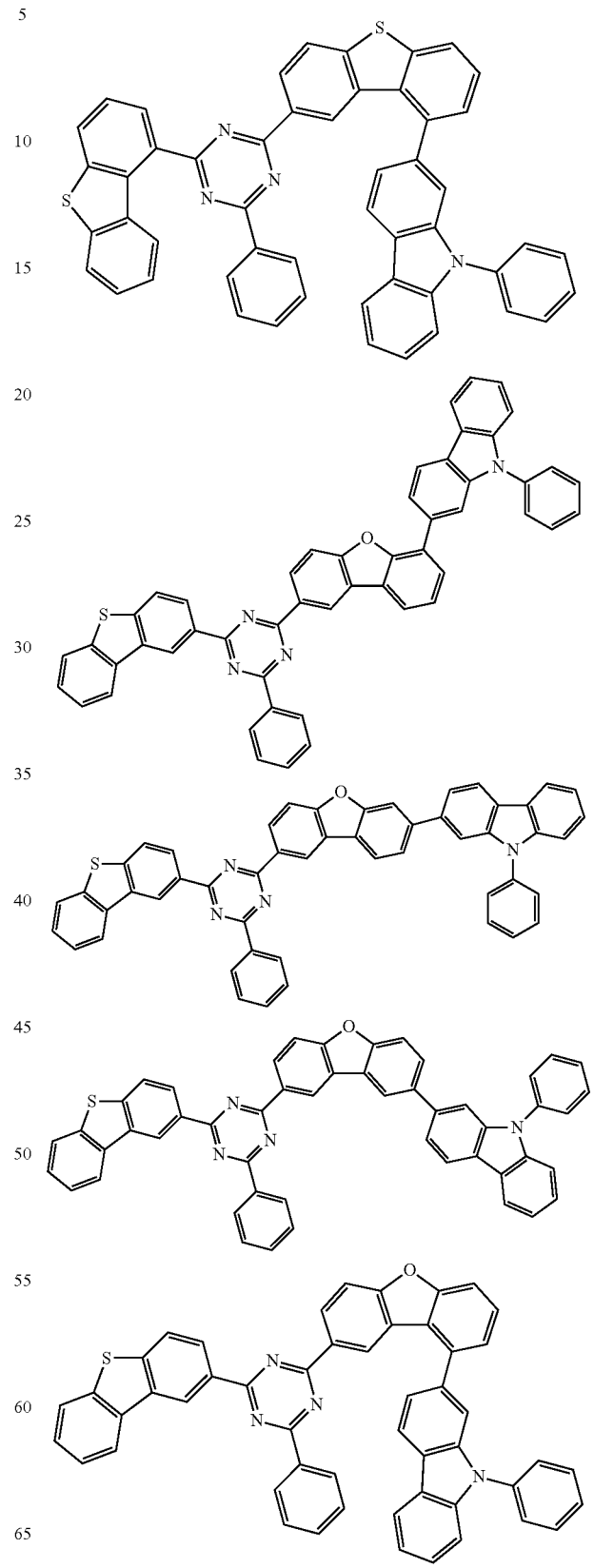

227
-continued
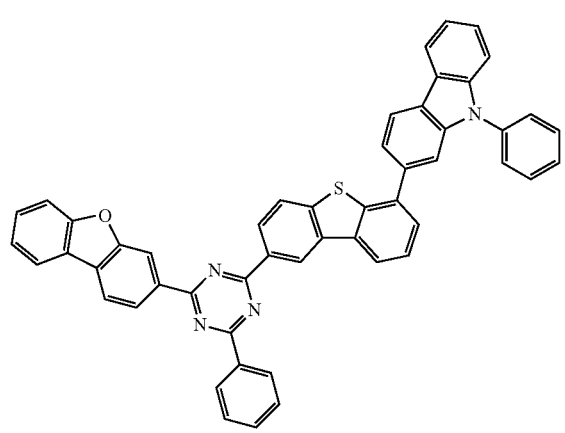
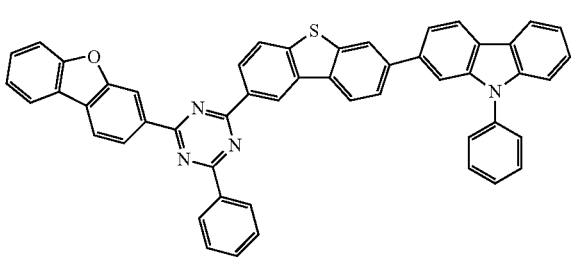
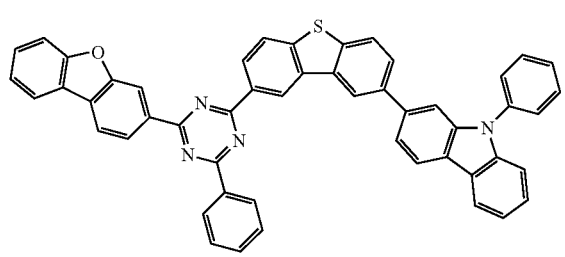
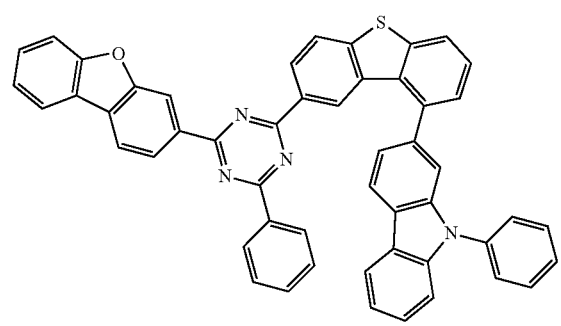
228
-continued
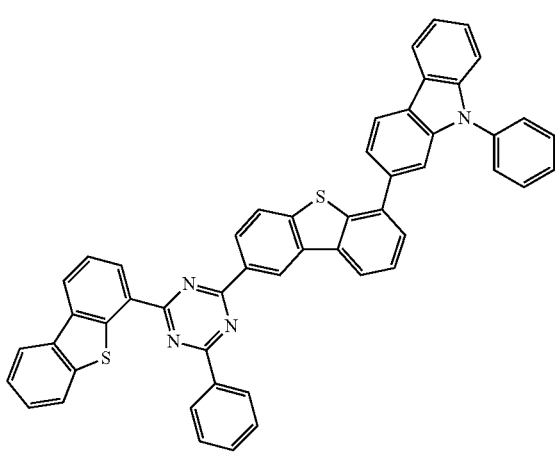
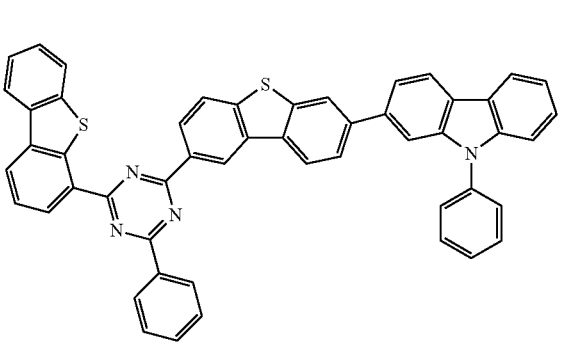
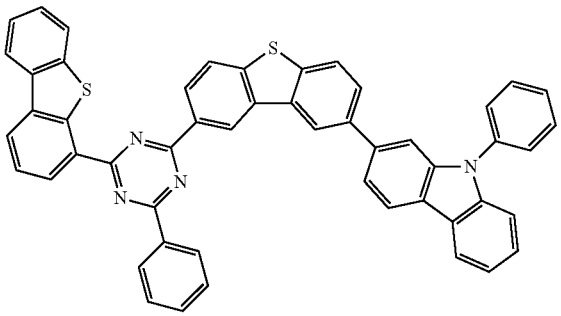
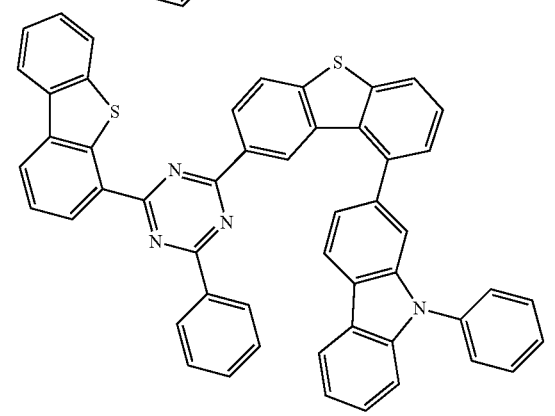

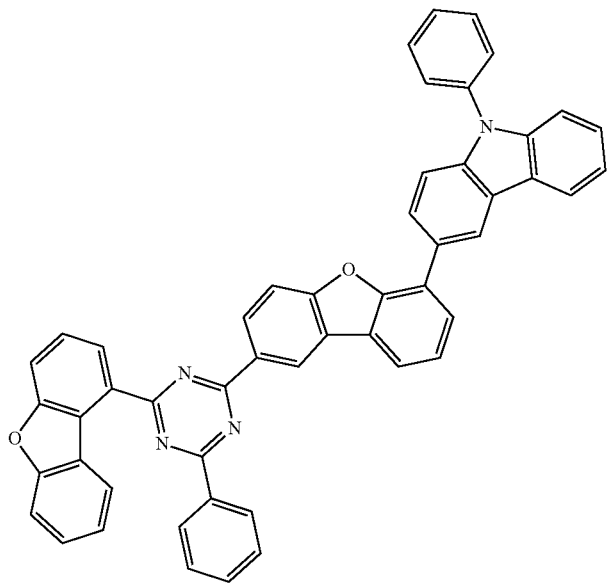 [SMILES: c1ccc(-c2nc(-c3ccc4oc5c(-c6ccc7c(c6)c6ccccc6n7-c6ccccc6)cccc5c4c3)nc(-c3cccc4oc5ccccc5c34)n2)cc1]
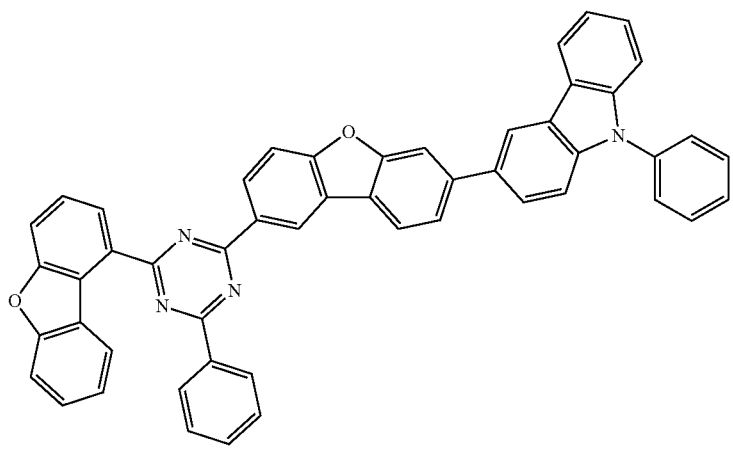
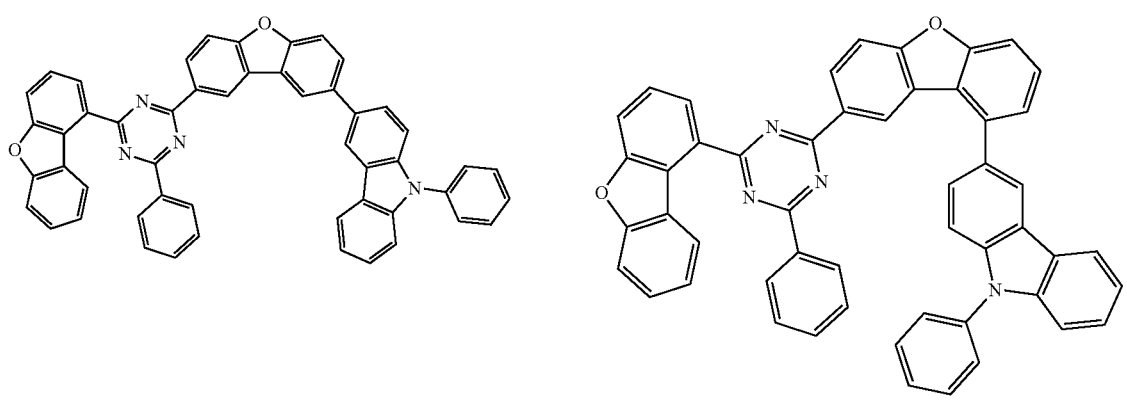

-continued
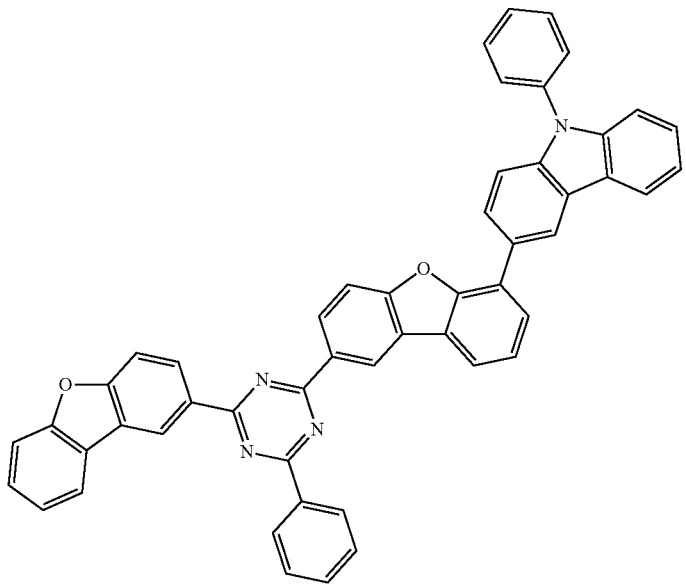
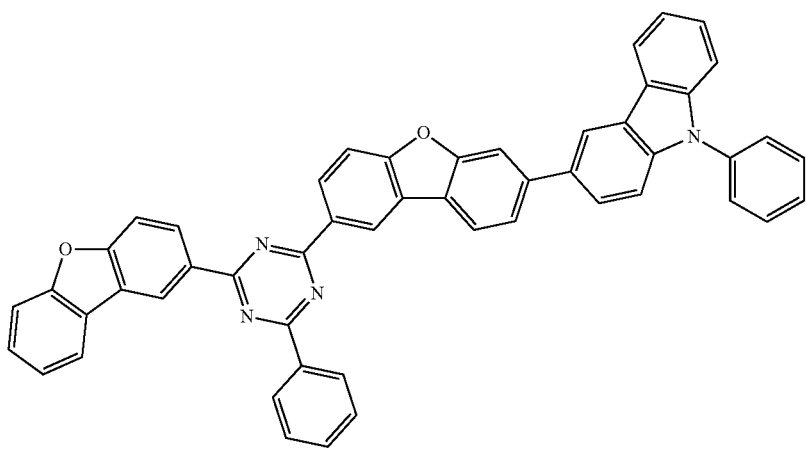
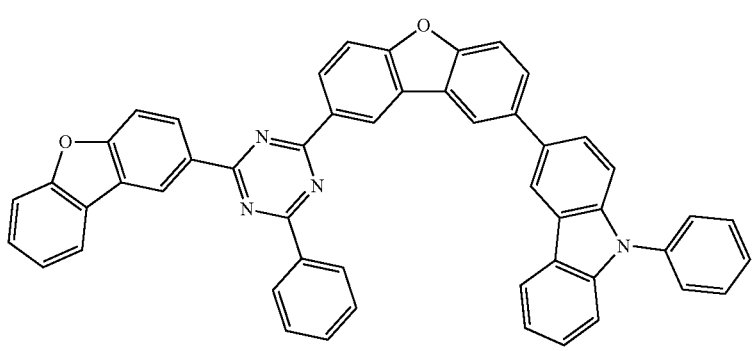

-continued
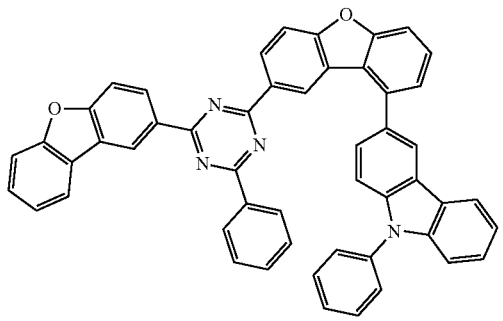
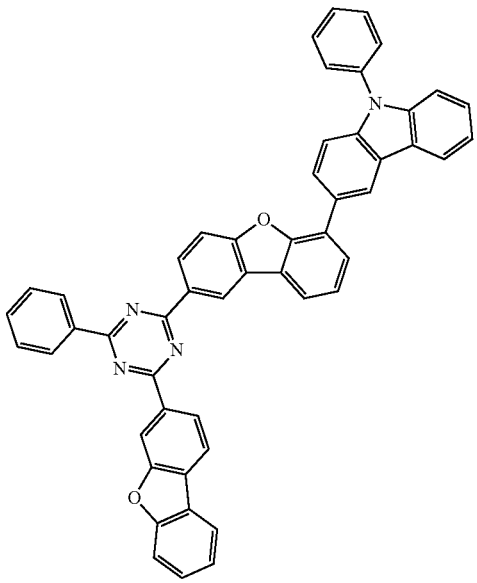
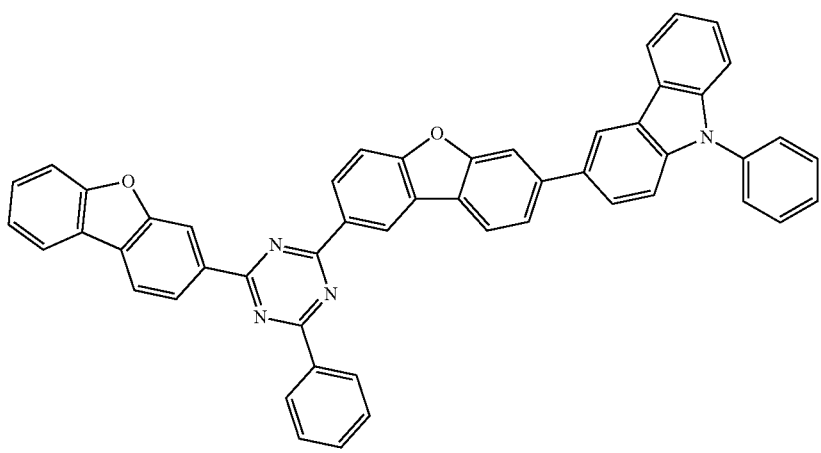
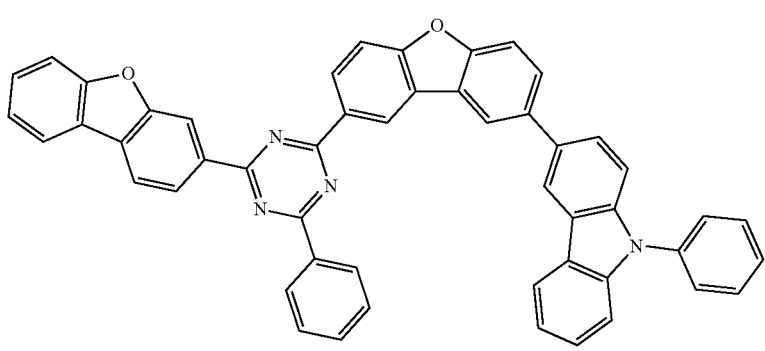

-continued
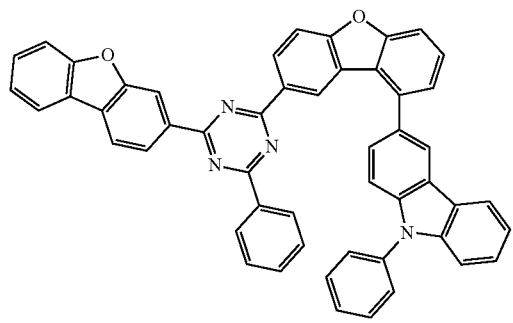
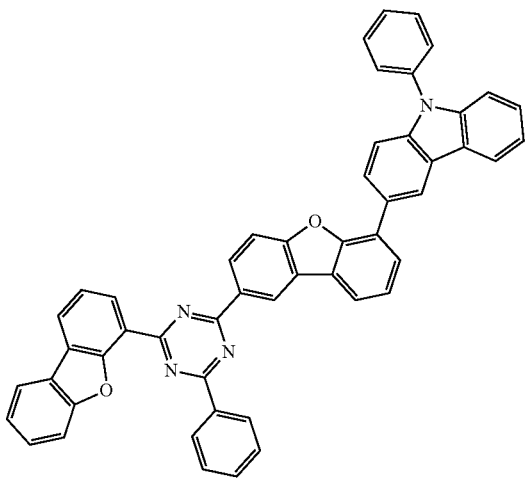
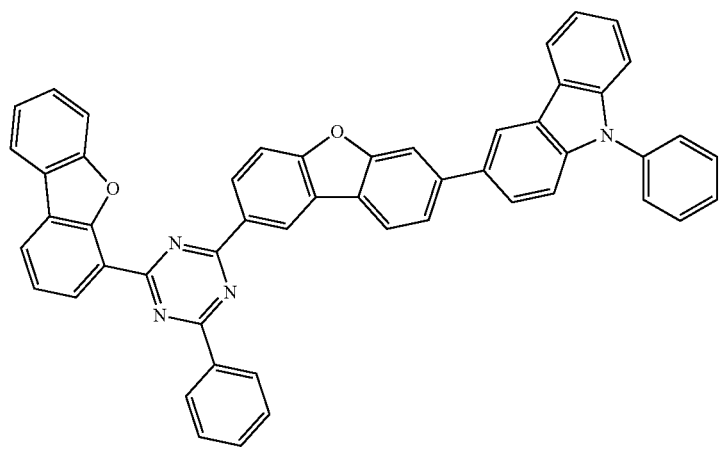
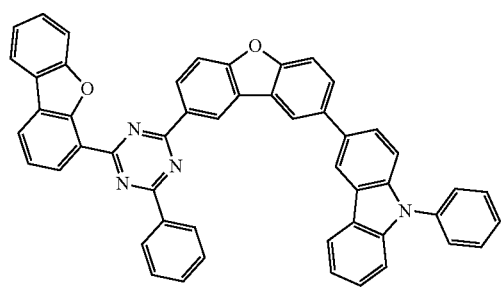
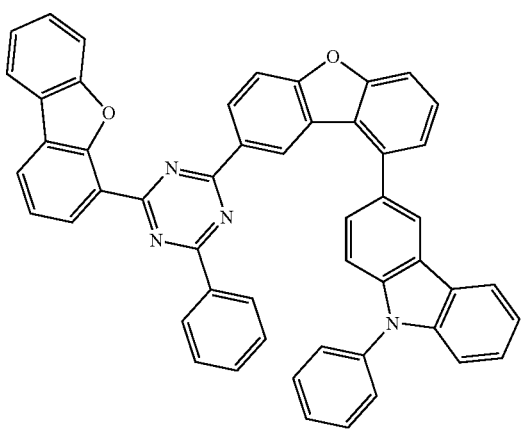

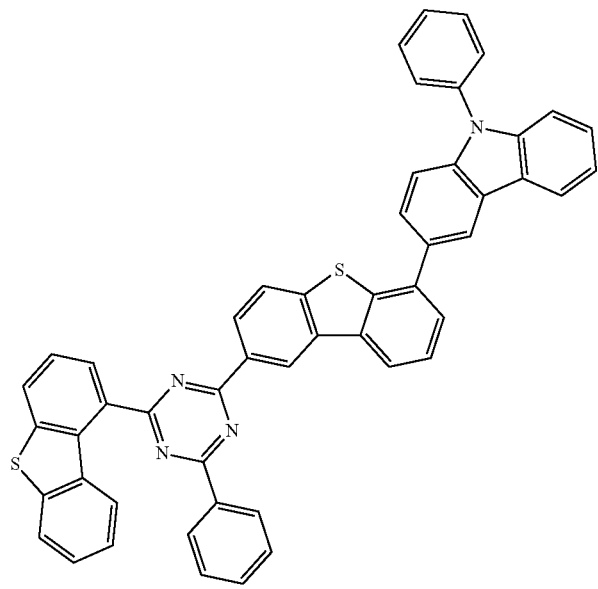
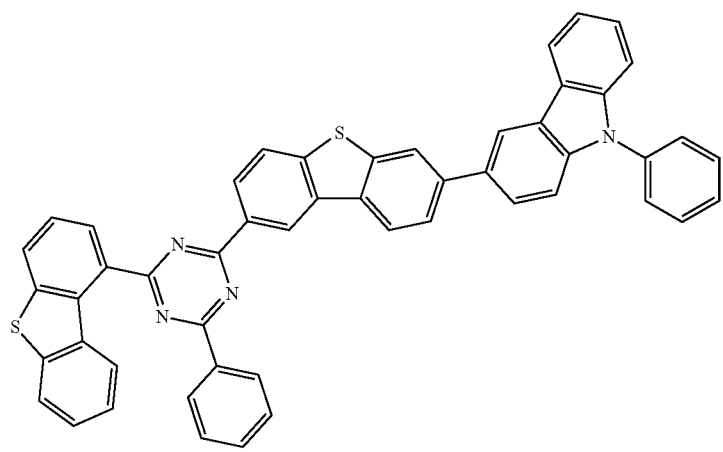
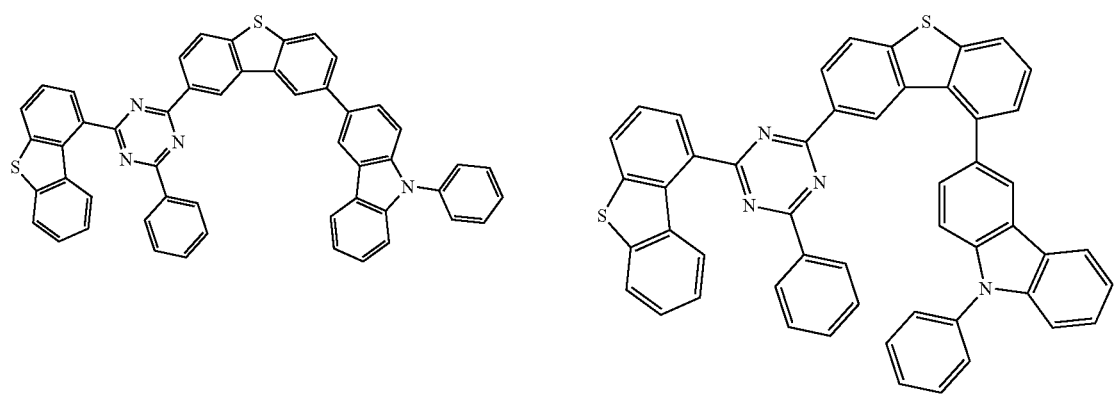

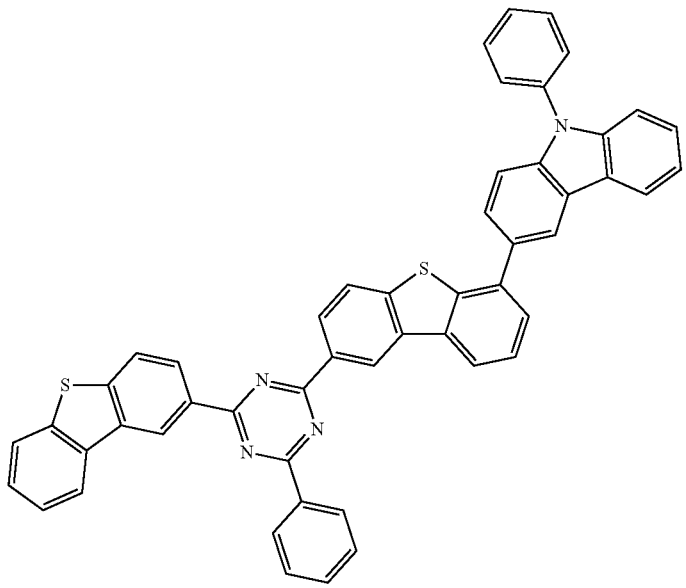
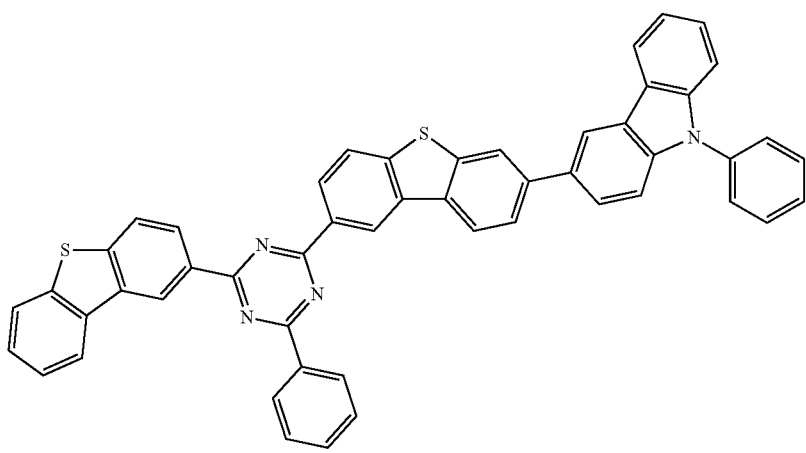
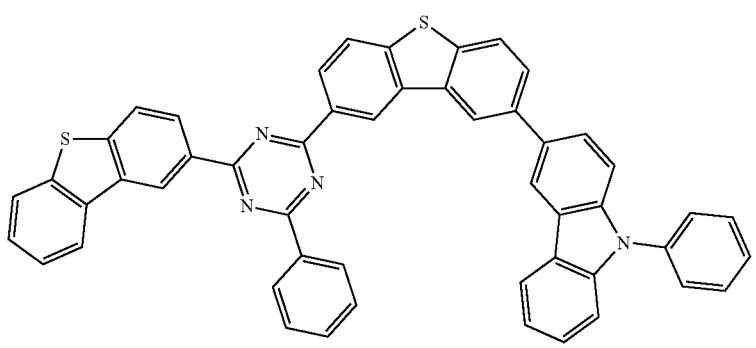

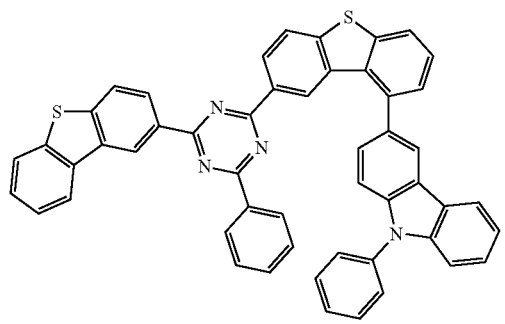
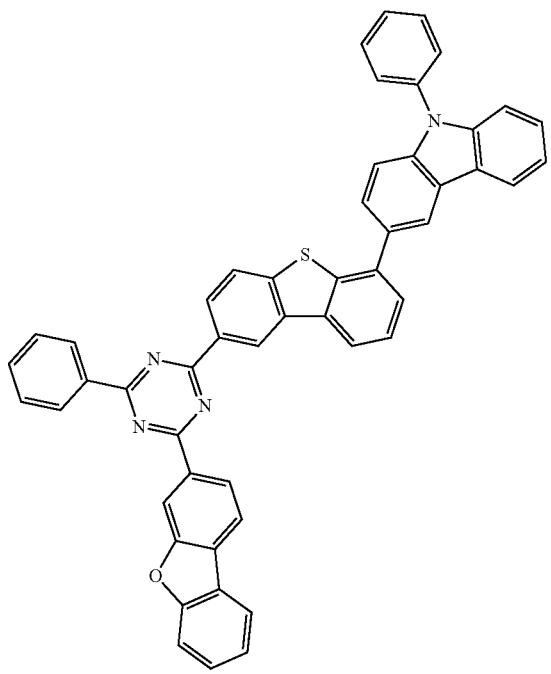
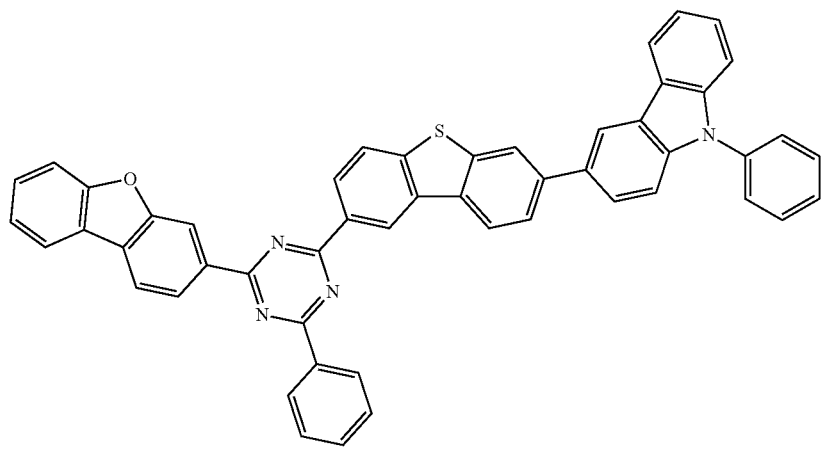
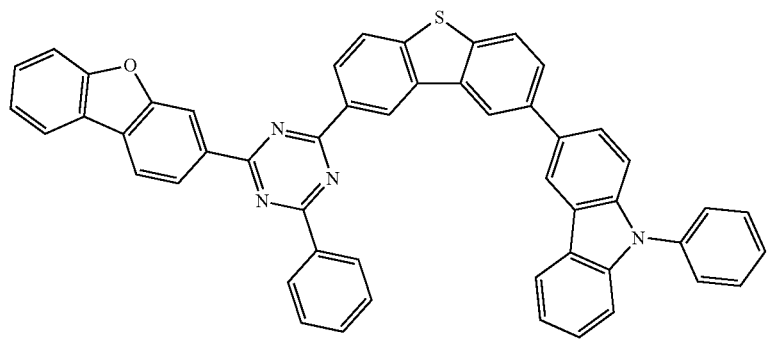

243
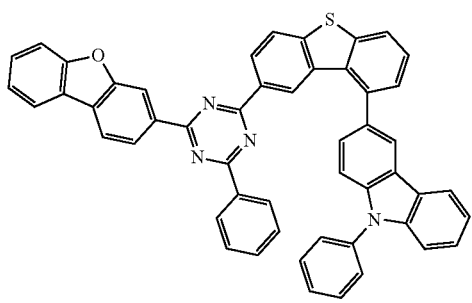
244
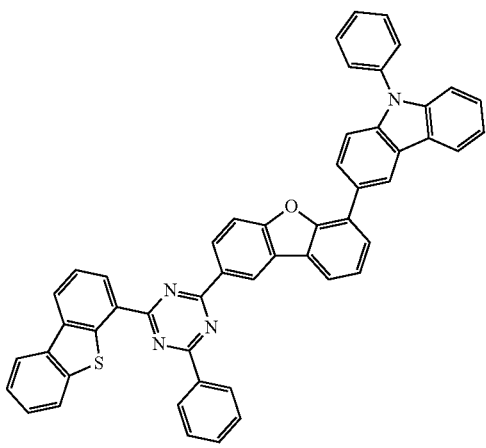
-continued
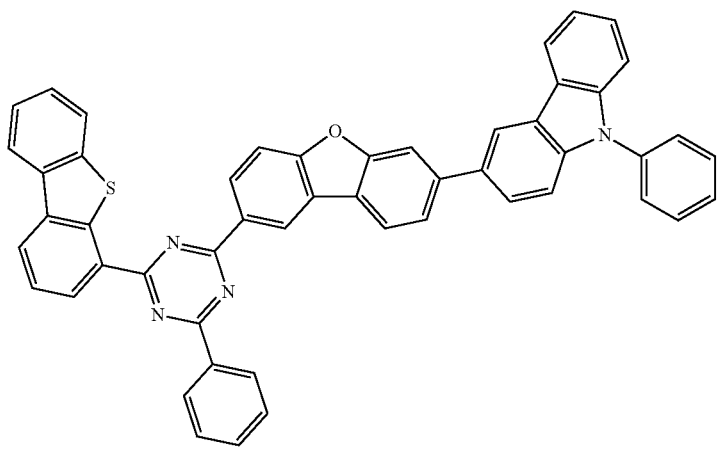
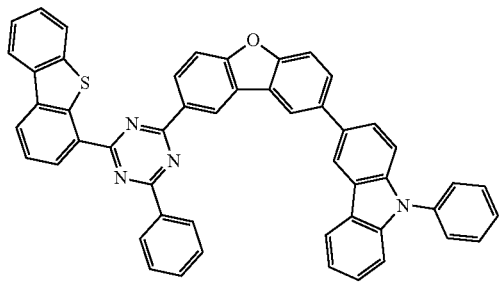
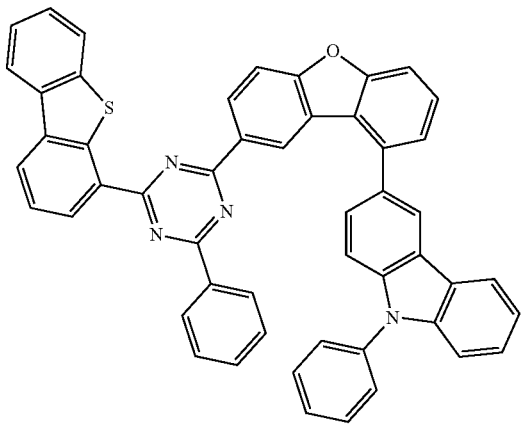
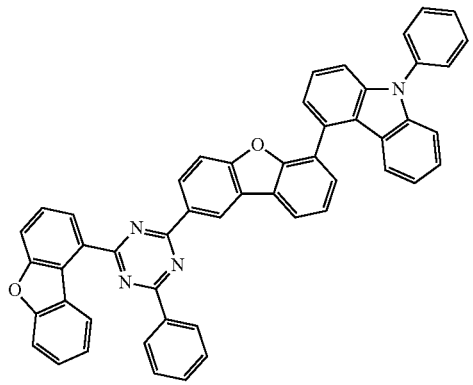
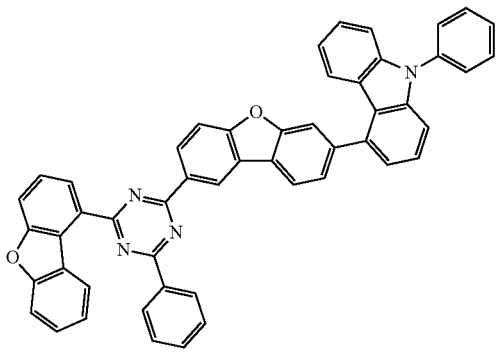

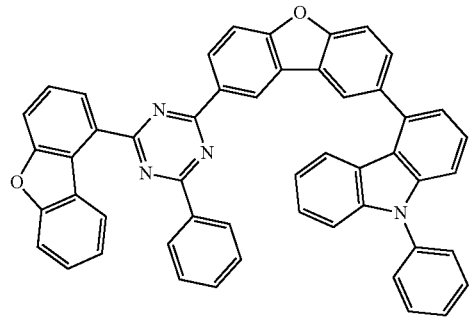
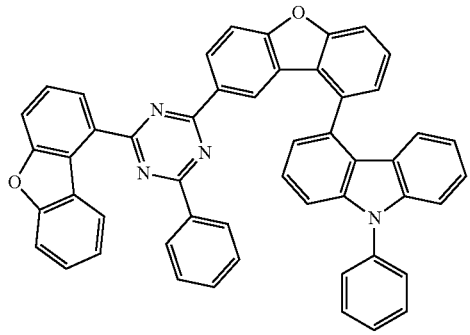
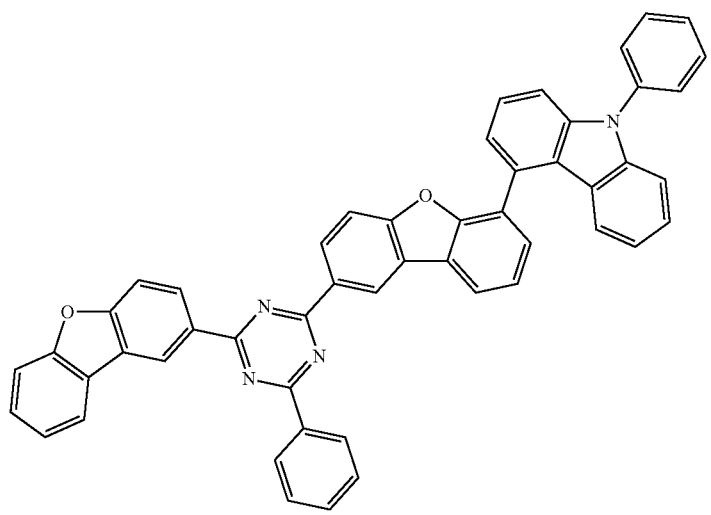
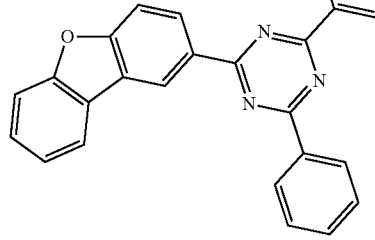
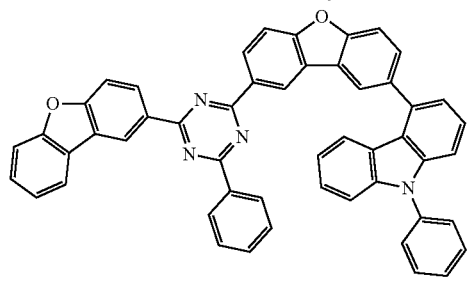
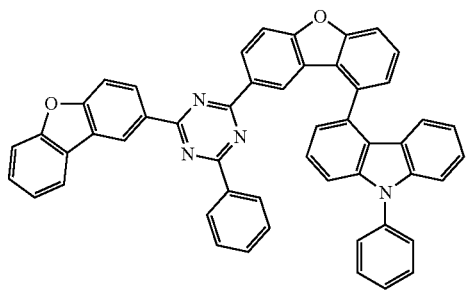

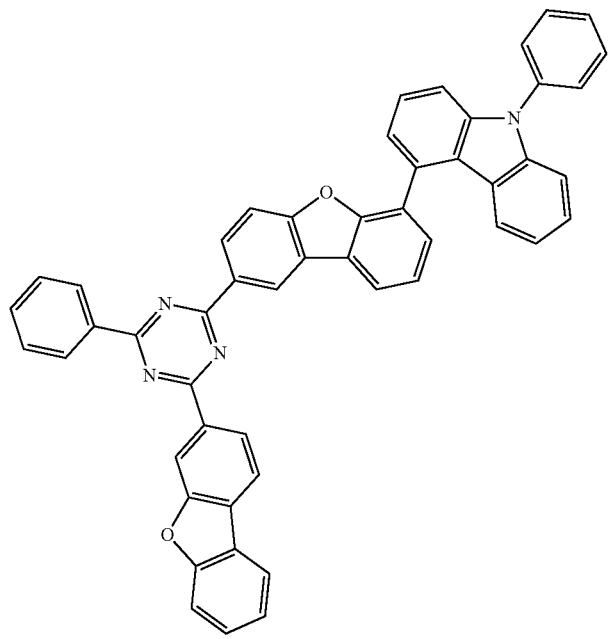
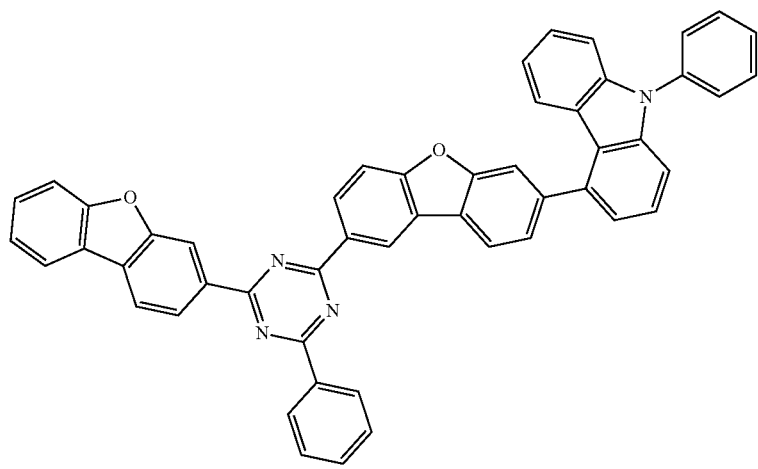
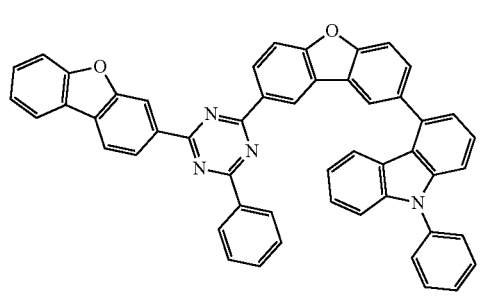
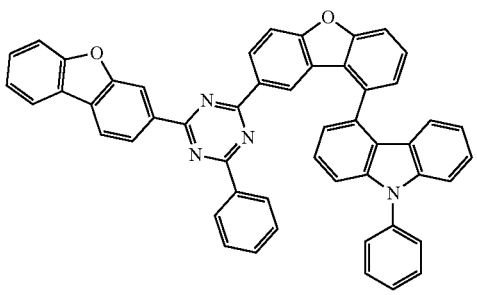

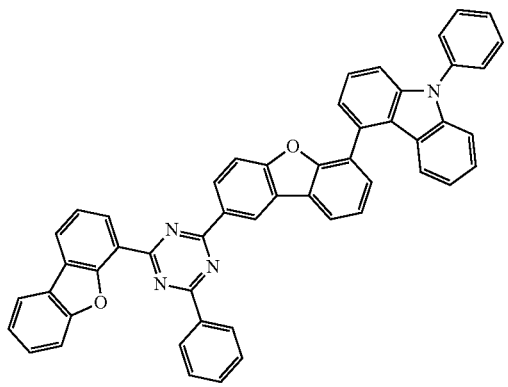
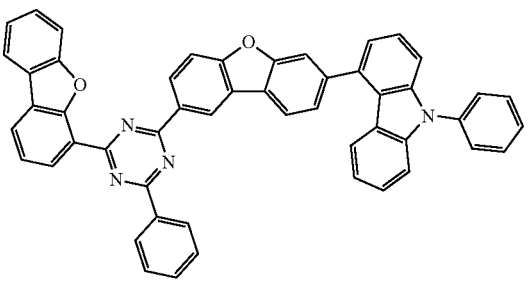
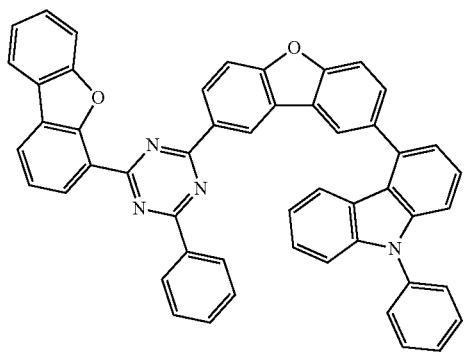
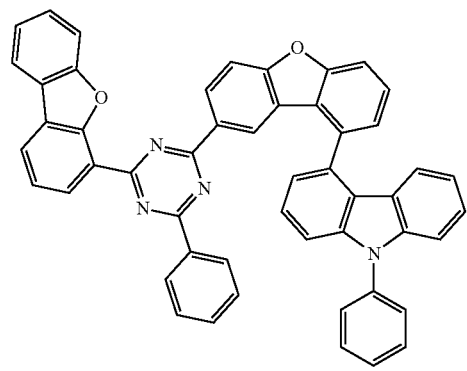
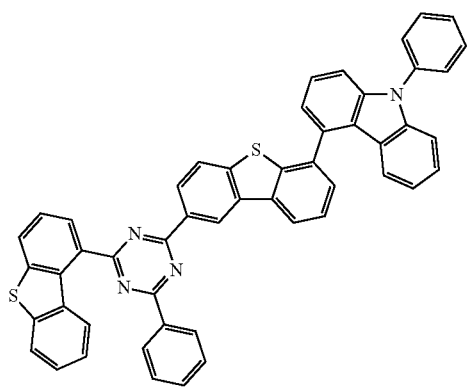
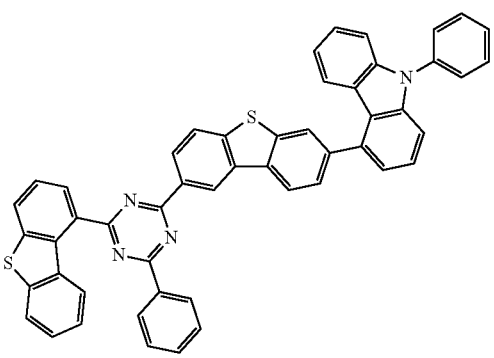
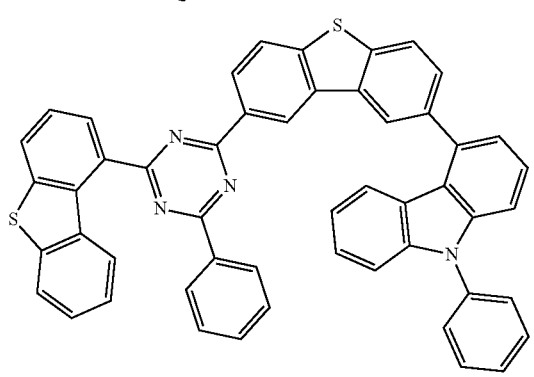
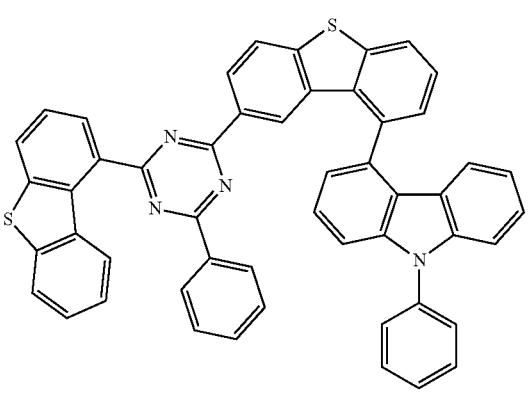

-continued
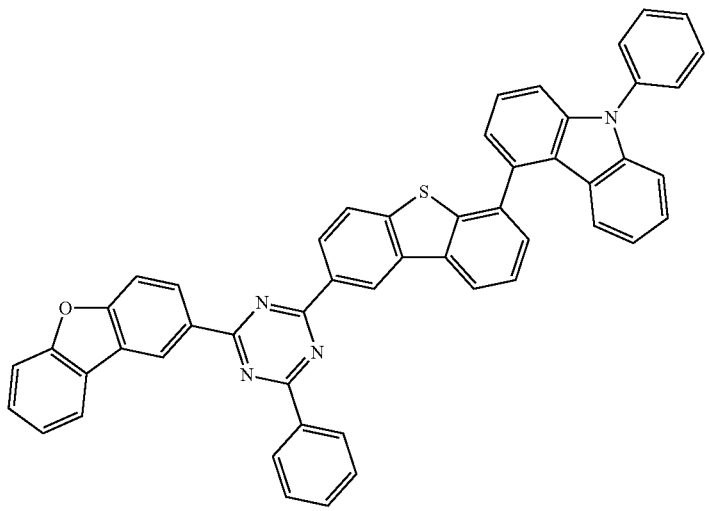
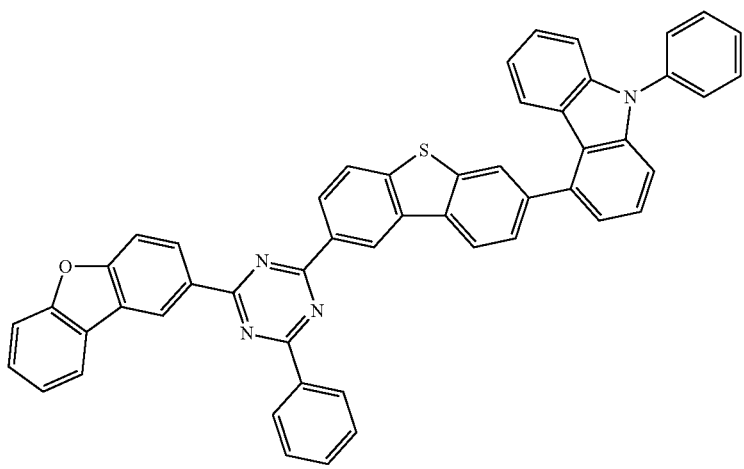
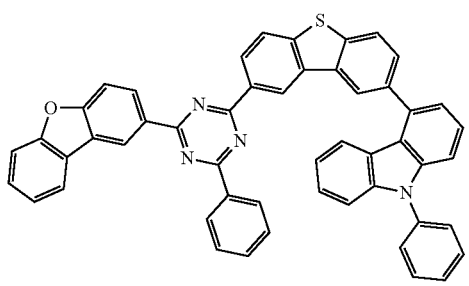
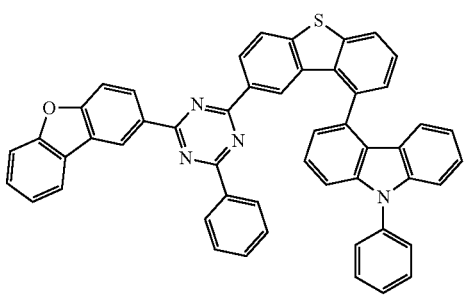

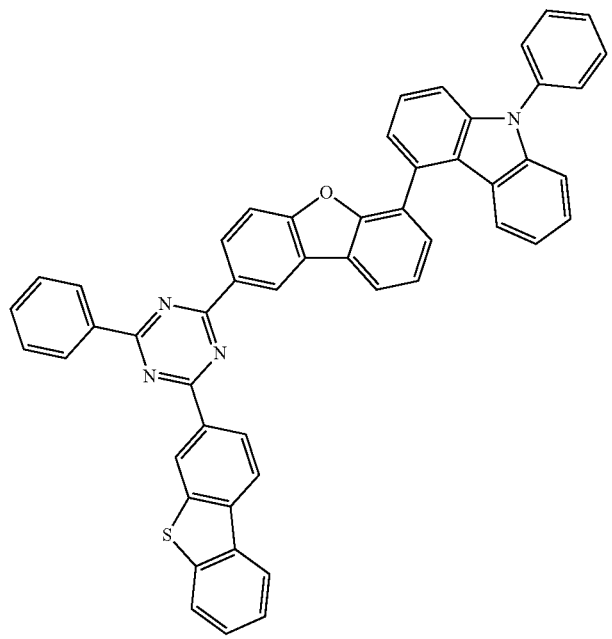
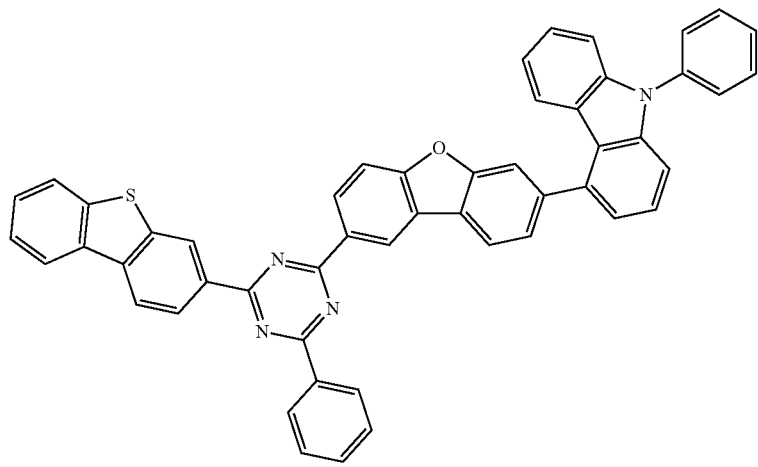
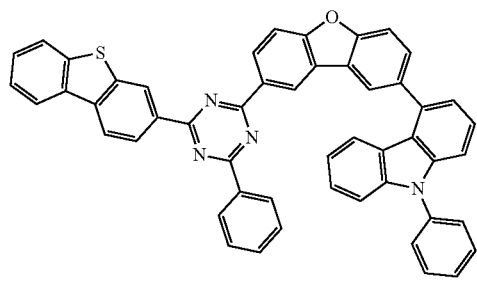
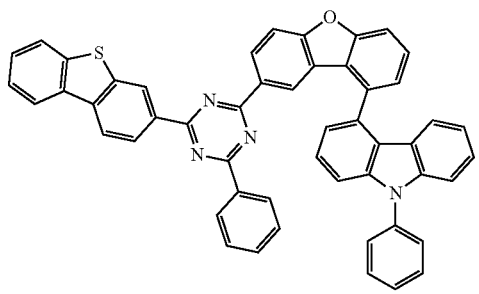

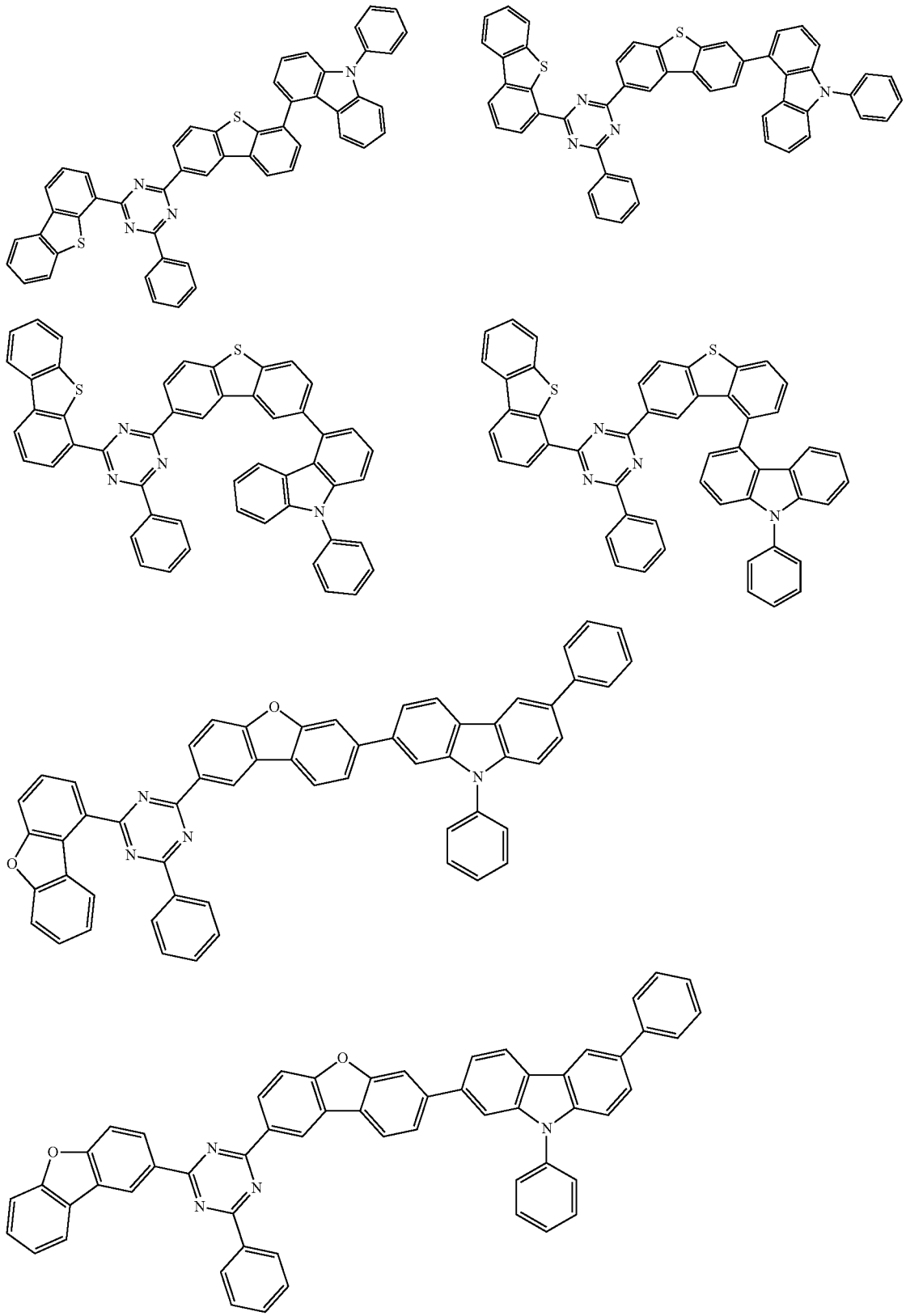

-continued
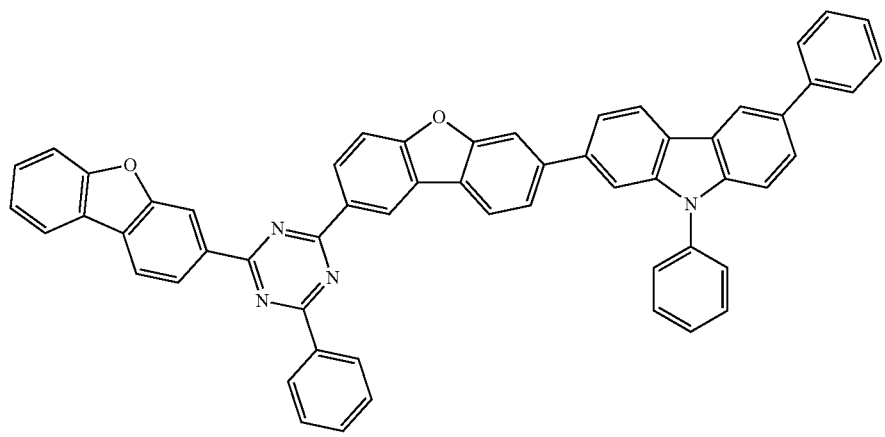 [SMILES: c1ccc(-c2ccc3c(c2)c2ccc(-c4ccc5c(c4)oc4ccc(-c6nc(-c7ccccc7)nc(-c7ccc8c(c7)oc7ccccc78)n6)cc45)cc2n3-c2ccccc2)cc1]
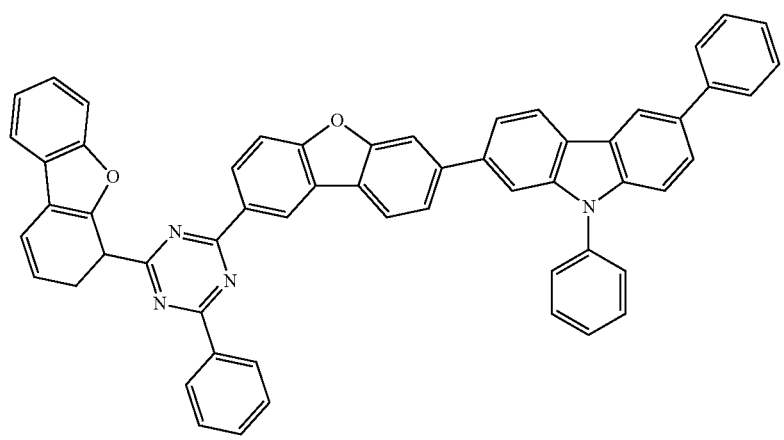 [SMILES: C1=Cc2c(oc3ccccc23)C(c2nc(-c3ccccc3)nc(-c3ccc4oc5cc(-c6ccc7c8cc(-c9ccccc9)ccc8n(-c8ccccc8)c7c6)ccc5c4c3)n2)C1]
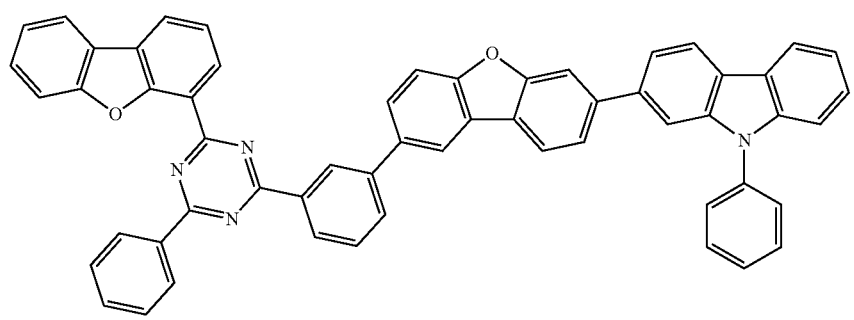

-continued
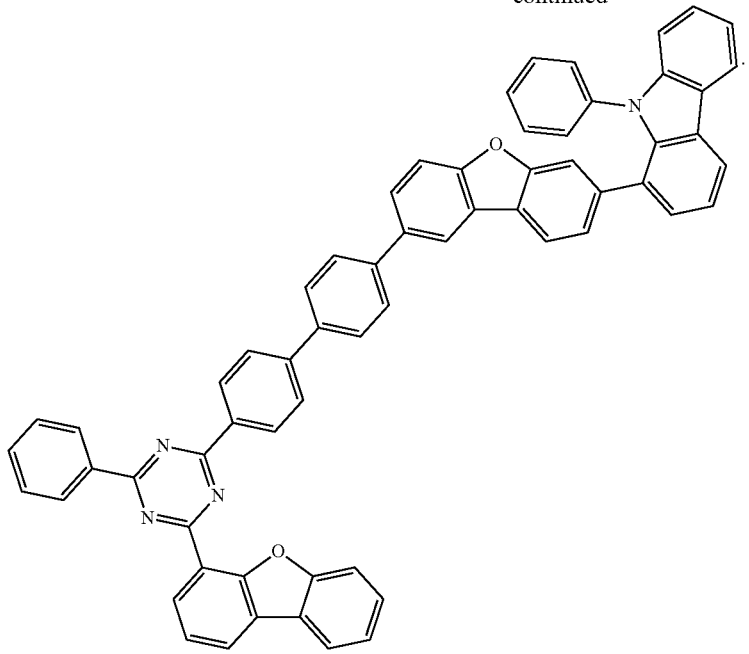
8. An organic light emitting device, comprising:
a first electrode;
a second electrode provided opposite to the first electrode; and
one or more organic material layers provided between the first electrode and the second electrode, wherein one or more one layers of the organic material layers comprise the compound of claim 1.
* * * * *